US008288393B2

(12) United States Patent
Iwata et al.

(10) Patent No.: US 8,288,393 B2
(45) Date of Patent: Oct. 16, 2012

(54) NITROGEN-CONTAINING HETEROCYCLIC COMPOUND AND PEST CONTROL AGENT

(75) Inventors: Jyun Iwata, Naka-gun (JP); Masahiro Kawaguchi, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 124 days.

(21) Appl. No.: 12/672,617

(22) PCT Filed: Aug. 11, 2008

(86) PCT No.: PCT/JP2008/064664
§ 371 (c)(1),
(2), (4) Date: Feb. 8, 2010

(87) PCT Pub. No.: WO2009/022746
PCT Pub. Date: Feb. 19, 2009

(65) Prior Publication Data
US 2011/0124858 A1  May 26, 2011

(30) Foreign Application Priority Data

Aug. 10, 2007  (JP) ................. 2007-208855
Dec. 26, 2007  (JP) ................. 2007-333470

(51) Int. Cl.
C07D 261/04  (2006.01)
C07D 413/04  (2006.01)
A01N 43/74  (2006.01)
A01N 47/20  (2006.01)
A01N 47/38  (2006.01)

(52) U.S. Cl. ............. 514/256; 514/230.5; 514/299; 514/300; 514/378; 544/105; 544/333; 546/112; 546/113; 548/240

(58) Field of Classification Search .......... None
See application file for complete search history.

(56) References Cited

U.S. PATENT DOCUMENTS

| 5,156,669 | A | 10/1992 | Zierke et al. | |
| 6,339,099 | B1 * | 1/2002 | Lam et al. | 514/378 |
| 2005/0250822 | A1 * | 11/2005 | Mita et al. | 514/365 |
| 2007/0066617 | A1 | 3/2007 | Mita et al. | |
| 2008/0312285 | A1 | 12/2008 | Palle et al. | |
| 2009/0156643 | A1 | 6/2009 | Mita et al. | |
| 2010/0254960 | A1 * | 10/2010 | Long et al. | 424/93.461 |
| 2011/0159107 | A1 * | 6/2011 | Koerber et al. | 424/605 |

FOREIGN PATENT DOCUMENTS

| EP | 0 455 052 | 11/1991 |
| EP | 1 731 512 | 12/2006 |
| JP | 4-224577 | 8/1992 |
| WO | WO 98/57951 * | 12/1998 |
| WO | 2005/021516 | 3/2005 |
| WO | 2005/085216 | 9/2005 |
| WO | 2006/090234 | 8/2006 |
| WO | WO 2006/129158 | 12/2006 |
| WO | WO 2007/029077 | 3/2007 |
| WO | WO 2007/031838 * | 3/2007 |
| WO | 2007/105814 | 9/2007 |
| WO | 2009/066009 | 5/2009 |
| WO | 2009/112275 | 9/2009 |
| WO | WO 2012/026403 * | 3/2012 |

OTHER PUBLICATIONS

Quan et al, Bioorganic and Medicinal Chemistry Letters, 13(6), 1023-1028, 2003.*
Japanese Patent Office, International Search Report (translated) mailed Sep. 22, 2008, from related International Patent Application No. PCT/JP2008/064664.
Parmar et al., "Synthesis, Characterization and In Vitro Anti-invasive Activity Screening of Polyphenolic and Heterocyclic Compounds," Bioorganic & Medicinal Chemistry, 11 (2003) pp. 913-929.

(Continued)

Primary Examiner — Fiona T Powers
(74) Attorney, Agent, or Firm — Kenyon & Kenyon LLP

(57) ABSTRACT

The present invention relates to a nitrogen-containing heterocyclic compound or salt thereof, represented by the following formula (I), and a pest control agent containing the compound or salt thereof, as an active ingredient of the pest control agent:

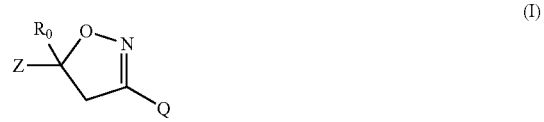

(I)

(wherein, $R_0$ represents a halogen atom, or the like; Z represents an unsubstituted or substituted aryl group, or the like; Y represents a nitro group, or the like; n represents an integer of 0 to 3; D represents a 5-membered to 8-membered hydrocarbon ring group or heterocyclic group; X represents a functional group represented by the following formula (II)-1 or formula (II)-2:

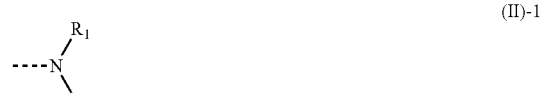

(II)-1

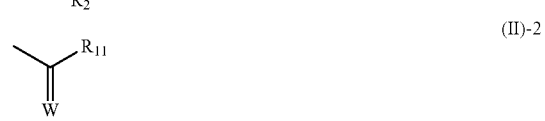

(II)-2

(wherein, in the formula (II)-1, the dotted line represents a single bond or double bond, and $R_1$ and $R_2$ respectively and independently represent a hydrogen atom, nitro group, hydroxyl group, mercapto group, unsubstituted or substituted amino group, or organic group; and, in the formula (II-2), W represents an oxygen atom or sulfur atom; and, $R_{11}$ represents a hydrogen atom, hydroxyl group, mercapto group, unsubstituted or substituted amino group, or the like); n1 represents an integer of 0 to 2; and, A represents a carbon atom or nitrogen atom).

18 Claims, No Drawings

OTHER PUBLICATIONS

Janusz et al., "New Cyclooxygenase-2/5-Lipoxygenase Inhibitors. 3. 7-tert-Butyl-2,3-dihydro-3,-dimethylbenzofuran Derivatives as Gastrointestinal Safe Antiflammatory and Analgesic Agents: Variations at the 5 Position," *J. Med. Chem.* (1998), 41, pp. 3515-3529.

Walters et al., "The Preparation of 5-Aryl-5-methyl-4,5-dihydroisoxazoles from Dilithiated C($\alpha$),O-Oximes and Select Acetyl Ketones," *Synthetic Communications*, vol. 33, No. 23, pp. 4163-4171, 2003.

RN 885890-19-7 Registry, ED Entered STN: May 29, 2006, CN 5-Isoxazolol,5-(difluoromethyl)-4,5-dihydro-3-(6-hydroxy-4,7-dimethoxy-5-benzoferanyl); retrieval date Sep. 2, 2008, URL: http://stnweb-japan.cas.org/.

RN 885890-13-1 Registry, ED Entered STN: May 29, 2006, CN 5-Isoxazolol, 4,5-dihydro-3-(6-hydroxy-4,7-dimethoxy-5-benzofuranyl)-5-(1,1,2,2-tetrafluoroethyl); retrieval date Sep. 2, 2008, URL: http://stnweb-japan.cas.org/.

RN 878436-08-9 Registry, ED Entered STN Mar. 29, 2006, CN 5-Isoxazolol, 4,5-dihydro-3-(6-hydroxy-4,7-dimethoxy-5-benzofuranyl)-5-(trifluoromethyl); retrieval date Sep. 2, 2008, URL: http://stnweb-japan.cas.org/.

RN 328285-44-5 Registry ED Entered STN: Mar. 21, 2001, CN 5-Isoxazolol, 4,5-dihydro-3-(2-naphthalenyl)-5-(trifluoromethyl); retrieval date Sep. 2, 2008, URL: http://stnweb-japan.cas.org/.

Townsend, Jessica D., et al., "The Preparation of 4,5-Dihydro-5-Phenyl-5-(2-Phenylethenyl)Isoxazoles, 4,5-Dihydro-5-Methyl-5-(2-Phenylethenyl)Isoxazoles, or 4,5-Dihydro-5,5-Di-(2-Phenylethenyl)Isoxazoles From Dilithiated C($\alpha$),O-Oximes and Select $\alpha,\beta$-Unsaturated Ketones", Synthetic Communications, 2000, vol. 30, No. 12, pp. 2175-2189.

Dang, Tuan Thanh, et al., "Synthesis of Isoxazole-5-carboxylates by Cyclization of Oxime 1,4-Dianions with Diethyl Oxalate", Synthesis, 2006, No. 15, pp. 2515-2522.

Fukui, Hiroki, et al, "NMR Determination of the Absolute Configuration of an $\alpha$-Exo-methylene-$\gamma$-lactone", Biosci. Biotechnol. Biochem., 2000, vol. 64, No. 7, pp. 1345-1351.

De Mattos, et al., "Cycloaddition of nitrile oxides to limonene: chemo- and regiospecific synthesis of 3-substituted 2-isoxazolines", 1994, vol. 17, No. 2, Abstract only, Database Caplus [Online], Chemical Abstract Service, Database accession No. 1994:483129, pages.

Shinohara, Toshio, et al., "Synthesis and Character of New Bis(Isoxazoline) Ligands", Heterocycles, 2003, vol. 59, No. 2, pp. 587-593.

Nabeta, Kensuke, et al., "Absolute Configuration of Kelsoene and Prespatane", Biosci. Biotechnol. Biochem., 1999, vol. 63, No. 10, pp. 1772-1776.

Database Registry [Online], Chemical Abstract Service, Database accession No. 328285-44-5, 1 page.

Jassbi, Amir Reza, et al., "Determination of Absolute Configuration of Decipinone, a Diterpenoid Ester with a Myrsinane-Type Carbon Skeleton, by NMR Spectroscopy", Helvetica Chimica Acta, 2002, vol. 85, No. 5, pp. 1706-1713.

European Search Report for 08792510.3, issued on Aug. 25, 2011, 12 pages.

\* cited by examiner

NITROGEN-CONTAINING HETEROCYCLIC COMPOUND AND PEST CONTROL AGENT

This application is a national phase application of PCT/JP2008/064664 filed on Aug. 11, 2008 which claims priority under 35 U.S.C. 119 to Japanese Patent Application Nos. 2007-208855 filed Aug. 10, 2007 and 2007-333470 filed Dec. 26, 2007.

TECHNICAL FIELD

The present invention relates to a novel nitrogen-containing heterocyclic compound or salt thereof, and to a pest control agent containing as an active ingredient thereof at least one type of these compounds.

The present application claims priority on Japanese Patent Application No. 2007-208855 filed in Japan on Aug. 10, 2007, and on Japanese Patent Application No. 2007-333470 filed in Japan on Dec. 26, 2007, the contents of which are incorporated herein by reference.

BACKGROUND ART

Although numerous insecticides, miticides and other pest control agents have been used in the past, since their efficacy has been inadequate, their use has been limited due to problems with drug resistance, or they have caused damage or contamination of plant bodies or demonstrated potent toxicity against human beings, livestock or fish, there have been more than a few cases in which these conventional pest control agents were hardly considered to be satisfactory control agents. Thus, there has been a desire for the development of a chemical having few of these disadvantages that can also be used safely.

Patent Document 1 relating to the present invention describes the following compound having a backbone that resembles that of the compound according to the present invention.

However, the compound according to the present invention is not described in this document.

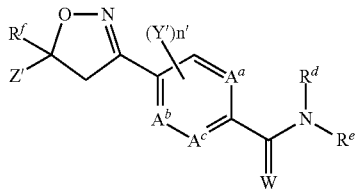

In the above formula, W' represents an oxygen atom or sulfur atom, $A^a$, $A^b$ and A' respectively and independently represent a carbon atom or nitrogen atom, Y' represents a halogen atom or the like, n' represents an integer of 0 to 4, $R^d$ and $R^e$ respectively and independently represent a hydrogen atom or C1 to C12 alkyl group or the like, $R^f$ represents a halogen atom or the like, and Z' represents a phenyl group or the like.

In addition, Patent Document 2 describes a compound represented by the following general formula. However, this compound was not considered to always demonstrate adequate control effects.

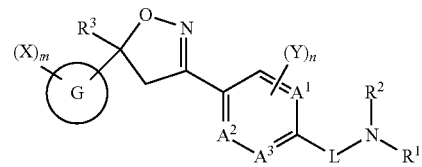

In the above formula, in the case $R^2$ and Y are present at adjacent locations, $R^2$ may form —$CH_2$—, —$CH_2CH_2$—, —$CH_2O$—, —$CH_2S$— or —$CH_2N(R^6)$— (wherein, $R^6$ represents a C1 to C6 alkyl group or the like) together with Y, or may form a 5-membered or 6-membered ring together with atoms respectively bonded thereto.

Patent Document 1: WO 2005/085216
Patent Document 2: WO 2007/105814

DISCLOSURE OF THE INVENTION

Problems to be Solved by the Invention

An object of the present invention is to provide a novel nitrogen-containing heterocyclic compound or salt thereof, which can be advantageously synthesized industrially and can function as an active ingredient of a pest control agent that has reliable effects and can be used safely, and a pest control agent that contains as an active ingredient thereof at least one type of these compounds.

Means for Solving the Problems

In order to solve the aforementioned problems, a first aspect of the present invention relates to a nitrogen-containing heterocyclic compound represented by the following formula (I), or salt thereof.

In the formula (I), $R_0$ represents a nitro group, hydroxyl group, mercapto group, halogen atom, unsubstituted or substituted amino group, or organic group.

Z represents an unsubstituted or substituted aryl group, unsubstituted or substituted heterocyclic group, unsubstituted or substituted alkyl group, unsubstituted or substituted alkenyl group, or unsubstituted or substituted alkynyl group.

Q represents a group represented by the following formula (I').

In the formula (I'), A represents a carbon atom or nitrogen atom, and in the case where A is a carbon atom and does not have a substituent represented by Y on the carbon atom, a hydrogen atom bonds thereto or A forms a ring by bonding with $R_1$ or $R_2$ as defined below.

Y represents a nitro group, hydroxyl group, mercapto group, halogen atom, unsubstituted or substituted amino group, or organic group, n represents an integer of 0 to 3, a plurality of Y are identical to or different from each other when n is 2 or more. Two Y may form a 4-membered to 6-membered ring by bonding together in the case where two Y are mutually adjacent.

D represents a 5-membered to 8-membered hydrocarbon ring group or heterocyclic group that has or does not have a substituent other than substituent X.

n1 represents an integer of 0 to 2, and two X are identical to or different from each other when n1 is 2.

X represents a functional group represented by the following formula (II)-1 or formula (II)-2.

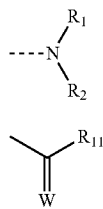

(II)-1

(II)-2

In the formula (II)-1, a dotted line represents a single bond or double bond, and either $R_1$ or $R_2$ is bonded to a nitrogen atom when the dotted line represents a double bond.

$R_1$ and $R_2$ respectively and independently represent a hydrogen atom, nitro group, hydroxyl group, mercapto group, unsubstituted or substituted amino group, or organic group. $R_1$ and $R_2$ may bond together to form a 3-membered to 8-membered ring, or $R_1$ and $R_2$ may together form a double bond to represent a group represented by the following formula:

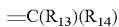

(in the formula, $R_{13}$ and $R_{14}$ respectively and independently represent a hydrogen atom, nitro group, hydroxyl group, mercapto group, halogen atom, unsubstituted or substituted amino group, or organic group), or $R_1$ or $R_2$ may bond with A to form a 5-membered to 8-membered ring.

In the aforementioned formula (II-2), W represents an oxygen atom or sulfur atom.

$R_{11}$ represents a hydrogen atom, hydroxyl group, mercapto group, unsubstituted or substituted amino group, or organic group.

In the aforementioned formula (I'), X is preferably represented by formula (II)-1.

In the aforementioned formula (II)-1, $R_1$ is preferably a group represented by formula (III):

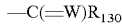

(III)

(in the formula, $R_{130}$ represents a hydrogen atom, unsubstituted or substituted amino group or organic group, and W represents an oxygen atom or sulfur atom).

In the aforementioned formula (I), Q preferably represents any of the groups represented by the following formulas:

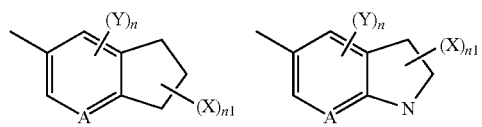

-continued

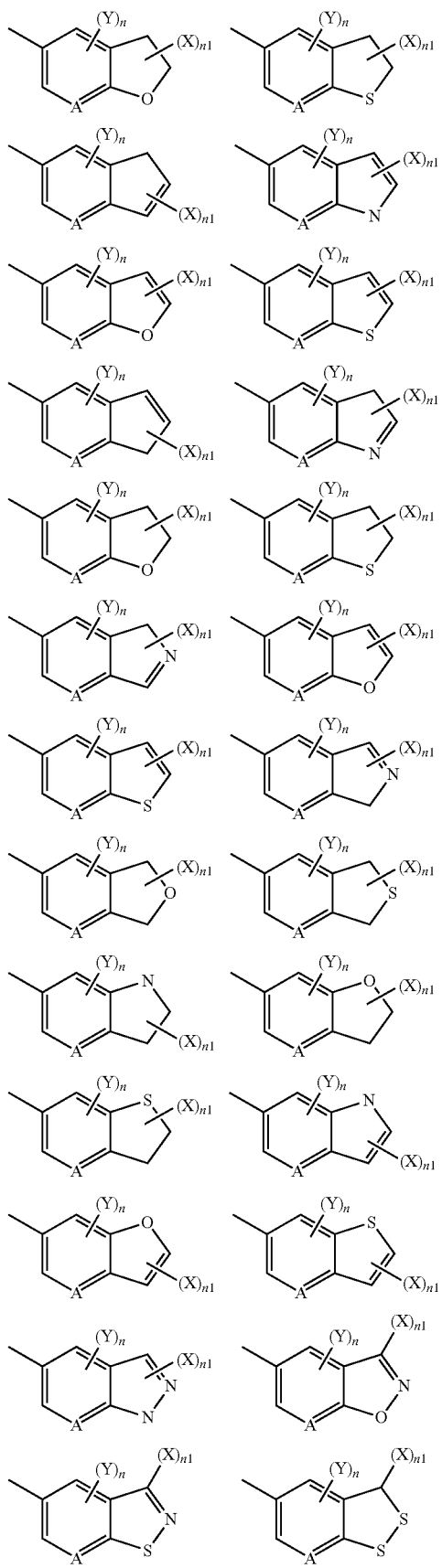

-continued

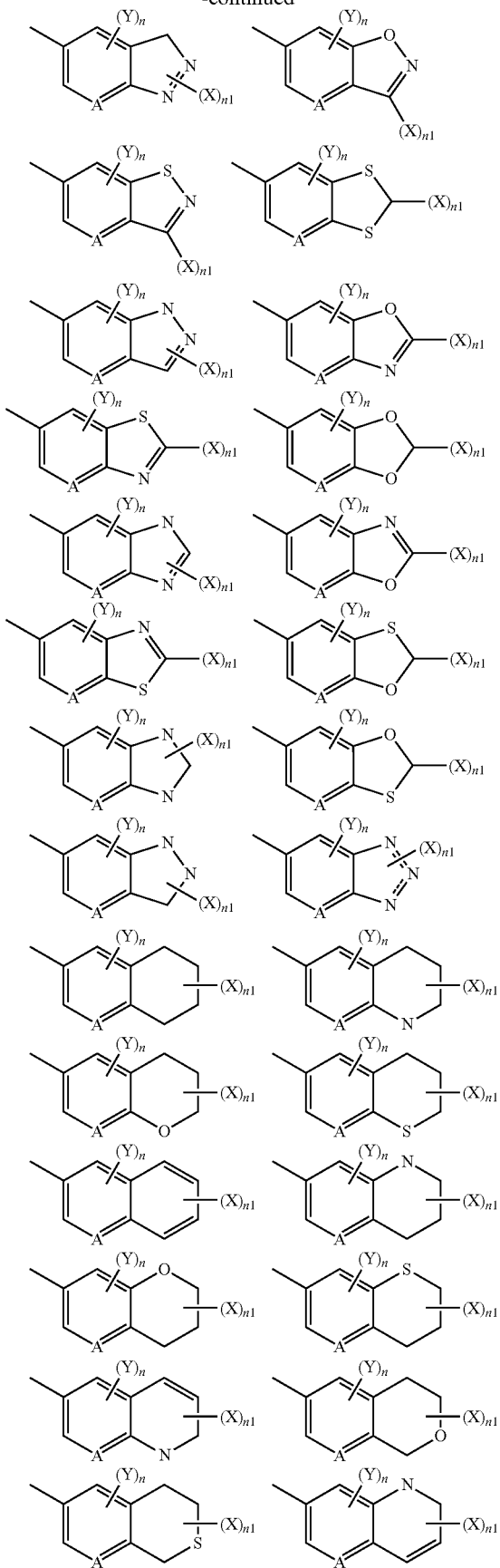
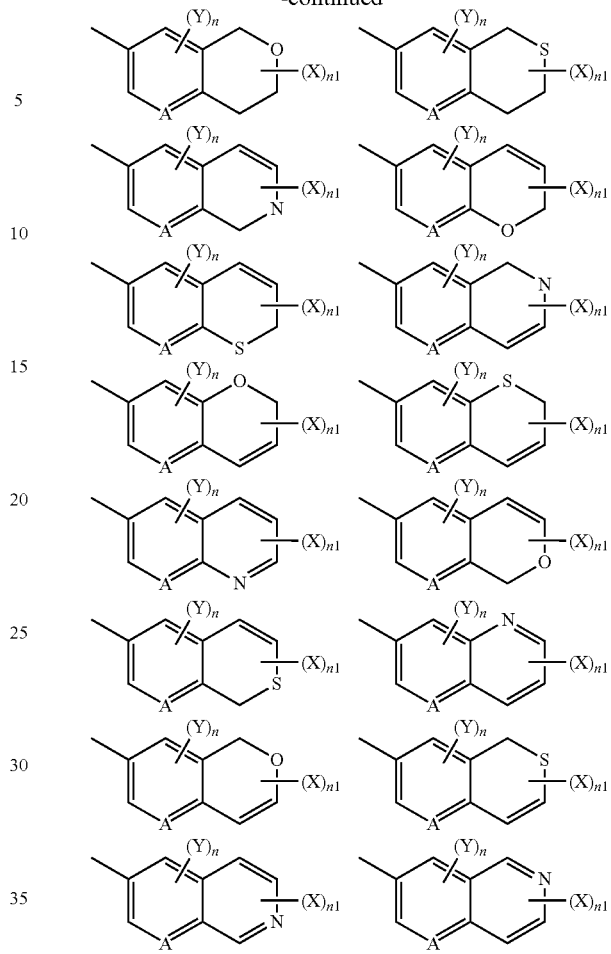

(in the formulas, A, Y, n, X and n1 have the same meanings as previously defined, and X, a hydrogen atom or a substituent other than X is bonded to a saturated nitrogen atom).

In the aforementioned formula (I), Z is preferably an unsubstituted or substituted phenyl group, or unsubstituted or substituted 5-membered or 6-membered heterocyclic group containing at least one heteroatom selected from the group consisting of a nitrogen atom, oxygen atom and sulfur atom.

In the aforementioned formula (I), $R_0$ preferably represents a C1 to C12 haloalkyl group.

In the aforementioned formula (I'), Y preferably represents a halogen atom, C1 to C6 alkyl group, C1 to C6 alkoxy group, C1 to C6 haloalkyl group or C1 to C6 haloalkoxy group, or n represents 0.

A second aspect of the present invention relates to an insecticide containing as an active ingredient thereof at least one type of the nitrogen-containing heterocyclic compound of the first aspect of the present invention, or salt thereof.

A third aspect of the present invention relates to a miticide containing as an active ingredient thereof at least one type of the nitrogen-containing heterocyclic compound of the first aspect of the present invention, or salt thereof.

A fourth aspect of the present invention relates to a pest control agent containing as an active ingredient thereof at least one type of the nitrogen-containing heterocyclic compound of the first aspect of the present invention, or salt thereof.

Effects of the Invention

According to the present invention, a novel nitrogen-containing heterocyclic compound or salt thereof, which can be advantageously synthesized industrially and can function as an active ingredient of a pest control agent that has reliable effects and can be used safely, as well as an insecticide, miticide and pest control agent, which contain as an active ingredient thereof at least one type of the compound, are provided.

BEST MODE FOR CARRYING OUT THE INVENTION

The following provides a detailed explanation of the present invention.

1) Nitrogen-Containing Heterocyclic Compound Represented by Formula (I) or Salt Thereof A first aspect of the present invention relates to a nitrogen-containing heterocyclic compound represented by the following formula (I) (hereinafter to be referred to as the "nitrogen-containing heterocyclic compound according to the present invention") and a salt thereof.

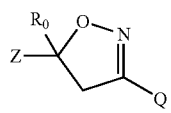

In formula (I), $R_0$ represents a nitro group, hydroxyl group, mercapto group, halogen atom, unsubstituted or substituted amino group, or organic group.

Examples of the halogen atom include a fluorine atom, chlorine atom and bromine atom.

Examples of the unsubstituted or substituted amino group include an amino group; mono-C1 to C6 alkylamino groups such as a methylamino group, ethylamino group or i-propylamino group; di-C1 to C6 alkylamino groups such as a dimethylamino group or methylamino group; acylamino groups such as an acetylamine group or benzoylamino group; and unsubstituted or substituted arylamino groups such as a phenylamino group or 4-methylphenylamino group.

The aforementioned organic group typically refers to an atom group that contains a carbon atom, and there are no particular limitations thereon provided that the atom group contains a carbon atom. Examples of the organic group include a cyano group; C1 to C6 alkyl groups such as a methyl group, ethyl group, n-propyl group, i-propyl group, n-butyl group, i-butyl group, s-butyl group, t-butyl group, n-pentyl group or n-hexyl group; C2 to C6 alkenyl groups such as a vinyl group, propenyl group, 1-propenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group; C2 to C6 alkynyl groups such as an ethynyl group, 1-propynyl group, 2-propynyl group, 1-butynyl group, 2-butynyl group, propargyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; C1 to C12 haloalkyl groups such as a chloromethyl group, dichloromethyl group, chloroethyl group, 1,2-dichloro-n-propyl group, 1-fluoro-n-butyl group, perfluoro-n-pentyl group, bromomethyl group, difluoromethyl group, trichloromethyl group, 2,2,2-trifluoroethyl group, trifluoromethyl group or pentafluoroethyl group; C3 to C8 cycloalkyl groups such as a cyclopropyl group, cyclobutyl group, cyclopentyl group, cyclohexyl group or cycloheptyl group; C3 to C8 halocycloalkyl groups such as a 2-chlorocyclopropyl group, 2,2-dichlorocyclopropyl group, 3-chlorocyclopentyl group or 4-bromocyclohexyl group; C1 to C6 alkoxy groups such as a methoxy group, ethoxy group, n-propoxy group, i-propoxy group, n-butoxy group, t-butoxy group, i-butoxy group, s-butoxy group or n-hexyloxy group; C1 to C6 haloalkoxy groups such as a 2-chloro-n-propoxy group, 2,3-dichlorobutoxy group, trichloromethoxy group or trifluoromethoxy group; C1 to C6 alkylsulfonyloxy groups such as a methylsulfonyloxy group, ethylsulfonyloxy group or i-propylsulfonyloxy group; arylsulfonyloxy groups such as a phenylsulfonyloxy group or 4-methylphenylsulfonyloxy group; C1 to C6 alkylthio groups such as a methylthio group, ethylthio group, n-propylthio group, i-propylthio group, n-butylthio group, i-butylthio group, s-butylthio group or t-butylthio group; C1 to C6 alkylsulfinyl groups such as a methylsulfinyl group, ethylsulfonyl group, n-propylsulfinyl group or t-butylsulfinyl group; C1 to C6 alkylsulfonyl groups such as a methylsulfonyl group, ethylsulfonyl group, n-propylsulfonyl group or t-butylsulfonyl group; C1 to C6 haloalkylthio groups such as a chloromethylthio group, trichloromethylthio group or trifluoromethylthio group; C1 to C6 haloalkylsulfinyl groups such as a chloromethylsulfinyl group, trichloromethylsulfinyl group or trifluoromethylsulfinyl group; C1 to C6 haloalkylsulfonyl groups such as a chloromethylsulfonyl group, trichloromethylsulfonyl group or trifluoromethylsulfonyl group; arylthio groups such as a phenylthio group, 4-methylphenylthio group or 2,4-dichlorophenylthio group; arylsulfinyl groups such as a phenylsulfinyl group, 4-methylphenylsulfinyl group or 2,4-dichlorophenylsulfinyl group; arylsulfonyl groups such as a phenylsulfonyl group, 4-methylphenylsulfonyl group or 2,4-dichlorophenylsulfonyl group; groups represented by —N=C($R_3$)$OR_4$; groups represented by —$COR_3$; groups represented by —C(=S)$R_3$; groups represented by —Si($R_5$)($R_6$)($R_7$); aryl groups such as a phenyl group, 4-methylphenyl group, 2-fluorophenyl group, 2,4-dichlorophenyl group, 2,4,6-trimethylphenyl group or 2-naphthyl group; and heterocyclic groups.

There are no limitations on the heterocyclic group and particularly on the composite elements thereof, and is preferably a 3-membered to 8-membered ring and more preferably a 5-membered or 6-membered ring. Specific examples of the heterocyclic group include unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group or 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group, unsaturated heterocyclic 6-membered ring group such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group, and saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, piperazino group, N-methylpiperazino group, aziridino group, azetidino group, pyrrolidino group, morpholino group or oxazolin-2-yl group. Among them, the unsaturated heterocyclic groups are preferable, and the unsaturated nitrogen-containing heterocyclic groups are more preferable. Specific examples thereof include a pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group, 1,2,4-triazol-5-yl group, pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group, 1,2,4-triazin-3-yl group, piperidin-3-yl group, pyrrolidin-2-yl group, morpholino group, piperidino group, piperazino group, N-methylpiperazino group, aziridino group, azetidino group, pyrrolidino group, morpholino group and oxazolin-2-yl group.

The aforementioned organic group may have a substituent at an arbitrary location within a chemically allowable range. The following lists examples of functional groups capable of serving as such substituents:

(1) halogen atoms such as a fluorine atom, chlorine atom, bromine atom or iodine atom;

(2) alkyl groups such as a methyl group, ethyl group, n-propyl group, i-propyl group, n-butyl group, s-butyl group, i-butyl group, s-butyl group, t-butyl group, n-pentyl group or n-hexyl group;

(3) cycloalkyl groups such as a cyclopropyl group, cyclobutyl group, cyclopentyl group, cyclohexyl group or cycloheptyl group;

(4) alkoxy groups such as a methoxy group, ethoxy group, n-propoxy group, isopropoxy group, n-butoxy group, i-butoxy group, s-butoxy group or t-butoxy group;

(5) alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group;

(6) cycloalkenyl groups such as a 2-cyclopropenyl group, 2-cyclopentenyl group, 3-cyclohexenyl group or 4-cyclooctenyl group;

(7) alkenyloxy groups such as a vinyloxy group, allyloxy group, 1-propenyloxy group or 2-butenyloxy group;

(8) alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group;

(9) alkynyloxy groups such as an ethynyloxy group or propargyloxy group;

(10) aryl groups such as a phenyl group, 1-napthyl group or 2-naphthyl group;

(11) aryloxy groups such as a phenoxy group or 1-naphthoxy group;

(12) aralkyl groups such as a benzyl group or phenethyl group;

(13) aralkyloxy groups such as a benzyloxy group or phenethyloxy group;

(14) acyl groups such as a formyl group, acetyl group, propionyl group, benzoyl group, cyclohexylcarbonyl group or phthaloyl group;

(15) alkoxycarbonyl groups such as a methoxycarbonyl group, ethoxycarbonyl group, n-propoxycarbonyl group, isopropoxycarbonyl group, n-butoxycarbonyl group or t-butoxycarbonyl group;

(16) carboxyl groups;

(17) hydroxyl groups;

(18) haloalkyl groups such as a chloromethyl group, chloroethyl group, 1,2-dichloro-n-propyl group, 1-fluoro-n-butyl group or perfluoro-n-pentyl group;

haloalkoxy groups such as 2-chloro-n-propoxy group, or 2,3-dichlorobutoxy group, trifluoromethoxy group;

(19) haloalkenyl groups such as a 2-chloro-1-propenyl group or 2-fluoro-1-butenyl group;

(20) haloalkynyl groups such as a 4,4-dichloro-1-butynyl group, 4-fluoro-1-pentynyl group or 5-bromo-2-pentynyl group;

(21) haloalkenyloxy groups such as a 2-chloro-1-propenyloxy group or 3-bromo-2-butenyloxy group;

(22) haloalkynyl groups such as a 3-chloro-propargyl group or 3-iodo-propargyl group;

(23) haloalkynyloxy groups such as a 3-chloro-propargyloxy group or 3-iodo-propargyloxy group;

(24) haloaryl groups such as a 4-chlorophenyl group, 4-fluorophenyl group or 2,4-dichlorophenyl group;

(25) haloaryloxy groups such as a 4-fluorophenoxy group or 4-chloro-1-naphthoxy group;

(26) halogen-substituted acyl groups such as a chloroacetyl group, trifluoroacetyl group, trichloroacetyl group or 4-chlorobenzoyl group;

(27) alkoxyalkyl groups such as a methoxymethyl group, ethoxymethyl group, 1-ethoxyethyl group or 2-ethoxyethyl group;

(28) alkoxyalkoxy groups such as a methoxymethoxy group, ethoxymethoxy group, 1-ethoxyethoxy group or 2-ethoxyethoxy group;

(29) cyano groups;

(30) isocyano groups;

(31) nitro groups;

(32) isocyanato groups;

(33) cyanato groups;

(34) amino groups;

(35) alkylamino groups such as a methylamino group, dimethylamino group or diethylamine group;

(36) arylamino groups such as an anilino group, naphthylamino group or anthranylamino group;

(37) aralkylamino groups such as a benzylamino group or phenethylamino group;

(38) alkylsulfonylamino groups such as a methylsulfonylamino group, ethylsulfonylamino group, n-propylsulfonylamino group, isopropylsulfonylamino group or n-butylsulfonylamino group;

(39) arylsulfonylamino groups such as a phenylsulfonylamino group;

(40) heteroarylsulfonylarnino groups such as a piperazinylsulfonylamino group;

(41) acylamino groups such as a formylarnino group, acetylamino group, propanoylamino group, butyrylamino group, isopropylcarbonylamino group or benzoylamino group;

(42) alkoxycarbonylamino groups such as a methoxycarbonylamino group or ethoxycarbonylamino group;

(43) haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 2,2,2-trifluoroethylsulfonylamino group or pentafluorosulfonylamino group;

(44) bis(alkylsulfonyl)amino groups such as a bis(methylsulfonyl)amino group, bis(ethylsulfonyl)amino group, (ethylsulfonyl)(methylsulfonyl)amino group, bis(n-propylsulfonyl)amino group, bis(isopropylsulfonyl)amino group, bis(n-butylsulfonyl) amino group or bis(t-butylsulfonyl)amino group;

(45) bis(haloalkylsulfonyl)amino groups such as a bis(fluoromethylsulfonyl)amino group, bis(chloromethylsulfonyl)amino group, bis(bromomethylsulfonyl)amino group, bis(dichloromethylsulfonyl)amino group, bis(1,1-difluoroethylsulfonyl)amino group, bis(trifluoromethylsulfonyl)amino group, bis(2,2,2 trifluoroethylsulfonyl)amino group or bis(pentafluoroethylsulfonyl)amino group;

(46) unsubstituted or substituted hydrazino groups such as a hydrazino group, N'-phenylhydrazino group, N'-methoxycarbonylhydrazino group, N'-acetylhydrazino group or N'-methylhydrazino group;

(47) unsubstituted or substituted aminocarbonyl groups such as an aminocarbonyl group, dimethylaminocarbonyl group, phenylaminocarbonyl group or N-phenyl-N-methylcarbonyl group;

(48) unsubstituted or substituted hydrazinocarbonyl groups such as a hydrazinocarbonyl group, N-methylhydrazinocarbonyl group or N'-phenylhydrazinocarbonyl group;

(49) unsubstituted or substituted iminoalkyl groups such as an N-methyliminomethyl group, 1-N-phenyliminoethyl group, N-hydroxyiminomethyl group or N-methoxyiminomethyl group;

(50) thiol groups;

(51) isothiocyanato groups;

(52) thiocyanato groups;

(53) alkylthio groups such as a methylthio group, ethylthio group, n-propylthio group, isopropylthio group, n-butylthio group, isobutylthio group, s-butylthio group or t-butylthio group;

(54) alkenylthio groups such as a vinylthio group or allylthio group;

(55) alkynylthio groups such as an ethynylthio group or propargylthio group;

(56) arylthio groups such as a phenylthio group or naphthylthio group;

(57) heteroarylthio groups such as a 2-piperidylthio group or 3-pyridazylthio group;

(58) aralkylthio groups such as a benzylthio group or phenethylthio group;

(59) heteroarylalkylthio groups such as a 2-ppidylmethylthio group or 2-furylmethylthio group;

(60) alkylthiocarbonyl groups such as a methylthiocarbonyl group, ethylthiocarhonyl group, n-propylthiocarbonyl group, isopropylthiocarbonyl group, 11-butylthiocarbonyl group, isobutylthiocarbonyl group, s-butylthiocarbonyl group or t-butylthiocarbonyl group;

(61) alkylthioalkyl groups such as a methylthiomethyl group or 1-methylthioethyl group;

(62) arylthioalkyl groups such as a phenylthiomethyl group or 1-phenylthioethyl group;

(63) alkylthioalkoxy groups such as a methylthiomethoxy group or 1-methylthioethoxy group;

(64) arylthioalkoxy groups such as a phenylthiomethoxy group or 1-phenylthioethoxy group;

(65) alkylsulfenyl groups such as a methylsulfenyl group, ethylsulfenyl group or t-butylsulfenyl group;

(66) alkenylsulfinyl groups such as an allylsulfinyl group;

(67) alkynylsulfinyl groups such as a propargylsulfinyl group;

(68) arylsulfinyl groups such as a phenylsulfinyl group;

(69) heteroarylsulfinyl groups such as a 2-pyridylsulfinyl group or 3-pyridylsulfinyl group;

(70) aralkylsulfinyl groups such as a benzylsulfinyl group or phenethylsulfinyl group;

(71) heteroarylalkylsulfinyl groups such as a 2-pyridylmethylsulfinyl group or 3-pyridylmethylsulfinyl group;

(72) alkylsulfonyl groups such as a methylsulfonyl group, ethylsulfonyl group or t-butylsulfonyl group;

(73) alkenylsulfonyl groups such as an allylsulfonyl group;

(74) alkynylsulfonyl groups such as a propargylsulfonyl group;

(75) arylsulfonyl groups such as a phenylsulfonyl group;

(76) heteroarylsulfonyl groups such as a 2-pyridylsulfonyl group or 3-pyridylsulfonyl group;

(77) aralkylsulfonyl groups such as a benzylsulfonyl group or phenethylsulfonyl group;

(78) heteroarylalkylsulfonyl groups such as a 2-pyridylmethylsulfonyl group or 3-pyridylmethylsulfonyl group;

(79) unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl gaup, isoxazol-5-yl group, isothiazol-3-yl group, isothiazol-4-yl group, isothiazol-5- yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 2,4-triazol- 3-yl group or 1,2,4-triazol-5-yl group;

(80) unsaturated heterocyclic 6-membered ring groups such as a pyridin-2-yl group, pyridin-3-yl group, pyridin-4-yl group, 5-chloro-3-pyridyl group, 3- trifluoromethyl-2-pyridyl group, pyridazin-3-yl group, pyridazin-4-yl group, pyrazin- 2-yl group, pyrimidin-5-yl group, 1,3,5-triazin-2-yl group or 1,2,4-triazin-3-yl group;

(81) saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, N-methylpiperazino group or oxazolin-2-yl group;

(82) heterocyclooxy groups such as a 2-pyridyloxy group or 3-isoxazolyloxy group;

(83) heteroarylalkyl groups such as a 2-pyridylmethyl group or 3-pyridylmethyl group; and, (84) heteroarylalkoxy groups such as a 2-pyridylmethoxy group or 3-pyridylmethoxy group.

These substituents exemplified in (1) to (84) above can also have substituents exemplified in (1) to (84).

Specific examples of the heterocyclic groups having substituents include a 3-trifluoromethylpyridin-2-yl group, 4-trifluoromethoxy-2-pyridyl group, 3-methyl-1-pyrazolyl group, 4-trifluoromethyl-1-imidazolyl group, 3,4,-difluoropyrrolidino group and 2-trifluoromethyl-4-pyrimidyl group.

$R_3$ and $R_4$ respectively and independently represent a hydrogen atom or an unsubstituted or substituted amino group or organic group.

Among these, $R_3$ is preferably a hydrogen atom; C1 to C12 alkyl group such as a methyl group or ethyl group; C1 to C12 haloalkyl group such as a trifluoromethyl group or pentafluoroethyl group; C3 to C12 cycloalkyl group such as a cyclopropyl group, cyclopentyl group or cyclohexyl group; C2 to C12 alkenyl group such as a vinyl group or allyl group; C2 to C12 haloalkenyl group such as a 3-chloroallyl group; C2 to C12 alkynyl group such as a propargyl group or 3-butynyl group; C2 to C12 haloalkynyl group such as a 2-chloroethynyl group, 2-bromoethynyl group or 3,3,3-trifluoro-1-propynyl group; C1 to C12 alkylthio group such as a methylthio group or ethylthio group; hydroxyl group; C1 to C12 alkoxy group such as a methoxy group or ethoxy group; amino group; mono-C1 to C6 alkylamino group such as a methylamino group or ethylamino group; di-C1 to C6 alkylamino group such as a dimethylamino group or diethylamino group; acylamino group such as an acetylamino group or benzoylamino group; unsubstituted or substituted arylamino group such as a phenylamino group or 4-methylphenylamino group; unsubstituted or substituted aryl group such as a phenyl group, 4-methylphenyl group, 2-chlorophenyl group or 2,4-difluorophenyl group; unsubstituted or substituted heterocyclic group; or unsubstituted or substituted hydrazdino group such as an N'-methylhydrazino group, N'-phenylhydrazino group or N,N'-dimethylhydrazino group.

$R_4$ is preferably a hydrogen atom; C1 to C12 alkyl group such as a methyl group or ethyl group; C1 to C12 haloalkyl group such as a trifluoromethyl group or pentafluoroethyl group; C3 to C12 cycloalkyl group such as a cyclopropyl group, cyclopentyl group or cyclohexyl group; C2 to C12 alkenyl group such as a vinyl group or allyl group; C2 to C12 haloalkenyl group such as a 3-chloroallyl group; C2 to C12 alkynyl group such as a propargyl group or 3-butynyl group; C2 to C12 haloalkynyl group such as a 2-chloroethynyl group, 2-bromoethynyl group or 3,3,3-trifluoro-1-propynyl group; amino group; di-C1 to C6 alkylamino group such as a dimethylamino group or diethylamino group; unsubstituted or substituted arylamino group such as a phenylamino group or 4-methylphenylamino group; unsubstituted or substituted aryl group such as a phenyl group, 4-methylphenyl group, 2-chlorophenyl group or 2,4-difluorophenyl group; or unsubstituted or substituted heterocyclic group.

Specific examples of the group represented by the aforementioned formula $-N=C(R_3)OR_4$ include $-N=C(H)OCH_3$, $-N=C(CH_3)OCH_3$, $-N=C(CH_3)OPh$, $-N=C(CF_3)OC_2H_5$, $-N=C(CH_3)OCH_2CH=CH_2$ and $-N=C(CH_3)OcPr$. Here, cPr represents a cyclopropyl group (and to mean the same hereinafter).

Specific examples of the group represented by the aforementioned formula $-COR_3$ include $-C(=O)NH(CH_3)$, $-C(=O)N(CH_3)_2$, $-C(=O)N(CH_3)Ph$, $-C(=O)N(CF_3)C_2H_5$, $-C(=O)N(CH_3)CH_2CH=CH_2$, $-C(=O)N(CH_3)(cPen)$, $-CHO$, $-CO_2CH_3$, $-CO_2C_2H_5$, $-CO_2Ph$, $-CO_2CH_2CH=CH_2$ and $-CO_2CF_3$. The aforementioned cPen represents a cyclopentyl group (and to mean the same hereinafter).

Specific examples of the group represented by the aforementioned formula $-C(=S)R_3$ include $-C(=S)NH(C_3H_7)$, $-C(=S)N(C_2H_5)_2$, $-C(=S)N(CH_3)Ph$, $-C(=S)N(CF_3)(n-C_4H_9)$, $-C(=S)N(CH_3)CH_2CH=CFl_2$, $-C(=S)N(CH_3)(cHex)$, $-C(=S)Ph$ and $-C(=S)(n-C_4H_9)$. The aforementioned cHex represents a cyclohexyl group (and to mean the same hereinafter).

$R_5$ to $R_7$ respectively and independently represent a hydrogen atom; C1 to C12 alkyl group such as a methyl group, ethyl group, n-propyl group, i-propyl group, n-butyl group or t-butyl group; unsubstituted or substituted aryl group such as a phenyl group or 4-methylphenyl group; or C1 to C12 alkoxy group such as a methoxy group, ethoxy group, isopropoxy group or t-butoxy group.

Specific examples of the group represented by the aforementioned formula $-Si(R_5)(R_6)(R_7)$ include $-Si(CH_3)_3$, $-Si(C_2H_5)_3$, $-Si(CH_3)_2(Ph)$, $-Si(Ph)_3$, $-Si(t-C_4H_9)(CH_3)_2$, $-Si(OCH_3)_3$, $-Si(OC_2H_5)_3$ and $-Si(OCH_3)_2CH_3$.

Among these, $R_0$ is preferably an organic group, and particularly preferably a C1 to C12 haloalkyl group.

Z represents an unsubstituted or substituted aryl group, unsubstituted or substituted heterocyclic group, unsubstituted or substituted alkyl group, unsubstituted or substituted alkenyl group or unsubstituted or substituted alkynyl group.

Specific examples of the unsubstituted or substituted aryl group and the unsubstituted or substituted heterocyclic group include the same groups as those indicated as specific examples of $R_0$. Specific examples of an alkyl group of the unsubstituted or substituted alkyl group, alkenyl group of the unsubstituted or substituted alkenyl group, and alkynyl group of the unsubstituted or substituted alkynyl group include the same groups as those indicated as specific examples of $R_0$. There are no particular limitations on these substituents provided that they are within a chemically allowable range, and specific examples thereof include the same substituents as those indicated as examples of substituents of organic groups of $R_0$.

Specific examples of the substituted alkyl group include a chloromethyl group, 2-chloroethyl group, trifluoromethyl group, 2,2,2-trifluoroethyl group, methoxymethyl group and methylthiomethyl group.

Specific examples of the substituted alkenyl group include a 2-chloroethenyl group, 2-fluoroethenyl group, 3,3,3-trifluoro-1-pentenyl group, 1,2,2-trifluoroethenyl group, 2,3,3-trifluoro-2-propenyl group, 2,3,3-triiodo-2-propenyl group and 2-methoxyethenyl group.

Specific examples of the substituted alkynyl group include a 2-chloroethynyl group, 2-fluoroethynyl group, 3-fluoro-1-propynyl group, 3,3,3-trifluoro-1-propynyl group, 3-fluoro-2-propynyl group and 3-iodo-2-propynyl group.

Among these, Z is preferably an unsubstituted or substituted aryl group or unsubstituted or substituted heterocyclic group, and is particularly preferably an unsubstituted or substituted phenyl group or unsubstituted or substituted 5-membered or 6-membered heterocyclic group containing at least one heteroatom selected from the group consisting of a nitrogen atom, oxygen atom and sulfur atom.

Specific examples of the unsubstituted or substituted aryl group or unsubstituted or substituted heterocyclic group of the aforementioned Z include, but are not limited to, the following (Z-1) to (Z-32).

(Z-1)

(Z-2)

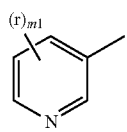 (Z-3)
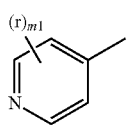 (Z-4)
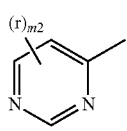 (Z-5)
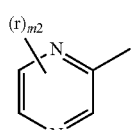 (Z-6)
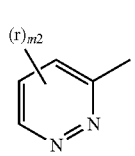 (Z-7)
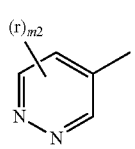 (Z-8)
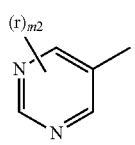 (Z-9)
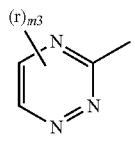 (Z-10)
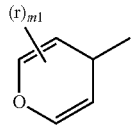 (Z-11)
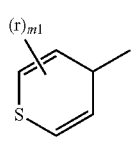 (Z-12)
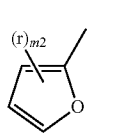 (Z-13)

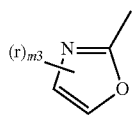 (Z-25)

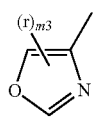 (Z-26)

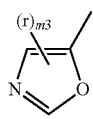 (Z-27)

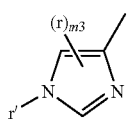 (Z-28)

 (Z-29)

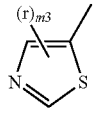 (Z-30)

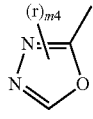 (Z-31)

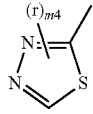 (Z-32)

In the aforementioned formulas, r represents a halogen atom such as a fluorine atom, chlorine atom or bromine atom; cyano group; nitro group; C1 to C6 alkyl group such as a methyl group or ethyl group; C1 to C6 haloalkyl group such as a trifluoromethyl group or pentafluoroethyl group; C3 to C8 cycloalkyl group such as a cyclopropyl group, cyclopentyl group or cyclohexyl group; C2 to C6 alkenyl group such as a vinyl group or propenyl group; C2 to C6 alkynyl group such as an ethynyl group or propargyl group; hydroxyl group; C1 to C6 alkoxy group such as a methoxy group, ethoxy group or i-propoxy group; unsubstituted or substituted aryloxy group such as a phenoxy group or 4-methylphenoxy group; mercapto group; C1 to C6 alkylthio group such as a methylthio group or ethylthio group; C1 to C6 alkylsulfinyl group such as a methylsulfinyl group or ethylsulfinyl group; C1 to C6 alkylsulfonyl group such as a methylsulfonyl group or ethylsulfonyl group; unsubstituted or substituted arylthio group such as a phenylthio group or 4-chlorophenylthio group; unsubstituted or substituted arylsulfonyl group such as a phenylsulfonyl group or 4-methylphenylsulfonyl group; C1 to C6 alkylsulfonyloxy group such as a methylsulfonyloxy group or ethylsulfonyloxy group; unsubstituted or substituted arylsulfonyloxy group such as a phenylsulfonyloxy group or 2-chlorophenylsulfonyloxy group; C1 to C6 alkoxycarbonyl group such as a methoxycarbonyl group or ethoxycarbonyl group; acyl group such as a formyl group, acetyl group, propionyl group or benzoyl group; unsubstituted or substituted aminocarbonyl group such as an aminocarbonyl group, N-methylaminocarbonyl group, N-phenylaminocarbonyl group or N,N-dimethylaminocarbonyl group; or a substituted aminothiocarbonyl group such as an N-methylaminothiocarbonyl group or N-phenylaminothiocarbonyl group. Among these, r preferably represents a halogen atom, C1 to C6 alkyl group or C1 to C6 haloalkyl group.

m0 represents an integer of 0 to 5, m1 represents an integer of 0 to 4, m2 represents an integer of 0 to 3, m3 represents an integer of 0 to 2, and m4 represents an integer of 0 or 1. A plurality of r may be the same or different when m0 to m3 represent an integer of 2 or more, respectively.

Q represents a group represented by the following formula (I').

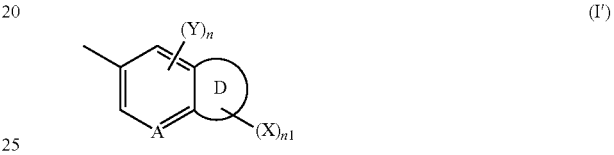 (I')

In the above formula (I'), A represents a carbon atom or nitrogen atom, and in the case where A is a carbon atom and the carbon atom does not have a substituent represented by Y, a hydrogen atom bonds thereto, or A forms a ring by bonding with $R_1$ or $R_2$.

Y represents a nitro group, hydroxyl group, mercapto group, halogen atom, unsubstituted or substituted amino group or organic group.

Specific examples of the halogen atom, unsubstituted or substituted amino group and organic group include the same groups as those indicated as specific examples of halogen atoms, unsubstituted or substituted amino groups and organic groups of $R_0$.

n represents an integer of 0 to 3, and a plurality of Y may be the same or different when n is 2 or more.

In addition, in the case of two adjacent Y, the two Y together may form a ring, and may form a 4- to 6-membered ring together with atoms respectively bonded by the two Y by forming, for example, —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—.

In addition, the hydrogen atoms bonded to each atom that forms a ring at this time may be substituted by a substituent T, and in the case of being simultaneously substituted by two or more T, each T may be the same or different.

Here, examples of T include a cyano group, nitro group, formyl group, halogen atom, C1 to C6 alkyl group, C1 to C6 alkoxy group, C3 to C8 cycloalkyl group, C3 to C8 cycloalkyloxy group, C3 to C8 cycloalkyl C1 to C6 alkyl group, C3 to C8 cycloalkyl C1 to C6 alkoxy group, C2 to C6 alkenyloxy group, C1 to C6 haloalkyl group, C1 to C6 haloalkoxy group, C2 to C6 haloalkenyloxy group, C1 to C6 alkoxycarbonyl group and unsubstituted or substituted phenyl group. Specific examples thereof include the same groups as those indicated as examples of the substituents of heterocyclic group of $R_0$.

Among these, in the present invention, Y preferably represents a halogen atom or C1 to C6 haloalkyl group, and n preferably represents 0.

D represents a 5- to 8-membered hydrocarbon ring group or heterocyclic group not having or having a substituent other than substituent X.

There are no particular limitations on the substituent other than substituent X provided that the substituent is chemically allowed, and examples thereof include the same as those indicated for the aforementioned r.

n1 represents an integer of 0 to 2, and in the case where n1 is 2, two X may be the same or different.

X represents a functional group represented by the following formula (II)-1 or (II)-2.

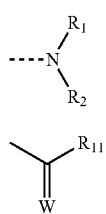

(II)-1

(II)-2

In the formula (II)-1 above, the dotted line represents a single bond or double bond, and in the case of a double bond, $R_1$ or $R_2$ is bonded to the nitrogen atom.

$R_1$ and $R_2$ respectively and independently represent a hydrogen atom, nitro group, hydroxyl group, mercapto group, unsubstituted or substituted amino group or organic group.

Specific examples of the unsubstituted or substituted amino group and organic group of $R_1$ and $R_2$ include the same as those indicated as specific examples of the unsubstituted or substituted amino group and organic group of the aforementioned $R_0$.

In addition, $R_1$ and $R_2$ may bond together to form a group represented by $=C(R_{13})(R_{14})$ or a 3- to 8-membered ring. Moreover, $R_1$ or $R_2$ may bond with A to form a 5- to 8-membered ring. In addition, the 3- to 8-membered ring and the 5- to 8-membered ring may be substituted with a substituent such as an alkyl group such as a methyl group or ethyl group; a halogen atom such as a fluorine atom or chlorine atom; an oxo group (=O); or an alkoxy group such as a methoxy group or ethoxy group.

Here, $R_{13}$ and $R_{14}$ respectively and independently represent a hydrogen atom, nitro group, hydroxyl group, mercapto group, halogen atom, unsubstituted or substituted amino group or organic group. Specific examples of the halogen atom, unsubstituted or substituted amino group and organic group of the aforementioned $R_{13}$ and $R_{14}$ are the same as those indicated as specific examples of the halogen atom, unsubstituted or substituted amino group and organic group of the aforementioned $R_0$.

In the aforementioned formula (II)-2, W represents an oxygen atom or sulfur atom.

$R_{11}$ represents a hydrogen atom, mercapto group, unsubstituted or substituted amino group or organic group. Specific examples of the unsubstituted or substituted amino group and organic group of $R_{11}$ are the same as those indicated as specific examples of the unsubstituted or substituted amino group and organic group of the aforementioned $R_0$. Among these, an unsubstituted or substituted C1 to C12 alkyl group, unsubstituted or substituted C1 to C12 alkoxy group, alkylamino group, unsubstituted or substituted aryl group, C1 to C1-2 alkyl group substituted with an unsubstituted or substituted heterocycle, and unsubstituted or substituted arylamino group are preferable.

In the aforementioned formula (I'), X is preferably represented by the formula (II)-1, and $R_1$ is preferably a group represented by the following formula (III):

$$-C(=W)R_{130} \quad (III)$$

(in the formula (III), $R_{130}$ represents a hydrogen atom, hydroxyl group, mercapto group, halogen atom, unsubstituted or substituted amino group or organic group, and more preferably a hydrogen atom, unsubstituted or substituted amino group or organic group, and W represents an oxygen atom or sulfur atom), and more preferably a group represented by:

$$-C(=O)R_{130}$$

(wherein, $R_{130}$ has the same meaning as previously described).

Specific examples of the halogen atom, unsubstituted or substituted amino group and organic group of $R_{130}$ are the same as those indicated as specific examples of the halogen atom, unsubstituted or substituted amino group and organic group of the aforementioned $R_0$. Among these, $R_{130}$ is preferably a C1 to C12 alkyl group, C1 to C12 alkyl group substituted with a C1 to C12 alkoxy group, cyano group, acyl group, unsubstituted or substituted aryl group or unsubstituted or substituted heterocyclic group, unsubstituted or substituted heterocyclic group, C3 to C12 cycloalkyl group, or unsubstituted or substituted C3 to C12 cycloalkenyl group.

In the aforementioned formula (I), Q is preferably represented by any one of the groups represented by the following formulas.

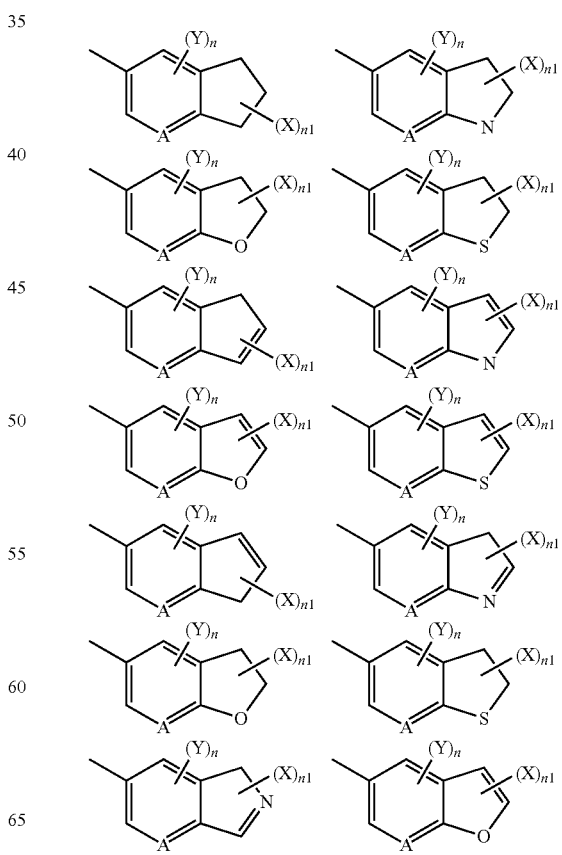

-continued
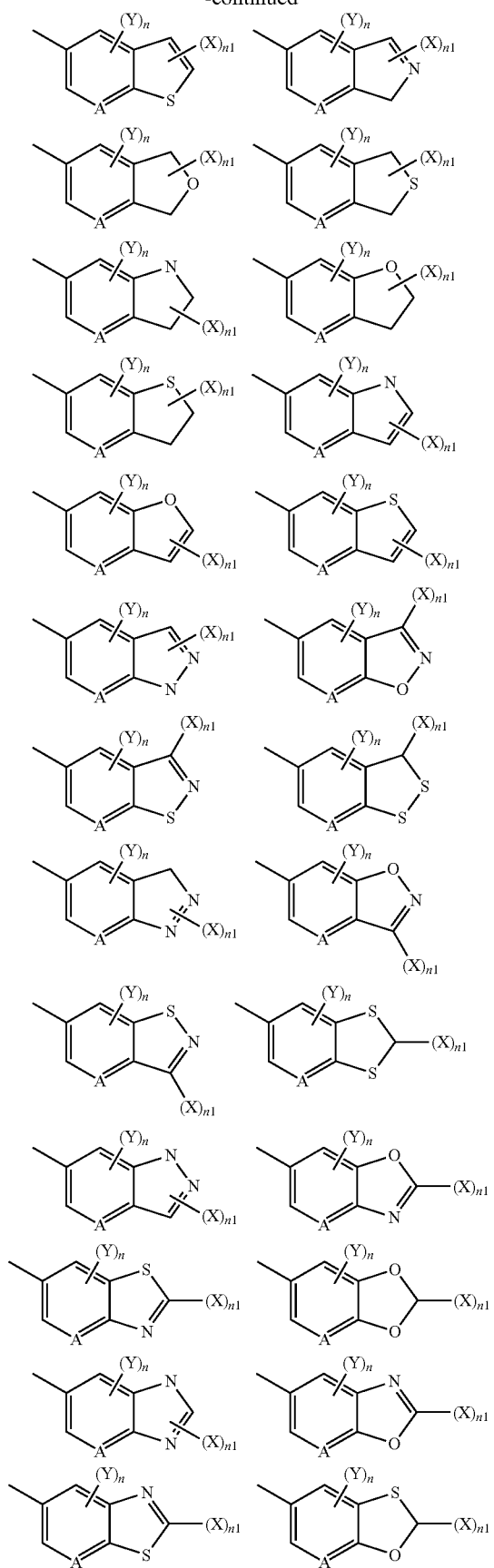
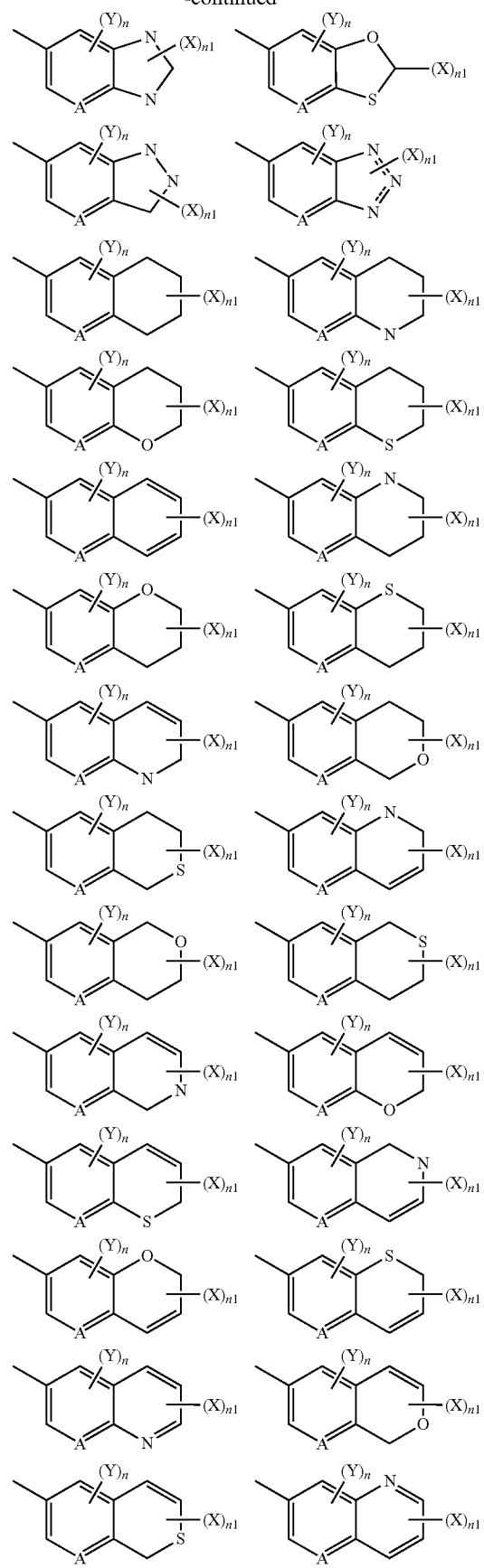

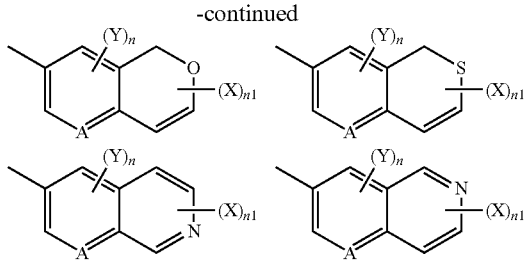

Among these, Q is particularly preferably represented by any one of the groups represented by the following formulas.

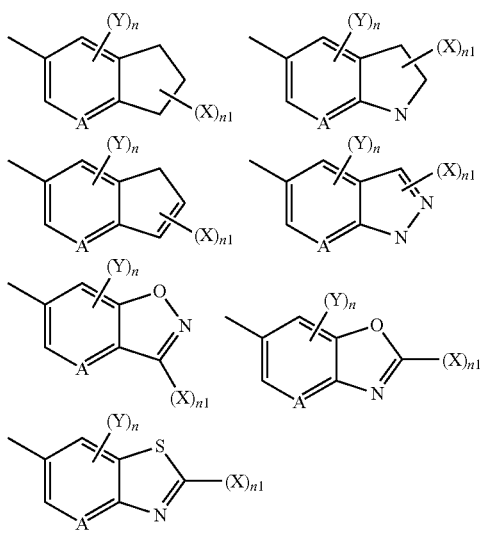

In the above formulas, A, Y, n, X and n1 are the same as previously defined, and X, a hydrogen atom or a substituent other than X is bonded to the saturated nitrogen atom.

A compound represented by the following formula (I″), which is a compound represented by formula (I) according to the present invention, can be produced according to the method indicated below.

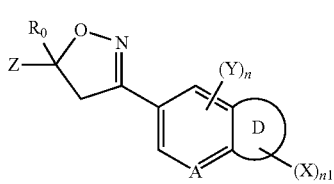

In the formula (I″) above, $R_0$, Z, Y, n, D, X, n1 and A are the same as previously defined.

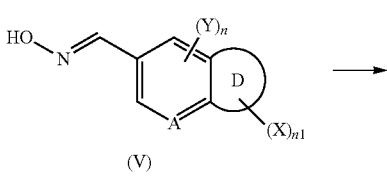

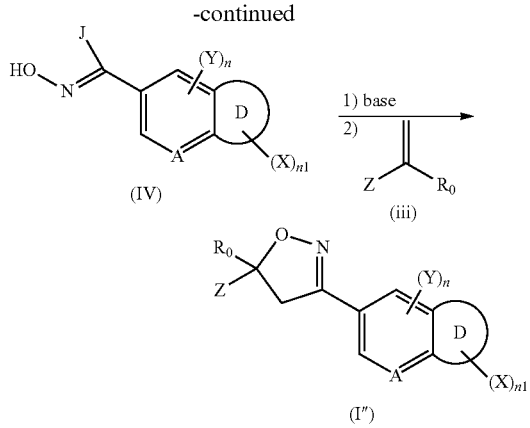

(In the above formulas, $R_0$, Z, Y, n, D, X, n1 and A are the same as previously defined, and J represents a halogen atom.)

Namely, a compound represented by formula (IV) is first obtained by allowing a halogenating agent to act on a compound represented by formula (V).

Examples of the halogenating agent used include N-halogenosuccinic acid imides such as N-chlorosuccinic acid imide or N-bromosuccinic acid imide; alkaline metal hypohalogenites such as sodium hypochlorite, hypohalogenous acid esters such as hypochlorous acid t-butyl ester; and carrier halogens such as chlorine gas.

The halogenating agent is normally used at 1 to 10 equivalents based on the compound represented by formula (V).

This reaction is preferably carried out in a solvent. There are no particular restrictions on the solvent used provided that it is inert in the reaction. Examples of the solvent used include aromatic hydrocarbons such as benzene, toluene or xylene; aliphatic hydrocarbons such as hexane or heptane; alicyclic hydrocarbons such as cyclohexane; aromatic halogenated hydrocarbons such as chlorobenzene or dichlorobenzene; aliphatic halogenated hydrocarbons such as dichloromethane, chloroform, carbon tetrachloride, 1,2-dichloroethane, 1,1,1-trichloroethane, trichloroethylene or tetrachloroethylene; ethers such as diethyl ether, 1,2-dimethoxyethane, tetrahydrofuran or 1,4-dioxane; esters such as ethyl acetate or ethyl propionate; amides such as N,N-dimethylformamide, N,N-dimethylacetoamide or N-methyl-2-pyrrolidone; alcohols such as methanol, ethanol or ethylene glycol; carboxylic acids such as acetic acid or propionic acid; acetonitrile; and, water.

One type of these solvents can be used or two or more types thereof can be used as a mixture.

The reaction temperature is normally within a temperature range of −60° C. to the reflux temperature of the reaction mixture.

The resulting compound represented by formula (IV) can normally be supplied to the next reaction without isolating.

Next, after allowing a base to act on the compound represented by formula (IV), a compound represented by formula (I″) can be obtained by allowing a compound represented by formula (iii) to act on the compound represented by formula (IV).

Examples of the base used include alkaline metal hydroxides such as sodium hydroxide or potassium hydroxide; alkaline metal carbonates such as sodium carbonate or potassium carbonate; alkaline metal bicarbonates such as sodium bicarbonate or potassium bicarbonate; and, organic bases such as triethylamine, imidazole or 1,8-diazabicyclo[5.4.0]-7-undecene.

The base is normally used at 1 to 5 equivalents based on the compound represented by formula (IV).

This reaction is preferably carried out in a solvent. There are no particular restrictions on the solvent used provided that it is inert in the reaction, and examples thereof are the same as those used in the reaction to obtain the compound represented by formula (IV).

The reaction temperature is normally within a temperature range of −60° C. to the reflux temperature of the reaction mixture.

There are no particular limitations on salts of compounds represented by formula (I) provided that they are horticulturally and agriculturally allowable salts. Examples of the salts of the compounds represented by formula (I) include salts of inorganic acids such as hydrochlorides, nitrates, sulfates and phosphates; and, salts of organic acids such as acetic acid, propionic acid or lactic acid.

A salt of a compound represented by formula (I) can be produced by, for example, allowing an inorganic acid or organic acid to act on the compound represented by formula (I).

After the reactions are completed and then an ordinary post-treatment procedure is carried out, a target compound can be purified by a known method such as distillation, recrystallization, or column chromatography, if needed, to isolate the target compound.

The structure of the target compound can be identified and confirmed by a known analysis such as elementary analysis, NMR spectroscopy, IR spectroscopy or mass spectroscopy.

A nitrogen-containing heterocyclic compound according to the present invention, or salt thereof (to be referred to as a compound according to the present invention), obtained in the manner described above can be used to control agriculturally harmful organisms, sanitary insect pests, stored grain insect pests, clothing insect pests, household insect pests and the like, and has adult insecticidal, nymph insecticidal, larval insecticidal and ovicidal action.

Thus, as will be described subsequently, the compound according to the present invention is useful as an active ingredient of a pest control agent.

Furthermore, among the compounds according to the present invention, there are those that demonstrate antimicrobial activity, herbicidal activity or plant growth regulatory action. In addition, the compounds according to the present invention can also be used as an antifouling agent to prevent adhesion of marine organisms to objects in contact with water such as ship bottoms or fishnets. In addition, some intermediates of the compounds according to the present invention also demonstrate insecticidal and/or miticidal activity.

2) Pest Control Agent

The pest control agent according to the present invention contains as an active ingredient thereof at least one type of the nitrogen-containing heterocyclic compound or salt thereof of the aforementioned first aspect of the present invention. The pest control agent according to the present invention is preferably an insecticide, miticide or sanitary insect pest control agent. Namely, a second aspect of the present invention relates to an insecticide containing as an active ingredient thereof at least one type of the aforementioned nitrogen-containing heterocyclic compound or salt thereof. In addition, a third aspect of the present invention relates to a miticide containing as an active ingredient thereof at least one type of the aforementioned nitrogen-containing heterocyclic compound or salt thereof. A fourth aspect of the present invention relates to a sanitary insect pest control agent containing as an active ingredient thereof at least one type of the aforementioned nitrogen-containing heterocyclic compound or salt thereof.

The pest control agent (insecticide, miticide or sanitary insect pest control agent) according to the present invention can be used to control agriculturally harmful organisms, sanitary insect pests, stored grain insect pests, clothing insect pests, household insect pests and the like, and has adult insecticidal, nymph insecticidal, larval insecticidal and ovicidal action.

The following lists typical examples thereof.

The compounds according to the present invention demonstrate superior control effects against harmful organisms such as order Orthoptera pests, order Thysanoptera pests, order Hemiptera pests, order Coleoptera pests, order Diptera pests, order Lepidoptera pests, order Hymenoptera pests, order Collembola pests, order Zygentoma pests, order Blattodea pests, order Isoptera pests, order Psocoptera pests, order Mallophaga pests, order Phthiraptera pests, plant parasitic mites, plant parasitic nematodes, plant parasitic mollusks, and other harmful animals, nuisance animals, sanitary insect pests and parasites. Examples of such harmful organisms include the biological species indicated below.

Examples of the order Orthoptera pests include *Ruspolia lineosa* of the family Tettigoniidae, *Teleogryllus emma* of the family Gryllidae, *Grylloptalpa orientalis* of the family Gryllotalpidae, *Oxya hyla intricate, Locusta migratoria* or *Melanoplus sanguinipes* of the family Acrididae, *Attractomorpha lata* of the family Pyrgomorphidae, and *Euscyrtus japonicus* of the family Eneopteridae.

Examples of the order Thysanoptera pests include *Frankliniella intonsa, Frankliniella occidentalis, Scirtothrips dorsalis, Thrips palmi* or *Thrips tabaci* of the family Thripidae, and *Ponticulothrips diospyrosi* or *Haplothrips aculeatus* of the family Phlaeothripidae.

Examples of the order Hemiptera pests include *Mogannia minute* of the family Cicadidae, *Aphrophora intermedia* of the family Aphrophoridae, *Machaerotypus sibiricus* of the family Membracidae, *Arboridia apicalis, Empoasca onukii, Nephotettix cincticeps* or *Recilia dorsalis* of the family Cicadellidae, *Pentastiridius apicalis* of the family Cixiidae, *Laodelphax striatellus, Nilaparvata lugens* or *Sogatella furcifera* of the family Delphacidae, *Nisia nervosa* of the family Meenoplidae, *Kamendaka saccharivora* of the family Derbidae, *Achilus flammeus* of the family Achilidae, *Orosanga japonicus* of the family Udoteaceae, *Mimophantia maritima* of the family Flatidae, *Cacopsylla pyrisuga* of the family Psyllidae, *Calophya mangiferae* of the family Calophyidae, *Daktulosphaira vitifoliae* of the family Phylloxera, *Adelges iaricis* or *Adelges tsugae* of the family Adelgidae, *Acyrthosiphon pisum, Aphis gossypii, Aphis spiraecola, Lipaphis erysimi, Myzus persicae, Schizaphis graninum* or *Rhopalosiphum padi* of the family Aphididae, *Aleurocanthus spiniferus, Bemisia tabaci, Bemisia argentifolii* or *Trialeurodes vaporariorum* of the family Aleyrodidae, *Drosicha corpulenta* or *Icerya purchasi* of the family Margarodidae, *Dysmicoccus brevipes, Planococcus citri* or *Pseudococcus comstocki* of the family Pseudococcidae, *Ceroplastes ceriferus* of the family Coccidae, *Aclerda takahashii* of the family Aclerididae, *Aonidiella aurantii, Diaspidiotus perniciosus* or *Unaspis yanonensis* of the family Diaspididae, *Lygus hesperus* or *Trigonotylus caclestialium* of the family Miridae, *Stephanitis pyrioides* or *Stephanitis nashi* of the family Tingidae, *Eysarcoris aeneus, Lagynotomus elongatus, Nezara viridula* or *Plautia crossota* of the family Pentatomidae, *Megacopta cribraria* of the family Plataspidae, *Cavelerius saccharivorus* of the family Lygaeidae, *Malcus japoni-* cus of the family Malcidae, *Dysdercus cingulatus* of the family Pyrrhocoridae, *Leptocorisa acuta* or *Leptocorisa chinensis* of the family Alydidae, *Anacanthocoris striicornis* of the family Coreidae, *Rhopalus maculatus* of the family Rhopalidae, and *Cimex lectularis* of the family Cimicidae.

Examples of the order Coleoptera pests include *Anomara cuprea, Anomara rufocuprea, Popillia japonica* or *Oryctes rhinoceros* of the family Scarabaeidae, *Agriotes ogurae, Melanotus okinawensis* or *Melanotus fortnumi fortnumi* of the family Rhynchophoridae, *Anthrenus verbasci* of the family Dermestidae, *Heterobostrychus hamatipennis* of the family Bostrychidae, *Stegobium paniceum* of the family Anobiidae, *Pitinus clavipes* of the family Ptinidae, *Tenebroides manritanicus* of the family Trogossitidae, *Necrobia rufipes* of the family Cleridae, *Carpophilus hemipterus* of the family Nitidulidae, *Ahasverus advena* of the family Silvanidae, *Cryptolestes ferrugineus* of the family Laemophloeidae, *Epilachna varivestis* or *Henosepilachna vigintioctopunctata* of the family Coccinellidae, *Tenebrio molitor* or *Tribolium castaneum* of the family Tenebrionidae, *Epicauta gorhami* of the family Meloidae, *Anoplophora glabripennis, Xylotrechus pyrrhoderus* or *Monochamus alternatus* of the family Cerambycidae, *Callosobruchus chinensis* of the family Bruchidae, *Leptinotarsa decemlineata, Diabrotica virgifera, Phaedon brassicae* or *Phyllotreta striolata* of the family Chrysomelidae, *Cylas formicarius* of the family Brentidae, *Hypera postica, Listroderes costirostris* or *Euscepes postfasciatus* of the family Curculionidae, *Echinocnemus bipunctatus* or *Lissorhoptus oryzophilus* of the family Erirhinidae, *Sitophilus zeamais* or *Sphenophrus venatus* of the family Rhynchophoridae, *Tomicus piniperda* of the family Scolytidae, *Crossotarsus niponicus* of the family Platypodidae, and *Lyctus brunneus* of the family Lyctidae.

Examples of the order Diptera pests include *Tipula aino* of the family Tipulidae, *Plecia nearctica* of the family Bibionidae, *Exechia shiitakevora* of the family Mycetophilidae, *Pnyxia scabiei* of the family Sciaridae, *Asphondylia yushimai* or *Mayetiola destructor* of the family Cecidomyiidae, *Aedes aegypti* or *Culex pipiens pallens* of the family Culicidae, *Simulium takahashii* of the family Simuliidae, *Chironomus oryzae* of the family Chironomidae, *Chrysops suavis* or *Tabanus trigonus* of the family Tabanidae, *Eumerus strigatus* of the family Syrphidae, *Bactrocera dorsalis, Euphranta japonica* or *Ceratitis capitata* of the family Tephritidae, *Liriomyza trifolii* or *Chromatomyia horticola* of the family Agromyzidae, *Meromyza nigriventris* of the family Chloropidae, *Drosophila suzukii* or *Drosophila melanogaster* of the family Drosophilidae, *Hydrellia griseola* of the family Ephydridae, *Hippobosca equina* of the family Hippoboscidae, *Parallelpmma sasakawae* of the family Scathophagidae, *Delia antiqua* or *Delia platura* of the family Anthomyiidae, *Fannia canicularis* of the family Fanniidae, *Musca domestica* or *Stomoxys calcitrans* of the family Muscidae, *Sarcophaga peregrina* of the family Sarcophagidae, *Gasterophilus intestinalis* of the family Gasterophilidae, *Hypoderma lineatum* of the family Hypodermatidae, and *Oestrus ovis* of the family Oestridae.

Examples of the order Lepidoptera pests include *Endoclita excrescens* of the family Hepialidae, *Antispila ampelopsia* of the family Heliozelidae, *Zeuzera leuconotum* of the family Cossidae, *Archips fuscocupreanus, Adoxophyes orana fasciata, Grapholita molesta, Homona magnanima, Leguminivora glycinivorella* or *Cydia pomonella* of the family Tortricidae, *Eupoecilia ambiguella* of the family Cochylidae, *Bambalina* sp. or *Eumeta minuscule* of the family Psychidae, *Nemapogon granella* or *Tinea translucens* of the family Tineidae, *Bucculatrix pyrivorella* of the family Bucculatricidae, *Lyonetia clerkella* of the family Lyonetiidae, *Caloptilia theivora* or *Phyllonorycter ringoniella* of the family Gracillariidae, *Phyllocnistis citrella* of the family Phyllocnistidae, *Acrolepiopsis sapporensis* of the family Acrolepiidae, *Plutella xylostella* or *Yponomeuta orientalis* of the family Yponomeutidae, *Argyresthia conjugella* of the family Argyresthiidae, *Nokona regalis* of the family Sesiidae, *Phthorimaea operculella, Sitotroga cerealella* or *Pectinophora gossypiella* of the family Gelechiidae, *Carposina sasakii* of the family Carposinidae, *Illiberis pruni* of the family Zygaenidae, *Monema flavescens* of the family Limacodidae, *Ancylolomia japonica, Chilo suppressalis, Cnaphalocrocis medinalis, Ostrinia furnacalis* or *Ostrinia nubilalis* of the family Crambidae, *Cadra cautella* or *Galleria mellonella* of the family Pyralidae, *Nippoptilia vitis* of the family Pterophoridae, *Papilio xuthus* of the family Papilionidae, *Pieris rapae* of the family Pieridae, *Parnara guttata guttata* of the family Hesperiidae, *Ascotis selenaria* of the family Geometridae, *Dendrolimus spectabilis* or *Malacosoma neustrium testaceum* of the family Lasiocampidae, *Agrius convulvuli* of the family Sphingidae, *Alma pseudoconspersa* or *Lymantria dispar* of the family Lymantriidae, *Hyphantria cunea* of the family Arctiidae, and *Agrotis ipsilon, Autographa nigrisigna, Helicoverpa armigera, Helicoverpa zea, Heliothis virescens, Spodoptera exigua* or *Spodoptera litura* of the family Noctuidae.

Examples of the order Hymenoptera pests include *Arge pagana* of the family Argidae, *Apethymus kuri* or *Athalia rosae ruficornis* of the family Tenthredinidae, *Dryocosmus kuriphilus* of the family Cynipidae, *Vespa simillima xanthoptera* of the family Vespidae, *Solenopsis invicta* of the family Formicidae, and *Megachile nipponica* of the family Megachilidae.

Examples of the order Collembola pests include *Bourletiella hortensis* of the family Sminthuridae.

Examples of the order Zygentoma pests include *Lepisma sacharina* or *Ctenolepisma villosa* of the family Lepismatidae.

Examples of the order Blattodea pests include *Periplaneta americana* of the family Blattidae, and *Blattela germanica* of the family Blattellidae.

Examples of the order Isoptera pests include *Incisitermes minor* of the family Kalotermitidae, *Coptotermes formosanus* of the family Rhinotermitidae, and *Odontotermes formosanus* of the family Termitidae.

Examples of the order Psocoptera pests include *Trogium pulsatorium* of the family Trogiidae, and *Liposcelis corrodens* of the family Liposcelidae.

Examples of the order Mallophaga pests include *Menopon gallinae* of the family Menoponidae, and *Damalinia Bovis* of the family Gyropidae.

Examples of the order Phthiraptera pests include *Haematopinus suis* of the family Haematopinidae, *Pediculus humanus* of the family Pediculidae, *Linognathus setosus* of the family Linognathidae, and *Pediculus pubis* of the family Pthiridae.

Examples of plant parasitic mites include *Penthaleus major* of the family Eupodidae, *Phytonemus pallidus* or *Polyphagotarsonemus latus* of the family Tarsonemidae, *Siteroptes* sp. of the family Pyemotidae, *Brevipalpus lewisi* of the family Tenuipalpidae, *Tuckerella pavoniformis* of the family Tuckerellidae, *Eotetranychus boreus, Panonychus citri, Panonychus ulmi, Tetranychus urticae* or *Tetranychus kanzawai* of the family Tetranychidae, *Trisetacus pini* of the family Nalepellidae, *Aculops pelekassi, Epitrimerus pyri* or *Phyllocoptruta oleivora* of the family Eriophyidae, *Diptacus*

*crenatae* of the family Diptilomiopidae, and *Aleuroglyphus ovatus, Tyrophagus putrescentiae* or *Rhizoglyphus robini* of the family Acaridae.

Examples of plant parasitic nematodes include *Xiphinema index* of the family Longidoridae, *Paratrichodorus minor* of the family Trichodoridae, *Rhabditella* sp. of the family Rhabditidae, *Aglenchus* sp. of the family Tylenchidae, *Cephalenchus* sp. of the family Tylodoridae, *Nothotylenchus acris* or *Ditylenchus destructor* of the family Anguinidae, *Rotylenchulus reniformis* or *Helicotylenchus dihystera* of the family Hoplolaimidae, *Paratylenchus curvigtatus* of the family Paratylenchidae, *Meloidogyne incognita* or *Meloidogyne hapla* of the family Meloidogynidae, *Globodera rostochiensis* or *Heterodera glycines* of the family Heteroderidae, Tylenchorhynchus claytoni of the family Tylenchorhynchidae, *Psilenchus* sp. of the family Tylenchidae, *Criconemoides* sp. of the family Criconematidae, *Tylenchulus semipenetrans* of the family Tylenchulidae, *Sphaeronema camelliae* of the family Sphaeronematinae, *Sphaeronema camelliae, Radopholus citrophilus, Radopholus similis, Nacobbus aberrans, Pratylenchus penetrans* or *Pratylenchus coffeae* of the family Pratylenchidae, *Iotonchium ungulatum* of the family Iotonchiidae, *Aphelenchus avenae* of the family Aphelenchoididae, *Aphelenchoides besseyi* or *Aphelenchoides fragariae* of the family Aphelenchoididae, and *Bursaphelenchus xylophilus* of the family Parasitaphelenchidae.

Examples of plant parasitic mollusks include *Pomacea canaliculata* of the family Helicodiscidae, *Leavicaulis alte* of the family Veronicellidae, *Achatina fulica* of the family Achatimidae, *Meghimatium bilineatum* of the family Philomycidae, *Succinea lauta* of the family Succineacea, *Discus pauper* of the family Discidae, *Zonitoides yessoensis* of the family Zonitidae, *Limax flavus* or *Deroceras reticulatum* of the family Limacidae, *Parakeliella harimensis* of the family Helicarionidae, and *Acusta despecta sieboldiana* or *Bradybaena similaris* of the family Bradybaenidae.

Examples of other harmful animals, nuisance animals, sanitary insect pests and parasites include members of the order Parasitiformes such as *Ornithonyssus sylvialum* of the family Macronyssidae, *Varma jacobsoni* of the family Varroidae, *Dermanyssus gallinae* of the family Dermanyssidae, *Ornithonyssus sylvialum* of the family Macronyssidae, *Boophilus microplus, Rhipicephalus sanguineus* or *Haemaphysalis longicornis* of the family Ixodidae, or *Sarcoptes scabiei* of the family Sarcoptidae, members of the order Isopoda such as *Armadillidium vulgare* of the family Armadillidiidae, members of the order Isopoda such as *Armadillidium vulgare* of the family Porcellionidae, Chilopoda class pests such as *Thereuonema tuberculata* of the order Scutigeromorpha, family Scutigeridae or *Scolopendra subspinipes* of the order Scolopendromorpha, Helminthomorpha class pests such as *Oxidus gracilis* of the order Polydesmida, family Paradoxosomatidae, *Theridiidae hasseltii* of the order Araneae, family Theridiidae, *Chiracanthium japonicum* of the order Araneae, family Clubionidae, *Androctonus crassicauda* of the order Scorpiones, nematode internal parasites in the form of *Ascaris lumbricoides, Syphacia* sp. and *Wuchereria bancrofti*, and flatworm internal parasites in the form of *Distomum* sp., *Paragonimus westermanii, Metagonimus yokokawaii, Schistosoma japonicum, Taenia solium, Taeniarhynchus saginatus, Echinococcus* sp. and *Diphyllobothrium latum*.

The compounds according to the present invention also demonstrate control effects against harmful organisms and the like as exemplified above that have acquired resistance to existing pest control agents.

In addition, the compounds according to the present invention can also be used in plants that have acquired characteristics such as pest resistance, disease resistance or herbicide resistance and the like through gene recombination or artificial hybridization.

In addition, numerous pests such as diamondback moths, planthoppers, leafhoppers and aphids have recently developed resistance to organic phosphorous agents, carbamate agents and miticides, and problems have occurred regarding the inadequate effects of these chemicals, thus resulting in the desire for an effective chemical against resistant strains of pests and mites. The compounds according to the present invention demonstrate superior insecticidal and miticidal effects against strains of pests resistant to organic phosphorous agents, carbamate agents and pyrethroid agents, and miticide-resistant strains of mites as well as sensitive strains of pests or mites. In addition, the pest control agent according to the present invention has low levels of chemical damage, low toxicity with respect to fish and mammals, and is highly safe.

In the case of an actual application of the pest control agent according to the present invention, although one type or two or more types of compounds according to the present invention can be used as is without adding other components, it is normally mixed with a solid vehicle, liquid vehicle or gaseous vehicle, or impregnated into a base material such as a porous ceramic plate or non-woven fabric, followed by the addition of a surfactant or other auxiliary agent as necessary, and is used by formulating into a form that can be adopted by ordinary agricultural chemicals for the purpose of use as an agricultural chemical, examples of which include wettable powders, granules, powders, emulsions, aqueous solutions, suspensions, water-dispersible granules, flowable preparations, aerosols, spraying agents, heat transpiration agents, smoking agents, poison bait and microcapsules.

In the case of using an additive or vehicle for the purpose of obtaining a solid agent, a plant-based powder such as powdered soybeans or powdered wheat, a mineral-based fine powder such as diatomaceous earth, apatite, gypsum, talc, bentonite, pyrophyllite or clay, or an organic or inorganic compound such as sodium benzoate, urea or sodium sulfate can be used. In the case of using for the purpose of obtaining a liquid agent, a petroleum distillate such as kerosene, xylene or solvent naphtha, or cyclohexane, cyclohexanone, dimethylformamide, dimethylsulfoxide, alcohol, acetone, methyl isobutyl ketone, mineral oil, vegetable oil, water, or the like can be used as a solvent. Examples of gaseous vehicles used in a spraying agent include butane gas, LG, dimethylether and carbon dioxide gas.

Examples of base materials of the poison bait include bait components such as grains, vegetable oils, sugars, or crystalline cellulose, antioxidants such as dibutylhydroxytoluene or nordihydroguaiaretic acid, preservatives such as dehydroacetic acid, agents for preventing accidental ingestion by children or pets such as powdered cayenne pepper, and pest-attracting aromatic components such as cheese fragrance or onion fragrance.

A surfactant can be added to these preparations as necessary in order to obtain a homogeneous and stable preparation form. There are no particular limitations on the surfactant used, and examples thereof include nonionic surfactants such as polyoxyethylene-added alkyl ethers, polyoxyethylene-added higher fatty acid esters, polyoxyethylene-added sorbitan higher fatty acid esters or polyoxyethylene-added tristyrylphenyl ethers, sulfate ester salts of polyoxyethylene-added alkylphenyl ethers, alkyl naphthalene sulfonates, polycarboxylates, lignin sulfonates, formaldehyde condensation products of alkyl naphthalene sulfonates and copolymers such as isobutylene-maleic anhydride copolymer.

Although there are no particular limitations on the amount of active ingredient in the pest control agent according to the present invention, it is preferably 0.01 to 90% by weight and particularly preferably 0.05 to 85% by weight.

In the case of using the pest control agent according to the present invention in agricultural applications, the preparation form is in the form of a wettable powder, emulsion, suspension, flowable preparation, aqueous solution or water-dispersible granules, and can be used by diluting these preparations to a prescribed concentration with water to obtain a solution, suspension or emulsion, and then spraying a powder or granules directly onto plants or soil.

In addition, in the case of using the compound according to the present invention as a pest control agent for preventing disease, the preparation form thereof is in the form of an emulsion, wettable powder, flowable preparation, or the like, and these preparations can be applied by diluting to a prescribed concentration with water. In addition, the compound according to the present invention can be used directly in the case where the preparation form thereof is an oily agent, aerosol, spraying agent, poison bait or miticidal sheet.

In the case of using the compound according to the present invention as a pest control agent for controlling external parasites of livestock such as cows or pigs or pets such as dogs or cats, a preparation of the compound according to the present invention can normally be used according to a known veterinary method.

Examples of such methods include administration in the form of a tablet, capsule, permeating liquid, feed additive, suppository or injection (intramuscular, subcutaneous, intravenous or intraperitoneal injection) in the case of aiming systemic control, and administration by spraying, pouring or spotting an oily or aqueous liquid, or forming a resin preparation into a suitable shape such as that of a collar, ear tag, or the like to attach the resin preparation to the animal in the case of aiming non-systemic control. In this case, the preparation is normally used at the rate of 0.01 to 1000 mg of the compound according to the present invention per 1 kg of body weight of the host animal.

Although the miticidal agent according to the present invention naturally demonstrates adequate effects when used alone, it can also be mixed or used in combination with one type or two or more types of other miticidal agents, antimicrobial agents, insecticidal and acaricidal agents, herbicides, plant growth regulators, synergists, fertilizers, soil conditioners or animal feeds.

In addition, in the case of using the compound according to the present invention as an agricultural chemical, it may be applied after mixing with other types of herbicides, various types of insecticides, miticides, nematocides, antimicrobial agents, plant growth regulators, synergists, fertilizers or soil conditioners as necessary either during formulation or during spraying.

By applying after mixing with other agricultural chemicals or plant hormones in particular, reduced costs resulting from decreasing the amount of chemical applied, and a broader insecticidal spectrum and greater pest control effects due to the synergistic action of the mixed chemicals, can be expected. At this time, the compound according to the present invention can be simultaneously combined with a plurality of known agricultural chemicals. Examples of types of the agricultural chemicals used by mixing with the compound according to the present invention include compounds listed in the 2007 edition of the Crop Protection Handbook. Specific examples thereof include, but are not limited to, agricultural chemicals listed below using their generic names.

Examples of active ingredient compounds of antimicrobial agents (generic name, including those for which application is currently pending) include:

anilinopyrimidine-based compounds such as mepanipyrim, pyrimethanil or cyprodinil;

pyridinamine-based compounds such as fluazinam;

azole-based compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole or imazalil;

quinoxaline-based compounds such as quinomethionate;

dithiocarbamate-based compounds such as maneb, zineb, mancozeb, polycarbamate, metiram, propineb, ferbam, nabam, metam, thiram or ziram;

organic chlorine-based compounds such as fthalide, chlorothalonil or quintozene;

imidazole-based compounds such as benomyl, thiophanate-methyl, carbendazim, thiabendazole, fuberiazole or cyazofamid;

cyanoacetoamide-based compounds such as cymoxanil;

phenylamide-based compounds such as metalaxyl, metalaxyl-M, mefenoxam, oxadixyl, ofurace, benalaxyl, benalaxyl-M, furalaxyl or cyprofuram;

sulfenic acid-based compounds such as dichlofluanid;

nitrophenyl-based compounds such as dinocap;

copper-based compounds such as cupric hydroxide or oxine copper;

isoxazole-based compounds such as hymexazol;

organic phosphorous-based compounds such as fosetyl-Al, tolcofos-methyl, S-benzyl-O,O-diisopropyl phosphorothioate, O-ethyl-S,S-diphenyl phosphorodithioate or aluminum ethyl hydrogen phosphonate;

N-halogenothioalkyl-based compounds such as captan, captafol or folpet;

dicarboxylmide-based compounds such as procymidone, iprodone or vinclozolin;

benzanilide-based compounds such as flutolanil, mepronil, zoxamid or tiadinil;

anilide-based compounds such as carboxin, oxycarboxin, thifluzamide, penthiopyrad, boscalid, fluopicolide, fluopyram or bixafen;

piperazine-based compounds such as triforine;

pyridine-based compounds such as pyrifenox;

carbinol-based compounds such as fenarimol or flutriafol;

piperidine-based compounds such as fenpropidine;

morpholine-based compounds such as fenpropimorph or tridemorph;

organic tin-based compounds such as fentin hydroxide or fentin acetate;

urea-based compounds such as pencycuron;

cinnamic acid-based compounds such as dimethomorph, flumorph or flumetover;

phenylcarbamate-based compounds such as diethofencarb;

cyanopyrrole-based compounds such as fludioxonil or fenpiclonil;

strobilurin-based compounds such as azoxystrobin, kresoxim-methyl, metominofen, metominostrobin, trifloxystrobin, picoxystrobin, oryzastrobin, dimoxystrobin, pyraclostrobin or fluoxastrobin;

oxazolidinone-based compounds such as famoxadone;

thiazole carboxamide-based compounds such as ethaboxam;

silyl amide-based compounds such as silthiopham;

amino acid amide carbamate-based compounds such as benthiavalicarb-isopropyl;

imidazolidine-based compounds such as fenamidone;

hydroxyanilide-based compounds such as fenhexamid;

benzenesulfonamide-based compounds such as flusulfamide;

oxime ether-based compounds such as cyflufenamid;

phenoxyamide-based compounds such as fenoxanil;

antibiotics such as validamycin, kasugamycin or polyoxins; and, guanidine-based compounds such as iminoctadine.

In addition, examples of other compounds include tolyfluanid, isoprothiolane, pyroquilon, diclomezine, quinoxyfen, propamocarb hydrochloride, spiroxamine, chloropicrin, dazomet, metam-sodium, nicobifen, metrafenone, UBF-307, diclocymet, proquinazid, amisulbrom, pyribencarb, mandipropamid, 5-chlor-7-(4-methyl-piperidin-1-yl)-6-(2,4,6-trifluor-phenyl)-[1,2,4]triazolo[1,5-a]pyrimidin and OK-5203.

Examples of active ingredient compounds of insecticides, miticides, nematocides or soil pest control agents that are agricultural chemicals used in sprayed liquids (generic name, including those for which application is currently pending) include:

organic phosphate ester-based compounds such as profenofos, dichlorvos, fenamiphos, fenitrothion, EPN, diazinon, chlorpyrifos-methyl, acephate, prothiofos, fosthiazate, phosphocarb, cadusafos, dislufoton, chlorpyrifos, demeton-S-methyl, dimethoate, methamidophos, isoxathion, isofenphos, ethion, etrimfos, quinalphos, dimethylvinphos, sulprofos, thiometon, vamidothion, pyraclofos, pyridaphenthion, pirimiphos-methyl, propaphos, phosalone, formothion, malathion, tetraclovinphos, chlorfenvinphos, cyanophos, trichlorfon, methidathion, phenthoate, ESP, azinphos-methyl, fenthion, heptenophos, methoxychlor, paration, monocrotophos, imicyafos, parathion-methyl, terbufos, phosphamidon, phosmet or phorate;

carbamate-based compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC or fenothiocarb;

nereistoxin derivatives such as cartap, thiocyclam, bensultap or thiosultap-sodium;

organic chlorine-based compounds such as dicofol, tetradifon, endosulufan, dienochloror dieldrin;

organic metal-based compounds such as fenbutatin oxide or cyhexatin;

pyrethroid-based compounds fenvalerate, permethrin, cypermethrin, deltamethrin, cyhalothrin, tefluthrin, ethofenprox, cyfluthrin, fenpropathrin, bifenthrin, flucythrinate, fluvalinate, cycloprothrin, lambda-cyhalothrin, pyrethrins, esfenvalerate, tetramethrin, resmethrin, protrifenbute, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin or phenothrin;

benzoylurea-based compounds such as diflubenzuron, chlorfluazuron, teflubenzuron, flufenoxuron, lufenuron, novaluron, triflumuron, hexaflumuron, noviflumuron, bistrifluoron or fluazuron;

juvenile hormone-like compounds such as methoprene, pyriproxyfen, fenoxycarb or diofenolan;

pyridazinone-based compounds such as pyridaben;

pyrazole-based compounds such as fenpyroximate, fipronil, tebufenpyrad, ethiprole, tolfenpyrad, acetoprole, pyrafluprole or pyriprole;

neonicotinoids such as imidacloprid, nitenpyram, acetamiprid, thiacloprid, thiamethoxam, clothianidin, dinotefuran or nithiazine; and, hydrazine-based compounds such as tebufenozide, methoxyfenozide, chromafenozide or halofenozide.

Examples of other compounds include flonicamid, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, flufenerim, pyridalyl, spirodiclofen, bifenazate, spiromesifen, spirotetramat, propargite, clofentezine, fluacrypyrim, metaflumizone, flubendiamide, cyflumetofen, chlorantraniliprole, cyenopyrafen, pyrifluquinazon, fenazaquin, amidoflumet, chlorobenzoate, sulfluramid, hydramethylnon, metaldehyde and ryanodine.

Moreover, additional examples of compounds include crystal protein toxins produced by *Bacillus thuringienses aizawai, Bacillus thuringienses kurstaki, Bacillus thuringienses israelensis, Bacillus thuringienses japonensis, Bacillus thuringienses tenebrionis* or *Bacillus thuringienses*; microbial agricultural chemicals such as insect pathogen viral agents, insect pathogen fungal agents or nematode pathogen fungal agents; antibiotics or semi-synthetic antibiotics such as avermectin, emamectin-benzoate, milbemectin, spinosad, ivermectin or lepimectin;

naturally-occurring substances such as azadirachtin or rotenone;

cooperative agents such as piperonyl butoxide; and repellents such as deet.

EXAMPLES

Although the following provides a more detailed explanation of the present invention through examples thereof, the present invention is not limited to the following examples.

Example 1

Production of N-{[5-(3,5-dichlorophenyl)-5-trifluoromethyl-4,5-dihydroisoxazol-3-yl]indan-1-yl}-propionic acid amide (Compound No.: 1-6)

Step 1

Production of N-(5-bromoindan-1-yl)propionic acid amide 2.7 g of 5-bromoindan-1-ylamine were dissolved in 30 ml of dichloromethane. 2.2 g of pyridine were added to this solution followed by the addition of 1.4 g of propionic anhydride while cooling with ice. After returning the reaction solution to room temperature and stirring overnight, the reaction solution was poured into ice water and extracted with chloroform. The organic layer was washed with water and saturated brine followed by drying with anhydrous magnesium sulfate. The solvent was distilled off under reduced pressure and the resulting residue was purified by silica gel column chromatography (developing solvent: ethyl acetate/n-hexane=1/1 (volume ratio)) to obtain 2.4 g of the target compound. Yield: 70%

$^1$H-NMR (CDCl$_3$, δppm): 1.20 (t, 3H), 1.73-1.85 (m, 1H), 2.25 (q, 2H), 2.55-2.65 (m, 1H), 2.80-3.00 (m, 2H), 5.41-5.59 (m, 2H), 7.14 (d, 1H), 7.33 (d, 1H), 7.38 (s, 1H)

Step 2

Production of N-(5-cyanoindan-1-yl)propionic acid amide 3.64 g of N-(5-bromoindan-1-yl)propionic acid amide were dissolved in 30 ml of 1-methyl-2-pyrrolidone. 1.8 g of cuprous cyanide were added to this solution followed by heating and refluxing for 2 hours. After returning the reaction solution to room temperature, the reaction solution was poured into water, and stirred for 1 hour. The resulting reaction mixture was filtered with CELITE and the filtrate was extracted with ethyl acetate. The organic layer was washed with water and saturated brine followed by drying with anhydrous magnesium sulfate. The solvent was distilled off under reduced pressure and the resulting residue was purified by silica gel column chromatography (developing solvent: ethyl acetate/n-hexane=7/3 (volume ratio)) to obtain 1.46 g of the target compound. Yield: 50%

$^1$H-NMR (CDCl$_3$, δppm): 1.21 (t, 3H), 1.79-1.86 (m, 1H), 2.28 (q, 2H), 2.61-2.68 (m, 1H), 2.85-3.01 (m, 2H), 5.52-5.69 (m, 2H), 7.37 (d, 1H), 7.50 (d, 1H), 7.51 (s, 1H)

Step 3

Production of N-(5-formylindan-1-yl)propionic acid amide 1.46 g of N-(5-cyanoindan-1-yl)propionic acid amide were dissolved in 20 ml of a 75% aqueous formic acid solution. 1.1 g of Rainey nickel were added to this solution followed by heating and refluxing for 2 hours. After returning the reaction solution to room temperature and filtering with CELITE, the solvent was distilled off under reduced pressure. The resulting residue was added to water, and extracted with ethyl acetate. After washing the organic layer with saturated aqueous sodium bicarbonate and saturated brine, the organic layer was dried with anhydrous magnesium sulfate. The solvent was distilled off under reduced pressure to obtain 1.18 g of the target compound. Yield: 80%

$^1$H-NMR (CDCl$_3$, δppm): 1.22 (t, 3H), 1.78-1.88 (m, 1H), 2.30 (q, 2H), 2.62-2.72 (m, 1H), 2.85-3.06 (m, 2H), 5.57 (q, 1H), 5.67 (m, 1H), 7.42 (d, 1H), 7.73 (d, 1H), 7.75 (s, 1H), 9.99 (s, 1H)

Step 4

Production of N-[5-(hydroxyiminomethyl)-indan-1-yl] propionic acid amide 1.18 g of N-(5-formylindan-1-yl)propionic acid amide were suspended in 20 ml of ethanol and 10 ml of water. 0.57 g of hydroxyamine hydrochloride and 0.67 g of sodium acetate were added to this suspension followed by stirring overnight at room temperature. The reaction liquid was concentrated under reduced pressure followed by pouring into ice water and extracting with ethyl acetate. After washing the organic layer with saturated aqueous sodium bicarbonate and saturated brine, the organic layer was dried with anhydrous magnesium sulfate. The solvent was distilled off under reduced pressure to obtain 1.25 g of the target compound. Yield: 100%

$^1$H-NMR (CDCl$_3$, δppm): 1.21 (t, 3H), 1.76-1.86 (m, 1H), 2.27 (q, 2H), 2.58-2.69 (m, 1H), 2.84-3.03 (m, 2H), 5.49-5.59 (m, 2H), 7.26 (d, 1H), 7.40 (d, 1H), 7.47 (s, 1H), 8.12 (s, 1H)

Step 5

Production of N-{5-(3,5-dichlorophenyl)-5-trifluoromethyl-4,5-dihydroisoxazol-3-yl]indan-1-yl}-propionic acid amide 1.25 g of N-[5-(hydroxyiminomethyl)-indan-1-yl]propionic acid amide were dissolved in 20 ml of N,N-dimethylformamide. 0.8 g of N-chlorosuccinimide were added to this solution followed by stirring for 1 hour at 50° C. The reaction solution was cooled to 0° C. followed by adding 1.44 g of 3,5-dichloro-1-(1-trifluoromethylethenyl)benzene and 0.6 g of triethylamine and stirring overnight at room temperature. The reaction solution was poured into ice water followed by extracting with ethyl acetate, washing with water and saturated brine and drying with anhydrous magnesium sulfate. The solvent was distilled off under reduced pressure and the resulting residue was purified by silica gel column chromatography (developing solvent: ethyl acetate/n-hexane=1/1 (volume ratio)) to obtain 1.99 g of the target compound. Yield: 77%

$^1$H-NMR (CDCl$_3$, δppm): 1.21 (t, 3H), 1.76-1.87 (m, 1H), 2.27 (q, 2H), 2.58-2.69 (m, 1H), 2.83-3.05 (m, 2H), 5.49-5.62 (m, 2H), 7.32 (d, 1H), 7.41-7.57 (m, 5H)

The structural formulas and physical constants of compounds according to the present invention produced in the same manner as Example 1, including the compound obtained in Example 1, are shown in Tables 1 to 20. In addition, $^1$H-NMR data are shown in Table 21. Furthermore, in the tables, figures in brackets [ ] indicate melting point (° C.). In addition, the meanings of abbreviations used in the tables are as indicated below.

Ph: phenyl
Py: pyridyl
Pr: propyl
c: cyclo
Hex: hexyl

TABLE 1

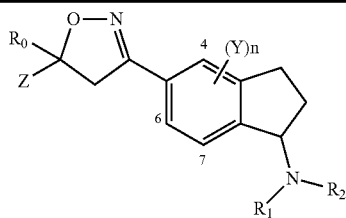

| Compound No. | Z | R₀ | (Y)n | R₁ | R₂ | Physical constant |
|---|---|---|---|---|---|---|
| 1-1 | 3,5-Cl₂Ph | CF₃ | — | CH₂CH₂(2-Py) | H | |
| 1-2 | 3,5-Cl₂Ph | CF₃ | — | CH₂CH₂COCH₃ | H | |
| 1-3 | 3,5-Cl₂Ph | CF₃ | — | CH₂CH₂OCH₃ | H | |
| 1-4 | 3,5-Cl₂Ph | CF₃ | — | COCH₃ | H | |
| 1-5 | 3,5-Cl₂Ph | CF₃ | — | COC₂H₅ | H | amorphous |
| 1-6 | 3,5-Cl₂Ph | CF₃ | — | COPr-n | H | [142-145] |
| 1-7 | 3,5-Cl₂Ph | CF₃ | — | COCH₂CH₂OCH₃ | H | [146-150] |
| 1-8 | 3,5-Cl₂Ph | CF₃ | — | COCH₂CH₂OCH₂CH₃ | H | [100-110] |
| 1-9 | 3,5-Cl₂Ph | CF₃ | — | COCH₂CH(CH₃)OCH₃ | H | amorphous |
| 1-10 | 3,5-Cl₂Ph | CF₃ | — | COCH₂CH(CH₃)OCH₂CH₃ | H | [101-136] |
| 1-11 | 3,5-Cl₂Ph | CF₃ | — | COCH₂CH(CH₃)OH | H | [68-129] |
| 1-12 | 3,5-Cl₂Ph | CF₃ | — | COCH₂CH₂OCH₂CH=CH₂ | H | amorphous |
| 1-13 | 3,5-Cl₂Ph | CF₃ | — | COCH₂COCH₃ | H | amorphous |
| 1-14 | 3,5-Cl₂Ph | CF₃ | — | COCH₂(1,3-dioxolane-2-yl) | H | amorphous |
| 1-15 | 3,5-Cl₂Ph | CF₃ | — | CH₂CH₂(2-Py) | H | amorphous |
| 1-16 | 3,5-Cl₂Ph | CF₃ | — | COCH₂(2-methyl-1,3-dioxolane-2-yl) | H | amorphous |
| 1-17 | 3,5-Cl₂Ph | CF₃ | — | COCH₂(2-trifluoromethyl-1,3-dioxolane-2-yl) | H | amorphous |
| 1-18 | 3,5-CL₂Ph | CF₃ | — | COCH₂(2-methyl-1,3-dioxane-2-yl) | H | amorphous |
| 1-19 | 3,5-Cl₂Ph | CF₃ | — | COCH₂CH₂(1,3-dioxolane-2-yl) | H | amorphous |
| 1-20 | 3,5-Cl₂Ph | CF₃ | — | COCH₂CH₂(2-methyl-1,3-dioxolane-2-yl) | H | amorphous |
| 1-21 | 3,5-Cl₂Ph | CF₃ | — | CO(tetrahydropyran-4-yl) | H | amorphous |
| 1-22 | 3,5-Cl₂Ph | CF₃ | — | CO(2,6-dimethyl-4H-pyran-4-one-3-yl) | H | amorphous |
| 1-23 | 3,5-Cl₂Ph | CF₃ | — | COCH₂CH₂CN | H | [174-178] |
| 1-24 | 3,5-Cl₂Ph | CF₃ | — | COCH₂CH₂Ph | H | amorphous |
| 1-25 | 3,5-Cl₂Ph | CF₃ | — | COCH₂CH₂(1,2,4-triazole-1-yl) | H | amorphous |
| 1-26 | 3,5-Cl₂Ph | CF₃ | — | COCH₂CH₂(pyrazole-1-yl) | H | amorphous |
| 1-27 | 3-CF₃Ph | CF₃ | — | COC₂H₅ | H | [110-120] |
| 1-28 | 3-CF₃Ph | CF₃ | — | COCH₂CH₂OCH₃ | H | [77-80] |
| 1-29 | 3-CF₃Ph | CF₃ | — | COCH₂CH(CH₃)OCH₃ | H | [58-81] |
| 1-30 | 3-CF₃Ph | CF₃ | — | COCH₂(2-methyl-1,3-dioxolane-2-yl) | H | amorphous |
| 1-31 | 3-CF₃Ph | CF₃ | — | COCH₂CH₂CN | H | amorphous |
| 1-32 | 3,5-Cl₂Ph | CF₃ | — | COPr-c | H | [178-185] |
| 1-33 | 3,5-Cl₂Ph | CF₃ | — | COHex-c | H | |
| 1-34 | 2-F-3-CF₃Ph | CF₃ | — | COC₂H₅ | H | [176-179] |
| 1-35 | 2-F-3-CF₃Ph | CF₃ | — | COCH₂CH₂OCH₃ | H | [147-151] |
| 1-36 | 3-CF₃-4-ClPh | CF₃ | — | COC₂H₅ | H | [125-129] |
| 1-37 | 3-CF₃-4-ClPh | CF₃ | — | COCH₂CH₂OCH₃ | H | [95-100] |
| 1-38 | 3-CF₃-4-ClPh | CF₃ | — | COCH₂CH(CH₃)OCH₃ | H | amorphous |
| 1-39 | 3,5-Cl₂Ph | CF₃ | — | CSC₂H₅ | H | amorphous |
| 1-40 | 3,5-Cl₂Ph | CF₃ | — | 2-cyclohexenone-3-yl | H | amorphous |
| 1-41 | 3,5-Cl₂Ph | CF₃ | — | CH₂(4-methyl-1,3-dioxolene-2-one-5-yl) | H | amorphous |
| 1-42 | 3,5-Cl₂Ph | CF₃ | — | CH₂(4-methyl-1,3-dioxolene-2-one-5-yl) | CH₂(4-methyl-1,3-dioxolene-2-one-5-yl) | amorphous |
| 1-43 | 3,5-Cl₂Ph | CF₃ | — | COC₂H₅ | CH₃ | |
| 1-44 | 3,5-Cl₂Ph | CF₃ | — | H | H | amorphous |
| 1-45 | 3-CF₃Ph | CF₃ | — | H | H | amorphous |
| 1-46 | 2-F-3-CF₃Ph | CF₃ | — | H | H | amorphous |
| 1-47 | 3-CF₃-4-ClPh | CF₃ | — | H | H | amorphous |
| 1-48 | 3,5-Cl₂Ph | CF₃ | 4-F | COC₂H₅ | H | |
| 1-49 | 3,5-Cl₂Ph | CF₃ | 4-Cl | COC₂H₅ | H | |
| 1-50 | 3,5-Cl₂Ph | CF₃ | 4-CH₃ | COC₂H₅ | H | |
| 1-51 | 3,5-Cl₂Ph | CF₃ | 4-CF₃ | COC₂H₅ | H | |
| 1-52 | 3,5-Cl₂Ph | CF₃ | 4-CH₂OCH₃ | COC₂H₅ | H | |

TABLE 1-continued

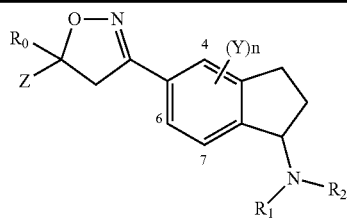

| Compound No. | Z | $R_0$ | (Y)n | $R_1$ | $R_2$ | Physical constant |
|---|---|---|---|---|---|---|
| 1-53 | 3,5-$Cl_2$Ph | $CF_3$ | 4-$NO_2$ | $COC_2H_5$ | H | |
| 1-54 | 3,5-$Cl_2$Ph | $CF_3$ | 4-OH | $COC_2H_5$ | H | |
| 1-55 | 3,5-$Cl_2$Ph | $CF_3$ | 4-$OCH_3$ | $COC_2H_5$ | H | |
| 1-56 | 3,5-$Cl_2$Ph | $CF_3$ | 4-$OCF_3$ | $COC_2H_5$ | H | |
| 1-57 | 3,5-$Cl_2$Ph | $CF_3$ | 4-$OCH_2COCH_3$ | $COC_2H_5$ | H | |
| 1-58 | 3,5-$Cl_2$Ph | $CF_3$ | 4-SH | $COC_2H_5$ | H | |
| 1-59 | 3,5-$Cl_2$Ph | $CF_3$ | 4-$SCH_3$ | $COC_2H_5$ | H | |
| 1-60 | 3,5-$Cl_2$Ph | $CF_3$ | 4-$SCF_3$ | $COC_2H_5$ | H | |
| 1-61 | 3,5-$Cl_2$Ph | $CF_3$ | 4-$NH_2$ | $COC_2H_5$ | H | |
| 1-62 | 3,5-$Cl_2$Ph | $CF_3$ | 4-$NHCH_3$ | $COC_2H_5$ | H | |
| 1-63 | 3,5-$Cl_2$Ph | $CF_3$ | 4-$N(CH_3)_2$ | $COC_2H_5$ | H | |
| 1-64 | 3,5-$Cl_2$Ph | $CF_3$ | 4-NHPh | $COC_2H_5$ | H | |
| 1-65 | 3,5-$Cl_2$Ph | $CF_3$ | 4-$NHCOCH_3$ | $COC_2H_5$ | H | |
| 1-66 | 3,5-$Cl_2$Ph | $CF_3$ | 4-$NHCO_2C_2H_5$ | $COC_2H_5$ | H | |
| 1-67 | 3,5-$Cl_2$Ph | $CF_3$ | 4-$NHCO_2$Bu-t | $COC_2H_5$ | H | |
| 1-68 | 3,5-$Cl_2$Ph | $CF_3$ | 4-$NHCH_2$Ph | $COC_2H_5$ | H | |
| 1-69 | 3,5-$Cl_2$Ph | $CF_3$ | 7-F | $COC_2H_5$ | H | |
| 1-70 | 3,5-$Cl_2$Ph | $NO_2$ | — | $COC_2H_5$ | H | |
| 1-71 | 3,5-$Cl_2$Ph | OH | — | $COC_2H_5$ | H | |
| 1-72 | 3,5-$Cl_2$Ph | OMe | — | $COC_2H_5$ | H | |
| 1-73 | 3,5-$Cl_2$Ph | $OCF_3$ | — | $COC_2H_5$ | H | |
| 1-74 | 3,5-$Cl_2$Ph | SH | — | $COC_2H_5$ | H | |
| 1-75 | 3,5-$Cl_2$Ph | $SCF_3$ | — | $COC_2H_5$ | H | |
| 1-76 | 3,5-$Cl_2$Ph | Cl | — | $COC_2H_5$ | H | |
| 1-77 | 3,5-$Cl_2$Ph | $NH_2$ | — | $COC_2H_5$ | H | |
| 1-78 | 3,5-$Cl_2$Ph | $NHCOCH_3$ | — | $COC_2H_5$ | H | |
| 1-79 | 3,5-$Cl_2$Ph | $NHCO_2C_2H_5$ | — | $COC_2H_5$ | H | |
| 1-80 | 3,5-$Cl_2$Ph | $CO_2C_2H_5$ | — | $COC_2H_5$ | H | |
| 1-81 | 3,5-$Cl_2$Ph | $SO_2CH_3$ | — | $COC_2H_5$ | H | |
| 1-82 | 3,5-$Cl_2$Ph | $SO_2CF_3$ | — | $COC_2H_5$ | H | |
| 1-83 | 3,5-$Cl_2$Ph | Ph | — | $COC_2H_5$ | H | |
| 1-84 | 3,5-$Cl_2$Ph | $COCH_3$ | — | $COC_2H_5$ | H | |
| 1-85 | 3,5-$Cl_2$Ph | Cl | — | $COC_2H_5$ | H | |
| 1-86 | 3,5-$Cl_2$Ph | CF2H | — | $COC_2H_5$ | H | |
| 1-87 | 3,5-$Cl_2$Ph | $CCl_3$ | — | $COC_2H_5$ | H | |
| 1-88 | 3,5-$Cl_2$Ph | $CF_2Cl$ | — | $COC_2H_5$ | H | |
| 1-89 | $CH_3CH=CH$ | $CF_3$ | — | $COC_2H_5$ | H | |
| 1-90 | Propargyl | $CF_3$ | — | $COC_2H_5$ | H | |
| 1-91 | $CH_2=CHCH_2$ | $CF_3$ | — | $COC_2H_5$ | H | |
| 1-92 | 2-butyryl | $CF_3$ | — | $COC_2H_5$ | H | |
| 1-93 | 3,5-$Cl_2$Ph | $CF_3$ | — | $COC_2H_5$ | -(nitrogen atom forms double bond with indane ring) | |
| 1-94 | 3,5-$Cl_2$Ph | $CF_3$ | — | =CHOCH$_3$ | | |
| 1-95 | 3,5-$Cl_2$Ph | $CF_3$ | — | =C(OCH$_3$)$_2$ | | |
| 1-96 | 3,5-$Cl_2$Ph | $CF_3$ | — | =CHNO$_2$ | | |
| 1-97 | 3,5-$Cl_2$Ph | $CF_3$ | — | =C(OCH$_2$CH$_2$O) | | |
| 1-98 | 3,5-$Cl_2$Ph | $CF_3$ | — | $CONHCH_3$ | H | |
| 1-99 | 3,5-$Cl_2$Ph | $CF_3$ | — | $CONHC_2H_5$ | H | |
| 1-100 | 3,5-$Cl_2$Ph | $CF_3$ | — | CONHPr-n | H | |
| 1-101 | 3,5-$Cl_2$Ph | $CF_3$ | — | $CONHCH_2CH_2OCH_3$ | H | |
| 1-102 | 3,5-$Cl_2$Ph | $CF_3$ | — | $CONHCH_2CH_2OCH_2CH_3$ | H | |
| 1-103 | 3,5-$Cl_2$Ph | $CF_3$ | — | $CONHCH_2CH(CH_3)OCH_3$ | H | |
| 1-104 | 3,5-$Cl_2$Ph | $CF_3$ | — | $CON(CH_3)_2$ | H | |
| 1-105 | 3,5-$Cl_2$Ph | $CF_3$ | — | $CONHCH_2CH_2CN$ | H | |
| 1-106 | 3,5-$Cl_2$Ph | $CF_3$ | — | $CONHCH_2CH_2Ph$ | H | |
| 1-107 | 3,5-$Cl_2$Ph | $CF_3$ | — | $CONHCH_2CH_2$(1,2,4-triazole-1-yl) | H | |
| 1-108 | 3,5-$Cl_2$Ph | $CF_3$ | — | $CONHCH_2CH_2$(pyrazole-1-yl) | H | |
| 1-109 | 3,5-$Cl_2$Ph | $CF_3$ | — | CONHOH | H | |
| 1-110 | 3,5-$Cl_2$Ph | $CF_3$ | — | $CONHOCH_3$ | H | |
| 1-111 | 3,5-$Cl_2$Ph | $CF_3$ | — | CONHPr-c | H | |
| 1-112 | 3,5-$Cl_2$Ph | $CF_3$ | — | CONHPh | H | |
| 1-113 | 3,5-$Cl_2$Ph | $CF_3$ | — | $CSNHCH_3$ | H | |
| 1-114 | 3,5-$Cl_2$Ph | $CF_3$ | — | $CO_2C_2H_5$ | H | |

TABLE 1-continued

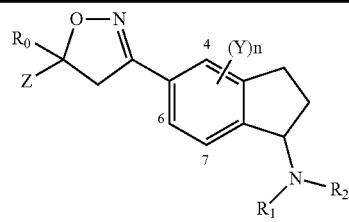

| Compound No. | Z | R₀ | (Y)n | R₁ | R₂ | Physical constant |
|---|---|---|---|---|---|---|
| 1-115 | 3,5-Cl₂Ph | CF₃ | — | CO₂Pr-n | H | |
| 1-116 | 3,5-Cl₂Ph | CF₃ | — | CO₂Pr-c | H | |
| 1-117 | 3,5-Cl₂Ph | CF₃ | — | CO₂CH₂CH₂OCH₃ | H | |
| 1-118 | 3,5-Cl₂Ph | CF₃ | — | CO₂CH₂CH₂OCH₂CH₃ | H | |
| 1-119 | 3,5-Cl₂Ph | CF₃ | — | CO₂CH₂CH(CH₃)OCH₃ | H | |
| 1-120 | 3,5-Cl₂Ph | CF₃ | — | CO₂CH₂CH₂CN | H | |
| 1-121 | 3,5-Cl₂Ph | CF₃ | — | CO₂CH₂CH₂Ph | H | |
| 1-122 | 3,5-Cl₂Ph | CF₃ | — | CO₂CH₂CH₂(1,2,4-triazole-1-yl) | H | |
| 1-123 | 3,5-Cl₂Ph | CF₃ | — | CO₂CH₂CH₂(pyrazole-1-yl) | H | |
| 1-124 | 3,5-Cl₂Ph | CF₃ | — | —CH₂CH₂CH₂CH₂— | | |
| 1-125 | 3,5-Cl₂Ph | CF₃ | — | —C(=O)CH₂CH₂CH₂— | | |
| 1-126 | 3,5-Cl₂Ph | CF₃ | — | —C(=O)CH₂C(=O)— | | |
| 1-127 | 3,5-Cl₂Ph | CF₃ | — | phthaloyl | | |
| 1-128 | 2,4-diCF₃-pyrimidine-6-yl | CF₃ | — | COCH₂CH(CH₃)OCH₃ | H | [105-125] |
| 1-129 | 2-CH₃S-4-CF₃-pyrimidine-6-yl | CF₃ | — | COCH₂CH(CH₃)OCH₃ | H | amorphous |
| 1-130 | 2-CH₃O-4-CF₃-pyrimidine-6-yl | CF₃ | — | COCH₂CH(CH₃)OCH₃ | H | amorphous |
| 1-131 | 2-Cl-4-CF₃-pyrimidine-6-yl | CF₃ | — | COCH₂CH(CH₃)OCH₃ | H | [99-109] |
| 1-132 | 2-Br-4-CF₃-pyrimidine-6-yl | CF₃ | — | COCH₂CH(CH₃)OCH₃ | H | amorphous |
| 1-133 | 3,5-Cl₂Ph | CF₃ | — | COCH₂Pr-c | H | |
| 1-134 | 3,5-Cl₂Ph | CF₃ | — | 2-cyclopentenone-3-yl | H | amorphous |
| 1-135 | 3-CF₃-4-CH₃Ph | CF₃ | — | COC₂H₅ | H | [138-140] |
| 1-136 | 3-CF₃-4-OCH₃Ph | CF₃ | — | COC₂H₅ | H | amorphous |
| 1-137 | 3-CF₃-4-CNPh | CF₃ | — | COC₂H₅ | H | amorphous |
| 1-138 | 3-CH₃-5-CF₃Ph | CF₃ | — | COC₂H₅ | H | amorphous |
| 1-139 | 3-OCH₃-5-CF₃Ph | CF₃ | — | COC₂H₅ | H | amorphous |
| 1-140 | 3-CN-5-CF₃Ph | CF₃ | — | COC₂H₅ | H | [160-165] |
| 1-141 | 2-CH₃-4-CF₃-pyrimidine-6-yl | CF₃ | — | COCH₂CH(CH₃)OCH₃ | H | amorphous |
| 1-142 | 2-CF₃-4-CF₃-pyrimidine-6-yl | CF₃ | — | COC₂H₅ | H | [148-151] |
| 1-143 | 2,6-di-Cl-pyridine-4-yl | CF₃ | — | COC₂H₅ | H | amorphous |
| 1-144 | 1-phenyl-pyrazole-4-yl | CF₃ | — | COC₂H₅ | H | amorphous |
| 1-145 | 1-phenyl-pyrazole-3-yl | CF₃ | — | COC₂H₅ | H | [170-178] |

TABLE 2

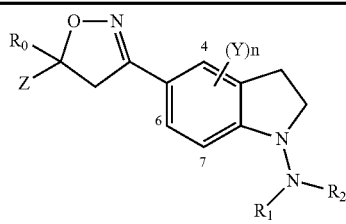

| Compound No. | Z | R₀ | (Y)n | R₁ | R₂ | Physical constant |
|---|---|---|---|---|---|---|
| 2-1 | 3,5-Cl₂Ph | CF₃ | — | n-Pr | H | |
| 2-2 | 3,5-Cl₂Ph | CF₃ | — | CH₂CH₂(2-Py) | H | |
| 2-3 | 3,5-Cl₂Ph | CF₃ | — | CH₂CH₂COCH₃ | H | |
| 2-4 | 3,5-Cl₂Ph | CF₃ | — | CH₂CH₂OCH₃ | H | |
| 2-5 | 3,5-Cl₂Ph | CF₃ | — | COCH₃ | H | |

TABLE 2-continued

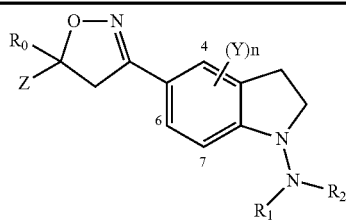

| Compound No. | Z | $R_0$ | (Y)n | $R_1$ | $R_2$ | Physical constant |
|---|---|---|---|---|---|---|
| 2-6 | 3,5-Cl$_2$Ph | CF$_3$ | — | COC$_2$H$_5$ | H | |
| 2-7 | 3,5-Cl$_2$Ph | CF$_3$ | — | COPr-n | H | |
| 2-8 | 3,5-Cl$_2$Ph | CF$_3$ | — | COCH$_2$CH$_2$OCH$_3$ | H | |
| 2-9 | 3,5-Cl$_2$Ph | CF$_3$ | — | COCH$_2$CH$_2$OCH$_2$CH$_3$ | H | |
| 2-10 | 3,5-Cl$_2$Ph | CF$_3$ | — | COCH$_2$CH(CH$_3$)OCH$_3$ | H | |
| 2-11 | 3,5-Cl$_2$Ph | CF$_3$ | — | COCH$_2$CH(CH$_3$)OCH$_2$CH$_3$ | H | |
| 2-12 | 3,5-Cl$_2$Ph | CF$_3$ | — | COCH$_2$CH(CH$_3$)OH | H | |
| 2-13 | 3,5-Cl$_2$Ph | CF$_3$ | — | COCH$_2$CH$_2$OCH$_2$CH=CH$_2$ | H | |
| 2-14 | 3,5-Cl$_2$Ph | CF$_3$ | — | COCH$_2$COCH$_3$ | H | |
| 2-15 | 3,5-Cl$_2$Ph | CF$_3$ | — | COCH$_2$(1,3-dioxolane-2-yl) | H | |
| 2-16 | 3,5-Cl$_2$Ph | CF$_3$ | — | COCH2(2-methyl-1,3-dioxolane-2-yl) | H | |
| 2-17 | 3,5-Cl$_2$Ph | CF$_3$ | — | COCH2(2-trifluoromethyl-1,3-dioxolane-2-yl) | H | |
| 2-18 | 3,5-Cl$_2$Ph | CF$_3$ | — | COCH2(2-methyl-1,3-dioxane-2-yl) | H | |
| 2-19 | 3,5-Cl$_2$Ph | CF$_3$ | — | COCH2CH2(1,3-dioxolane-2-yl) | H | |
| 2-20 | 3,5-Cl$_2$Ph | CF$_3$ | — | COCH2CH2(2-methyl-1,3-dioxolane-2-yl) | H | |
| 2-21 | 3,5-Cl$_2$Ph | CF$_3$ | — | CO(tetrahydropyran-4-yl) | H | |
| 2-22 | 3,5-Cl$_2$Ph | CF$_3$ | — | CO(2,6-dimethyl-4H-pyran-4-one-3-yl) | H | |
| 2-23 | 3,5-Cl$_2$Ph | CF$_3$ | — | COCH$_2$CH$_2$CN | H | |
| 2-24 | 3,5-Cl$_2$Ph | CF$_3$ | — | COCH$_2$CH$_2$Ph | H | |
| 2-25 | 3,5-Cl$_2$Ph | CF$_3$ | — | COCH$_2$CH$_2$(1,2,4-triazole-1-yl) | H | |
| 2-26 | 3,5-Cl$_2$Ph | CF$_3$ | — | COCH$_2$CH$_2$(pyrazole-1-yl) | H | |
| 2-27 | 3-CF$_3$Ph | CF$_3$ | — | COC$_2$H$_5$ | H | |
| 2-28 | 3-CF$_3$Ph | CF$_3$ | — | COCH$_2$CH$_2$OCH$_3$ | H | |
| 2-29 | 3-CF$_3$Ph | CF$_3$ | — | COCH$_2$CH(CH$_3$)OCH$_3$ | H | |
| 2-30 | 3-CF$_3$Ph | CF$_3$ | — | COCH$_2$(2-methyl-1,3-dioxolane-2-yl) | H | |
| 2-31 | 3-CF$_3$Ph | CF$_3$ | — | COCH$_2$CH$_2$CN | H | |
| 2-32 | 3,5-Cl$_2$Ph | CF$_3$ | — | COPr-c | H | |
| 2-33 | 3,5-Cl$_2$Ph | CF$_3$ | — | COHex-c | H | |
| 2-34 | 2-F-3-CF$_3$Ph | CF$_3$ | — | COC$_2$H$_5$ | H | |
| 2-35 | 2-F-3-CF$_3$Ph | CF$_3$ | — | COCH$_2$CH$_2$OCH$_3$ | H | |
| 2-36 | 3-CF$_3$-4-ClPh | CF$_3$ | — | COC$_2$H$_5$ | H | |
| 2-37 | 3-CF$_3$-4-ClPh | CF$_3$ | — | COCH$_2$CH$_2$OCH$_3$ | H | |
| 2-38 | 3-CF$_3$-4-ClPh | CF$_3$ | — | COCH$_2$CH(CH$_3$)OCH$_3$ | H | |
| 2-39 | 3,5-Cl$_2$Ph | CF$_3$ | — | COC$_2$H$_5$ | CH$_3$ | |
| 2-40 | 3,5-Cl$_2$Ph | CF$_3$ | — | CSC$_2$H$_5$ | H | |
| 2-41 | 3,5-Cl$_2$Ph | CF$_3$ | — | 2-cyclohexenone-3-yl | H | |
| 2-42 | 3,5-Cl$_2$Ph | CF$_3$ | — | CH$_2$(4-methyl-1,3-dioxolene-2-one-5-yl) | H | |
| 2-43 | 3,5-Cl$_2$Ph | CF$_3$ | — | CH$_2$(4-methyl-1,3-dioxolene-2-one-5-yl) | CH$_2$(4-methyl-1,3-dioxolene-2-one-5-yl) | |
| 2-44 | 3,5-Cl$_2$Ph | CF$_3$ | — | H | H | |
| 2-45 | 3-CF$_3$Ph | CF$_3$ | — | H | H | |
| 2-46 | 2-F-3-CF$_3$Ph | CF$_3$ | — | H | H | |
| 2-47 | 3-CF$_3$-4-ClPh | CF$_3$ | — | H | H | |
| 2-48 | 3,5-Cl$_2$Ph | CF$_3$ | 4-F | COC$_2$H$_5$ | H | |
| 2-49 | 3,5-Cl$_2$Ph | CF$_3$ | 4-Cl | COC$_2$H$_5$ | H | |
| 2-50 | 3,5-Cl$_2$Ph | CF$_3$ | 4-CH$_3$ | COC$_2$H$_5$ | H | |
| 2-51 | 3,5-Cl$_2$Ph | CF$_3$ | 4-CF$_3$ | COC$_2$H$_5$ | H | |
| 2-52 | 3,5-Cl$_2$Ph | CF$_3$ | 4-CH$_2$OCH$_3$ | COC$_2$H$_5$ | H | |
| 2-53 | 3,5-Cl$_2$Ph | CF$_3$ | 4-NO$_2$ | COC$_2$H$_5$ | H | |
| 2-54 | 3,5-Cl$_2$Ph | CF$_3$ | 4-OH | COC$_2$H$_5$ | H | |
| 2-55 | 3,5-Cl$_2$Ph | CF$_3$ | 4-OCH$_3$ | COC$_2$H$_5$ | H | |
| 2-56 | 3,5-Cl$_2$Ph | CF$_3$ | 4-OCF$_3$ | COC$_2$H$_5$ | H | |
| 2-57 | 3,5-Cl$_2$Ph | CF$_3$ | 4-OCH$_2$COCH$_3$ | COC$_2$H$_5$ | H | |
| 2-58 | 3,5-Cl$_2$Ph | CF$_3$ | 4-SH | COC$_2$H$_5$ | H | |
| 2-59 | 3,5-Cl$_2$Ph | CF$_3$ | 4-SCH$_3$ | COC$_2$H$_5$ | H | |
| 2-60 | 3,5-Cl$_2$Ph | CF$_3$ | 4-SCF$_3$ | COC$_2$H$_5$ | H | |
| 2-61 | 3,5-Cl$_2$Ph | CF$_3$ | 4-NH$_2$ | COC$_2$H$_5$ | H | |
| 2-62 | 3,5-Cl$_2$Ph | CF$_3$ | 4-NHCH$_3$ | COC$_2$H$_5$ | H | |
| 2-63 | 3,5-Cl$_2$Ph | CF$_3$ | 4-N(CH$_3$)$_2$ | COC$_2$H$_5$ | H | |
| 2-64 | 3,5-Cl$_2$Ph | CF$_3$ | 4-NHPh | COC$_2$H$_5$ | H | |
| 2-65 | 3,5-Cl$_2$Ph | CF$_3$ | 4-NHCOCH$_3$ | COC$_2$H$_5$ | H | |

TABLE 2-continued

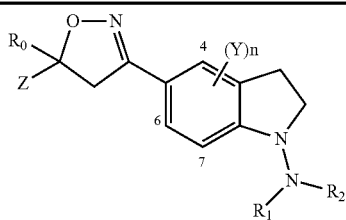

| Compound No. | Z | $R_0$ | $(Y)n$ | $R_1$ | $R_2$ | Physical constant |
|---|---|---|---|---|---|---|
| 2-66 | 3,5-Cl$_2$Ph | CF$_3$ | 4-NHCO$_2$C$_2$H$_5$ | COC$_2$H$_5$ | H | |
| 2-67 | 3,5-Cl$_2$Ph | CF$_3$ | 4-NHCO$_2$Bu-t | COC$_2$H$_5$ | H | |
| 2-68 | 3,5-Cl$_2$Ph | CF$_3$ | 4-NHCH$_2$Ph | COC$_2$H$_5$ | H | |
| 2-69 | 3,5-Cl$_2$Ph | CF$_3$ | 7-F | COC$_2$H$_5$ | H | |
| 2-70 | 3,5-Cl$_2$Ph | NO$_2$ | — | COC$_2$H$_5$ | H | |
| 2-71 | 3,5-Cl$_2$Ph | OH | — | COC$_2$H$_5$ | H | |
| 2-72 | 3,5-Cl$_2$Ph | OMe | — | COC$_2$H$_5$ | H | |
| 2-73 | 3,5-Cl$_2$Ph | OCF$_3$ | — | COC$_2$H$_5$ | H | |
| 2-74 | 3,5-Cl$_2$Ph | SH | — | COC$_2$H$_5$ | H | |
| 2-75 | 3,5-Cl$_2$Ph | SCF$_3$ | — | COC$_2$H$_5$ | H | |
| 2-76 | 3,5-Cl$_2$Ph | Cl | — | COC$_2$H$_5$ | H | |
| 2-77 | 3,5-Cl$_2$Ph | NH$_2$ | — | COC$_2$H$_5$ | H | |
| 2-78 | 3,5-Cl$_2$Ph | NHCOCH$_3$ | — | COC$_2$H$_5$ | H | |
| 2-79 | 3,5-Cl$_2$Ph | NHCO$_2$C$_2$H$_5$ | — | COC$_2$H$_5$ | H | |
| 2-80 | 3,5-Cl$_2$Ph | CO$_2$C$_2$H$_5$ | — | COC$_2$H$_5$ | H | |
| 2-81 | 3,5-Cl$_2$Ph | SO$_2$CH$_3$ | — | COC$_2$H$_5$ | H | |
| 2-82 | 3,5-Cl$_2$Ph | SO$_2$CF$_3$ | — | COC$_2$H$_5$ | H | |
| 2-83 | 3,5-Cl$_2$Ph | Ph | — | COC$_2$H$_5$ | H | |
| 2-84 | 3,5-Cl$_2$Ph | COCH$_3$ | — | COC$_2$H$_5$ | H | |
| 2-85 | 3,5-Cl$_2$Ph | Cl | — | COC$_2$H$_5$ | H | |
| 2-86 | 3,5-Cl$_2$Ph | CF$_2$H | — | COC$_2$H$_5$ | H | |
| 2-87 | 3,5-Cl$_2$Ph | CCl$_3$ | — | COC$_2$H$_5$ | H | |
| 2-88 | 3,5-Cl$_2$Ph | CF$_2$Cl | — | COC$_2$H$_5$ | H | |
| 2-89 | CH$_3$CH=CH | CF$_3$ | — | COC$_2$H$_5$ | H | |
| 2-90 | Propargyl | CF$_3$ | — | COC$_2$H$_5$ | H | |
| 2-91 | CH$_3$CH=CH | CF$_3$ | — | COC$_2$H$_5$ | H | |
| 2-92 | 2-butynyl | CF$_3$ | — | COC$_2$H$_5$ | H | |
| 2-93 | 3,5-Cl$_2$Ph | CF$_3$ | — | =CHOCH$_3$ | | |
| 2-94 | 3,5-Cl$_2$Ph | CF$_3$ | — | =C(OCH$_3$)$_2$ | | |
| 2-95 | 3,5-Cl$_2$Ph | CF$_3$ | — | =CHNO$_2$ | | |
| 2-96 | 3,5-Cl$_2$Ph | CF$_3$ | — | =C(OCH$_2$CH$_2$O) | | |
| 2-97 | 3,5-Cl$_2$Ph | CF$_3$ | — | CONHCH$_3$ | H | |
| 2-98 | 3,5-Cl$_2$Ph | CF$_3$ | — | CONHC$_2$H$_5$ | H | |
| 2-99 | 3,5-Cl$_2$Ph | CF$_3$ | — | CONHPr-n | H | |
| 2-100 | 3,5-Cl$_2$Ph | CF$_3$ | — | CONHCH$_2$CH$_2$OCH$_3$ | H | |
| 2-101 | 3,5-Cl$_2$Ph | CF$_3$ | — | CONHCH$_2$CH$_2$OCH$_2$CH$_3$ | H | |
| 2-102 | 3,5-Cl$_2$Ph | CF$_3$ | — | CONHCH$_2$CH(CH$_3$)OCH$_3$ | H | |
| 2-103 | 3,5-Cl$_2$Ph | CF$_3$ | — | CON(CH$_3$)$_2$ | H | |
| 2-104 | 3,5-Cl$_2$Ph | CF$_3$ | — | CONHCH$_2$CH$_2$CN | H | |
| 2-105 | 3,5-Cl$_2$Ph | CF$_3$ | — | CONHCH$_2$CH$_2$Ph | H | |
| 2-106 | 3,5-Cl$_2$Ph | CF$_3$ | — | CONHCH$_2$CH$_2$(1,2,4-triazole-1-yl) | H | |
| 2-107 | 3,5-Cl$_2$Ph | CF$_3$ | — | CONHCH$_2$CH$_2$(pyrazole-1-yl) | H | |
| 2-108 | 3,5-Cl$_2$Ph | CF$_3$ | — | CONHOH | H | |
| 2-109 | 3,5-Cl$_2$Ph | CF$_3$ | — | CONHOCH$_3$ | H | |
| 2-110 | 3,5-Cl$_2$Ph | CF$_3$ | — | CONHPr-c | H | |
| 2-111 | 3,5-Cl$_2$Ph | CF$_3$ | — | CONHPh | H | |
| 2-112 | 3,5-Cl$_2$Ph | CF$_3$ | — | CSNHCH$_3$ | H | |
| 2-113 | 3,5-Cl$_2$Ph | CF$_3$ | — | CO$_2$C$_2$H$_5$ | H | |
| 2-114 | 3,5-Cl$_2$Ph | CF$_3$ | — | CO$_2$Pr-n | H | |
| 2-115 | 3,5-Cl$_2$Ph | CF$_3$ | — | CO$_2$Pr-c | H | |
| 2-116 | 3,5-Cl$_2$Ph | CF$_3$ | — | CO$_2$CH$_2$CH$_2$OCH$_3$ | H | |
| 2-117 | 3,5-Cl$_2$Ph | CF$_3$ | — | CO$_2$CH$_2$CH$_2$OCH$_2$CH$_3$ | H | |
| 2-118 | 3,5-Cl$_2$Ph | CF$_3$ | — | CO$_2$CH$_2$CH(CH$_3$)OCH$_3$ | H | |
| 2-119 | 3,5-Cl$_2$Ph | CF$_3$ | — | CO$_2$CH$_2$CH$_2$CN | H | |
| 2-120 | 3,5-Cl$_2$Ph | CF$_3$ | — | CO$_2$CH$_2$CH$_2$Ph | H | |
| 2-121 | 3,5-Cl$_2$Ph | CF$_3$ | — | CO$_2$CH$_2$CH$_2$(1,2,4-triazole-1-yl) | H | |
| 2-122 | 3,5-Cl$_2$Ph | CF$_3$ | — | CO$_2$CH$_2$CH$_2$(pyrazole-1-yl) | H | |
| 2-123 | 3,5-Cl$_2$Ph | CF$_3$ | — | —CH$_2$CH$_2$CH$_2$CH$_2$— | | |
| 2-124 | 3,5-Cl$_2$Ph | CF$_3$ | — | —C(=O)CH$_2$CH$_2$CH$_2$— | | |
| 2-125 | 3,5-Cl$_2$Ph | CF$_3$ | — | —C(=O)CH$_2$CH$_2$C(=O)— | | |
| 2-126 | 3,5-Cl$_2$Ph | CF$_3$ | — | phthaloyl | | |

TABLE 2-continued

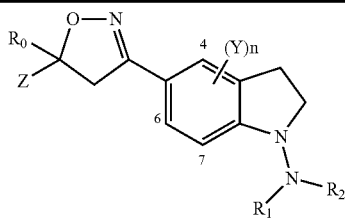

| Compound No. | Z | $R_0$ | (Y)n | $R_1$ | $R_2$ | Physical constant |
|---|---|---|---|---|---|---|
| 2-127 | 2,4-diCF$_3$-pyrimidine-6-yl | CF$_3$ | — | COCH$_2$CH(CH$_3$)OCH$_3$ | H | |
| 2-128 | 2-CH$_3$S-4-CF$_3$-pyrimidine-6-yl | CF$_3$ | — | COCH$_2$CH(CH$_3$)OCH$_3$ | H | |
| 2-129 | 2-CH$_3$O-4-CF$_3$-pyrimidine-6-yl | CF$_3$ | — | COCH$_2$CH(CH$_3$)OCH$_3$ | H | |
| 2-130 | 2-Cl-4-CF$_3$-pyrimidine-6-yl | CF$_3$ | — | COCH$_2$CH(CH$_3$)OCH$_3$ | H | |
| 2-131 | 2-Br-4-CF$_3$-pyrimidine-6-yl | CF$_3$ | — | COCH$_2$CH(CH$_3$)OCH$_3$ | H | |

TABLE 3

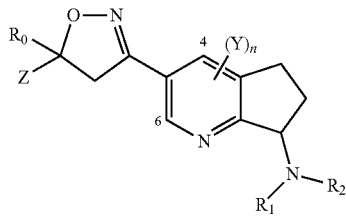

| Compound No. | Z | $R_0$ | (Y)n | $R_1$ | $R_2$ | Physical constant |
|---|---|---|---|---|---|---|
| 3-1 | 3,5-Cl$_2$Ph | CF$_3$ | — | n-Pr | H | |
| 3-2 | 3,5-Cl$_2$Ph | CF$_3$ | — | CH$_2$CH$_2$(2-Py) | H | |
| 3-3 | 3,5-Cl$_2$Ph | CF$_3$ | — | CH$_2$CH$_2$COCH$_3$ | H | |
| 3-4 | 3,5-Cl$_2$Ph | CF$_3$ | — | CH$_2$CH$_2$OCH$_3$ | H | |
| 3-5 | 3,5-Cl$_2$Ph | CF$_3$ | — | COCH$_3$ | H | |
| 3-6 | 3,5-Cl$_2$Ph | CF$_3$ | — | COC$_2$H$_5$ | H | amorphous |
| 3-7 | 3,5-Cl$_2$Ph | CF$_3$ | — | COPr-n | H | |
| 3-8 | 3,5-Cl$_2$Ph | CF$_3$ | — | COCH$_2$CH$_2$OCH$_3$ | H | |
| 3-9 | 3,5-Cl$_2$Ph | CF$_3$ | — | COCH$_2$CH$_2$OCH$_2$CH$_3$ | H | |
| 3-10 | 3,5-Cl$_2$Ph | CF$_3$ | — | COCH$_2$CH(CH$_3$)OCH$_3$ | H | |
| 3-11 | 3,5-Cl$_2$Ph | CF$_3$ | — | COCH$_2$CH(CH$_3$)OCH$_2$CH$_3$ | H | |
| 3-12 | 3,5-Cl$_2$Ph | CF$_3$ | — | COCH$_2$CH(CH$_3$)OH | H | |
| 3-13 | 3,5-Cl$_2$Ph | CF$_3$ | — | COCH$_2$CH$_2$OCH$_2$CH=CH$_2$ | H | |
| 3-14 | 3,5-Cl$_2$Ph | CF$_3$ | — | COCH$_2$COCH$_3$ | H | |
| 3-15 | 3,5-Cl$_2$Ph | CF$_3$ | — | COCH$_2$(1,3-dioxolane-2-yl) | H | |
| 3-16 | 3,5-Cl$_2$Ph | CF$_3$ | — | COCH$_2$(2-methyl-1,3-dioxolane-2-yl) | H | |
| 3-17 | 3,5-Cl$_2$Ph | CF$_3$ | — | COCH$_2$(2-trifluoromethyl-1,3-dioxolane-2-yl) | H | |
| 3-18 | 3,5-Cl$_2$Ph | CF$_3$ | — | COCH$_2$(2-methyl-1,3-dioxane-2-yl) | H | |
| 3-19 | 3,5-Cl$_2$Ph | CF$_3$ | — | COCH$_2$CH$_2$(1,3-dioxolane-2-yl) | H | |
| 3-20 | 3,5-Cl$_2$Ph | CF$_3$ | — | COCH$_2$CH$_2$(2-methyl-1,3-dioxolane-2-yl) | H | |
| 3-21 | 3,5-Cl$_2$Ph | CF$_3$ | — | CO(tetrahydropyran-4-yl) | H | |
| 3-22 | 3,5-Cl$_2$Ph | CF$_3$ | — | CO(2,6-dimethyl-4H-pyran-4-one-3-yl) | H | |
| 3-23 | 3,5-Cl$_2$Ph | CF$_3$ | — | COCH$_2$CH$_2$CN | H | |
| 3-24 | 3,5-Cl$_2$Ph | CF$_3$ | — | COCH$_2$CH$_2$Ph | H | |
| 3-25 | 3,5-Cl$_2$Ph | CF$_3$ | — | COCH$_2$CH$_2$(1,2,4-triazole-1-yl) | H | |
| 3-26 | 3,5-Cl$_2$Ph | CF$_3$ | — | COCH$_2$CH$_2$(pyrazole-1-yl) | H | |
| 3-27 | 3-CF$_3$Ph | CF$_3$ | — | COC$_2$H$_5$ | H | |
| 3-28 | 3-CF$_3$Ph | CF$_3$ | — | COCH$_2$CH$_2$OCH$_3$ | H | |

TABLE 3-continued

| Compound No. | Z | $R_0$ | (Y)n | $R_1$ | $R_2$ | Physical constant |
|---|---|---|---|---|---|---|
| 3-29 | 3-CF$_3$Ph | CF$_3$ | — | COCH$_2$CH(CH$_3$)OCH$_3$ | H | |
| 3-30 | 3-CF$_3$Ph | CF$_3$ | — | COCH$_2$(2-methyl-1,3-dioxolane-2-yl) | H | |
| 3-31 | 3-CF$_3$Ph | CF$_3$ | — | COCH$_2$CH$_2$CN | H | |
| 3-32 | 3,5-Cl$_2$Ph | CF$_3$ | — | COPr-c | H | |
| 3-33 | 3,5-Cl$_2$Ph | CF$_3$ | — | COHex-c | H | |
| 3-34 | 2-F-3-CF$_3$Ph | CF$_3$ | — | COC$_2$H$_5$ | H | |
| 3-35 | 2-F-3-CF$_3$Ph | CF$_3$ | — | COCH$_2$CH$_2$OCH$_3$ | H | |
| 3-36 | 3-CF$_3$-4-ClPh | CF$_3$ | — | COC$_2$H$_5$ | H | |
| 3-37 | 3-CF$_3$-4-ClPh | CF$_3$ | — | COCH$_2$CH$_2$OCH$_3$ | H | |
| 3-38 | 3-CF$_3$-4-ClPh | CF$_3$ | — | COCH$_2$CH(CH$_3$)OCH$_3$ | H | |
| 3-39 | 3,5-Cl$_2$Ph | CF$_3$ | — | CSC$_2$H$_5$ | H | |
| 3-40 | 3,5-Cl$_2$Ph | CF$_3$ | — | 2-cyclohexenone-3-yl | H | |
| 3-41 | 3,5-Cl$_2$Ph | CF$_3$ | — | CH$_2$(4-methyl-1,3-dioxolene-2-one-5-yl) | H | |
| 3-42 | 3,5-Cl$_2$Ph | CF$_3$ | — | CH$_2$(4-methyl-1,3-dioxolene-2-one-5-yl) | CH2(4-methyl-1,3-dioxolene-2-one-5-yl) | |
| 3-43 | 3,5-Cl$_2$Ph | CF$_3$ | — | COC$_2$H$_5$ | CH$_3$ | |
| 3-44 | 3,5-Cl$_2$Ph | CF$_3$ | — | H | H | amorphous |
| 3-45 | 3-CF$_3$Ph | CF$_3$ | — | H | H | |
| 3-46 | 2-F-3-CF$_3$Ph | CF$_3$ | — | H | H | |
| 3-47 | 3-CF$_3$-4-ClPh | CF$_3$ | — | H | H | |
| 3-48 | 3,5-Cl$_2$Ph | CF$_3$ | 4-F | COC$_2$H$_5$ | H | |
| 3-49 | 3,5-Cl$_2$Ph | CF$_3$ | 4-Cl | COC$_2$H$_5$ | H | |
| 3-50 | 3,5-Cl$_2$Ph | CF$_3$ | 4-CH$_3$ | COC$_2$H$_5$ | H | |
| 3-51 | 3,5-Cl$_2$Ph | CF$_3$ | 4-CF$_3$ | COC$_2$H$_5$ | H | |
| 3-52 | 3,5-Cl$_2$Ph | CF$_3$ | 4-CH$_2$OCH$_3$ | COC$_2$H$_5$ | H | |
| 3-53 | 3,5-Cl$_2$Ph | CF$_3$ | 4-NO$_2$ | COC$_2$H$_5$ | H | |
| 3-54 | 3,5-Cl$_2$Ph | CF$_3$ | 4-OH | COC$_2$H$_5$ | H | |
| 3-55 | 3,5-Cl$_2$Ph | CF$_3$ | 4-OCH$_3$ | COC$_2$H$_5$ | H | |
| 3-56 | 3,5-Cl$_2$Ph | CF$_3$ | 4-OCF$_3$ | COC$_2$H$_5$ | H | |
| 3-57 | 3,5-Cl$_2$Ph | CF$_3$ | 4-OCH$_2$COCH$_3$ | COC$_2$H$_5$ | H | |
| 3-58 | 3,5-Cl$_2$Ph | CF$_3$ | 4-SH | COC$_2$H$_5$ | H | |
| 3-59 | 3,5-Cl$_2$Ph | CF$_3$ | 4-SCH$_3$ | COC$_2$H$_5$ | H | |
| 3-60 | 3,5-Cl$_2$Ph | CF$_3$ | 4-SCF$_3$ | COC$_2$H$_5$ | H | |
| 3-61 | 3,5-Cl$_2$Ph | CF$_3$ | 4-NH$_2$ | COC$_2$H$_5$ | H | |
| 3-62 | 3,5-Cl$_2$Ph | CF$_3$ | 4-NHCH$_3$ | COC$_2$H$_5$ | H | |
| 3-63 | 3,5-Cl$_2$Ph | CF$_3$ | 4-N(CH$_3$)$_2$ | COC$_2$H$_5$ | H | |
| 3-64 | 3,5-Cl$_2$Ph | CF$_3$ | 4-NHPh | COC$_2$H$_5$ | H | |
| 3-65 | 3,5-Cl$_2$Ph | CF$_3$ | 4-NHCOCH$_3$ | COC$_2$H$_5$ | H | |
| 3-66 | 3,5-Cl$_2$Ph | CF$_3$ | 4-NHCO$_2$C$_2$H$_5$ | COC$_2$H$_5$ | H | |
| 3-67 | 3,5-Cl$_2$Ph | CF$_3$ | 4-NHCO$_2$Bu-t | COC$_2$H$_5$ | H | |
| 3-68 | 3,5-Cl$_2$Ph | CF$_3$ | 4-NHCH$_2$Ph | COC$_2$H$_5$ | H | |
| 3-69 | 3,5-Cl$_2$Ph | NO$_2$ | — | COC$_2$H$_5$ | H | |
| 3-70 | 3,5-Cl$_2$Ph | OH | — | COC$_2$H$_5$ | H | |
| 3-71 | 3,5-Cl$_2$Ph | OMe | — | COC$_2$H$_5$ | H | |
| 3-72 | 3,5-Cl$_2$Ph | OCF$_3$ | — | COC$_2$H$_5$ | H | |
| 3-73 | 3,5-Cl$_2$Ph | SH | — | COC$_2$H$_5$ | H | |
| 3-74 | 3,5-Cl$_2$Ph | SCF$_3$ | — | COC$_2$H$_5$ | H | |
| 3-75 | 3,5-Cl$_2$Ph | Cl | — | COC$_2$H$_5$ | H | |
| 3-76 | 3,5-Cl$_2$Ph | NH$_2$ | — | COC$_2$H$_5$ | H | |
| 3-77 | 3,5-Cl$_2$Ph | NHCOCH$_3$ | — | COC$_2$H$_5$ | H | |
| 3-78 | 3,5-Cl$_2$Ph | NHCO$_2$C$_2$H$_5$ | — | COC$_2$H$_5$ | H | |
| 3-79 | 3,5-Cl$_2$Ph | CO$_2$C$_2$H$_5$ | — | COC$_2$H$_5$ | H | |
| 3-80 | 3,5-Cl$_2$Ph | SO$_2$CH$_3$ | — | COC$_2$H$_5$ | H | |
| 3-81 | 3,5-Cl$_2$Ph | SO$_2$CF$_3$ | — | COC$_2$H$_5$ | H | |
| 3-82 | 3,5-Cl$_2$Ph | Ph | — | COC$_2$H$_5$ | H | |
| 3-83 | 3,5-Cl$_2$Ph | COCH$_3$ | — | COC$_2$H$_5$ | H | |
| 3-84 | 3,5-Cl$_2$Ph | Cl | — | COC$_2$H$_5$ | H | |
| 3-85 | 3,5-Cl$_2$Ph | CF$_2$H | — | COC$_2$H$_5$ | H | |
| 3-86 | 3,5-Cl$_2$Ph | CCl$_3$ | — | COC$_2$H$_5$ | H | |
| 3-87 | 3,5-Cl$_2$Ph | CF$_2$Cl | — | COC$_2$H$_5$ | H | |
| 3-88 | CH$_3$CH=CH | CF$_3$ | — | COC$_2$H$_5$ | H | |
| 3-89 | Propargyl | CF$_3$ | — | COC$_2$H$_5$ | H | |
| 3-90 | CH$_2$=CHCH$_2$ | CF$_3$ | — | COC$_2$H$_5$ | H | |
| 3-91 | 2-butynyl | CF$_3$ | — | COC$_2$H$_5$ | H | |

TABLE 3-continued

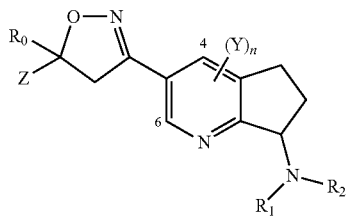

| Compound No. | Z | $R_0$ | $(Y)n$ | $R_1$ | $R_2$ | Physical constant |
|---|---|---|---|---|---|---|
| 3-92 | 3,5-$Cl_2$Ph | $CF_3$ | — | $COC_2H_5$ | -(nitrogen atom forms double bond with indane ring) | |
| 3-93 | 3,5-$Cl_2$Ph | $CF_3$ | — | =CHOCH$_3$ | | |
| 3-94 | 3,5-$Cl_2$Ph | $CF_3$ | — | =C(OCH$_3$)$_2$ | | |
| 3-95 | 3,5-$Cl_2$Ph | $CF_3$ | — | =CHNO$_2$ | | |
| 3-96 | 3,5-$Cl_2$Ph | $CF_3$ | — | =C(OCH$_2$CH$_2$O) | | |
| 3-97 | 3,5-$Cl_2$Ph | $CF_3$ | — | CONHCH$_3$ | H | |
| 3-98 | 3,5-$Cl_2$Ph | $CF_3$ | — | CONHC$_2$H$_5$ | H | |
| 3-99 | 3,5-$Cl_2$Ph | $CF_3$ | — | CONHPr-n | H | |
| 3-100 | 3,5-$Cl_2$Ph | $CF_3$ | — | CONHCH$_2$CH$_2$OCH$_3$ | H | |
| 3-101 | 3,5-$Cl_2$Ph | $CF_3$ | — | CONHCH$_2$CH$_2$OCH$_2$CH$_3$ | H | |
| 3-102 | 3,5-$Cl_2$Ph | $CF_3$ | — | CONHCH$_2$CH(CH$_3$)OCH$_3$ | H | |
| 3-103 | 3,5-$Cl_2$Ph | $CF_3$ | — | CON(CH$_3$)$_2$ | H | |
| 3-104 | 3,5-$Cl_2$Ph | $CF_3$ | — | CONHCH$_2$CH$_2$CN | H | |
| 3-105 | 3,5-$Cl_2$Ph | $CF_3$ | — | CONHCH$_2$CH$_2$Ph | H | |
| 3-106 | 3,5-$Cl_2$Ph | $CF_3$ | — | CONHCH$_2$CH$_2$(1,2,4-triazole-1-yl) | H | |
| 3-107 | 3,5-$Cl_2$Ph | $CF_3$ | — | CONHCH$_2$CH$_2$(pyrazole-1-yl) | H | |
| 3-108 | 3,5-$Cl_2$Ph | $CF_3$ | — | CONHOH | H | |
| 3-109 | 3,5-$Cl_2$Ph | $CF_3$ | — | CONHOCH$_3$ | H | |
| 3-110 | 3,5-$Cl_2$Ph | $CF_3$ | — | CONHPr-c | H | |
| 3-111 | 3,5-$Cl_2$Ph | $CF_3$ | — | CONHPh | H | |
| 3-112 | 3,5-$Cl_2$Ph | $CF_3$ | — | CSNHCH$_3$ | H | |
| 3-113 | 3,5-$Cl_2$Ph | $CF_3$ | — | CO$_2$C$_2$H$_5$ | H | |
| 3-114 | 3,5-$Cl_2$Ph | $CF_3$ | — | CO$_2$Pr-n | H | |
| 3-115 | 3,5-$Cl_2$Ph | $CF_3$ | — | CO$_2$Pr-c | H | |
| 3-116 | 3,5-$Cl_2$Ph | $CF_3$ | — | CO$_2$CH$_2$CH$_2$OCH$_3$ | H | |
| 3-117 | 3,5-$Cl_2$Ph | $CF_3$ | — | CO$_2$CH$_2$CH$_2$OCH$_2$CH$_3$ | H | |
| 3-118 | 3,5-$Cl_2$Ph | $CF_3$ | — | CO$_2$CH$_2$CH(CH$_3$)OCH$_3$ | H | |
| 3-119 | 3,5-$Cl_2$Ph | $CF_3$ | — | CO$_2$CH$_2$CH$_2$CN | H | |
| 3-120 | 3,5-$Cl_2$Ph | $CF_3$ | — | CO$_2$CH$_2$CH$_2$Ph | H | |
| 3-121 | 3,5-$Cl_2$Ph | $CF_3$ | — | CO$_2$CH$_2$CH$_2$(1,2,4-triazole-1-yl) | H | |
| 3-122 | 3,5-$Cl_2$Ph | $CF_3$ | — | CO$_2$CH$_2$CH$_2$(pyrazole-1-yl) | H | |
| 3-123 | 3,5-$Cl_2$Ph | $CF_3$ | — | CH$_2$CH$_2$CH$_2$CH$_2$ | | |
| 3-124 | 3,5-$Cl_2$Ph | $CF_3$ | — | C(=O)CH$_2$CH$_2$CH$_2$ | | |
| 3-125 | 3,5-$Cl_2$Ph | $CF_3$ | — | C(=O)CH$_2$CH$_2$C(=O) | | |
| 3-126 | 3,5-$Cl_2$Ph | $CF_3$ | — | phthaloyl | | |
| 3-127 | 2,4-di$CF_3$-pyrimidine-6-yl | $CF_3$ | — | COCH$_2$CH(CH$_3$)OCH$_3$ | H | |
| 3-128 | 2-CH$_3$S-4-$CF_3$-pyrimidine-6-yl | $CF_3$ | — | COCH$_2$CH(CH$_3$)OCH$_3$ | H | |
| 3-129 | 2-CH$_3$O-4-$CF_3$-pyrimidine-6-yl | $CF_3$ | — | COCH$_2$CH(CH$_3$)OCH$_3$ | H | |
| 3-130 | 2-Cl-4-$CF_3$-pyrimidine-6-yl | $CF_3$ | — | COCH$_2$CH(CH$_3$)OCH$_3$ | H | |
| 3-131 | 2-Br-4-$CF_3$-pyrimidine-6-yl | $CF_3$ | — | COCH$_2$CH(CH$_3$)OCH$_3$ | H | |

TABLE 4

| Compound No. | Z | $R_0$ | (Y)n | $R_1$ | $R_2$ | Physical constant |
|---|---|---|---|---|---|---|
| 4-1 | 3,5-Cl$_2$Ph | CF$_3$ | — | n-Pr | H | |
| 4-2 | 3,5-Cl$_2$Ph | CF$_3$ | — | CH$_2$CH$_2$(2-Py) | H | |
| 4-3 | 3,5-Cl$_2$Ph | CF$_3$ | — | CH$_2$CH$_2$COCH$_3$ | H | |
| 4-4 | 3,5-Cl$_2$Ph | CF$_3$ | — | CH$_2$CH$_2$OCH$_3$ | H | |
| 4-5 | 3,5-Cl$_2$Ph | CF$_3$ | — | COCH$_3$ | H | |
| 4-6 | 3,5-Cl$_2$Ph | CF$_3$ | — | COC$_2$H$_5$ | H | |
| 4-7 | 3,5-Cl$_2$Ph | CF$_3$ | — | COPr-n | H | |
| 4-8 | 3,5-Cl$_2$Ph | CF$_3$ | — | COCH$_2$CH$_2$OCH$_3$ | H | |
| 4-9 | 3,5-Cl$_2$Ph | CF$_3$ | — | COCH$_2$CH$_2$OCH$_2$CH$_3$ | H | |
| 4-10 | 3,5-Cl$_2$Ph | CF$_3$ | — | COCH$_2$CH(CH$_3$)OCH$_3$ | H | |
| 4-11 | 3,5-Cl$_2$Ph | CF$_3$ | — | COCH$_2$CH(CH$_3$)OCH$_2$CH$_3$ | H | |
| 4-12 | 3,5-Cl$_2$Ph | CF$_3$ | — | COCH$_2$CH(CH$_3$)OH | H | |
| 4-13 | 3,5-Cl$_2$Ph | CF$_3$ | — | COCH$_2$CH$_2$OCH$_2$CH=CH$_2$ | H | |
| 4-14 | 3,5-Cl$_2$Ph | CF$_3$ | — | COCH$_2$COCH$_3$ | H | |
| 4-15 | 3,5-Cl$_2$Ph | CF$_3$ | — | COCH$_2$(1,3-dioxolane-2-yl) | H | |
| 4-16 | 3,5-Cl$_2$Ph | CF$_3$ | — | COCH$_2$(2-methyl-1,3-dioxolane-2-yl) | H | |
| 4-17 | 3,5-Cl$_2$Ph | CF$_3$ | — | COCH$_2$(2-trifluoromethyl-1,3-dioxolane-2-yl) | H | |
| 4-18 | 3,5-Cl$_2$Ph | CF$_3$ | — | COCH$_2$(2-methyl-1,3-dioxane-2-yl) | H | |
| 4-19 | 3,5-Cl$_2$Ph | CF$_3$ | — | COCH$_2$CH$_2$(1,3-dioxolane-2-yl) | H | |
| 4-20 | 3,5-Cl$_2$Ph | CF$_3$ | — | COCH$_2$CH$_2$(2-methyl-1,3-dioxolane-2-yl) | H | |
| 4-21 | 3,5-Cl$_2$Ph | CF$_3$ | — | CO(tetrahydropyran-4-yl) | H | |
| 4-22 | 3,5-Cl$_2$Ph | CF$_3$ | — | CO(2,6-dimethyl-4H-pyran-4-one-3-yl) | H | |
| 4-23 | 3,5-Cl$_2$Ph | CF$_3$ | — | COCH$_2$CH$_2$CN | H | |
| 4-24 | 3,5-Cl$_2$Ph | CF$_3$ | — | COCH$_2$CH$_2$Ph | H | |
| 4-25 | 3,5-Cl$_2$Ph | CF$_3$ | — | COCH$_2$CH$_2$(1,2,4-triazole-1-yl) | H | |
| 4-26 | 3,5-Cl$_2$Ph | CF$_3$ | — | COCH$_2$CH$_2$(pyrazole-1-yl) | H | |
| 4-27 | 3-CF$_3$Ph | CF$_3$ | — | COC$_2$H$_5$ | H | |
| 4-28 | 3-CF$_3$Ph | CF$_3$ | — | COCH$_2$CH$_2$OCH$_3$ | H | |
| 4-29 | 3-CF$_3$Ph | CF$_3$ | — | COCH$_2$CH(CH$_3$)OCH$_3$ | H | |
| 4-30 | 3-CF$_3$Ph | CF$_3$ | — | COCH$_2$(2-methyl-1,3-dioxolane-2-yl) | H | |
| 4-31 | 3-CF$_3$Ph | CF$_3$ | — | COCH$_2$CH$_2$CN | H | |
| 4-32 | 3,5-Cl$_2$Ph | CF$_3$ | — | COPr-c | H | |
| 4-33 | 3,5-Cl$_2$Ph | CF$_3$ | — | COHex-c | H | |
| 4-34 | 2-F-3-CF$_3$Ph | CF$_3$ | — | COC$_2$H$_5$ | H | |
| 4-35 | 2-F-3-CF$_3$Ph | CF$_3$ | — | COCH$_2$CH$_2$OCH$_3$ | H | |
| 4-36 | 3-CF$_3$-4-ClPh | CF$_3$ | — | COC$_2$H$_5$ | H | |
| 4-37 | 3-CF$_3$-4-ClPh | CF$_3$ | — | COCH$_2$CH$_2$OCH$_3$ | H | |
| 4-38 | 3-CF$_3$-4-ClPh | CF$_3$ | — | COCH$_2$CH(CH$_3$)OCH$_3$ | H | |
| 4-39 | 3,5-Cl$_2$Ph | CF$_3$ | — | COC$_2$H$_5$ | CH$_3$ | |
| 4-40 | 3,5-Cl$_2$Ph | CF$_3$ | — | CSC$_2$H$_5$ | H | |
| 4-41 | 3,5-Cl$_2$Ph | CF$_3$ | — | 2-cyclohexenone-3-yl | H | |
| 4-42 | 3,5-Cl$_2$Ph | CF$_3$ | — | CH$_2$(4-methyl-1,3-dioxolene-2-one-5-yl) | H | |
| 4-43 | 3,5-Cl$_2$Ph | CF$_3$ | — | CH$_2$(4-methyl-1,3-dioxolene-2-one-5-yl) | CH$_2$(4-methyl-1,3-dioxolene-2-one-5-yl) | |
| 4-44 | 3,5-Cl$_2$Ph | CF$_3$ | — | H | H | |
| 4-45 | 3-CF$_3$Ph | CF$_3$ | — | H | H | |
| 4-46 | 2-F-3-CF$_3$Ph | CF$_3$ | — | H | H | |
| 4-47 | 3-CF$_3$-4-ClPh | CF$_3$ | — | H | H | |
| 4-48 | 3,5-Cl$_2$Ph | CF$_3$ | 4-F | COC$_2$H$_5$ | H | |
| 4-49 | 3,5-Cl$_2$Ph | CF$_3$ | 4-Cl | COC$_2$H$_5$ | H | |
| 4-50 | 3,5-Cl$_2$Ph | CF$_3$ | 4-CH$_3$ | COC$_2$H$_5$ | H | |
| 4-51 | 3,5-Cl$_2$Ph | CF$_3$ | 4-CF$_3$ | COC$_2$H$_5$ | H | |
| 4-52 | 3,5-Cl$_2$Ph | CF$_3$ | 4-CH$_2$OCH$_3$ | COC$_2$H$_5$ | H | |
| 4-53 | 3,5-Cl$_2$Ph | CF$_3$ | 4-NO$_2$ | COC$_2$H$_5$ | H | |
| 4-54 | 3,5-Cl$_2$Ph | CF$_3$ | 4-OH | COC$_2$H$_5$ | H | |

TABLE 4-continued

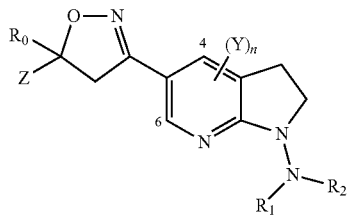

| Compound No. | Z | $R_0$ | (Y)n | $R_1$ | $R_2$ | Physical constant |
|---|---|---|---|---|---|---|
| 4-55 | 3,5-$Cl_2$Ph | $CF_3$ | 4-$OCH_3$ | $COC_2H_5$ | H | |
| 4-56 | 3,5-$Cl_2$Ph | $CF_3$ | 4-$OCF_3$ | $COC_2H_5$ | H | |
| 4-57 | 3,5-$Cl_2$Ph | $CF_3$ | 4-$OCH_2COCH_3$ | $COC_2H_5$ | H | |
| 4-58 | 3,5-$Cl_2$Ph | $CF_3$ | 4-SH | $COC_2H_5$ | H | |
| 4-59 | 3,5-$Cl_2$Ph | $CF_3$ | 4-$SCH_3$ | $COC_2H_5$ | H | |
| 4-60 | 3,5-$Cl_2$Ph | $CF_3$ | 4-$SCF_3$ | $COC_2H_5$ | H | |
| 4-61 | 3,5-$Cl_2$Ph | $CF_3$ | 4-$NH_2$ | $COC_2H_5$ | H | |
| 4-62 | 3,5-$Cl_2$Ph | $CF_3$ | 4-$NHCH_3$ | $COC_2H_5$ | H | |
| 4-63 | 3,5-$Cl_2$Ph | $CF_3$ | 4-$N(CH_3)_2$ | $COC_2H_5$ | H | |
| 4-64 | 3,5-$Cl_2$Ph | $CF_3$ | 4-NHPh | $COC_2H_5$ | H | |
| 4-65 | 3,5-$Cl_2$Ph | $CF_3$ | 4-NHCOCH3 | $COC_2H_5$ | H | |
| 4-66 | 3,5-$Cl_2$Ph | $CF_3$ | 4-$NHCO_2C_2H_5$ | $COC_2H_5$ | H | |
| 4-67 | 3,5-$Cl_2$Ph | $CF_3$ | 4-$NHCO_2$Bu-t | $COC_2H_5$ | H | |
| 4-68 | 3,5-$Cl_2$Ph | $CF_3$ | 4-$NHCH_2$Ph | $COC_2H_5$ | H | |
| 4-69 | 3,5-$Cl_2$Ph | $NO_2$ | — | $COC_2H_5$ | H | |
| 4-70 | 3,5-$Cl_2$Ph | OH | — | $COC_2H_5$ | H | |
| 4-71 | 3,5-$Cl_2$Ph | OMe | — | $COC_2H_5$ | H | |
| 4-72 | 3,5-$Cl_2$Ph | $OCF_3$ | — | $COC_2H_5$ | H | |
| 4-73 | 3,5-$Cl_2$Ph | SH | — | $COC_2H_5$ | H | |
| 4-74 | 3,5-$Cl_2$Ph | $SCF_3$ | — | $COC_2H_5$ | H | |
| 4-75 | 3,5-$Cl_2$Ph | Cl | — | $COC_2H_5$ | H | |
| 4-76 | 3,5-$Cl_2$Ph | $NH_2$ | — | $COC_2H_5$ | H | |
| 4-77 | 3,5-$Cl_2$Ph | $NHCOCH_3$ | — | $COC_2H_5$ | H | |
| 4-78 | 3,5-$Cl_2$Ph | $NHCO_2C_2H_5$ | — | $COC_2H_5$ | H | |
| 4-79 | 3,5-$Cl_2$Ph | $CO_2C_2H_5$ | — | $COC_2H_5$ | H | |
| 4-80 | 3,5-$Cl_2$Ph | $SO_2CH_3$ | — | $COC_2H_5$ | H | |
| 4-81 | 3,5-$Cl_2$Ph | $SO_2CF_3$ | — | $COC_2H_5$ | H | |
| 4-82 | 3,5-$Cl_2$Ph | Ph | — | $COC_2H_5$ | H | |
| 4-83 | 3,5-$Cl_2$Ph | $COCH_3$ | — | $COC_2H_5$ | H | |
| 4-84 | 3,5-$Cl_2$Ph | Cl | — | $COC_2H_5$ | H | |
| 4-85 | 3,5-$Cl_2$Ph | $CF_2H$ | — | $COC_2H_5$ | H | |
| 4-86 | 3,5-$Cl_2$Ph | $CCl_3$ | — | $COC_2H_5$ | H | |
| 4-87 | 3,5-$Cl_2$Ph | $CF_2Cl$ | — | $COC_2H_5$ | H | |
| 4-88 | $CH_3CH=CH$ | $CF_3$ | — | $COC_2H_5$ | H | |
| 4-89 | Propargyl | $CF_3$ | — | $COC_2H_5$ | H | |
| 4-90 | $CH_2=CHCH_2$ | $CF_3$ | — | $COC_2H_5$ | H | |
| 4-91 | 2-butynyl | $CF_3$ | — | $COC_2H_5$ | H | |
| 4-92 | 3,5-$Cl_2$Ph | $CF_3$ | — | =$CHOCH_3$ | | |
| 4-93 | 3,5-$Cl_2$Ph | $CF_3$ | — | =$C(OCH_3)_2$ | | |
| 4-94 | 3,5-$Cl_2$Ph | $CF_3$ | — | =$CHNO_2$ | | |
| 4-95 | 3,5-$Cl_2$Ph | $CF_3$ | — | =$C(OCH_2CH_2O)$ | | |
| 4-96 | 3,5-$Cl_2$Ph | $CF_3$ | — | $CONHCH_3$ | H | |
| 4-97 | 3,5-$Cl_2$Ph | $CF_3$ | — | $CONHC_2H_5$ | H | |
| 4-98 | 3,5-$Cl_2$Ph | $CF_3$ | — | CONHPr-n | H | |
| 4-99 | 3,5-$Cl_2$Ph | $CF_3$ | — | $CONHCH_2CH_2OCH_3$ | H | |
| 4-100 | 3,5-$Cl_2$Ph | $CF_3$ | — | $CONHCH_2CH_2OCH_2CH_3$ | H | |
| 4-101 | 3,5-$Cl_2$Ph | $CF_3$ | — | $CONHCH_2CH(CH_3)OCH_3$ | H | |
| 4-102 | 3,5-$Cl_2$Ph | $CF_3$ | — | $CON(CH_3)_2$ | H | |
| 4-103 | 3,5-$Cl_2$Ph | $CF_3$ | — | $CONHCH_2CH_2CN$ | H | |
| 4-104 | 3,5-$Cl_2$Ph | $CF_3$ | — | $CONHCH_2CH_2$Ph | H | |
| 4-105 | 3,5-$Cl_2$Ph | $CF_3$ | — | $CONHCH_2CH_2$ (1,2,4-triazole-1-yl) | H | |
| 4-106 | 3,5-$Cl_2$Ph | $CF_3$ | — | $CONHCH_2CH_2$ (pyrazole-1-yl) | H | |
| 4-107 | 3,5-$Cl_2$Ph | $CF_3$ | — | CONHOH | H | |
| 4-108 | 3,5-$Cl_2$Ph | $CF_3$ | — | $CONHOCH_3$ | H | |
| 4-109 | 3,5-$Cl_2$Ph | $CF_3$ | — | CONHPr-c | H | |
| 4-110 | 3,5-$Cl_2$Ph | $CF_3$ | — | CONHPh | H | |
| 4-111 | 3,5-$Cl_2$Ph | $CF_3$ | — | $CSNHCH_3$ | H | |
| 4-112 | 3,5-$Cl_2$Ph | $CF_3$ | — | $CO_2C_2H_5$ | H | |
| 4-113 | 3,5-$Cl_2$Ph | $CF_3$ | — | $CO_2$Pr-n | H | |
| 4-114 | 3,5-$Cl_2$Ph | $CF_3$ | — | $CO_2$Pr-c | H | |
| 4-115 | 3,5-$Cl_2$Ph | $CF_3$ | — | $CO_2CH_2CH_2OCH_3$ | H | |
| 4-116 | 3,5-$Cl_2$Ph | $CF_3$ | — | $CO_2CH_2CH_2OCH_2CH_3$ | H | |
| 4-117 | 3,5-$Cl_2$Ph | $CF_3$ | — | $CO_2CH_2CH(CH_3)OCH_3$ | H | |
| 4-118 | 3,5-$Cl_2$Ph | $CF_3$ | — | $CO_2CH_2CH_2CN$ | H | |

TABLE 4-continued

| Compound No. | Z | $R_0$ | (Y)n | $R_1$ | $R_2$ | Physical constant |
|---|---|---|---|---|---|---|
| 4-119 | 3,5-Cl$_2$Ph | CF$_3$ | — | CO$_2$CH$_2$CH$_2$Ph | H | |
| 4-120 | 3,5-Cl$_2$Ph | CF$_3$ | — | CO$_2$CH$_2$CH$_2$(1,2,4-triazole-1-yl) | H | |
| 4-121 | 3,5-Cl$_2$Ph | CF$_3$ | — | CO$_2$CH$_2$CH$_2$(pyrazole-1-yl) | H | |
| 4-122 | 3,5-Cl$_2$Ph | CF$_3$ | — | —CH$_2$CH$_2$CH$_2$CH$_2$— | | |
| 4-123 | 3,5-Cl$_2$Ph | CF$_3$ | — | —C(=O)CH$_2$CH$_2$CH$_2$— | | |
| 4-124 | 3,5-Cl$_2$Ph | CF$_3$ | — | —C(=O)CH$_2$CH$_2$C(=O)— | | |
| 4-125 | 3,5-Cl$_2$Ph | CF$_3$ | — | phthaloyl | | |
| 4-126 | 2,4-diCF$_3$-pyrimidine-6-yl | CF$_3$ | — | COCH$_2$CH(CH$_3$)OCH$_3$ | H | |
| 4-127 | 2-CH$_3$S-4-CF$_3$-pyrimidine-6-yl | CF$_3$ | — | COCH$_2$CH(CH$_3$)OCH$_3$ | H | |
| 4-128 | 2-CH$_3$O-4-CF$_3$-pyrimidine-6-yl | CF$_3$ | — | COCH$_2$CH(CH$_3$)OCH$_3$ | H | |
| 4-129 | 2-Cl-4-CF$_3$-pyrimidine-6-yl | CF$_3$ | — | COCH$_2$CH(CH$_3$)OCH$_3$ | H | |
| 4-130 | 2-Br-4-CF$_3$-pyrimidine-6-yl | CF$_3$ | — | COCH$_2$CH(CH$_3$)OCH$_3$ | H | |

TABLE 5

| Compound No. | Z | $R_0$ | (Y)n | $R_1$ | $R_2$ | G | Physical constant |
|---|---|---|---|---|---|---|---|
| 5-1 | 3,5-Cl$_2$Ph | CF$_3$ | — | n-Pr | H | CH$_2$ | |
| 5-2 | 3,5-Cl$_2$Ph | CF$_3$ | — | CH$_2$CH$_2$(2-Py) | H | O | |
| 5-3 | 3,5-Cl$_2$Ph | CF$_3$ | — | CH$_2$CH$_2$COCH$_3$ | H | CH$_2$ | |
| 5-4 | 3,5-Cl$_2$Ph | CF$_3$ | — | CH$_2$CH$_2$OCH$_3$ | H | O | |
| 5-5 | 3,5-Cl$_2$Ph | CF$_3$ | — | COCH$_3$ | H | CH$_2$ | |
| 5-6 | 3,5-Cl$_2$Ph | CF$_3$ | — | COC$_2$H$_5$ | H | CH$_2$ | [173-177] |
| 5-7 | 3,5-Cl$_2$Ph | CF$_3$ | — | COC$_2$H$_5$ | H | O | amorphous |
| 5-8 | 3,5-Cl$_2$Ph | CF$_3$ | — | COPr-n | H | CH$_2$ | [152-155] |
| 5-9 | 3,5-Cl$_2$Ph | CF$_3$ | — | COCH$_2$CH$_2$OCH$_3$ | H | CH$_2$ | |
| 5-10 | 3,5-Cl$_2$Ph | CF$_3$ | — | COCH$_2$CH$_2$OCH$_3$ | H | O | [125-135] |
| 5-11 | 3,5-Cl$_2$Ph | CF$_3$ | — | COCH$_2$CH$_2$OCH$_2$CH$_3$ | H | O | |
| 5-12 | 3,5-Cl$_2$Ph | CF$_3$ | — | COCH$_2$CH(CH$_3$)OCH$_3$ | H | CH$_2$ | amorphous |
| 5-13 | 3,5-Cl$_2$Ph | CF$_3$ | — | COCH$_2$CH(CH$_3$)OCH$_2$CH$_3$ | H | O | |
| 5-14 | 3,5-Cl$_2$Ph | CF$_3$ | — | COCH$_2$CH(CH$_3$)OH | H | CH$_2$ | |
| 5-15 | 3,5-Cl$_2$Ph | CF$_3$ | — | COCH$_2$CH$_2$OCH$_2$CH=CH$_2$ | H | O | |
| 5-16 | 3,5-Cl$_2$Ph | CF$_3$ | — | COCH$_2$COCH$_3$ | H | CH$_2$ | |
| 5-17 | 3,5-Cl$_2$Ph | CF$_3$ | — | COCH$_2$(1,3-dioxolane-2-yl) | H | O | |
| 5-18 | 3,5-Cl$_2$Ph | CF$_3$ | — | COCH$_2$(2-methyl-1,3-dioxolane-2-yl) | H | CH$_2$ | |
| 5-19 | 3,5-Cl$_2$Ph | CF$_3$ | — | COCH$_2$(2-trifluoromethyl-1,3-dioxolane-2-yl) | H | O | |
| 5-20 | 3,5-Cl$_2$Ph | CF$_3$ | — | COCH$_2$(2-methyl-1,3-dioxane-2-yl) | H | CH$_2$ | |
| 5-21 | 3,5-Cl$_2$Ph | CF$_3$ | — | COCH$_2$CH$_2$(1,3-dioxolane-2-yl) | H | O | |

TABLE 5-continued

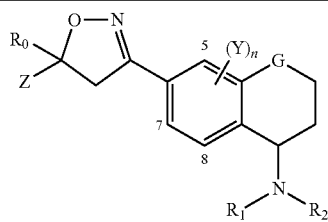

| Compound No. | Z | R₀ | (Y)n | R₁ | R₂ | G | Physical constant |
|---|---|---|---|---|---|---|---|
| 5-22 | 3,5-Cl₂Ph | CF₃ | — | COCH₂CH₂(2-methyl-1,3-dioxolane-2-yl) | H | CH₂ | |
| 5-23 | 3,5-Cl₂Ph | CF₃ | — | CO(tetrahydropyran-4-yl) | H | O | |
| 5-24 | 3,5-Cl₂Ph | CF₃ | — | CO(2,6-dimethyl-4H-pyran-4-one-3-yl) | H | CH₂ | |
| 5-25 | 3,5-Cl₂Ph | CF₃ | — | COCH₂CH₂CN | H | O | |
| 5-26 | 3,5-Cl₂Ph | CF₃ | — | COCH₂CH₂Ph | H | CH₂ | |
| 5-27 | 3,5-Cl₂Ph | CF₃ | — | COCH₂CH₂(1,2,4-triazole-1-yl) | H | O | |
| 5-28 | 3,5-Cl₂Ph | CF₃ | — | COCH₂CH₂(pyrazole-1-yl) | H | CH₂ | |
| 5-29 | 3-CF₃Ph | CF₃ | — | COC₂H₅ | H | O | |
| 5-30 | 3-CF₃Ph | CF₃ | — | COCH₂CH₂OCH₃ | H | CH₂ | |
| 5-31 | 3-CF₃Ph | CF₃ | — | COCH₂CH(CH₃)OCH₃ | H | O | |
| 5-32 | 3-CF₃Ph | CF₃ | — | COCH₂(2-methyl-1,3-dioxolane-2-yl) | H | CH₂ | |
| 5-33 | 3-CF₃Ph | CF₃ | — | COCH₂CH₂CN | H | O | |
| 5-34 | 3,5-Cl₂Ph | CF₃ | — | COPr-c | H | CH₂ | |
| 5-35 | 3,5-Cl₂Ph | CF₃ | — | COHex-c | H | O | |
| 5-36 | 2-F-3-CF₃Ph | CF₃ | — | COC₂H₅ | H | CH₂ | |
| 5-37 | 2-F-3-CF₃Ph | CF₃ | — | COCH₂CH₂OCH₃ | H | O | |
| 5-38 | 3-CF₃-4-ClPh | CF₃ | — | COC₂H₅ | H | CH₂ | |
| 5-39 | 3-CF₃-4-ClPh | CF₃ | — | COCH₂CH₂OCH₃ | H | O | |
| 5-40 | 3-CF₃-4-ClPh | CF₃ | — | COCH₂CH(CH₃)OCH₃ | H | CH₂ | |
| 5-41 | 3,5-Cl₂Ph | CF₃ | — | CSC₂H₅ | H | O | |
| 5-42 | 3,5-Cl₂Ph | CF₃ | — | 2-cyclohexenone-3-yl | H | CH₂ | |
| 5-43 | 3,5-Cl₂Ph | CF₃ | — | CH₂(4-methyl-1,3-dioxolene-2-one-5-yl) | H | O | |
| 5-44 | 3,5-Cl₂Ph | CF₃ | — | CH₂(4-methyl-1,3-dioxolene-2-one-5-yl) | CH₂(4-methyl-1,3-3-dioxolene-2-one-5-yl) | CH₂ | |
| 5-45 | 3,5-Cl₂Ph | CF₃ | — | COC₂H₅ | CH₃ | O | |
| 5-46 | 3,5-Cl₂Ph | CF₃ | — | H | H | CH₂ | amorphous |
| 5-47 | 3,5-Cl₂Ph | CF₃ | — | H | H | O | amorphous |
| 5-48 | 3-CF₃Ph | CF₃ | — | H | H | CH₂ | |
| 5-49 | 2-F-3-CF₃Ph | CF₃ | — | H | H | O | |
| 5-50 | 3-CF₃-4-ClPh | CF₃ | — | H | H | CH₂ | |
| 5-51 | 3,5-Cl₂Ph | CF₃ | 5-F | COC₂H₅ | H | O | |
| 5-52 | 3,5-Cl₂Ph | CF₃ | 5-Cl | COC₂H₅ | H | CH₂ | |
| 5-53 | 3,5-Cl₂Ph | CF₃ | 5-CH₃ | COC₂H₅ | H | O | |
| 5-54 | 3,5-Cl₂Ph | CF₃ | 5-CF₃ | COC₂H₅ | H | CH₂ | |
| 5-55 | 3,5-Cl₂Ph | CF₃ | 5-CH₂OCH₃ | COC₂H₅ | H | O | |
| 5-56 | 3,5-Cl₂Ph | CF₃ | 5-NO₂ | COC₂H₅ | H | CH₂ | |
| 5-57 | 3,5-Cl₂Ph | CF₃ | 5-OH | COC₂H₅ | H | O | |
| 5-58 | 3,5-Cl₂Ph | CF₃ | 5-OCH₃ | COC₂H₅ | H | CH₂ | |
| 5-59 | 3,5-Cl₂Ph | CF₃ | 5-OCF₃ | COC₂H₅ | H | O | |
| 5-60 | 3,5-Cl₂Ph | CF₃ | 5-OCH₂COCH₃ | COC₂H₅ | H | CH₂ | |
| 5-61 | 3,5-Cl₂Ph | CF₃ | 5-SH | COC₂H₅ | H | O | |
| 5-62 | 3,5-Cl₂Ph | CF₃ | 5-SCH₃ | COC₂H₅ | H | CH₂ | |
| 5-63 | 3,5-Cl₂Ph | CF₃ | 5-SCF₃ | COC₂H₅ | H | O | |
| 5-64 | 3,5-Cl₂Ph | CF₃ | 5-NH₂ | COC₂H₅ | H | CH₂ | |
| 5-65 | 3,5-Cl₂Ph | CF₃ | 5-NHCH₃ | COC₂H₅ | H | O | |
| 5-66 | 3,5-Cl₂Ph | CF₃ | 5-N(CH₃)₂ | COC₂H₅ | H | CH₂ | |
| 5-67 | 3,5-Cl₂Ph | CF₃ | 5-NHPh | COC₂H₅ | H | O | |
| 5-68 | 3,5-Cl₂Ph | CF₃ | 5-NHCOCH₃ | COC₂H₅ | H | CH₂ | |
| 5-69 | 3,5-Cl₂Ph | CF₃ | 5-NHCO₂C₂H₅ | COC₂H₅ | H | O | |
| 5-70 | 3,5-Cl₂Ph | CF₃ | 5-NHCO₂Bu-t | COC₂H₅ | H | CH₂ | |
| 5-71 | 3,5-Cl₂Ph | CF₃ | 5-NHCH₂Ph | COC₂H₅ | H | O | |
| 5-72 | 3,5-Cl₂Ph | CF₃ | 8-F | COC₂H₅ | H | CH₂ | |
| 5-73 | 3,5-Cl₂Ph | NO₂ | — | COC₂H₅ | H | O | |
| 5-74 | 3,5-Cl₂Ph | OH | — | COC₂H₅ | H | CH₂ | |
| 5-75 | 3,5-Cl₂Ph | OMe | — | COC₂H₅ | H | O | |
| 5-76 | 3,5-Cl₂Ph | OCF₃ | — | COC₂H₅ | H | CH₂ | |
| 5-77 | 3,5-Cl₂Ph | SH | — | COC₂H₅ | H | O | |
| 5-78 | 3,5-Cl₂Ph | SCF₃ | — | COC₂H₅ | H | CH₂ | |
| 5-79 | 3,5-Cl₂Ph | Cl | — | COC₂H₅ | H | O | |
| 5-80 | 3,5-Cl₂Ph | NH₂ | — | COC₂H₅ | H | CH₂ | |

TABLE 5-continued

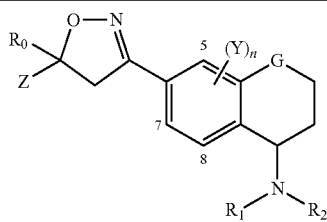

| Compound No. | Z | R₀ | (Y)n | R₁ | R₂ | G | Physical constant |
|---|---|---|---|---|---|---|---|
| 5-81 | 3,5-Cl₂Ph | NHCOCH₃ | — | COC₂H₅ | H | O | |
| 5-82 | 3,5-Cl₂Ph | NHCO₂C₂H₅ | — | COC₂H₅ | H | CH₂ | |
| 5-83 | 3,5-Cl₂Ph | CO₂C₂H₅ | — | COC₂H₅ | H | O | |
| 5-84 | 3,5-Cl₂Ph | SO₂CH₃ | — | COC₂H₅ | H | CH₂ | |
| 5-85 | 3,5-Cl₂Ph | SO₂CF₃ | — | COC₂H₅ | H | O | |
| 5-86 | 3,5-Cl₂Ph | Ph | — | COC₂H₅ | H | CH₂ | |
| 5-87 | 3,5-Cl₂Ph | COCH₃ | — | COC₂H₅ | H | O | |
| 5-88 | 3,5-Cl₂Ph | Cl | — | COC₂H₅ | H | CH₂ | |
| 5-89 | 3,5-Cl₂Ph | CF₂H | — | COC₂H₅ | H | O | |
| 5-90 | 3,5-Cl₂Ph | CCl₃ | — | COC₂H₅ | H | CH₂ | |
| 5-91 | 3,5-Cl₂Ph | CF₂Cl | — | COC₂H₅ | H | O | |
| 5-92 | CH₃CH=CH | CF₃ | — | COC₂H₅ | H | CH₂ | |
| 5-93 | Propargyl | CF₃ | — | COC₂H₅ | H | O | |
| 5-94 | CH₂=CHCH₂ | CF₃ | — | COC₂H₅ | H | CH₂ | |
| 5-95 | 2-butynyl | CF₃ | — | COC₂H₅ | H | O | |
| 5-96 | 3,5-Cl₂Ph | CF₃ | — | COC₂H₅ | -(nitrogen atom forms double bond with indane ring) | CH₂ | |
| 5-97 | 3,5-Cl₂Ph | CF₃ | — | =CHOCH₃ | | CH₂ | |
| 5-98 | 3,5-Cl₂Ph | CF₃ | — | =C(OCH₃)₂ | | O | |
| 5-99 | 3,5-Cl₂Ph | CF₃ | — | =CHNO₂ | | CH₂ | |
| 5-100 | 3,5-Cl₂Ph | CF₃ | — | =C(OCH₂CH₂O) | | O | |
| 5-101 | 3,5-Cl₂Ph | CF₃ | — | CONHCH₃ | H | CH₂ | |
| 5-102 | 3,5-Cl₂Ph | CF₃ | — | CONHC₂H₅ | H | O | |
| 5-103 | 3,5-Cl₂Ph | CF₃ | — | CONHPr-n | H | CH₂ | |
| 5-104 | 3,5-Cl₂Ph | CF₃ | — | CONHCH₂CH₂OCH₃ | H | O | |
| 5-105 | 3,5-Cl₂Ph | CF₃ | — | CONHCH₂CH₂OCH₂CH₃ | H | CH₂ | |
| 5-106 | 3,5-Cl₂Ph | CF₃ | — | CONHCH₂CH(CH₃)OCH₃ | H | O | |
| 5-107 | 3,5-Cl₂Ph | CF₃ | — | CON(CH₃)₂ | H | CH₂ | |
| 5-108 | 3,5-Cl₂Ph | CF₃ | — | CONHCH₂CN | H | O | |
| 5-109 | 3,5-Cl₂Ph | CF₃ | — | CONHCH₂CH₂Ph | H | CH₂ | |
| 5-110 | 3,5-Cl₂Ph | CF₃ | — | CONHCH₂CH₂(1,2,4-triazole-1-yl) | H | O | |
| 5-111 | 3,5-Cl₂Ph | CF₃ | — | CONHCH₂CH₂(pyrazole-1-yl) | H | CH₂ | |
| 5-112 | 3,5-Cl₂Ph | CF₃ | — | CONHOH | H | O | |
| 5-113 | 3,5-Cl₂Ph | CF₃ | — | CONHOCH₃ | H | CH₂ | |
| 5-114 | 3,5-Cl₂Ph | CF₃ | — | CONHPr-c | H | O | |
| 5-115 | 3,5-Cl₂Ph | CF₃ | — | CONHPh | H | CH₂ | |
| 5-116 | 3,5-Cl₂Ph | CF₃ | — | CSNHCH₃ | H | O | |
| 5-117 | 3,5-Cl₂Ph | CF₃ | — | CO₂C₂H₅ | H | CH₂ | |
| 5-118 | 3,5-Cl₂Ph | CF₃ | — | CO₂Pr-n | H | O | |
| 5-119 | 3,5-Cl₂Ph | CF₃ | — | CO₂Pr-c | H | CH₂ | |
| 5-120 | 3,5-Cl₂Ph | CF₃ | — | CO₂CH₂CH₂OCH₃ | H | O | |
| 5-121 | 3,5-Cl₂Ph | CF₃ | — | CO₂CH₂CH₂OCH₂CH₃ | H | CH₂ | |
| 5-122 | 3,5-Cl₂Ph | CF₃ | — | CO₂CH₂CH(CH₃)OCH₃ | H | O | |
| 5-123 | 3,5-Cl₂Ph | CF₃ | — | CO₂CH₂CH₂CN | H | CH₂ | |
| 5-124 | 3,5-Cl₂Ph | CF₃ | — | CO₂CH₂CH₂Ph | H | O | |
| 5-125 | 3,5-Cl₂Ph | CF₃ | — | CO₂CH₂CH₂(1,2,4-triazole-1-yl) | H | CH₂ | |
| 5-126 | 3,5-Cl₂Ph | CF₃ | — | CO₂CH₂CH₂(pyrazole-1-yl) | H | O | |
| 5-127 | 3,5-Cl₂Ph | CF₃ | — | CH₂CH₂CH₂CH₂ | | CH₂ | |
| 5-128 | 3,5-Cl₂Ph | CF₃ | — | C(=O)CH₂CH₂CH₂ | | O | |
| 5-129 | 3,5-Cl₂Ph | CF₃ | — | C(=O)CH₂CH₂C(=O) | | CH₂ | |
| 5-130 | 3,5-Cl₂Ph | CF₃ | — | phthaloyl | | O | |
| 5-131 | 2,4-diCF₃-pyrimidine-6-yl | CF₃ | — | COCH₂CH(CH₃)OCH₃ | H | CH₂ | |
| 5-132 | 2-CH₃S-4-CF₃-pyrimidine-6-yl | CF₃ | — | COCH₂CH(CH₃)OCH₃ | H | O | |
| 5-133 | 2-CH₃O-4-CF₃-pyrimidine-6-yl | CF₃ | — | COCH₂CH(CH₃)OCH₃ | H | CH₂ | |

TABLE 5-continued

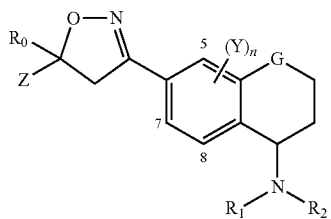

| Compound No. | Z | $R_0$ | (Y)n | $R_1$ | $R_2$ | G | Physical constant |
|---|---|---|---|---|---|---|---|
| 5-134 | 2-Cl-4-CF$_3$-pyrimidine-6-yl | CF$_3$ | — | COCH$_2$CH(CH$_3$)OCH$_3$ | H | O | |
| 5-135 | 2-Br-4-CF$_3$-pyrimidine-6-yl | CF$_3$ | — | COCH$_2$CH(CH$_3$)OCH$_3$ | H | CH$_2$ | |

TABLE 6

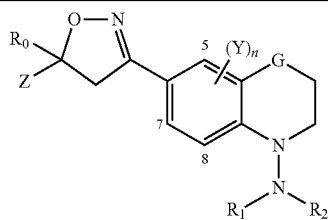

| Compound No. | Z | $R_0$ | (Y)n | $R_1$ | $R_2$ | G | Physical constant |
|---|---|---|---|---|---|---|---|
| 6-1 | 3,5-Cl$_2$Ph | CF$_3$ | — | n-Pr | H | CH$_2$ | |
| 6-2 | 3,5-Cl$_2$Ph | CF$_3$ | — | CH$_2$CH$_2$(2-Py) | H | O | |
| 6-3 | 3,5-Cl$_2$Ph | CF$_3$ | — | CH$_2$CH$_2$COCH$_3$ | H | CH$_2$ | |
| 6-4 | 3,5-Cl$_2$Ph | CF$_3$ | — | CH$_2$CH$_2$OCH$_3$ | H | O | |
| 6-5 | 3,5-Cl$_2$Ph | CF$_3$ | — | COCH$_3$ | H | CH$_2$ | |
| 6-6 | 3,5-Cl$_2$Ph | CF$_3$ | — | COC$_2$H$_5$ | H | CH$_2$ | |
| 6-7 | 3,5-Cl$_2$Ph | CF$_3$ | — | COC$_2$H$_5$ | H | O | |
| 6-8 | 3,5-Cl$_2$Ph | CF$_3$ | — | COPr-n | H | CH$_2$ | |
| 6-9 | 3,5-Cl$_2$Ph | CF$_3$ | — | COCH$_2$CH$_2$OCH$_3$ | H | CH$_2$ | |
| 6-10 | 3,5-Cl$_2$Ph | CF$_3$ | — | COCH$_2$CH$_2$OCH$_3$ | H | O | |
| 6-11 | 3,5-Cl$_2$Ph | CF$_3$ | — | COCH$_2$CH$_2$OCH$_2$CH$_3$ | H | O | |
| 6-12 | 3,5-Cl$_2$Ph | CF$_3$ | — | COCH$_2$CH(CH$_3$)OCH$_3$ | H | CH$_2$ | |
| 6-13 | 3,5-Cl$_2$Ph | CF$_3$ | — | COCH$_2$CH(CH$_3$)OCH$_2$CH$_3$ | H | O | |
| 6-14 | 3,5-Cl$_2$Ph | CF$_3$ | — | COCH$_2$CH(CH$_3$)OH | H | CH$_2$ | |
| 6-15 | 3,5-Cl$_2$Ph | CF$_3$ | — | COCH$_2$CH$_2$OCH=CH$_2$ | H | O | |
| 6-16 | 3,5-Cl$_2$Ph | CF$_3$ | — | COCH$_2$COCH$_3$ | H | CH$_2$ | |
| 6-17 | 3,5-Cl$_2$Ph | CF$_3$ | — | COCH$_2$(1,3-dioxolane-2-yl) | H | O | |
| 6-18 | 3,5-Cl$_2$Ph | CF$_3$ | — | COCH$_2$(2-methyl-1,3-dioxolane-2-yl) | H | CH$_2$ | |
| 6-19 | 3,5-Cl$_2$Ph | CF$_3$ | — | COCH$_2$(2-trifluoromethyl-1,3-dioxolane-2-yl) | H | O | |
| 6-20 | 3,5-Cl$_2$Ph | CF$_3$ | — | COCH$_2$(2-methyl-1,3-dioxolane-2-yl) | H | CH$_2$ | |
| 6-21 | 3,5-Cl$_2$Ph | CF$_3$ | — | COCH$_2$CH$_2$(1,3-dioxolane-2-yl) | H | O | |
| 6-22 | 3,5-Cl$_2$Ph | CF$_3$ | — | COCH$_2$CH$_2$(2-methyl-1,3-dioxolane-2-yl) | H | CH$_2$ | |
| 6-23 | 3,5-Cl$_2$Ph | CF$_3$ | — | CO(tetrahydropyran-4-yl) | H | O | |
| 6-24 | 3,5-Cl$_2$Ph | CF$_3$ | — | CO(2,6-dimethyl-4H-pyran-4-one-3-yl) | H | CH$_2$ | |
| 6-25 | 3,5-Cl$_2$Ph | CF$_3$ | — | COCH$_2$CH$_2$CN | H | O | |
| 6-26 | 3,5-Cl$_2$Ph | CF$_3$ | — | COCH$_2$CH$_2$Ph | H | CH$_2$ | |
| 6-27 | 3,5-Cl$_2$Ph | CF$_3$ | — | COCH$_2$CH$_2$(1,2,4-triazole-1-yl) | H | O | |
| 6-28 | 3,5-Cl$_2$Ph | CF$_3$ | — | COCH$_2$(pyrazole-1-yl) | H | CH$_2$ | |
| 6-29 | 3-CF$_3$Ph | CF$_3$ | — | COC$_2$H$_5$ | H | O | |
| 6-30 | 3-CF$_3$Ph | CF$_3$ | — | COCH$_2$CH$_2$OCH$_3$ | H | CH$_2$ | |
| 6-31 | 3-CF$_3$Ph | CF$_3$ | — | COCH$_2$CH(CH$_3$)OCH$_3$ | H | O | |
| 6-32 | 3-CF$_3$Ph | CF$_3$ | — | COCH$_2$(2-methyl-1,3-dioxolane-2-yl) | H | CH$_2$ | |
| 6-33 | 3-CF$_3$Ph | CF$_3$ | — | COCH$_2$CH$_2$CN | H | O | |
| 6-34 | 3,5-Cl$_2$Ph | CF$_3$ | — | COPr-c | H | CH$_2$ | |
| 6-35 | 3,5-Cl$_2$Ph | CF$_3$ | — | COHex-c | H | O | |

TABLE 6-continued

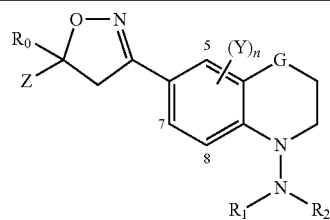

| Compound No. | Z | R₀ | (Y)n | R₁ | R₂ | G | Physical constant |
|---|---|---|---|---|---|---|---|
| 6-36 | 2-F-3-CF₃Ph | CF₃ | — | COC₂H₅ | H | CH₂ | |
| 6-37 | 2-F-3-CF₃Ph | CF₃ | — | COCH₂CH₂OCH₃ | H | O | |
| 6-38 | 3-CF₃-4-ClPh | CF₃ | — | COC₂H₅ | H | CH₂ | |
| 6-39 | 3-CF₃-4-ClPh | CF₃ | — | COCH₂CH₂OCH₃ | H | O | |
| 6-40 | 3-CF₃-4-ClPh | CF₃ | — | COCH₂CH(CH₃)OCH₃ | H | CH₂ | |
| 6-41 | 3,5-Cl₂Ph | CF₃ | — | CSC₂H₅ | H | O | |
| 6-42 | 3,5-Cl₂Ph | CF₃ | — | 2-cyclohexenone-3-yl | H | CH₂ | |
| 6-43 | 3,5-Cl₂Ph | CF₃ | — | CH₂(4-methyl-1,3-dioxolene-2-one-5-yl) | H | O | |
| 6-44 | 3,5-Cl₂Ph | CF₃ | — | CH₂(4-methyl-1,3-dioxolene-2-one-5-yl) | CH₂(4-methyl-1,3-dioxolene-2-one-5-yl) | CH₂ | |
| 6-45 | 3,5-Cl₂Ph | CF₃ | — | COC₂H₅ | CH₃ | O | |
| 6-46 | 3,5-Cl₂Ph | CF₃ | — | H | H | CH₂ | |
| 6-47 | 3,5-Cl₂Ph | CF₃ | — | H | H | O | |
| 6-48 | 3-CF₃Ph | CF₃ | — | H | H | CH₂ | |
| 6-49 | 2-F-3-CF₃Ph | CF₃ | — | H | H | O | |
| 6-50 | 3-CF₃-4-ClPh | CF₃ | — | H | H | CH₂ | |
| 6-51 | 3,5-Cl₂Ph | CF₃ | 5-F | COC₂H₅ | H | O | |
| 6-52 | 3,5-Cl₂Ph | CF₃ | 5-Cl | COC₂H₅ | H | CH₂ | |
| 6-53 | 3,5-Cl₂Ph | CF₃ | 5-CH3 | COC₂H₅ | H | O | |
| 6-54 | 3,5-Cl₂Ph | CF₃ | 5-CF3 | COC₂H₅ | H | CH₂ | |
| 6-55 | 3,5-Cl₂Ph | CF₃ | 5-CH₂OCH₃ | COC₂H₅ | H | O | |
| 6-56 | 3,5-Cl₂Ph | CF₃ | 5-NO₂ | COC₂H₅ | H | CH₂ | |
| 6-57 | 3,5-Cl₂Ph | CF₃ | 5-OH | COC₂H₅ | H | O | |
| 6-58 | 3,5-Cl₂Ph | CF₃ | 5-OCH₃ | COC₂H₅ | H | CH₂ | |
| 6-59 | 3,5-Cl₂Ph | CF₃ | 5-OCF₃ | COC₂H₅ | H | O | |
| 6-60 | 3,5-Cl₂Ph | CF₃ | 5-OCH₂COCH₃ | COC₂H₅ | H | CH₂ | |
| 6-61 | 3,5-Cl₂Ph | CF₃ | 5-SH | COC₂H₅ | H | O | |
| 6-62 | 3,5-Cl₂Ph | CF₃ | 5-SCH₃ | COC₂H₅ | H | CH₂ | |
| 6-63 | 3,5-Cl₂Ph | CF₃ | 5-SCF₃ | COC₂H₅ | H | O | |
| 6-64 | 3,5-Cl₂Ph | CF₃ | 5-NH₂ | COC₂H₅ | H | CH₂ | |
| 6-65 | 3,5-Cl₂Ph | CF₃ | 5-NHCH₃ | COC₂H₅ | H | O | |
| 6-66 | 3,5-Cl₂Ph | CF₃ | 5-N(CH3)₂ | COC₂H₅ | H | CH₂ | |
| 6-67 | 3,5-Cl₂Ph | CF₃ | 5-NHPh | COC₂H₅ | H | O | |
| 6-68 | 3,5-Cl₂Ph | CF₃ | 5-NHCOCH3 | COC₂H₅ | H | CH₂ | |
| 6-69 | 3,5-Cl₂Ph | CF₃ | 5-NHCO₂C₂H₅ | COC₂H₅ | H | O | |
| 6-70 | 3,5-Cl₂Ph | CF₃ | 5-NHCO₂Bu-t | COC₂H₅ | H | CH₂ | |
| 6-71 | 3,5-Cl₂Ph | CF₃ | 5-NHCH₂Ph | COC₂H₅ | H | O | |
| 6-72 | 3,5-Cl₂Ph | CF₃ | 8-F | COC₂H₅ | H | CH₂ | |
| 6-73 | 3,5-Cl₂Ph | NO₂ | — | COC₂H₅ | H | O | |
| 6-74 | 3,5-Cl₂Ph | OH | — | COC₂H₅ | H | CH₂ | |
| 6-75 | 3,5-Cl₂Ph | OMe | — | COC₂H₅ | H | O | |
| 6-76 | 3,5-Cl₂Ph | OCF₃ | — | COC₂H₅ | H | CH₂ | |
| 6-77 | 3,5-Cl₂Ph | SH | — | COC₂H₅ | H | O | |
| 6-78 | 3,5-Cl₂Ph | SCF₃ | — | COC₂H₅ | H | CH₂ | |
| 6-79 | 3,5-Cl₂Ph | Cl | — | COC₂H₅ | H | O | |
| 6-80 | 3,5-Cl₂Ph | NH₂ | — | COC₂H₅ | H | CH₂ | |
| 6-81 | 3,5-Cl₂Ph | NHCOCH₃ | — | COC₂H₅ | H | O | |
| 6-82 | 3,5-Cl₂Ph | NHCO₂C₂H₅ | — | COC₂H₅ | H | CH₂ | |
| 6-83 | 3,5-Cl₂Ph | CO₂C₂H₅ | — | COC₂H₅ | H | O | |
| 6-84 | 3,5-Cl₂Ph | SO₂CH₃ | — | COC₂H₅ | H | CH₂ | |
| 6-85 | 3,5-Cl₂Ph | SO₂CF₃ | — | COC₂H₅ | H | O | |
| 6-86 | 3,5-Cl₂Ph | Ph | — | COC₂H₅ | H | CH₂ | |
| 6-87 | 3,5-Cl₂Ph | COCH₃ | — | COC₂H₅ | H | O | |
| 6-88 | 3,5-Cl₂Ph | Cl | — | COC₂H₅ | H | CH₂ | |
| 6-89 | 3,5-Cl₂Ph | CF₂H | — | COC₂H₅ | H | O | |
| 6-90 | 3,5-Cl₂Ph | CCl₃ | — | COC₂H₅ | H | CH₂ | |
| 6-91 | 3,5-Cl₂Ph | CF₂Cl | — | COC₂H₅ | H | O | |
| 6-92 | CH₃CH=CH | CF₃ | — | COC₂H₅ | H | CH₂ | |
| 6-93 | Propargyl | CF₃ | — | COC₂H₅ | H | O | |
| 6-94 | CH₂=CHCH₂ | CF₃ | — | COC₂H₅ | H | CH₂ | |
| 6-95 | 2-butynyl | CF₃ | — | COC₂H₅ | H | O | |
| 6-96 | 3,5-Cl₂Ph | CF₃ | — | =CHOCH₃ | | CH₂ | |
| 6-97 | 3,5-Cl₂Ph | CF₃ | — | =C(OCH₃)₂ | | O | |

TABLE 6-continued

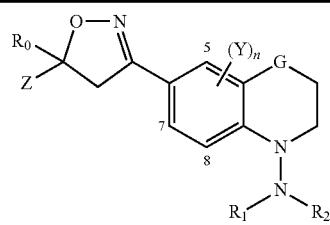

| Compound No. | Z | $R_0$ | (Y)n | $R_1$ | $R_2$ | G | Physical constant |
|---|---|---|---|---|---|---|---|
| 6-98 | 3,5-$Cl_2$Ph | $CF_3$ | — | =CHNO$_2$ | | $CH_2$ | |
| 6-99 | 3,5-$Cl_2$Ph | $CF_3$ | — | =C(OCH$_2$CH$_2$O) | | O | |
| 6-100 | 3,5-$Cl_2$Ph | $CF_3$ | — | CONHCH$_3$ | H | $CH_2$ | |
| 6-101 | 3,5-$Cl_2$Ph | $CF_3$ | — | CONHC$_2$H$_5$ | H | O | |
| 6-102 | 3,5-$Cl_2$Ph | $CF_3$ | — | CONHPr-n | H | $CH_2$ | |
| 6-103 | 3,5-$Cl_2$Ph | $CF_3$ | — | CONHCH$_2$CH$_2$OCH$_3$ | H | O | |
| 6-104 | 3,5-$Cl_2$Ph | $CF_3$ | — | CONHCH$_2$CH$_2$OCH$_2$CH$_3$ | H | $CH_2$ | |
| 6-105 | 3,5-$Cl_2$Ph | $CF_3$ | — | CONHCH$_2$CH(CH$_3$)OCH$_3$ | H | O | |
| 6-106 | 3,5-$Cl_2$Ph | $CF_3$ | — | CON(CH$_3$)$_2$ | H | $CH_2$ | |
| 6-107 | 3,5-$Cl_2$Ph | $CF_3$ | — | CONHCH$_2$CH$_2$CN | H | O | |
| 6-108 | 3,5-$Cl_2$Ph | $CF_3$ | — | CONHCH$_2$Ph | H | $CH_2$ | |
| 6-109 | 3,5-$Cl_2$Ph | $CF_3$ | — | CONHCH$_2$CH$_2$(1,2,4-triazole-1-yl) | H | O | |
| 6-110 | 3,5-$Cl_2$Ph | $CF_3$ | — | CONHCH$_2$CH$_2$(pyrazole-1-yl) | H | $CH_2$ | |
| 6-111 | 3,5-$Cl_2$Ph | $CF_3$ | — | CONHOH | H | O | |
| 6-112 | 3,5-$Cl_2$Ph | $CF_3$ | — | CONHOCH$_3$ | H | $CH_2$ | |
| 6-113 | 3,5-$Cl_2$Ph | $CF_3$ | — | CONHPr-c | H | O | |
| 6-114 | 3,5-$Cl_2$Ph | $CF_3$ | — | CONHPh | H | $CH_2$ | |
| 6-115 | 3,5-$Cl_2$Ph | $CF_3$ | — | CSNHCH$_3$ | H | O | |
| 6-116 | 3,5-$Cl_2$Ph | $CF_3$ | — | CO$_2$C$_2$H$_5$ | H | $CH_2$ | |
| 6-117 | 3,5-$Cl_2$Ph | $CF_3$ | — | CO$_2$Pr-n | H | O | |
| 6-118 | 3,5-$Cl_2$Ph | $CF_3$ | — | CO$_2$Pr-c | H | $CH_2$ | |
| 6-119 | 3,5-$Cl_2$Ph | $CF_3$ | — | CO$_2$CH$_2$CH$_2$OCH$_3$ | H | O | |
| 6-120 | 3,5-$Cl_2$Ph | $CF_3$ | — | CO$_2$CH$_2$CH$_2$OCH$_2$CH$_3$ | H | $CH_2$ | |
| 6-121 | 3,5-$Cl_2$Ph | $CF_3$ | — | CO$_2$CH$_2$CH(CH$_3$)OCH$_3$ | H | O | |
| 6-122 | 3,5-$Cl_2$Ph | $CF_3$ | — | CO$_2$CH$_2$CH$_2$CN | H | $CH_2$ | |
| 6-123 | 3,5-$Cl_2$Ph | $CF_3$ | — | CO$_2$CH$_2$CH$_2$Ph | H | O | |
| 6-124 | 3,5-$Cl_2$Ph | $CF_3$ | — | CO$_2$CH$_2$CH$_2$(1,2,4-triazole-1-yl) | H | $CH_2$ | |
| 6-125 | 3,5-$Cl_2$Ph | $CF_3$ | — | CO$_2$CH$_2$CH$_2$(pyrazole-1-yl) | H | O | |
| 6-126 | 3,5-$Cl_2$Ph | $CF_3$ | — | CH$_2$CH$_2$CH$_2$CH$_2$ | | $CH_2$ | |
| 6-127 | 3,5-$Cl_2$Ph | $CF_3$ | — | C(=O)CH$_2$CH$_2$CH$_2$CH$_2$ | | O | |
| 6-128 | 3,5-$Cl_2$Ph | $CF_3$ | — | C(=O)CH$_2$CH$_2$C(=O) | | $CH_2$ | |
| 6-129 | 3,5-$Cl_2$Ph | $CF_3$ | — | phthaloyl | | O | |
| 6-130 | 2,4-diCF$_3$-pyrimidine-6-yl | $CF_3$ | — | COCH$_2$CH(CH$_3$)OCH$_3$ | H | $CH_2$ | |
| 6-131 | 2-CH$_3$S-4-CF$_3$-pyrimidine-6-yl | $CF_3$ | — | COCH$_2$CH(CH$_3$)OCH$_3$ | H | O | |
| 6-132 | 2-CH$_3$O-4-CF$_3$-pyrimidine-6-yl | $CF_3$ | — | COCH$_2$CH(CH$_3$)OCH$_3$ | H | $CH_2$ | |
| 6-133 | 2-Cl-4-CF$_3$-pyrimidine-6-yl | $CF_3$ | — | COCH$_2$CH(CH$_3$)OCH$_3$ | H | O | |
| 6-134 | 2-Br-4-CF$_3$-pyrimidine-6-yl | $CF_3$ | — | COCH$_2$CH(CH$_3$)OCH$_3$ | H | $CH_2$ | |

TABLE 7

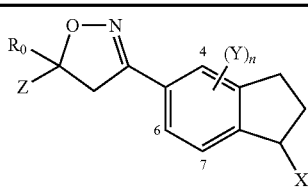

| Compound No. | Z | $R_0$ | (Y)n | X | Physical constant |
|---|---|---|---|---|---|
| 7-1 | 3,5-$Cl_2$Ph | $CF_3$ | — | — | |
| 7-2 | 3,5-$Cl_2$Ph | $CF_3$ | — | COCH$_3$ | |
| 7-3 | 3,5-$Cl_2$Ph | $CF_3$ | — | COC$_2$H$_5$ | |

TABLE 7-continued

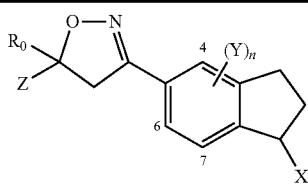

| Compound No. | Z | $R_0$ | (Y)n | X | Physical constant |
|---|---|---|---|---|---|
| 7-4 | 3,5-$Cl_2$Ph | $CF_3$ | — | COPr-n | |
| 7-5 | 3,5-$Cl_2$Ph | $CF_3$ | — | $COCH_2CH_2OCH_3$ | |
| 7-6 | 3,5-$Cl_2$Ph | $CF_3$ | — | $COCH_2CH_2OCH_2CH_3$ | |
| 7-7 | 3,5-$Cl_2$Ph | $CF_3$ | — | $COCH_2CH(CH_3)OCH_3$ | |
| 7-8 | 3,5-$Cl_2$Ph | $CF_3$ | — | $COCH_2CH(CH_3)OCH_2CH_3$ | |
| 7-9 | 3,5-$Cl_2$Ph | $CF_3$ | — | $COCH_2CH(CH_3)OH$ | |
| 7-10 | 3,5-$Cl_2$Ph | $CF_3$ | — | $COCH_2CH_2OCH_2CH=CH_2$ | |
| 7-11 | 3,5-$Cl_2$Ph | $CF_3$ | — | $COCH_2COCH_3$ | |
| 7-12 | 3,5-$Cl_2$Ph | $CF_3$ | — | $COCH_2$(1,3-dioxolane-2-yl) | |
| 7-13 | 3,5-$Cl_2$Ph | $CF_3$ | — | $COCH_2$(2-methyl-1,3-dioxolane-2-yl) | |
| 7-14 | 3,5-$Cl_2$Ph | $CF_3$ | — | $COCH_2$(2-trifluoromethyl-1,3-dioxolane-2-yl) | |
| 7-15 | 3,5-$Cl_2$Ph | $CF_3$ | — | $COCH_2$(2-methyl-1,3-dioxolane-2-yl) | |
| 7-16 | 3,5-$Cl_2$Ph | $CF_3$ | — | $COCH_2CH_2$(1,3-dioxolane-2-yl) | |
| 7-17 | 3,5-$Cl_2$Ph | $CF_3$ | — | $COCH_2CH_2$(2-methyl-1,3-dioxolane-2-yl) | |
| 7-18 | 3,5-$Cl_2$Ph | $CF_3$ | — | CO(tetrahydropyran-4-yl) | |
| 7-19 | 3,5-$Cl_2$Ph | $CF_3$ | — | CO(2,6-dimethyl-4H-pyran-4-one-3-yl) | |
| 7-20 | 3,5-$Cl_2$Ph | $CF_3$ | — | $COCH_2CH_2CN$ | |
| 7-21 | 3,5-$Cl_2$Ph | $CF_3$ | — | $COCH_2CH_2Ph$ | |
| 7-22 | 3,5-$Cl_2$Ph | $CF_3$ | — | $COCH_2CH_2$(1,2,4-triazole-1-yl) | |
| 7-23 | 3,5-$Cl_2$Ph | $CF_3$ | — | $COCH_2CH_2$(pyrazole-1-yl) | |
| 7-24 | 3-$CF_3$Ph | $CF_3$ | — | $COC_2H_5$ | |
| 7-25 | 3-$CF_3$Ph | $CF_3$ | — | $COCH_2CH_2OCH_3$ | |
| 7-26 | 3-$CF_3$Ph | $CF_3$ | — | $COCH_2CH(CH_3)OCH_3$ | |
| 7-27 | 3-$CF_3$Ph | $CF_3$ | — | $COCH_2$(2-methyl-1,3-dioxolane-2-yl) | |
| 7-28 | 3-$CF_3$Ph | $CF_3$ | — | $COCH_2CH_2CN$ | |
| 7-29 | 3,5-$Cl_2$Ph | $CF_3$ | — | COPr-c | |
| 7-30 | 3,5-$Cl_2$Ph | $CF_3$ | — | COHex-c | |
| 7-31 | 2-F-3-$CF_3$Ph | $CF_3$ | — | $COC_2H_5$ | |
| 7-32 | 2-F-3-$CF_3$Ph | $CF_3$ | — | $COCH_2CH_2OCH_3$ | |
| 7-33 | 3-$CF_3$-4-ClPh | $CF_3$ | — | $COC_2H_5$ | |
| 7-34 | 3-$CF_3$-4-ClPh | $CF_3$ | — | $COCH_2CH_2OCH_3$ | |
| 7-35 | 3-$CF_3$-4-ClPh | $CF_3$ | — | $COCH_2CH(CH_3)OCH_3$ | |
| 7-36 | 3,5-$Cl_2$Ph | $CF_3$ | — | $CSC_2H_5$ | |
| 7-37 | 3,5-$Cl_2$Ph | $CF_3$ | — | 2-cyclohexenone-3-yl | |
| 7-38 | 3,5-$Cl_2$Ph | $CF_3$ | — | H | |
| 7-39 | 3-$CF_3$Ph | $CF_3$ | — | H | |
| 7-40 | 2-F-3-$CF_3$Ph | $CF_3$ | — | H | |
| 7-41 | 2-$CF_3$-4-ClPh | $CF_3$ | — | H | |
| 7-42 | 3,5-$Cl_2$Ph | $CF_3$ | 4-F | $COC_2H_5$ | |
| 7-43 | 3,5-$Cl_2$Ph | $CF_3$ | 4-Cl | $COC_2H_5$ | |
| 7-44 | 3,5-$Cl_2$Ph | $CF_3$ | 4-$CH_3$ | $COC_2H_5$ | |
| 7-45 | 3,5-$Cl_2$Ph | $CF_3$ | 4-$CF_3$ | $COC_2H_5$ | |
| 7-46 | 3,5-$Cl_2$Ph | $CF_3$ | 4-$CH_2OCH_3$ | $COC_2H_5$ | |
| 7-47 | 3,5-$Cl_2$Ph | $CF_3$ | 4-$NO_2$ | $COC_2H_5$ | |
| 7-48 | 3,5-$Cl_2$Ph | $CF_3$ | 4-OH | $COC_2H_5$ | |
| 7-49 | 3,5-$Cl_2$Ph | $CF_3$ | 4-$OCH_3$ | $COC_2H_5$ | |
| 7-50 | 3,5-$Cl_2$Ph | $CF_3$ | 4-$OCF_3$ | $COC_2H_5$ | |
| 7-51 | 3,5-$Cl_2$Ph | $CF_3$ | 4-$OCH_2COCH_3$ | $COC_2H_5$ | |
| 7-52 | 3,5-$Cl_2$Ph | $CF_3$ | 4-SH | $COC_2H_5$ | |
| 7-53 | 3,5-$Cl_2$Ph | $CF_3$ | 4-$SCH_3$ | $COC_2H_5$ | |
| 7-54 | 3,5-$Cl_2$Ph | $CF_3$ | 4-$SCF_3$ | $COC_2H_5$ | |
| 7-55 | 3,5-$Cl_2$Ph | $CF_3$ | 4-$NH_2$ | $COC_2H_5$ | |
| 7-56 | 3,5-$Cl_2$Ph | $CF_3$ | 4-$NHCH_3$ | $COC_2H_5$ | |
| 7-57 | 3,5-$Cl_2$Ph | $CF_3$ | 4-$N(CH_3)_2$ | $COC_2H_5$ | |
| 7-58 | 3,5-$Cl_2$Ph | $CF_3$ | 4-NHPh | $COC_2H_5$ | |
| 7-59 | 3,5-$Cl_2$Ph | $CF_3$ | 4-NHCOCH3 | $COC_2H_5$ | |
| 7-60 | 3,5-$Cl_2$Ph | $CF_3$ | 4-$NHCO_2C_2H_5$ | $COC_2H_5$ | |
| 7-61 | 3,5-$Cl_2$Ph | $CF_3$ | 4-$NHCO_2$Bu-t | $COC_2H_5$ | |
| 7-62 | 3,5-$Cl_2$Ph | $CF_3$ | 4-$NHCH_2$Ph | $COC_2H_5$ | |
| 7-63 | 3,5-$Cl_2$Ph | $CF_3$ | 7-F | $COC_2H_5$ | |
| 7-64 | 3,5-$Cl_2$Ph | $NO_2$ | — | $COC_2H_5$ | |

TABLE 7-continued

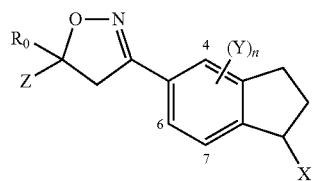

| Compound No. | Z | $R_0$ | (Y)n | X | Physical constant |
|---|---|---|---|---|---|
| 7-65 | 3,5-Cl$_2$Ph | OH | — | COC$_2$H$_5$ | |
| 7-66 | 3,5-Cl$_2$Ph | OMe | — | COC$_2$H$_5$ | |
| 7-67 | 3,5-Cl$_2$Ph | OCF$_3$ | — | COC$_2$H$_5$ | |
| 7-68 | 3,5-Cl$_2$Ph | SH | — | COC$_2$H$_5$ | |
| 7-69 | 3,5-Cl$_2$Ph | SCF$_3$ | — | COC$_2$H$_5$ | |
| 7-70 | 3,5-Cl$_2$Ph | Cl | — | COC$_2$H$_5$ | |
| 7-71 | 3,5-Cl$_2$Ph | NH$_2$ | — | COC$_2$H$_5$ | |
| 7-72 | 3,5-Cl$_2$Ph | NHCOCH$_3$ | — | COC$_2$H$_5$ | |
| 7-73 | 3,5-Cl$_2$Ph | NHCO$_2$C$_2$H$_5$ | — | COC$_2$H$_5$ | |
| 7-74 | 3,5-Cl$_2$Ph | CO$_2$C$_2$H$_5$ | — | COC$_2$H$_5$ | |
| 7-75 | 3,5-Cl$_2$Ph | SO$_2$CH$_3$ | — | COC$_2$H$_5$ | |
| 7-76 | 3,5-Cl$_2$Ph | SO$_2$CF$_3$ | — | COC$_2$H$_5$ | |
| 7-77 | 3,5-Cl$_2$Ph | Ph | — | COC$_2$H$_5$ | |
| 7-78 | 3,5-Cl$_2$Ph | COCH$_3$ | — | COC$_2$H$_5$ | |
| 7-79 | 3,5-Cl$_2$Ph | Cl | — | COC$_2$H$_5$ | |
| 7-80 | 3,5-Cl$_2$Ph | CF$_2$H | — | COC$_2$H$_5$ | |
| 7-81 | 3,5-Cl$_2$Ph | CCl$_3$ | — | COC$_2$H$_5$ | |
| 7-82 | 3,5-Cl$_2$Ph | CF$_2$Cl | — | COC$_2$H$_5$ | |
| 7-83 | CH$_3$CH=CH | CF$_3$ | — | COC$_2$H$_5$ | |
| 7-84 | Propargyl | CF$_3$ | — | COC$_2$H$_5$ | |
| 7-85 | CH$_2$=CHCH$_2$ | CF$_3$ | — | COC$_2$H$_5$ | |
| 7-86 | 2-butynyl | CF$_3$ | — | COC$_2$H$_5$ | |
| 7-87 | 3,5-Cl$_2$Ph | CF$_3$ | — | CONHCH$_3$ | |
| 7-88 | 3,5-Cl$_2$Ph | CF$_3$ | — | CONHC$_2$H$_5$ | |
| 7-89 | 3,5-Cl$_2$Ph | CF$_3$ | — | CONHPr-n | |
| 7-90 | 3,5-Cl$_2$Ph | CF$_3$ | — | CONHCH$_2$CH$_2$OCH$_3$ | |
| 7-91 | 3,5-Cl$_2$Ph | CF$_3$ | — | CONHCH$_2$CH$_2$OCH$_2$CH$_3$ | |
| 7-92 | 3,5-Cl$_2$Ph | CF$_3$ | — | CONHCH$_2$CH(CH$_3$)OCH$_3$ | |
| 7-93 | 3,5-Cl$_2$Ph | CF$_3$ | — | CON(CH$_3$)$_2$ | |
| 7-94 | 3,5-Cl$_2$Ph | CF$_3$ | — | CONHCH$_2$CH$_2$CN | |
| 7-95 | 3,5-Cl$_2$Ph | CF$_3$ | — | CONHCH$_2$CH$_2$Ph | |
| 7-96 | 3,5-Cl$_2$Ph | CF$_3$ | — | CONHCH$_2$CH$_2$(1,2,4-triazole-1-yl) | |
| 7-97 | 3,5-Cl$_2$Ph | CF$_3$ | — | CONHCH$_2$CH$_2$(pyrazole-1-yl) | |
| 7-98 | 3,5-Cl$_2$Ph | CF$_3$ | — | CONHOH | |
| 7-99 | 3,5-Cl$_2$Ph | CF$_3$ | — | CONHOCH$_3$ | |
| 7-100 | 3,5-Cl$_2$Ph | CF$_3$ | — | CONHPr-c | |
| 7-101 | 3,5-Cl$_2$Ph | CF$_3$ | — | CONHPh | |
| 7-102 | 3,5-Cl$_2$Ph | CF$_3$ | — | CSNHCH$_3$ | |
| 7-103 | 3,5-Cl$_2$Ph | CF$_3$ | — | CO$_2$C$_2$H$_5$ | |
| 7-104 | 3,5-Cl$_2$Ph | CF$_3$ | — | CO$_2$Pr-n | |
| 7-105 | 3,5-Cl$_2$Ph | CF$_3$ | — | CO$_2$Pr-c | |
| 7-106 | 3,5-Cl$_2$Ph | CF$_3$ | — | CO$_2$CH$_2$CH$_2$OCH$_3$ | |
| 7-107 | 3,5-Cl$_2$Ph | CF$_3$ | — | CO$_2$CH$_2$CH$_2$OCH$_2$CH$_3$ | |
| 7-108 | 3,5-Cl$_2$Ph | CF$_3$ | — | CO$_2$CH$_2$CH(CH$_3$)OCH$_3$ | |
| 7-109 | 3,5-Cl$_2$Ph | CF$_3$ | — | CO$_2$CH$_2$CH$_2$CN | |
| 7-110 | 3,5-Cl$_2$Ph | CF$_3$ | — | CO$_2$CH$_2$CH$_2$Ph | |
| 7-111 | 3,5-Cl$_2$Ph | CF$_3$ | — | CO$_2$CH$_2$CH$_2$(1,2,4-triazole-1-yl) | |
| 7-112 | 3,5-Cl$_2$Ph | CF$_3$ | — | CO$_2$CH$_2$CH$_2$(pyrazole-1-yl) | |
| 7-113 | 2,4-diCF$_3$-pyrimidine-6-yl | CF$_3$ | — | COCH$_2$CH(CH$_3$)OCH$_3$ | |
| 7-114 | 2-CH$_3$S-4-CF$_3$-pyrimidine-6-yl | CF$_3$ | — | COCH$_2$CH(CH$_3$)OCH$_3$ | |
| 7-115 | 2-CH$_3$O-4-CF$_3$-pyrimidine-6-yl | CF$_3$ | — | COCH$_2$CH(CH$_3$)OCH$_3$ | |
| 7-116 | 2-Cl-4-CF$_3$-pyrimidine-6-yl | CF$_3$ | — | COCH$_2$CH(CH$_3$)OCH$_3$ | |
| 7-117 | 2-Br-4-CF$_3$-pyrimidine-6-yl | CF$_3$ | — | COCH$_2$CH(CH$_3$)OCH$_3$ | |

TABLE 8

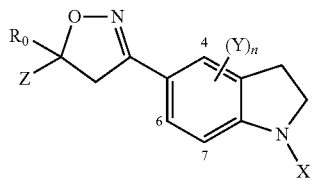

| Compound No. | Z | R₀ | (Y)n | X | Physical constant |
|---|---|---|---|---|---|
| 8-1 | 3,5-Cl₂Ph | CF₃ | — | — | amorphous |
| 8-2 | 3,5-Cl₂Ph | CF₃ | — | COCH₃ | |
| 8-3 | 3,5-Cl₂Ph | CF₃ | — | COC₂H₅ | |
| 8-4 | 3,5-Cl₂Ph | CF₃ | — | COPr-n | |
| 8-5 | 3,5-Cl₂Ph | CF₃ | — | COCH₂CH₂OCH₃ | |
| 8-6 | 3,5-Cl₂Ph | CF₃ | — | COCH₂CH₂OCH₂CH₃ | |
| 8-7 | 3,5-Cl₂Ph | CF₃ | — | COCH₂CH(CH₃)OCH₃ | |
| 8-8 | 3,5-Cl₂Ph | CF₃ | — | COCH₂CH(CH₃)OCH₂CH₃ | |
| 8-9 | 3,5-Cl₂Ph | CF₃ | — | COCH₂CH(CH₃)OH | |
| 8-10 | 3,5-Cl₂Ph | CF₃ | — | COCH₂CH₂OCH₂CH=CH₂ | |
| 8-11 | 3,5-Cl₂Ph | CF₃ | — | COCH₂COCH₃ | |
| 8-12 | 3,5-Cl₂Ph | CF₃ | — | COCH₂(1,3-dioxolane-2-yl) | |
| 8-13 | 3,5-Cl₂Ph | CF₃ | — | COCH₂(2-methyl-1,3-dioxolane-2-yl) | |
| 8-14 | 3,5-Cl₂Ph | CF₃ | — | COCH₂(2-trifluoromethyl-1,3-dioxolane-2-yl) | |
| 8-15 | 3,5-Cl₂Ph | CF₃ | — | COCH₂(2-methyl-1,3-dioxane-2-yl) | |
| 8-16 | 3,5-Cl₂Ph | CF₃ | — | COCH₂CH₂(1,3-dioxolane-2-yl) | |
| 8-17 | 3,5-Cl₂Ph | CF₃ | — | COCH₂CH₂(2-methyl-1,3-dioxolane-2-yl) | |
| 8-18 | 3,5-Cl₂Ph | CF₃ | — | CO(tetrahydropyran-4-yl) | |
| 8-19 | 3,5-Cl₂Ph | CF₃ | — | CO(2,6-dimethyl-4H-pyran-4-one-3-yl) | |
| 8-20 | 3,5-Cl₂Ph | CF₃ | — | COCH₂CH₂CN | |
| 8-21 | 3,5-Cl₂Ph | CF₃ | — | COCH₂CH₂Ph | |
| 8-22 | 3,5-Cl₂Ph | CF₃ | — | OCH₂CH₂(1,2,4-triazole-1-yl) | |
| 8-23 | 3,5-Cl₂Ph | CF₃ | — | COCH₂CH₂(pyrazole-1-yl) | |
| 8-24 | 3-CF₃Ph | CF₃ | — | COC₂H₅ | |
| 8-25 | 3-CF₃Ph | CF₃ | — | COCH₂CH₂OCH₃ | |
| 8-26 | 3-CF₃Ph | CF₃ | — | COCH₂CH(CH₃)OCH₃ | |
| 8-27 | 3-CF₃Ph | CF₃ | — | COCH₂(2-methyl-1,3-dioxolane-2-yl) | |
| 8-28 | 3-CF₃Ph | CF₃ | — | COCH₂CH₂CN | |
| 8-29 | 3,5-Cl₂Ph | CF₃ | — | COPr-c | |
| 8-30 | 3,5-Cl₂Ph | CF₃ | — | COHex-c | |
| 8-31 | 2-F-3-CF₃Ph | CF₃ | — | COC₂H₅ | |
| 8-32 | 2-F-3-CF₃Ph | CF₃ | — | COCH₂CH₂OCH₃ | |
| 8-33 | 3-CF₃-4-ClPh | CF₃ | — | COC₂H₅ | |
| 8-34 | 3-CF₃-4-ClPh | CF₃ | — | COCH₂CH₂OCH₃ | |
| 8-35 | 3-CF₃-4-ClPh | CF₃ | — | COCH₂CH(CH₃)OCH₃ | |
| 8-36 | 3,5-Cl₂Ph | CF₃ | — | CSC₂H₅ | |
| 8-37 | 3,5-Cl₂Ph | CF₃ | — | 2-cyclohexenone-3-yl | |
| 8-38 | 3,5-Cl₂Ph | CF₃ | — | H | |
| 8-39 | 3-CF₃Ph | CF₃ | — | H | |
| 8-40 | 2-F-3-CF₃Ph | CF₃ | — | H | |
| 8-41 | 3-CF₃-4-ClPh | CF₃ | — | H | |
| 8-42 | 3,5-Cl₂Ph | CF₃ | 4-F | COC₂H₅ | |
| 8-43 | 3,5-Cl₂Ph | CF₃ | 4-Cl | COC₂H₅ | |
| 8-44 | 3,5-Cl₂Ph | CF₃ | 4-CH₃ | COC₂H₅ | |
| 8-45 | 3,5-Cl₂Ph | CF₃ | 4-CF₃ | COC₂H₅ | |
| 8-46 | 3,5-Cl₂Ph | CF₃ | 4-CH₂OCH₃ | COC₂H₅ | |
| 8-47 | 3,5-Cl₂Ph | CF₃ | 4-NO₂ | COC₂H₅ | |
| 8-48 | 3,5-Cl₂Ph | CF₃ | 4-OH | COC₂H₅ | |
| 8-49 | 3,5-Cl₂Ph | CF₃ | 4-OCH₃ | COC₂H₅ | |
| 8-50 | 3,5-Cl₂Ph | CF₃ | 4-OCF₃ | COC₂H₅ | |
| 8-51 | 3,5-Cl₂Ph | CF₃ | 4-OCH₂COCH₃ | COC₂H₅ | |
| 8-52 | 3,5-Cl₂Ph | CF₃ | 4-SH | COC₂H₅ | |
| 8-53 | 3,5-Cl₂Ph | CF₃ | 4-SCH₃ | COC₂H₅ | |
| 8-54 | 3,5-Cl₂Ph | CF₃ | 4-SCF₃ | COC₂H₅ | |
| 8-55 | 3,5-Cl₂Ph | CF₃ | 4-NH₂ | COC₂H₅ | |
| 8-56 | 3,5-Cl₂Ph | CF₃ | 4-NHCH₃ | COC₂H₅ | |
| 8-57 | 3,5-Cl₂Ph | CF₃ | 4-N(CH₃)₂ | COC₂H₅ | |
| 8-58 | 3,5-Cl₂Ph | CF₃ | 4-NHPh | COC₂H₅ | |
| 8-59 | 3,5-Cl₂Ph | CF₃ | 4-NHCOCH₃ | COC₂H₅ | |
| 8-60 | 3,5-Cl₂Ph | CF₃ | 4-NHCO₂C₂H₅ | COC₂H₅ | |

TABLE 8-continued

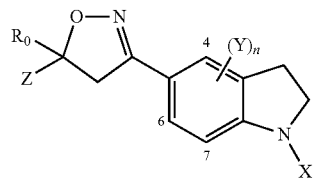

| Compound No. | Z | $R_0$ | (Y)n | X | Physical constant |
|---|---|---|---|---|---|
| 8-61 | 3,5-$Cl_2$Ph | $CF_3$ | 4-$NHCO_2$Bu-t | $COC_2H_5$ | |
| 8-62 | 3,5-$Cl_2$Ph | $CF_3$ | 4-$NHCH_2$Ph | $COC_2H_5$ | |
| 8-63 | 3,5-$Cl_2$Ph | $CF_3$ | 7-F | $COC_2H_5$ | |
| 8-64 | 3,5-$Cl_2$Ph | $NO_2$ | — | $COC_2H_5$ | |
| 8-65 | 3,5-$Cl_2$Ph | OH | — | $COC_2H_5$ | |
| 8-66 | 3,5-$Cl_2$Ph | OMe | — | $COC_2H_5$ | |
| 8-67 | 3,5-$Cl_2$Ph | $OCF_3$ | — | $COC_2H_5$ | |
| 8-68 | 3,5-$Cl_2$Ph | SH | — | $COC_2H_5$ | |
| 8-69 | 3,5-$Cl_2$Ph | $SCF_3$ | — | $COC_2H_5$ | |
| 8-70 | 3,5-$Cl_2$Ph | Cl | — | $COC_2H_5$ | |
| 8-71 | 3,5-$Cl_2$Ph | $NH_2$ | — | $COC_2H_5$ | |
| 8-72 | 3,5-$Cl_2$Ph | $NHCOCH_3$ | — | $COC_2H_5$ | |
| 8-73 | 3,5-$Cl_2$Ph | $NHCO_2C_2H_5$ | — | $COC_2H_5$ | |
| 8-74 | 3,5-$Cl_2$Ph | $CO_2C_2H_5$ | — | $COC_2H_5$ | |
| 8-75 | 3,5-$Cl_2$Ph | $SO_2CH_3$ | — | $COC_2H_5$ | |
| 8-76 | 3,5-$Cl_2$Ph | $SO_2CF_3$ | — | $COC_2H_5$ | |
| 8-77 | 3,5-$Cl_2$Ph | Ph | — | $COC_2H_5$ | |
| 8-78 | 3,5-$Cl_2$Ph | $COCH_3$ | — | $COC_2H_5$ | |
| 8-79 | 3,5-$Cl_2$Ph | Cl | — | $COC_2H_5$ | |
| 8-80 | 3,5-$Cl_2$Ph | $CF_2H$ | — | $COC_2H_5$ | |
| 8-81 | 3,5-$Cl_2$Ph | $CCl_3$ | — | $COC_2H_5$ | |
| 8-82 | 3,5-$Cl_2$Ph | $CF_2Cl$ | — | $COC_2H_5$ | |
| 8-83 | $CH_3CH=CH$ | $CF_3$ | — | $COC_2H_5$ | |
| 8-84 | Propargyl | $CF_3$ | — | $COC_2H_5$ | |
| 8-85 | $CH_2=CHCH_2$ | $CF_3$ | — | $COC_2H_5$ | |
| 8-86 | 2-butynyl | $CF_3$ | — | $COC_2H_5$ | |
| 8-87 | 3,5-$Cl_2$Ph | $CF_3$ | — | $CONHCH_3$ | |
| 8-88 | 3,5-$Cl_2$Ph | $CF_3$ | — | $CONHC_2H_5$ | [157-159] |
| 8-89 | 3,5-$Cl_2$Ph | $CF_3$ | — | CONHPr-n | |
| 8-90 | 3,5-$Cl_2$Ph | $CF_3$ | — | $CONHCH_2CH_2OCH_3$ | |
| 8-91 | 3,5-$Cl_2$Ph | $CF_3$ | — | $CONHCH_2CH_2OCH_2CH_3$ | |
| 8-92 | 3,5-$Cl_2$Ph | $CF_3$ | — | $CONHCH_2CH(CH_3)OCH_3$ | |
| 8-93 | 3,5-$Cl_2$Ph | $CF_3$ | — | $CON(CH_3)_2$ | |
| 8-94 | 3,5-$Cl_2$Ph | $CF_3$ | — | $CONHCH_2CH_2CN$ | |
| 8-95 | 3,5-$Cl_2$Ph | $CF_3$ | — | $CONHCH_2CH_2Ph$ | |
| 8-96 | 3,5-$Cl_2$Ph | $CF_3$ | — | $CONHCH_2CH_2$ (1,2,4-triazole-1-yl) | |
| 8-97 | 3,5-$Cl_2$Ph | $CF_3$ | — | $CONHCH_2CH_2$ (pyrazole-1-yl) | |
| 8-98 | 3,5-$Cl_2$Ph | $CF_3$ | — | CONHOH | |
| 8-99 | 3,5-$Cl_2$Ph | $CF_3$ | — | $CONHOCH_3$ | |
| 8-100 | 3,5-$Cl_2$Ph | $CF_3$ | — | CONHPr-c | |
| 8-101 | 3,5-$Cl_2$Ph | $CF_3$ | — | CONHPh | |
| 8-102 | 3,5-$Cl_2$Ph | $CF_3$ | — | $CSNHCH_3$ | |
| 8-103 | 3,5-$Cl_2$Ph | $CF_3$ | — | $CO_2C_2H_5$ | |
| 8-104 | 3,5-$Cl_2$Ph | $CF_3$ | — | $CO_2$Pr-n | |
| 8-105 | 3,5-$Cl_2$Ph | $CF_3$ | — | $CO_2$Pr-c | |
| 8-106 | 3,5-$Cl_2$Ph | $CF_3$ | — | $CO_2CH_2CH_2OCH_3$ | |
| 8-107 | 3,5-$Cl_2$Ph | $CF_3$ | — | $CO_2CH_2CH_2OCH_2CH_3$ | |
| 8-108 | 3,5-$Cl_2$Ph | $CF_3$ | — | $CO_2CH_2CH(CH_3)OCH_3$ | |
| 8-109 | 3,5-$Cl_2$Ph | $CF_3$ | — | $CO_2CH_2CH_2CN$ | |
| 8-110 | 3,5-$Cl_2$Ph | $CF_3$ | — | $CO_2CH_2CH_2Ph$ | |
| 8-111 | 3,5-$Cl_2$Ph | $CF_3$ | — | $CO_2CH_2CH_2$ (1,2,4-triazole-1-yl) | |
| 8-112 | 3,5-$Cl_2$Ph | $CF_3$ | — | $CO_2CH_2CH_2$ (pyrazole-1-yl) | |
| 8-113 | 2,4-di$CF_3$-pyrimidine-6-yl | $CF_3$ | — | $COCH_2CH(CH_3)OCH_3$ | |
| 8-114 | 2-$CH_3$S-4-$CF_3$-pyrimidine-6-yl | $CF_3$ | — | $COCH_2CH(CH_3)OCH_3$ | |
| 8-115 | 2-$CH_3$O-4-$CF_3$-pyrimidine-6-yl | $CF_3$ | — | $COCH_2CH(CH_3)OCH_3$ | |
| 8-116 | 2-Cl-4-$CF_3$-pyrimidine-6-yl | $CF_3$ | — | $COCH_2CH(CH_3)OCH_3$ | |
| 8-117 | 2-Br-$CF_3$-pyrimidine-6-yl | $CF_3$ | — | $COCH_2CH(CH_3)OCH_3$ | |

TABLE 9

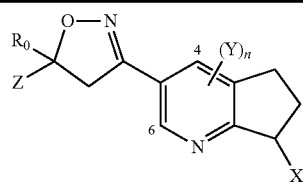

| Compound No. | Z | R₀ | (Y)n | X | Physical constant |
|---|---|---|---|---|---|
| 9-1 | 3,5-Cl₂Ph | CF₃ | — | COCH₃ | |
| 9-2 | 3,5-Cl₂Ph | CF₃ | — | COC₂H₅ | |
| 9-3 | 3,5-Cl₂Ph | CF₃ | — | COPr-n | |
| 9-4 | 3,5-Cl₂Ph | CF₃ | — | COCH₂CH₂OCH₃ | |
| 9-5 | 3,5-Cl₂Ph | CF₃ | — | COCH₂CH₂OCH₂CH₃ | |
| 9-6 | 3,5-Cl₂Ph | CF₃ | — | COCH₂CH(CH₃)OCH₃ | |
| 9-7 | 3,5-Cl₂Ph | CF₃ | — | COCH₂CH(CH₃)OCH₂CH₃ | |
| 9-8 | 3,5-Cl₂Ph | CF₃ | — | COCH₂CH(CH₃)OH | |
| 9-9 | 3,5-Cl₂Ph | CF₃ | — | COCH₂CH₂OCH₂CH=CH₂ | |
| 9-10 | 3,5-Cl₂Ph | CF₃ | — | COCH₂COCH₃ | |
| 9-11 | 3,5-Cl₂Ph | CF₃ | — | COCH₂(1,3-dioxolane-2-yl) | |
| 9-12 | 3,5-Cl₂Ph | CF₃ | — | COCH₂(2-methyl-1,3-dioxolane-2-yl) | |
| 9-13 | 3,5-Cl₂Ph | CF₃ | — | COCH₂(2-trifluoromethyl-1,3-dioxolane-2-yl) | |
| 9-14 | 3,5-Cl₂Ph | CF₃ | — | COCH₂(2-methyl-1,3-dioxane-2-yl) | |
| 9-15 | 3,5-Cl₂Ph | CF₃ | — | COCH₂CH₂ (1,3-dioxolane-2-yl) | |
| 9-16 | 3,5-Cl₂Ph | CF₃ | — | COCH₂CH₂ (2-methyl-1,3-dioxolane-2-yl) | |
| 9-17 | 3,5-Cl₂Ph | CF₃ | — | CO(tetrahydropyran-4-yl) | |
| 9-18 | 3,5-Cl₂Ph | CF₃ | — | CO(2,6-dimethyl-4H-pyran-4-one-3-yl) | |
| 9-19 | 3,5-Cl₂Ph | CF₃ | — | COCH₂CH₂CN | |
| 9-20 | 3,5-Cl₂Ph | CF₃ | — | COCH₂CH₂Ph | |
| 9-21 | 3,5-Cl₂Ph | CF₃ | — | COCH₂CH₂(1,2,4-triazole-1-yl) | |
| 9-22 | 3,5-Cl₂Ph | CF₃ | — | COCH₂CH₂(pyrazole-1-yl) | |
| 9-23 | 3-CF₃Ph | CF₃ | — | COC₂H₅ | |
| 9-24 | 3-CF₃Ph | CF₃ | — | COCH₂CH₂OCH₃ | |
| 9-25 | 3-CF₃Ph | CF₃ | — | COCH₂CH(CH₃)OCH₃ | |
| 9-26 | 3-CF₃Ph | CF₃ | — | COCH₂(2-methyl-1,3-dioxolane-2-yl) | |
| 9-27 | 3-CF₃Ph | CF₃ | — | COCH₂CH₂CN | |
| 9-28 | 3,5-Cl₂Ph | CF₃ | — | COPr-c | |
| 9-29 | 3,5-Cl₂Ph | CF₃ | — | COHex-c | |
| 9-30 | 2-F-3-CF₃Ph | CF₃ | — | COC₂H₅ | |
| 9-31 | 2-F-3-CF₃Ph | CF₃ | — | COCH₂CH₂OCH₃ | |
| 9-32 | 3-CF₃-4-ClPh | CF₃ | — | COC₂H₅ | |
| 9-33 | 3-CF₃-4-ClPh | CF₃ | — | COCH₂CH₂OCH₃ | |
| 9-34 | 3-CF₃-4-ClPh | CF₃ | — | COCH₂CH(CH₃)OCH₃ | |
| 9-35 | 3,5-Cl₂Ph | CF₃ | — | CSC₂H₅ | |
| 9-36 | 3,5-Cl₂Ph | CF₃ | — | 2-cyclohexenone-3-yl | |
| 9-37 | 3,5-Cl₂Ph | CF₃ | — | H | |
| 9-38 | 3-CF₃Ph | CF₃ | — | H | |
| 9-39 | 2-F-3-CF₃Ph | CF₃ | — | H | |
| 9-40 | 3-CF₃-4-ClPh | CF₃ | — | H | |
| 9-41 | 3,5-Cl₂Ph | CF₃ | 4-F | COC₂H₅ | |
| 9-42 | 3,5-Cl₂Ph | CF₃ | 4-Cl | COC₂H₅ | |
| 9-43 | 3,5-Cl₂Ph | CF₃ | 4-CH₃ | COC₂H₅ | |
| 9-44 | 3,5-Cl₂Ph | CF₃ | 4-CF₃ | COC₂H₅ | |
| 9-45 | 3,5-Cl₂Ph | CF₃ | 4-CH₂OCH₃ | COC₂H₅ | |
| 9-46 | 3,5-Cl₂Ph | CF₃ | 4-NO₂ | COC₂H₅ | |
| 9-47 | 3,5-Cl₂Ph | CF₃ | 4-OH | COC₂H₅ | |
| 9-48 | 3,5-Cl₂Ph | CF₃ | 4-OCH₃ | COC₂H₅ | |
| 9-49 | 3,5-Cl₂Ph | CF₃ | 4-OCF₃ | COC₂H₅ | |
| 9-50 | 3,5-Cl₂Ph | CF₃ | 4-OCH₂COCH₃ | COC₂H₅ | |
| 9-51 | 3,5-Cl₂Ph | CF₃ | 4-SH | COC₂H₅ | |
| 9-52 | 3,5-Cl₂Ph | CF₃ | 4-SCH₃ | COC₂H₅ | |
| 9-53 | 3,5-Cl₂Ph | CF₃ | 4-SCF₃ | COC₂H₅ | |
| 9-54 | 3,5-Cl₂Ph | CF₃ | 4-NH₂ | COC₂H₅ | |
| 9-55 | 3,5-Cl₂Ph | CF₃ | 4-NHCH₃ | COC₂H₅ | |
| 9-56 | 3,5-Cl₂Ph | CF₃ | 4-N(CH₃)₂ | COC₂H₅ | |
| 9-57 | 3,5-Cl₂Ph | CF₃ | 4-NHPh | COC₂H₅ | |
| 9-58 | 3,5-Cl₂Ph | CF₃ | 4-NHCOCH3 | COC₂H₅ | |
| 9-59 | 3,5-Cl₂Ph | CF₃ | 4-NHCO₂C₂H₅ | COC₂H₅ | |
| 9-60 | 3,5-Cl₂Ph | CF₃ | 4-NHCO₂Bu-t | COC₂H₅ | |
| 9-61 | 3,5-Cl₂Ph | CF₃ | 4-NHCH₂Ph | COC₂H₅ | |
| 9-62 | 3,5-Cl₂Ph | NO₂ | — | COC₂H₅ | |
| 9-63 | 3,5-Cl₂Ph | OH | — | COC₂H₅ | |

TABLE 9-continued

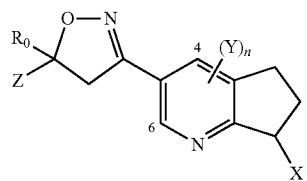

| Compound No. | Z | R₀ | (Y)n | X | Physical constant |
|---|---|---|---|---|---|
| 9-64 | 3,5-Cl₂Ph | OMe | — | COC₂H₅ | |
| 9-65 | 3,5-Cl₂Ph | OCF₃ | — | COC₂H₅ | |
| 9-66 | 3,5-Cl₂Ph | SH | — | COC₂H₅ | |
| 9-67 | 3,5-Cl₂Ph | SCF₃ | — | COC₂H₅ | |
| 9-68 | 3,5-Cl₂Ph | Cl | — | COC₂H₅ | |
| 9-69 | 3,5-Cl₂Ph | NH₂ | — | COC₂H₅ | |
| 9-70 | 3,5-Cl₂Ph | NHCOCH₃ | — | COC₂H₅ | |
| 9-71 | 3,5-Cl₂Ph | NHCO₂C₂H₅ | — | COC₂H₅ | |
| 9-72 | 3,5-Cl₂Ph | CO₂C₂H₅ | — | COC₂H₅ | |
| 9-73 | 3,5-Cl₂Ph | SO₂CH₃ | — | COC₂H₅ | |
| 9-74 | 3,5-Cl₂Ph | SO₂CF₃ | — | COC₂H₅ | |
| 9-75 | 3,5-Cl₂Ph | Ph | — | COC₂H₅ | |
| 9-76 | 3,5-Cl₂Ph | COCH₃ | — | COC₂H₅ | |
| 9-77 | 3,5-Cl₂Ph | Cl | — | COC₂H₅ | |
| 9-78 | 3,5-Cl₂Ph | CF₂H | — | COC₂H₅ | |
| 9-79 | 3,5-Cl₂Ph | CCl₃ | — | COC₂H₅ | |
| 9-80 | 3,5-Cl₂Ph | CF₂Cl | — | COC₂H₅ | |
| 9-81 | CH₃CH=CH | CF₃ | — | COC₂H₅ | |
| 9-82 | Propargyl | CF₃ | — | COC₂H₅ | |
| 9-83 | CH₂=CHCH₂ | CF₃ | — | COC₂H₅ | |
| 9-84 | 2-butynyl | CF₃ | — | COC₂H₅ | |
| 9-85 | 3,5-Cl₂Ph | CF₃ | — | CONHCH₃ | |
| 9-86 | 3,5-Cl₂Ph | CF₃ | — | CONHC₂H₅ | |
| 9-87 | 3,5-Cl₂Ph | CF₃ | — | CONHPr-n | |
| 9-88 | 3,5-Cl₂Ph | CF₃ | — | CONHCH₂CH₂OCH₃ | |
| 9-89 | 3,5-Cl₂Ph | CF₃ | — | CONHCH₂CH₂OCH₂CH₃ | |
| 9-90 | 3,5-Cl₂Ph | CF₃ | — | CONHCH₂CH(CH₃)OCH₃ | |
| 9-91 | 3,5-Cl₂Ph | CF₃ | — | CON(CH₃)₂ | |
| 9-92 | 3,5-Cl₂Ph | CF₃ | — | CONHCH₂CH₂CN | |
| 9-93 | 3,5-Cl₂Ph | CF₃ | — | CONHCH₂CH₂Ph | |
| 9-94 | 3,5-Cl₂Ph | CF₃ | — | CONHCH₂CH₂(1,2,4-triazole-1-yl) | |
| 9-95 | 3,5-Cl₂Ph | CF₃ | — | CONHCH₂CH₂(pyrazole-1-yl) | |
| 9-96 | 3,5-Cl₂Ph | CF₃ | — | CONHOH | |
| 9-97 | 3,5-Cl₂Ph | CF₃ | — | CONHOCH₃ | |
| 9-98 | 3,5-Cl₂Ph | CF₃ | — | CONHPr-c | |
| 9-99 | 3,5-Cl₂Ph | CF₃ | — | CONHPh | |
| 9-100 | 3,5-Cl₂Ph | CF₃ | — | CSNHCH₃ | |
| 9-101 | 3,5-Cl₂Ph | CF₃ | — | CO₂C₂H₅ | |
| 9-102 | 3,5-Cl₂Ph | CF₃ | — | CO₂Pr-n | |
| 9-103 | 3,5-Cl₂Ph | CF₃ | — | CO₂Pr-c | |
| 9-104 | 3,5-Cl₂Ph | CF₃ | — | CO₂CH₂CH₂OCH₃ | |
| 9-105 | 3,5-Cl₂Ph | CF₃ | — | CO₂CH₂CH₂OCH₂CH₃ | |
| 9-106 | 3,5-Cl₂Ph | CF₃ | — | CO₂CH₂CH(CH₃)OCH₃ | |
| 9-107 | 3,5-Cl₂Ph | CF₃ | — | CO₂CH₂CH₂CN | |
| 9-108 | 3,5-Cl₂Ph | CF₃ | — | CO₂CH₂CH₂Ph | |
| 9-109 | 3,5-Cl₂Ph | CF₃ | — | CO₂CH₂CH₂ (1,2,4-triazole-1-yl) | |
| 9-110 | 3,5-Cl₂Ph | CF₃ | — | CO₂CH₂CH₂ (pyrazole-1-yl) | |
| 9-111 | 2,4-diCF₃-pyrimidine-6-yl | CF₃ | — | COCH₂CH(CH₃)OCH₃ | |
| 9-112 | 2-CH₃S-4-CF₃-pyrimidine-6-yl | CF₃ | — | COCH₂CH(CH₃)OCH₃ | |
| 9-113 | 2-CH₃O-4-CF₃-pyrimidine-6-yl | CF₃ | — | COCH₂CH(CH₃)OCH₃ | |
| 9-114 | 2-Cl-4-CF₃-pyrimidine-6-yl | CF₃ | — | COCH₂CH(CH₃)OCH₃ | |
| 9-115 | 2-Br-4-CF₃-pyrimidine-6-yl | CF₃ | — | COCH₂CH(CH₃)OCH₃ | |

TABLE 10

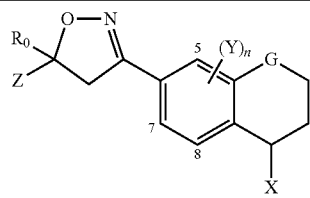

| Compound No. | Z | $R_0$ | (Y)n | X | Physical constant |
|---|---|---|---|---|---|
| 10-1 | 3,5-Cl$_2$Ph | CF$_3$ | — | — | |
| 10-2 | 3,5-Cl$_2$Ph | CF$_3$ | — | COCH$_3$ | |
| 10-3 | 3,5-Cl$_2$Ph | CF$_3$ | — | COC$_2$H$_5$ | |
| 10-4 | 3,5-Cl$_2$Ph | CF$_3$ | — | COPr-n | |
| 10-5 | 3,5-Cl$_2$Ph | CF$_3$ | — | COCH$_2$CH$_2$OCH$_3$ | |
| 10-6 | 3,5-Cl$_2$Ph | CF$_3$ | — | COCH$_2$CH$_2$OCH$_2$CH$_3$ | |
| 10-7 | 3,5-Cl$_2$Ph | CF$_3$ | — | COCH$_2$CH(CH$_3$)OCH$_3$ | |
| 10-8 | 3,5-Cl$_2$Ph | CF$_3$ | — | COCH$_2$CH(CH$_3$)OCH$_2$CH$_3$ | |
| 10-9 | 3,5-Cl$_2$Ph | CF$_3$ | — | COCH$_2$CH(CH$_3$)OH | |
| 10-10 | 3,5-Cl$_2$Ph | CF$_3$ | — | COCH$_2$CH$_2$OCH$_2$CH=CH$_2$ | |
| 10-11 | 3,5-Cl$_2$Ph | CF$_3$ | — | COCH$_2$COCH$_3$ | |
| 10-12 | 3,5-Cl$_2$Ph | CF$_3$ | — | COCH$_2$(1,3-dioxolane-2-yl) | |
| 10-13 | 3,5-Cl$_2$Ph | CF$_3$ | — | COCH$_2$ 2-methyl-1,3-dioxolane-2-yl) | |
| 10-14 | 3,5-Cl$_2$Ph | CF$_3$ | — | COCH$_2$(2-trifluoromethyl-1,3-dioxolane-2-yl) | |
| 10-15 | 3,5-Cl$_2$Ph | CF$_3$ | — | COCH$_2$(2-methyl-1,3-dioxane-2-yl) | |
| 10-16 | 3,5-Cl$_2$Ph | CF$_3$ | — | COCH$_2$CH$_2$ (1,3-dioxolane-2-yl) | |
| 10-17 | 3,5-Cl$_2$Ph | CF$_3$ | — | COCH$_2$CH$_2$(2-methyl-1,3-dioxolane-2-yl) | |
| 10-18 | 3,5-Cl$_2$Ph | CF$_3$ | — | CO(tetrahydropyran-4-yl) | |
| 10-19 | 3,5-Cl$_2$Ph | CF$_3$ | — | CO(2,6-dimethyl-4H-pyran-4-one-3-yl) | |
| 10-20 | 3,5-Cl$_2$Ph | CF$_3$ | — | COCH$_2$CH$_2$CN | |
| 10-21 | 3,5-Cl$_2$Ph | CF$_3$ | — | COCH$_2$CH$_2$Ph | |
| 10-22 | 3,5-Cl$_2$Ph | CF$_3$ | — | COCH$_2$CH$_2$(1,2,4-triazole-1-yl) | |
| 10-23 | 3,5-Cl$_2$Ph | CF$_3$ | — | COCH$_2$CH$_2$(pyrazole-1-yl) | |
| 10-24 | 3-CF$_3$Ph | CF$_3$ | — | COC$_2$H$_5$ | |
| 10-25 | 3-CF$_3$Ph | CF$_3$ | — | COCH$_2$CH$_2$OCH$_3$ | |
| 10-26 | 3-CF$_3$Ph | CF$_3$ | — | COCH$_2$CH(CH$_3$)OCH$_3$ | |
| 10-27 | 3-CF$_3$Ph | CF$_3$ | — | COCH$_2$(2-methyl-1,3-dioxolane-2-yl) | |
| 10-28 | 3-CF$_3$Ph | CF$_3$ | — | COCH$_2$CH$_2$CN | |
| 10-29 | 3,5-Cl$_2$Ph | CF$_3$ | — | COPr-c | |
| 10-30 | 3,5-Cl$_2$Ph | CF$_3$ | — | COHex-c | |
| 10-31 | 2-F-3-CF$_3$Ph | CF$_3$ | — | COC$_2$H$_5$ | |
| 10-32 | 2-F-3-CF$_3$Ph | CF$_3$ | — | COCH$_2$CH$_2$OCH$_3$ | |
| 10-33 | 3-CF$_3$-4-ClPh | CF$_3$ | — | COC$_2$H$_5$ | |
| 10-34 | 3-CF$_3$-4-ClPh | CF$_3$ | — | COCH$_2$CH$_2$OCH$_3$ | |
| 10-35 | 3-CF$_3$-4-ClPh | CF$_3$ | — | COCH$_2$CH(CH$_3$)OCH$_3$ | |
| 10-36 | 3,5-Cl$_2$Ph | CF$_3$ | — | CSC$_2$H$_5$ | |
| 10-37 | 3,5-Cl$_2$Ph | CF$_3$ | — | 2-cyclohexenone-3-yl | |
| 10-38 | 3,5-Cl$_2$Ph | CF$_3$ | — | H | |
| 10-39 | 3-CF$_3$Ph | CF$_3$ | — | H | |
| 10-40 | 2-F-3-CF$_3$Ph | CF$_3$ | — | H | |
| 10-41 | 3-CF$_3$-4-ClPh | CF$_3$ | — | H | |
| 10-42 | 3,5-Cl$_2$Ph | CF$_3$ | 4-F | COC$_2$H$_5$ | |
| 10-43 | 3,5-Cl$_2$Ph | CF$_3$ | 4-Cl | COC$_2$H$_5$ | |
| 10-44 | 3,5-Cl$_2$Ph | CF$_3$ | 4-CH$_3$ | COC$_2$H$_5$ | |
| 10-45 | 3,5-Cl$_2$Ph | CF$_3$ | 4-CF$_3$ | COC$_2$H$_5$ | |
| 10-46 | 3,5-Cl$_2$Ph | CF$_3$ | 4-CH$_2$OCH$_3$ | COC$_2$H$_5$ | |
| 10-47 | 3,5-Cl$_2$Ph | CF$_3$ | 4-NO$_2$ | COC$_2$H$_5$ | |
| 10-48 | 3,5-Cl$_2$Ph | CF$_3$ | 4-OH | COC$_2$H$_5$ | |
| 10-49 | 3,5-Cl$_2$Ph | CF$_3$ | 4-OCH$_3$ | COC$_2$H$_5$ | |
| 10-50 | 3,5-Cl$_2$Ph | CF$_3$ | 4-OCF$_3$ | COC$_2$H$_5$ | |
| 10-51 | 3,5-Cl$_2$Ph | CF$_3$ | 4-OCH$_2$COCH$_3$ | COC$_2$H$_5$ | |
| 10-52 | 3,5-Cl$_2$Ph | CF$_3$ | 4-SH | COC$_2$H$_5$ | |
| 10-53 | 3,5-Cl$_2$Ph | CF$_3$ | 4-SCH$_3$ | COC$_2$H$_5$ | |
| 10-54 | 3,5-Cl$_2$Ph | CF$_3$ | 4-SCF$_3$ | COC$_2$H$_5$ | |
| 10-55 | 3,5-Cl$_2$Ph | CF$_3$ | 4-NH$_2$ | COC$_2$H$_5$ | |
| 10-56 | 3,5-Cl$_2$Ph | CF$_3$ | 4-NHCH$_3$ | COC$_2$H$_5$ | |
| 10-57 | 3,5-Cl$_2$Ph | CF$_3$ | 4-N(CH$_3$)$_2$ | COC$_2$H$_5$ | |
| 10-58 | 3,5-Cl$_2$Ph | CF$_3$ | 4-NHPh | COC$_2$H$_5$ | |
| 10-59 | 3,5-Cl$_2$Ph | CF$_3$ | 4-NHCOCH$_3$ | COC$_2$H$_5$ | |
| 10-60 | 3,5-Cl$_2$Ph | CF$_3$ | 4-NHCO$_2$C$_2$H$_5$ | COC$_2$H$_5$ | |
| 10-61 | 3,5-Cl$_2$Ph | CF$_3$ | 4-NHCO$_2$Bu-t | COC$_2$H$_5$ | |

TABLE 10-continued

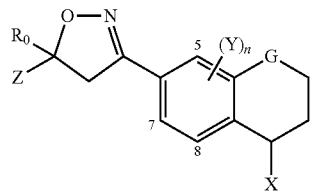

| Compound No. | Z | R₀ | (Y)n | X | Physical constant |
|---|---|---|---|---|---|
| 10-62 | 3,5-Cl₂Ph | CF₃ | 4-NHCH₂Ph | COC₂H₅ | |
| 10-63 | 3,5-Cl₂Ph | NO₂ | — | COC₂H₅ | |
| 10-64 | 3,5-Cl₂Ph | OH | — | COC₂H₅ | |
| 10-65 | 3,5-Cl₂Ph | OMe | — | COC₂H₅ | |
| 10-66 | 3,5-Cl₂Ph | OCF₃ | — | COC₂H₅ | |
| 10-67 | 3,5-Cl₂Ph | SH | — | COC₂H₅ | |
| 10-68 | 3,5-Cl₂Ph | SCF₃ | — | COC₂H₅ | |
| 10-69 | 3,5-Cl₂Ph | Cl | — | COC₂H₅ | |
| 10-70 | 3,5-Cl₂Ph | NH₂ | — | COC₂H₅ | |
| 10-71 | 3,5-Cl₂Ph | NHCOCH₃ | — | COC₂H₅ | |
| 10-72 | 3,5-Cl₂Ph | NHCO₂C₂H₅ | — | COC₂H₅ | |
| 10-73 | 3,5-Cl₂Ph | CO₂C₂H₅ | — | COC₂H₅ | |
| 10-74 | 3,5-Cl₂Ph | SO₂CH₃ | — | COC₂H₅ | |
| 10-75 | 3,5-Cl₂Ph | SO₂CF₃ | — | COC₂H₅ | |
| 10-76 | 3,5-Cl₂Ph | Ph | — | COC₂H₅ | |
| 10-77 | 3,5-Cl₂Ph | COCH₃ | — | COC₂H₅ | |
| 10-78 | 3,5-Cl₂Ph | Cl | — | COC₂H₅ | |
| 10-79 | 3,5-Cl₂Ph | CF₂H | — | COC₂H₅ | |
| 10-80 | 3,5-Cl₂Ph | CCl₃ | — | COC₂H₅ | |
| 10-81 | 3,5-Cl₂Ph | CF₂Cl | — | COC₂H₅ | |
| 10-82 | CH₃CH=CH | CF₃ | — | COC₂H₅ | |
| 10-83 | Propargyl | CF₃ | — | COC₂H₅ | |
| 10-84 | CH₂=CHCH₂ | CF₃ | — | COC₂H₅ | |
| 10-85 | 2-butynyl | CF₃ | — | COC₂H₅ | |
| 10-86 | 3,5-Cl₂Ph | CF₃ | — | CONHCH₃ | |
| 10-87 | 3,5-Cl₂Ph | CF₃ | — | CONHC₂H₅ | |
| 10-88 | 3,5-Cl₂Ph | CF₃ | — | CONHPr-n | |
| 10-89 | 3,5-Cl₂Ph | CF₃ | — | CONHCH₂CH₂OCH₃ | |
| 10-90 | 3,5-Cl₂Ph | CF₃ | — | CONHCH₂CH₂OCH₂CH₃ | |
| 10-91 | 3,5-Cl₂Ph | CF₃ | — | CONHCH₂CH(CH₃)OCH₃ | |
| 10-92 | 3,5-Cl₂Ph | CF₃ | — | CON(CH₃)₂ | |
| 10-93 | 3,5-Cl₂Ph | CF₃ | — | CONHCH₂CH₂CN | |
| 10-94 | 3,5-Cl₂Ph | CF₃ | — | CONHCH₂₂CH₂Ph | |
| 10-95 | 3,5-Cl₂Ph | CF₃ | — | CONHCH₂CH₂(1,2,4-triazole-1-yl) | |
| 10-96 | 3,5-Cl₂Ph | CF₃ | — | CONHCH₂CH₂(pyrazole-1-yl) | |
| 10-97 | 3,5-Cl₂Ph | CF₃ | — | CONHOH | |
| 10-98 | 3,5-Cl₂Ph | CF₃ | — | CONHOCH₃ | |
| 10-99 | 3,5-Cl₂Ph | CF₃ | — | CONHPr-c | |
| 10-100 | 3,5-Cl₂Ph | CF₃ | — | CONHPh | |
| 10-101 | 3,5-Cl₂Ph | CF₃ | — | CSNHCH₃ | |
| 10-102 | 3,5-Cl₂Ph | CF₃ | — | CO₂C₂H₅ | |
| 10-103 | 3,5-Cl₂Ph | CF₃ | — | CO₂Pr-n | |
| 10-104 | 3,5-Cl₂Ph | CF₃ | — | CO₂Pr-c | |
| 10-105 | 3,5-Cl₂Ph | CF₃ | — | CO₂CH₂CH₂OCH₃ | |
| 10-106 | 3,5-Cl₂Ph | CF₃ | — | CO₂CH₂CH₂OCH₂CH₃ | |
| 10-107 | 3,5-Cl₂Ph | CF₃ | — | CO₂CH₂CH(CH₃)OCH₃ | |
| 10-108 | 3,5-Cl₂Ph | CF₃ | — | CO₂CH₂CH₂CN | |
| 10-109 | 3,5-Cl₂Ph | CF₃ | — | CO₂CH₂CH₂Ph | |
| 10-110 | 3,5-Cl₂Ph | CF₃ | — | CO₂CH₂CH₂(1,2,4-triazole-1-yl) | |
| 10-111 | 3,5-Cl₂Ph | CF₃ | — | CO₂CH₂CH₂(pyrazole-1-yl) | |
| 10-112 | 2,4-diCF₃-pyrimidine-6-yl | CF₃ | — | COCH₂CH(CH₃)OCH₃ | |
| 10-113 | 2-CH₃S-4-CF₃-pyrimidine-6-yl | CF₃ | — | COCH₂CH(CH₃)OCH₃ | |
| 10-114 | 2-CH₃O-4-CF₃-pyrimidine-6-yl | CF₃ | — | COCH₂CH(CH₃)OCH₃ | |
| 10-115 | 2-Cl-4-CF₃-pyrimidine-6-yl | CF₃ | — | COCH₂CH(CH₃)OCH₃ | |
| 10-116 | 2-Br-4-CF₃-pyrimidine-6-yl | CF₃ | — | COCH₂CH(CH₃)OCH₃ | |

TABLE 11

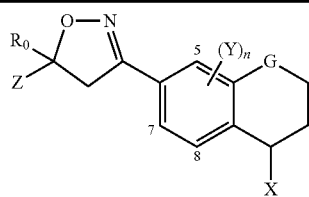

| Compound No. | Z | $R_0$ | (Y)n | X | G | Physical constant |
|---|---|---|---|---|---|---|
| 11-1 | 3,5-Cl$_2$Ph | CF$_3$ | — | — | CH$_2$ | |
| 11-2 | 3,5-Cl$_2$Ph | CF$_3$ | — | COCH$_3$ | O | |
| 11-3 | 3,5-Cl$_2$Ph | CF$_3$ | — | COC$_2$H$_5$ | CH$_2$ | |
| 11-4 | 3,5-Cl$_2$Ph | CF$_3$ | — | COPr-n | O | |
| 11-5 | 3,5-Cl$_2$Ph | CF$_3$ | — | COCH$_2$CH$_2$OCH$_3$ | CH$_2$ | |
| 11-6 | 3,5-Cl$_2$Ph | CF$_3$ | — | COCH$_2$CH$_2$OCH$_2$CH$_3$ | O | |
| 11-7 | 3,5-Cl$_2$Ph | CF$_3$ | — | COCH$_2$CH(CH$_3$)OCH$_3$ | CH$_2$ | |
| 11-8 | 3,5-Cl$_2$Ph | CF$_3$ | — | COCH$_2$CH(CH$_3$)OCH$_2$CH$_3$ | O | |
| 11-9 | 3,5-Cl$_2$Ph | CF$_3$ | — | COCH$_2$CH(CH$_3$)OH | CH$_2$ | |
| 11-10 | 3,5-Cl$_2$Ph | CF$_3$ | — | COCH$_2$CH$_2$OCH$_2$CH=CH$_2$ | O | |
| 11-11 | 3,5-Cl$_2$Ph | CF$_3$ | — | COCH$_2$COCH$_3$ | CH$_2$ | |
| 11-12 | 3,5-Cl$_2$Ph | CF$_3$ | — | COCH$_2$(1,3-dioxolane-2-yl) | O | |
| 11-13 | 3,5-Cl$_2$Ph | CF$_3$ | — | COCH$_2$(2-methyl-1,3-dioxolane-2-yl) | CH$_2$ | |
| 11-14 | 3,5-Cl$_2$Ph | CF$_3$ | — | COCH$_2$(2-trifluoromethyl-1,3-dioxolane-2-yl) | O | |
| 11-15 | 3,5-Cl$_2$Ph | CF$_3$ | — | COCH$_2$(2-methyl-1,3-dioxane-2-yl) | CH$_2$ | |
| 11-16 | 3,5-Cl$_2$Ph | CF$_3$ | — | COCH$_2$CH$_2$(1,3-dioxolane-2-yl) | O | |
| 11-17 | 3,5-Cl$_2$Ph | CF$_3$ | — | COCH$_2$CH$_2$(2-methyl-1,3-dioxolane-2-yl) | CH$_2$ | |
| 11-18 | 3,5-Cl$_2$Ph | CF$_3$ | — | CO(tetrahydropyran-4-yl) | O | |
| 11-19 | 3,5-Cl$_2$Ph | CF$_3$ | — | CO(2,6-dimethyl-4H-pyran-4-one-3-yl) | CH$_2$ | |
| 11-20 | 3,5-Cl$_2$Ph | CF$_3$ | — | COCH$_2$CH$_2$CN | O | |
| 11-21 | 3,5-Cl$_2$Ph | CF$_3$ | — | COCH$_2$CH$_2$Ph | CH$_2$ | |
| 11-22 | 3,5-Cl$_2$Ph | CF$_3$ | — | COCH$_2$CH$_2$(1,2,4-triazole-1-yl) | O | |
| 11-23 | 3,5-Cl$_2$Ph | CF$_3$ | — | COCH$_2$CH$_2$(pyrazole-1-yl) | CH$_2$ | |
| 11-24 | 3,5-Cl$_2$Ph | CF$_3$ | — | COC$_2$H$_5$ | O | |
| 11-25 | 3,5-Cl$_2$Ph | CF$_3$ | — | COCH$_2$CH$_2$OCH$_3$ | CH$_2$ | |
| 11-26 | 3,5-Cl$_2$Ph | CF$_3$ | — | COCH$_2$CH(CH$_3$)OCH$_3$ | O | |
| 11-27 | 3,5-Cl$_2$Ph | CF$_3$ | — | COCH$_2$(2-methyl-1,3-dioxolane-2-yl) | CH$_2$ | |
| 11-28 | 3,5-Cl$_2$Ph | CF$_3$ | — | COCH$_2$CH$_2$CN | O | |
| 11-29 | 3,5-Cl$_2$Ph | CF$_3$ | — | COPr-c | CH$_2$ | |
| 11-30 | 3,5-Cl$_2$Ph | CF$_3$ | — | COHex-c | O | |
| 11-31 | 2-F-3-CF$_3$Ph | CF$_3$ | — | COC$_2$H$_5$ | CH$_2$ | |
| 11-32 | 2-F-3-CF$_3$Ph | CF$_3$ | — | COCH$_2$CH$_2$OCH$_3$ | O | |
| 11-33 | 3-CF$_3$-4-ClPh | CF$_3$ | — | COC$_2$H$_5$ | CH$_2$ | |
| 11-34 | 3-CF$_3$-4-ClPh | CF$_3$ | — | COCH$_2$CH$_2$OCH$_3$ | O | |
| 11-35 | 3-CF$_3$-4-ClPh | CF$_3$ | — | COCH$_2$CH(CH$_3$)OCH$_3$ | CH$_2$ | |
| 11-36 | 3,5-Cl$_2$Ph | CF$_3$ | — | COC$_2$H$_5$ | O | |
| 11-37 | 3,5-Cl$_2$Ph | CF$_3$ | — | 2-cyclohexenone-3-yl | CH$_2$ | |
| 11-38 | 3,5-Cl$_2$Ph | CF$_3$ | — | H | O | |
| 11-39 | 3-CF$_3$Ph | CF$_3$ | — | H | CH$_2$ | |
| 11-40 | 2-F-3-CF$_3$Ph | CF$_3$ | — | H | O | |
| 11-41 | 3-CF$_3$-4-ClPh | CF$_3$ | — | H | CH$_2$ | |
| 11-42 | 3,5-Cl$_2$Ph | CF$_3$ | 5-F | COC$_2$H$_5$ | O | |
| 11-43 | 3,5-Cl$_2$Ph | CF$_3$ | 5-Cl | COC$_2$H$_5$ | CH$_2$ | |
| 11-44 | 3,5-Cl$_2$Ph | CF$_3$ | 5-CH$_3$ | COC$_2$H$_5$ | O | |
| 11-45 | 3,5-Cl$_2$Ph | CF$_3$ | 5-CF$_3$ | COC$_2$H$_5$ | CH$_2$ | |
| 11-46 | 3,5-Cl$_2$Ph | CF$_3$ | 5-CH$_2$OCH$_3$ | COC$_2$H$_5$ | O | |
| 11-47 | 3,5-Cl$_2$Ph | CF$_3$ | 5-NO$_2$ | COC$_2$H$_5$ | CH$_2$ | |
| 11-48 | 3,5-Cl$_2$Ph | CF$_3$ | 5-OH | COC$_2$H$_5$ | O | |
| 11-49 | 3,5-Cl$_2$Ph | CF$_3$ | 5-OCH$_3$ | COC$_2$H$_5$ | CH$_2$ | |
| 11-50 | 3,5-Cl$_2$Ph | CF$_3$ | 5-OCF$_3$ | COC$_2$H$_5$ | O | |
| 11-51 | 3,5-Cl$_2$Ph | CF$_3$ | 5-OCH$_2$COCH$_3$ | COC$_2$H$_5$ | CH$_2$ | |
| 11-52 | 3,5-Cl$_2$Ph | CF$_3$ | 5-SH | COC$_2$H$_5$ | O | |
| 11-53 | 3,5-Cl$_2$Ph | CF$_3$ | 5-SCH$_3$ | COC$_2$H$_5$ | CH$_2$ | |
| 11-54 | 3,5-Cl$_2$Ph | CF$_3$ | 5-SCF$_3$ | COC$_2$H$_5$ | O | |
| 11-55 | 3,5-Cl$_2$Ph | CF$_3$ | 5-NH$_2$ | COC$_2$H$_5$ | CH$_2$ | |
| 11-56 | 3,5-Cl$_2$Ph | CF$_3$ | 5-NHCH$_3$ | COC$_2$H$_5$ | O | |
| 11-57 | 3,5-Cl$_2$Ph | CF$_3$ | 5-NH(CH$_3$)$_2$ | COC$_2$H$_5$ | CH$_2$ | |
| 11-58 | 3,5-Cl$_2$Ph | CF$_3$ | 5-NHPh | COC$_2$H$_5$ | O | |
| 11-59 | 3,5-Cl$_2$Ph | CF$_3$ | 5-NHCOCH$_3$ | COC$_2$H$_5$ | CH$_2$ | |

TABLE 11-continued

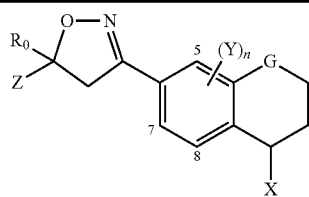

| Compound No. | Z | R₀ | (Y)n | X | G | Physical constant |
|---|---|---|---|---|---|---|
| 11-60 | 3,5-Cl₂Ph | CF₃ | 5-NHCO₂C₂H₅ | COC₂H₅ | O | |
| 11-61 | 3,5-Cl₂Ph | CF₃ | 5-NHCO₂Bu-t | COC₂H₅ | CH₂ | |
| 11-62 | 3,5-Cl₂Ph | CF₃ | 5-NHCH₂Ph | COC₂H₅ | O | |
| 11-63 | 3,5-Cl₂Ph | CF₃ | 8-F | COC₂H₅ | CH₂ | |
| 11-64 | 3,5-Cl₂Ph | NO₂ | — | COC₂H₅ | O | |
| 11-65 | 3,5-Cl₂Ph | OH | — | COC₂H₅ | CH₂ | |
| 11-66 | 3,5-Cl₂Ph | OMe | — | COC₂H₅ | O | |
| 11-67 | 3,5-Cl₂Ph | OCF₃ | — | COC₂H₅ | CH₂ | |
| 11-68 | 3,5-Cl₂Ph | SH | — | COC₂H₅ | O | |
| 11-69 | 3,5-Cl₂Ph | SCF₃ | — | COC₂H₅ | CH₂ | |
| 11-70 | 3,5-Cl₂Ph | Cl | — | COC₂H₅ | O | |
| 11-71 | 3,5-Cl₂Ph | NH₂ | — | COC₂H₅ | CH₂ | |
| 11-72 | 3,5-Cl₂Ph | NHCOCH₃ | — | COC₂H₅ | O | |
| 11-73 | 3,5-Cl₂Ph | NHCO₂C₂H₅ | — | COC₂H₅ | CH₂ | |
| 11-74 | 3,5-Cl₂Ph | CO₂C₂H₅ | — | COC₂H₅ | O | |
| 11-75 | 3,5-Cl₂Ph | SO₂CH₃ | — | COC₂H₅ | CH₂ | |
| 11-76 | 3,5-Cl₂Ph | SO₂CF₃ | — | COC₂H₅ | O | |
| 11-77 | 3,5-Cl₂Ph | Ph | — | COC₂H₅ | CH₂ | |
| 11-78 | 3,5-Cl₂Ph | COCH₃ | — | COC₂H₅ | O | |
| 11-79 | 3,5-Cl₂Ph | Cl | — | COC₂H₅ | CH₂ | |
| 11-80 | 3,5-Cl₂Ph | CF₂H | — | COC₂H₅ | O | |
| 11-81 | 3,5-Cl₂Ph | CCl₃ | — | COC₂H₅ | CH₂ | |
| 11-82 | 3,5-Cl₂Ph | CF₂Cl | — | COC₂H₅ | O | |
| 11-83 | CH₃CH=CH | CF₃ | — | COC₂H₅ | CH₂ | |
| 11-84 | Propargyl | CF₃ | — | COC₂H₅ | O | |
| 11-85 | CH₂=CHCH₂ | CF₃ | — | COC₂H₅ | CH₂ | |
| 11-86 | 2-butynyl | CF₃ | — | COC₂H₅ | O | |
| 11-87 | 3,5-Cl₂Ph | CF₃ | — | CONHCH₃ | CH₂ | |
| 11-88 | 3,5-Cl₂Ph | CF₃ | — | CONHC₂H₅ | O | |
| 11-89 | 3,5-Cl₂Ph | CF₃ | — | CONHPr-n | CH₂ | |
| 11-90 | 3,5-Cl₂Ph | CF₃ | — | CONHCH₂CH₂OCH₃ | O | |
| 11-91 | 3,5-Cl₂Ph | CF₃ | — | CONHCH₂CH₂OCH₂CH₃ | CH₂ | |
| 11-92 | 3,5-Cl₂Ph | CF₃ | — | CONHCH₂CH(CH₃)OCH₃ | O | |
| 11-93 | 3,5-Cl₂Ph | CF₃ | — | CON(CH₃)₂ | CH₂ | |
| 11-94 | 3,5-Cl₂Ph | CF₃ | — | CONHCH₂CH₂CN | O | |
| 11-95 | 3,5-Cl₂Ph | CF₃ | — | CONHCH₂CH₂Ph | CH₂ | |
| 11-96 | 3,5-Cl₂Ph | CF₃ | — | CONHCH₂CH₂ (1,2,4-triazole-1-yl) | O | |
| 11-97 | 3,5-Cl₂Ph | CF₃ | — | CONHCH₂CH₂ (pyrazole-1-yl) | CH₂ | |
| 11-98 | 3,5-Cl₂Ph | CF₃ | — | CONHOH | O | |
| 11-99 | 3,5-Cl₂Ph | CF₃ | — | CONHOCH₃ | CH₂ | |
| 11-100 | 3,5-Cl₂Ph | CF₃ | — | CONHPr-c | O | |
| 11-101 | 3,5-Cl₂Ph | CF₃ | — | CONHPh | CH₂ | |
| 11-102 | 3,5-Cl₂Ph | CF₃ | — | CSNHCH₃ | O | |
| 11-103 | 3,5-Cl₂Ph | CF₃ | — | CO₂C₂H₅ | CH₂ | |
| 11-104 | 3,5-Cl₂Ph | CF₃ | — | CO₂Pr-n | O | |
| 11-105 | 3,5-Cl₂Ph | CF₃ | — | CO₂Pr-c | CH₂ | |
| 11-106 | 3,5-Cl₂Ph | CF₃ | — | CO₂CH₂CH₂OCH₃ | O | |
| 11-107 | 3,5-Cl₂Ph | CF₃ | — | CO₂CH₂CH₂OCH₂CH₃ | CH₂ | |
| 11-108 | 3,5-Cl₂Ph | CF₃ | — | CO₂CH₂CH(CH₃)OCH₃ | O | |
| 11-109 | 3,5-Cl₂Ph | CF₃ | — | CO₂CH₂CH₂CN | CH₂ | |
| 11-110 | 3,5-Cl₂Ph | CF₃ | — | CO₂CH₂CH₂Ph | O | |
| 11-111 | 3,5-Cl₂Ph | CF₃ | — | CO₂CH₂CH₂ (1,2,4-triazole-1-yl) | CH₂ | |
| 11-112 | 3,5-Cl₂Ph | CF₃ | — | CO₂CH₂CH₂(pyrazole-1-yl) | O | |
| 11-113 | 2,4-diCF₃-pyrimidine-6-yl | CF₃ | — | COCH₂CH(CH₃)OCH₃ | CH₂ | |
| 11-114 | 2-CH₃S-4-CF₃-pyrimidine-6-yl | CF₃ | — | COCH₂CH(CH₃)OCH₃ | O | |
| 11-115 | 2-CH₃O-4-CF₃-pyrimidine-6-yl | CF₃ | — | COCH₂CH(CH₃)OCH₃ | CH₂ | |
| 11-116 | 2-Cl-4-CF₃-pyrimidine-6-yl | CF₃ | — | COCH₂CH(CH₃)OCH₃ | O | |
| 11-117 | 2-Br-4-CF₃-pyrimidine-6-yl | CF₃ | — | COCH₂CH(CH₃)OCH₃ | CH₂ | |

TABLE 12

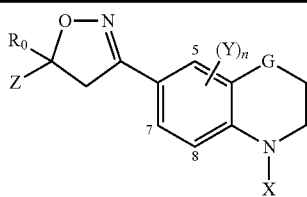

| Compound No. | Z | $R_0$ | (Y)n | X | G | Physical constant |
|---|---|---|---|---|---|---|
| 12-1 | 3,5-$Cl_2$Ph | $CF_3$ | — | — | $CH_2$ | |
| 12-2 | 3,5-$Cl_2$Ph | $CF_3$ | — | $COCH_3$ | O | |
| 12-3 | 3,5-$Cl_2$Ph | $CF_3$ | — | $COC_2H_5$ | $CH_2$ | |
| 12-4 | 3,5-$Cl_2$Ph | $CF_3$ | — | COPr-n | O | |
| 12-5 | 3,5-$Cl_2$Ph | $CF_3$ | — | $COCH_2CH_2OCH_3$ | $CH_2$ | |
| 12-6 | 3,5-$Cl_2$Ph | $CF_3$ | — | $COCH_2CH_2OCH_2CH_3$ | O | |
| 12-7 | 3,5-$Cl_2$Ph | $CF_3$ | — | $COCH_2CH(CH_3)OCH_3$ | $CH_2$ | |
| 12-8 | 3,5-$Cl_2$Ph | $CF_3$ | — | $COCH_2CH(CH_3)OCH_2CH_3$ | O | |
| 12-9 | 3,5-$Cl_2$Ph | $CF_3$ | — | $COCH_2CH(CH_3)OH$ | $CH_2$ | |
| 12-10 | 3,5-$Cl_2$Ph | $CF_3$ | — | $COCH_2CH_2OCH_2CH=CH_2$ | O | |
| 12-11 | 3,5-$Cl_2$Ph | $CF_3$ | — | $COCH_2COCH_3$ | $CH_2$ | |
| 12-12 | 3,5-$Cl_2$Ph | $CF_3$ | — | $COCH_2$(1,3-dioxolane-2-yl) | O | |
| 12-13 | 3,5-$Cl_2$Ph | $CF_3$ | — | $COCH_2$(2-methyl-1,3-dioxolane-2-yl) | $CH_2$ | |
| 12-14 | 3,5-$Cl_2$Ph | $CF_3$ | — | $COCH_2$(2-trifluoromethyl-1,3-dioxolane-2-yl) | O | |
| 12-15 | 3,5-$Cl_2$Ph | $CF_3$ | — | $COCH_2$(2-methyl-1,3-dioxane-2-yl) | $CH_2$ | |
| 12-16 | 3,5-$Cl_2$Ph | $CF_3$ | — | $COCH_2CH_2$(1,3-dioxolane-2-yl) | O | |
| 12-17 | 3,5-$Cl_2$Ph | $CF_3$ | — | $COCH_2CH_2$(2-methyl-1,3-dioxolane-2-yl) | $CH_2$ | |
| 12-18 | 3,5-$Cl_2$Ph | $CF_3$ | — | CO(tetrahydropyran-4-yl) | O | |
| 12-19 | 3,5-$Cl_2$Ph | $CF_3$ | — | CO(2,6-dimethyl-4H-pyran-4-one-3-yl) | $CH_2$ | |
| 12-20 | 3,5-$Cl_2$Ph | $CF_3$ | — | $COCH_2CH_2CN$ | O | |
| 12-21 | 3,5-$Cl_2$Ph | $CF_3$ | — | $COCH_2CH_2Ph$ | $CH_2$ | |
| 12-22 | 3,5-$Cl_2$Ph | $CF_3$ | — | $COCH_2CH_2$(1,2,4-triazole-1-yl) | O | |
| 12-23 | 3,5-$Cl_2$Ph | $CF_3$ | — | $COCH_2CH_2$(pyrazole-1-yl) | $CH_2$ | |
| 12-24 | 3,5-$Cl_2$Ph | $CF_3$ | — | $COC_2H_5$ | O | |
| 12-25 | 3,5-$Cl_2$Ph | $CF_3$ | — | $COCH_2CH_2OCH_3$ | $CH_2$ | |
| 12-26 | 3,5-$Cl_2$Ph | $CF_3$ | — | $COCH_2CH(CH_3)OCH_3$ | O | |
| 12-27 | 3,5-$Cl_2$Ph | $CF_3$ | — | $COCH_2$(2-methyl-1,3-dioxolane-2-yl) | $CH_2$ | |
| 12-28 | 3,5-$Cl_2$Ph | $CF_3$ | — | $COCH_2CH_2CN$ | O | |
| 12-29 | 3,5-$Cl_2$Ph | $CF_3$ | — | COPr-c | $CH_2$ | |
| 12-30 | 3,5-$Cl_2$Ph | $CF_3$ | — | COHex-c | O | |
| 12-31 | 2-F-3-$CF_3$Ph | $CF_3$ | — | $COC_2H_5$ | $CH_2$ | |
| 12-32 | 2-F-3-$CF_3$Ph | $CF_3$ | — | $COCH_2CH_2OCH_3$ | O | |
| 12-33 | 3-$CF_3$-4-ClPh | $CF_3$ | — | $COC_2H_5$ | $CH_2$ | |
| 12-34 | 3-$CF_3$-4-ClPh | $CF_3$ | — | $COCH_2CH_2OCH_3$ | O | |
| 12-35 | 3-$CF_3$-4-ClPh | $CF_3$ | — | $COCH_2CH(CH_3)OCH_3$ | $CH_2$ | |
| 12-36 | 3,5-$Cl_2$Ph | $CF_3$ | — | $CSC_2H_5$ | O | |
| 12-37 | 3,5-$Cl_2$Ph | $CF_3$ | — | 2-cyclohexenone-3-yl | $CH_2$ | |
| 12-38 | 3,5-$Cl_2$Ph | $CF_3$ | — | H | O | |
| 12-39 | 3-$CF_3$Ph | $CF_3$ | — | H | $CH_2$ | |
| 12-40 | 2-F-3-$CF_3$Ph | $CF_3$ | — | H | O | |
| 12-41 | 3-$CF_3$-4-ClPh | $CF_3$ | — | H | $CH_2$ | |
| 12-42 | 3,5-$Cl_2$Ph | $CF_3$ | 5-F | $COC_2H_5$ | O | |
| 12-43 | 3,5-$Cl_2$Ph | $CF_3$ | 5-Cl | $COC_2H_5$ | $CH_2$ | |
| 12-44 | 3,5-$Cl_2$Ph | $CF_3$ | 5-$CH_3$ | $COC_2H_5$ | O | |
| 12-45 | 3,5-$Cl_2$Ph | $CF_3$ | 5-$CF_3$ | $COC_2H_5$ | $CH_2$ | |
| 12-46 | 3,5-$Cl_2$Ph | $CF_3$ | 5-$CH_2OCH_3$ | $COC_2H_5$ | O | |
| 12-47 | 3,5-$Cl_2$Ph | $CF_3$ | 5-$NO_2$ | $COC_2H_5$ | $CH_2$ | |
| 12-48 | 3,5-$Cl_2$Ph | $CF_3$ | 5-OH | $COC_2H_5$ | O | |
| 12-49 | 3,5-$Cl_2$Ph | $CF_3$ | 5-$OCH_3$ | $COC_2H_5$ | $CH_2$ | |
| 12-50 | 3,5-$Cl_2$Ph | $CF_3$ | 5-$OCF_3$ | $COC_2H_5$ | O | |
| 12-51 | 3,5-$Cl_2$Ph | $CF_3$ | 5-$OCH_2COCH_3$ | $COC_2H_5$ | $CH_2$ | |
| 12-52 | 3,5-$Cl_2$Ph | $CF_3$ | 5-SH | $COC_2H_5$ | O | |
| 12-53 | 3,5-$Cl_2$Ph | $CF_3$ | 5-$SCH_3$ | $COC_2H_5$ | $CH_2$ | |
| 12-54 | 3,5-$Cl_2$Ph | $CF_3$ | 5-$SCF_3$ | $COC_2H_5$ | O | |
| 12-55 | 3,5-$Cl_2$Ph | $CF_3$ | 5-$NH_2$ | $COC_2H_5$ | $CH_2$ | |
| 12-56 | 3,5-$Cl_2$Ph | $CF_3$ | 5-$NHCH_3$ | $COC_2H_5$ | O | |
| 12-57 | 3,5-$Cl_2$Ph | $CF_3$ | 5-$NH(CH_3)_2$ | $COC_2H_5$ | $CH_2$ | |
| 12-58 | 3,5-$Cl_2$Ph | $CF_3$ | 5-NHPh | $COC_2H_5$ | O | |
| 12-59 | 3,5-$Cl_2$Ph | $CF_3$ | 5-$NHCOCH_3$ | $COC_2H_5$ | $CH_2$ | |

TABLE 12-continued

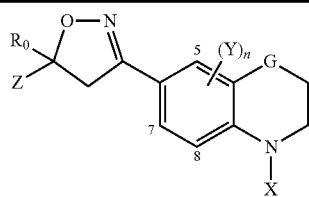

| Compound No. | Z | R₀ | (Y)n | X | G | Physical constant |
|---|---|---|---|---|---|---|
| 12-60 | 3,5-Cl₂Ph | CF₃ | 5-NHCO₂C₂H₅ | COC₂H₅ | O | |
| 12-61 | 3,5-Cl₂Ph | CF₃ | 5-NHCO₂Bu-t | COC₂H₅ | CH₂ | |
| 12-62 | 3,5-Cl₂Ph | CF₃ | 5-NHCH₂Ph | COC₂H₅ | O | |
| 12-63 | 3,5-Cl₂Ph | CF₃ | 8-F | COC₂H₅ | O | |
| 12-64 | 3,5-Cl₂Ph | NO₂ | — | COC₂H₅ | CH₂ | |
| 12-65 | 3,5-Cl₂Ph | OH | — | COC₂H₅ | O | |
| 12-66 | 3,5-Cl₂Ph | OMe | — | COC₂H₅ | CH₂ | |
| 12-67 | 3,5-Cl₂Ph | OCF₃ | — | COC₂H₅ | O | |
| 12-68 | 3,5-Cl₂Ph | SH | — | COC₂H₅ | CH₂ | |
| 12-69 | 3,5-Cl₂Ph | SCF₃ | — | COC₂H₅ | O | |
| 12-70 | 3,5-Cl₂Ph | Cl | — | COC₂H₅ | CH₂ | |
| 12-71 | 3,5-Cl₂Ph | NH₂ | — | COC₂H₅ | O | |
| 12-72 | 3,5-Cl₂Ph | NHCOCH₃ | — | COC₂H₅ | CH₂ | |
| 12-73 | 3,5-Cl₂Ph | NHCO₂C₂H₅ | — | COC₂H₅ | O | |
| 12-74 | 3,5-Cl₂Ph | CO₂C₂H₅ | — | COC₂H₅ | CH₂ | |
| 12-75 | 3,5-Cl₂Ph | SO₂CH₃ | — | COC₂H₅ | O | |
| 12-76 | 3,5-Cl₂Ph | SO₂CF₃ | — | COC₂H₅ | CH₂ | |
| 12-77 | 3,5-Cl₂Ph | Ph | — | COC₂H₅ | O | |
| 12-78 | 3,5-Cl₂Ph | COCH₃ | — | COC₂H₅ | CH₂ | |
| 12-79 | 3,5-Cl₂Ph | Cl | — | COC₂H₅ | O | |
| 12-80 | 3,5-Cl₂Ph | CF₂H | — | COC₂H₅ | CH₂ | |
| 12-81 | 3,5-Cl₂Ph | CCl₃ | — | COC₂H₅ | O | |
| 12-82 | 3,5-Cl₂Ph | CF₂Cl | — | COC₂H₅ | CH₂ | |
| 12-83 | CH₃CH=CH | CF₃ | — | COC₂H₅ | O | |
| 12-84 | Propargyl | CF₃ | — | COC₂H₅ | CH₂ | |
| 12-85 | CH₂=CHCH₂ | CF₃ | — | COC₂H₅ | O | |
| 12-86 | 2-butynyl | CF₃ | — | COC₂H₅ | CH₂ | |
| 12-87 | 3,5-Cl₂Ph | CF₃ | — | CONHCH₃ | O | |
| 12-88 | 3,5-Cl₂Ph | CF₃ | — | CONHC₂H₅ | CH₂ | |
| 12-89 | 3,5-Cl₂Ph | CF₃ | — | CONHPr-n | O | |
| 12-90 | 3,5-Cl₂Ph | CF₃ | — | CONHCH₂CH₂OCH₃ | CH₂ | |
| 12-91 | 3,5-Cl₂Ph | CF₃ | — | CONHCH₂CH₂OCH₂CH₃ | O | |
| 12-92 | 3,5-Cl₂Ph | CF₃ | — | CONHCH₂CH(CH₃)OCH₃ | CH₂ | |
| 12-93 | 3,5-Cl₂Ph | CF₃ | — | CON(CH₃)₂ | O | |
| 12-94 | 3,5-Cl₂Ph | CF₃ | — | CONHCH₂CH₂CN | CH₂ | |
| 12-95 | 3,5-Cl₂Ph | CF₃ | — | CONHCH₂CH₂Ph | O | |
| 12-96 | 3,5-Cl₂Ph | CF₃ | — | CONHCH₂CH₂(1,2,4-triazole-1-yl) | CH₂ | |
| 12-97 | 3,5-Cl₂Ph | CF₃ | — | CONHCH₂CH₂(pyrazole-1-yl) | O | |
| 12-98 | 3,5-Cl₂Ph | CF₃ | — | CONHOH | CH₂ | |
| 12-99 | 3,5-Cl₂Ph | CF₃ | — | CONHOCH₃ | O | |
| 12-100 | 3,5-Cl₂Ph | CF₃ | — | CONHPr-c | CH₂ | |
| 12-101 | 3,5-Cl₂Ph | CF₃ | — | CONHPh | O | |
| 12-102 | 3,5-Cl₂Ph | CF₃ | — | CSNHCH₃ | CH₂ | |
| 12-103 | 3,5-Cl₂Ph | CF₃ | — | CO₂C₂H₅ | O | |
| 12-104 | 3,5-Cl₂Ph | CF₃ | — | CO₂Pr-n | CH₂ | |
| 12-105 | 3,5-Cl₂Ph | CF₃ | — | CO₂Pr-c | O | |
| 12-106 | 3,5-Cl₂Ph | CF₃ | — | CO₂CH₂CH₂OCH₃ | CH₂ | |
| 12-107 | 3,5-Cl₂Ph | CF₃ | — | CO₂CH₂CH₂OCH₂CH₃ | O | |
| 12-108 | 3,5-Cl₂Ph | CF₃ | — | CO₂CH₂CH(CH₃)OCH₃ | CH₂ | |
| 12-109 | 3,5-Cl₂Ph | CF₃ | — | CO₂CH₂CH₂CN | O | |
| 12-110 | 3,5-Cl₂Ph | CF₃ | — | CO₂CH₂CH₂Ph | CH₂ | |
| 12-111 | 3,5-Cl₂Ph | CF₃ | — | CO₂CH₂CH₂(1,2,4-triazole-1-yl) | O | |
| 12-112 | 3,5-Cl₂Ph | CF₃ | — | CO₂CH₂CH₂(pyrazole-1-yl) | CH₂ | |
| 12-113 | 2,4-diCF₃-pyrimidine-6-yl | CF₃ | — | COCH₂CH(CH₃)OCH₃ | O | |
| 12-114 | 2-CH₃S-4-CF₃-pyrimidine-6-yl | CF₃ | — | COCH₂CH(CH₃)OCH₃ | CH₂ | |
| 12-115 | 2-CH₃O-4-CF₃-pyrimidine-6-yl | CF₃ | — | COCH₂CH(CH₃)OCH₃ | O | |
| 12-116 | 2-Cl-4-CF₃-pyrimidine-6-yl | CF₃ | — | COCH₂CH(CH₃)OCH₃ | CH₂ | |
| 12-117 | 2-Br-4-CF₃-pyrimidine-6-yl | CF₃ | — | COCH₂CH(CH₃)OCH₃ | O | |

TABLE 13

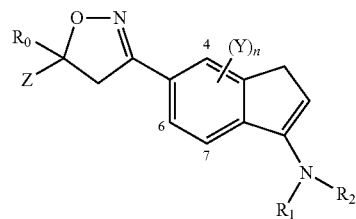

| Compound No. | Z | R₀ | (Y)n | R₁ | R₂ | Physical constant |
|---|---|---|---|---|---|---|
| 13-1 | 3,5-Cl₂Ph | CF₃ | — | n-Pr | H | |
| 13-2 | 3,5-Cl₂Ph | CF₃ | — | CH₂CH₂(2-Py) | H | |
| 13-3 | 3,5-Cl₂Ph | CF₃ | — | CH₂CH₂COCH₃ | H | |
| 13-4 | 3,5-Cl₂Ph | CF₃ | — | CH₂CH₂OCH₃ | H | |
| 13-5 | 3,5-Cl₂Ph | CF₃ | — | COCH₃ | H | [229-231] |
| 13-6 | 3,5-Cl₂Ph | CF₃ | — | COC₂H₅ | H | [213-216] |
| 13-7 | 3,5-Cl₂Ph | CF₃ | — | COPr-n | H | |
| 13-8 | 3,5-Cl₂Ph | CF₃ | — | COCH₂CH₂OCH₃ | H | |
| 13-9 | 3,5-Cl₂Ph | CF₃ | — | COCH₂CH₂OCH₂CH₃ | H | |
| 13-10 | 3,5-Cl₂Ph | CF₃ | — | COCH₂CH(CH₃)OCH₃ | H | |
| 13-11 | 3,5-Cl₂Ph | CF₃ | — | COCH₂CH(CH₃)OCH₂CH₃ | H | |
| 13-12 | 3,5-Cl₂Ph | CF₃ | — | COCH₂CH(CH₃)OH | H | |
| 13-13 | 3,5-Cl₂Ph | CF₃ | — | COCH₂CH₂OCH₂CH=CH₂ | H | |
| 13-14 | 3,5-Cl₂Ph | CF₃ | — | COCH₂COCH₃ | H | |
| 13-15 | 3,5-Cl₂Ph | CF₃ | — | COCH₂(1,3-dioxolane-2-yl) | H | |
| 13-16 | 3,5-Cl₂Ph | CF₃ | — | COCH₂(2-methyl-1,3-dioxolane-2-yl) | H | |
| 13-17 | 3,5-Cl₂Ph | CF₃ | — | COCH₂(2-trifluoromethyl-1,3-dioxolane-2-yl) | H | |
| 13-18 | 3,5-Cl₂Ph | CF₃ | — | COCH₂(2-methyl-1,3-dioxane-2-yl) | H | |
| 13-19 | 3,5-Cl₂Ph | CF₃ | — | COCH₂CH₂(1,3-dioxolane-2-yl) | H | |
| 13-20 | 3,5-Cl₂Ph | CF₃ | — | COCH₂CH₂(2-methyl-1,3-dioxolane-2-yl) | H | |
| 13-21 | 3,5-Cl₂Ph | CF₃ | — | CO(tetrahydropyran-4-yl) | H | |
| 13-22 | 3,5-Cl₂Ph | CF₃ | — | CO(2,6-dimethyl-4H-pyran-4-one-3-yl) | H | |
| 13-23 | 3,5-Cl₂Ph | CF₃ | — | COCH₂CH₂CN | H | |
| 13-24 | 3,5-Cl₂Ph | CF₃ | — | COCH₂CH₂Ph | H | |
| 13-25 | 3,5-Cl₂Ph | CF₃ | — | COCH₂CH₂(1,2,4-triazole-1-yl) | H | |
| 13-26 | 3,5-Cl₂Ph | CF₃ | — | COCH₂CH₂(pyrazole-1-yl) | H | |
| 13-27 | 3,5-Cl₂Ph | CF₃ | — | COC₂H₅ | H | |
| 13-28 | 3,5-Cl₂Ph | CF₃ | — | COCH₂CH₂CH₂OCH₃ | H | |
| 13-29 | 3,5-Cl₂Ph | CF₃ | — | COCH₂CH(CH₃)OCH₃ | H | |
| 13-30 | 3,5-Cl₂Ph | CF₃ | — | COCH₂(2-methyl-1,3-dioxolane-2-yl) | H | |
| 13-31 | 3-CF₃Ph | CF₃ | — | COCH₂CH₂CN | H | |
| 13-32 | 3,5-Cl₂Ph | CF₃ | — | COPr-c | H | |
| 13-33 | 3,5-Cl₂Ph | CF₃ | — | COHex-c | H | |
| 13-34 | 2-F-3-CF₃Ph | CF₃ | — | COC₂H₅ | H | |
| 13-35 | 2-F-3-CF₃Ph | CF₃ | — | COCH₂CH₂OCH₃ | H | |
| 13-36 | 3-CF₃-4-ClPh | CF₃ | — | COC₂H₅ | H | |
| 13-37 | 3-CF₃-4-ClPh | CF₃ | — | COCH₂CH₂OCH₃ | H | |
| 13-38 | 3-CF₃-4-ClPh | CF₃ | — | COCH₂CH(CH₃)OCH₃ | H | |
| 13-39 | 3,5-Cl₂Ph | CF₃ | — | CSC₂H₅ | H | |
| 13-40 | 3,5-Cl₂Ph | CF₃ | — | 2-cyclohexenone-3-yl | H | |
| 13-41 | 3,5-Cl₂Ph | CF₃ | — | CH₂(4-methyl-1,3-dioxolene-2-one-5-yl) | H | |
| 13-42 | 3,5-Cl₂Ph | CF₃ | — | CH₂(4-methyl-1,3-dioxolene-2-one-5-yl) | CH₂(4-methyl-1,3-dioxolene-2-one-5-yl) | |
| 13-43 | 3,5-Cl₂Ph | CF₃ | — | COC₂H₅ | CH₃ | |
| 13-44 | 3,5-Cl₂Ph | CF₃ | — | H | H | |
| 13-45 | 3-CF₃Ph | CF₃ | — | H | H | |
| 13-46 | 2-F-3-CF₃Ph | CF₃ | — | H | H | |
| 13-47 | 3-CF₃-4-ClPh | CF₃ | — | H | H | |
| 13-48 | 3,5-Cl₂Ph | CF₃ | 4-F | COC₂H₅ | H | |
| 13-49 | 3,5-Cl₂Ph | CF₃ | 4-Cl | COC₂H₅ | H | |
| 13-50 | 3,5-Cl₂Ph | CF₃ | 4-CH₃ | COC₂H₅ | H | |
| 13-51 | 3,5-Cl₂Ph | CF₃ | 4-CF₃ | COC₂H₅ | H | |
| 13-52 | 3,5-Cl₂Ph | CF₃ | 4-CH₂OCH₃ | COC₂H₅ | H | |
| 13-53 | 3,5-Cl₂Ph | CF₃ | 4-NO₂ | COC₂H₅ | H | |

TABLE 13-continued

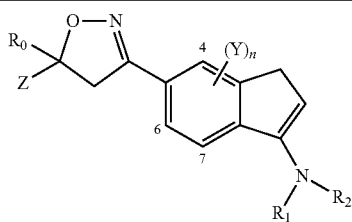

| Compound No. | Z | $R_0$ | (Y)n | $R_1$ | $R_2$ | Physical constant |
|---|---|---|---|---|---|---|
| 13-54 | 3,5-Cl$_2$Ph | CF$_3$ | 4-OH | COC$_2$H$_5$ | H | |
| 13-55 | 3,5-Cl$_2$Ph | CF$_3$ | 4-OCH$_3$ | COC$_2$H$_5$ | H | |
| 13-56 | 3,5-Cl$_2$Ph | CF$_3$ | 4-OCF$_3$ | COC$_2$H$_5$ | H | |
| 13-57 | 3,5-Cl$_2$Ph | CF$_3$ | 4-OCH$_2$COCH$_3$ | COC$_2$H$_5$ | H | |
| 13-58 | 3,5-Cl$_2$Ph | CF$_3$ | 4-SH | COC$_2$H$_5$ | H | |
| 13-59 | 3,5-Cl$_2$Ph | CF$_3$ | 4-SCH$_3$ | COC$_2$H$_5$ | H | |
| 13-60 | 3,5-Cl$_2$Ph | CF$_3$ | 4-SCF$_3$ | COC$_2$H$_5$ | H | |
| 13-61 | 3,5-Cl$_2$Ph | CF$_3$ | 4-NH$_2$ | COC$_2$H$_5$ | H | |
| 13-62 | 3,5-Cl$_2$Ph | CF$_3$ | 4-NHCH$_3$ | COC$_2$H$_5$ | H | |
| 13-63 | 3,5-Cl$_2$Ph | CF$_3$ | 4-N(CH$_3$)$_2$ | COC$_2$H$_5$ | H | |
| 13-64 | 3,5-Cl$_2$Ph | CF$_3$ | 4-NHPh | COC$_2$H$_5$ | H | |
| 13-65 | 3,5-Cl$_2$Ph | CF$_3$ | 4-NHCOCH$_3$ | COC$_2$H$_5$ | H | |
| 13-66 | 3,5-Cl$_2$Ph | CF$_3$ | 4-NHCO$_2$C$_2$H$_5$ | COC$_2$H$_5$ | H | |
| 13-67 | 3,5-Cl$_2$Ph | CF$_3$ | 4-NHCO$_2$Bu-t | COC$_2$H$_5$ | H | |
| 13-68 | 3,5-Cl$_2$Ph | CF$_3$ | 4-NHCH$_2$Ph | COC$_2$H$_5$ | H | |
| 13-69 | 3,5-Cl$_2$Ph | CF$_3$ | 7-F | COC$_2$H$_5$ | H | |
| 13-70 | 3,5-Cl$_2$Ph | NO$_2$ | — | COC$_2$H$_5$ | H | |
| 13-71 | 3,5-Cl$_2$Ph | OH | — | COC$_2$H$_5$ | H | |
| 13-72 | 3,5-Cl$_2$Ph | OMe | — | COC$_2$H$_5$ | H | |
| 13-73 | 3,5-Cl$_2$Ph | OCF$_3$ | — | COC$_2$H$_5$ | H | |
| 13-74 | 3,5-Cl$_2$Ph | SH | — | COC$_2$H$_5$ | H | |
| 13-75 | 3,5-Cl$_2$Ph | SCF$_3$ | — | COC$_2$H$_5$ | H | |
| 13-76 | 3,5-Cl$_2$Ph | Cl | — | COC$_2$H$_5$ | H | |
| 13-77 | 3,5-Cl$_2$Ph | NH$_2$ | — | COC$_2$H$_5$ | H | |
| 13-78 | 3,5-Cl$_2$Ph | NHCOCH$_3$ | — | COC$_2$H$_5$ | H | |
| 13-79 | 3,5-Cl$_2$Ph | NHCO$_2$C$_2$H$_5$ | — | COC$_2$H$_5$ | H | |
| 13-80 | 3,5-Cl$_2$Ph | CO$_2$C$_2$H$_5$ | — | COC$_2$H$_5$ | H | |
| 13-81 | 3,5-Cl$_2$Ph | SO$_2$CH$_3$ | — | COC$_2$H$_5$ | H | |
| 13-82 | 3,5-Cl$_2$Ph | SO$_2$CH$_3$ | — | COC$_2$H$_5$ | H | |
| 13-83 | 3,5-Cl$_2$Ph | Ph | — | COC$_2$H$_5$ | H | |
| 13-84 | 3,5-Cl$_2$Ph | COCH$_3$ | — | COC$_2$H$_5$ | H | |
| 13-85 | 3,5-Cl$_2$Ph | Cl | — | COC$_2$H$_5$ | H | |
| 13-86 | 3,5-Cl$_2$Ph | CF$_2$H | — | COC$_2$H$_5$ | H | |
| 13-87 | 3,5-Cl$_2$Ph | CCl$_3$ | — | COC$_2$H$_5$ | H | |
| 13-88 | 3,5-Cl$_2$Ph | CF$_2$Cl | — | COC$_2$H$_5$ | H | |
| 13-89 | CH$_3$CH=CH | CF$_3$ | — | COC$_2$H$_5$ | H | |
| 13-90 | Propargyl | CF$_3$ | — | COC$_2$H$_5$ | H | |
| 13-91 | CH$_2$=CHCH$_2$ | CF$_3$ | — | COC$_2$H$_3$ | H | |
| 13-92 | 2-butynyl | CF$_3$ | — | COC$_2$H$_5$ | H | |
| 13-93 | 3,5-Cl$_2$Ph | CF$_3$ | — | =CHOCH$_3$ | | |
| 13-94 | 3,5-Cl$_2$Ph | CF$_3$ | — | =C(OCH$_3$)$_2$ | | |
| 13-95 | 3,5-Cl$_2$Ph | CF$_3$ | — | =CHNO$_2$ | | |
| 13-96 | 3,5-Cl$_2$Ph | CF$_3$ | — | =C(OCH$_2$CH$_2$O) | | |
| 13-97 | 3,5-Cl$_2$Ph | CF$_3$ | — | CONHCH$_3$ | H | |
| 13-98 | 3,5-Cl$_2$Ph | CF$_3$ | — | CONHC$_2$H$_5$ | H | |
| 13-99 | 3,5-Cl$_2$Ph | CF$_3$ | — | CONHPr-n | H | |
| 13-100 | 3,5-Cl$_2$Ph | CF$_3$ | — | CONHCH$_2$CH$_2$OCH$_3$ | H | |
| 13-101 | 3,5-Cl$_2$Ph | CF$_3$ | — | CONHCH$_2$CH$_2$OCH$_2$CH$_3$ | H | |
| 13-102 | 3,5-Cl$_2$Ph | CF$_3$ | — | CONHCH$_2$CH(CH$_3$)OCH$_3$ | H | |
| 13-103 | 3,5-Cl$_2$Ph | CF$_3$ | — | CON(CH$_3$)$_2$ | H | |
| 13-104 | 3,5-Cl$_2$Ph | CF$_3$ | — | CONHCH$_2$CH$_2$CN | H | |
| 13-105 | 3,5-Cl$_2$Ph | CF$_3$ | — | CONHCH$_2$CH$_2$Ph | H | |
| 13-106 | 3,5-Cl$_2$Ph | CF$_3$ | — | CONHCH$_2$CH$_2$ (1,2,4-triazole-1-yl) | H | |
| 13-107 | 3,5-Cl$_2$Ph | CF$_3$ | — | CONHCH$_2$CH$_2$ (pyrazole-1-yl) | H | |
| 13-108 | 3,5-Cl$_2$Ph | CF$_3$ | — | CONHOH | H | |
| 13-109 | 3,5-Cl$_2$Ph | CF$_3$ | — | CONHOCH$_3$ | H | |
| 13-110 | 3,5-Cl$_2$Ph | CF$_3$ | — | CONHPr-c | H | |
| 13-111 | 3,5-Cl$_2$Ph | CF$_3$ | — | CONHPh | H | |
| 13-112 | 3,5-Cl$_2$Ph | CF$_3$ | — | CSNHCH$_3$ | H | |
| 13-113 | 3,5-Cl$_2$Ph | CF$_3$ | — | CO$_2$C$_2$H$_5$ | H | |
| 13-114 | 3,5-Cl$_2$Ph | CF$_3$ | — | CO$_2$Pr-n | H | |
| 13-115 | 3,5-Cl$_2$Ph | CF$_3$ | — | CO$_2$Pr-c | H | |
| 13-116 | 3,5-Cl$_2$Ph | CF$_3$ | — | CO$_2$CH$_2$CH$_2$OCH$_3$ | H | |

TABLE 13-continued

| Compound No. | Z | R₀ | (Y)n | R₁ | R₂ | Physical constant |
|---|---|---|---|---|---|---|
| 13-117 | 3,5-Cl₂Ph | CF₃ | — | CO₂CH₂CH₂OCH₂CH₃ | H | |
| 13-118 | 3,5-Cl₂Ph | CF₃ | — | CO₂CH₂CH(CH₃)OCH₃ | H | |
| 13-119 | 3,5-Cl₂Ph | CF₃ | — | CO₂CH₂CH₂CN | H | |
| 13-120 | 3,5-Cl₂Ph | CF₃ | — | CO₂CH₂CH₂Ph | H | |
| 13-121 | 3,5-Cl₂Ph | CF₃ | — | CO₂CH₂CH₂(1,2,4-triazole-1-yl) | H | |
| 13-122 | 3,5-Cl₂Ph | CF₃ | — | CO₂CH₂CH₂(pyrazole-1-yl) | H | |
| 13-123 | 3,5-Cl₂Ph | CF₃ | — | CH₂CH₂CH₂CH₂ | | |
| 13-124 | 3,5-Cl₂Ph | CF₃ | — | C(=O)CH₂CH₂CH₂ | | |
| 13-125 | 3,5-Cl₂Ph | CF₃ | — | C(=O)CH₂CH₂C(=O) | | |
| 13-126 | 3,5-Cl₂Ph | CF₃ | — | phthaloyl | | |
| 13-127 | 2,4-diCF₃-pyrimidine-6-yl | CF₃ | — | COCH₂CH(CH₃)OCH₃ | H | |
| 13-128 | 2-CH₃S-4-CF₃-pyrimidine-6-yl | CF₃ | — | COCH₂CH(CH₃)OCH₃ | H | |
| 13-129 | 2-CH₃O-4-CF₃-pyrimidine-6-yl | CF₃ | — | COCH₂CH(CH₃)OCH₃ | H | |
| 13-130 | 2-Cl-4-CF₃-pyrimidine-6-yl | CF₃ | — | COCH₂CH(CH₃)OCH₃ | H | |
| 13-131 | 2-Br-4-CF₃-pyrimidine-6-yl | CF₃ | — | COCH₂CH(CH₃)OCH₃ | H | |

TABLE 14

| Compound No. | Z | R₀ | (Y)n | R₁ | R₂ | G | Physical constant |
|---|---|---|---|---|---|---|---|
| 14-1 | 3,5-Cl₂Ph | CF₃ | — | n-Pr | H | O | |
| 14-2 | 3,5-Cl₂Ph | CF₃ | — | CH₂CH₂(2-Py) | H | NH | |
| 14-3 | 3,5-Cl₂Ph | CF₃ | — | CH₂CH₂COCH₃ | H | CH₂ | |
| 14-4 | 3,5-Cl₂Ph | CF₃ | — | CH₂CH₂OCH₃ | H | S | |
| 14-5 | 3,5-Cl₂Ph | CF₃ | — | COCH₃ | H | O | |
| 14-6 | 3,5-Cl₂Ph | CF₃ | — | COC₂H₅ | H | O | [162-165] |
| 14-7 | 3,5-Cl₂Ph | CF₃ | — | COC₂H₅ | COC₂H₅ | O | amorphous |
| 14-8 | 3,5-Cl₂Ph | CF₃ | — | COC₂H5 | H | NH | [133-137] |
| 14-9 | 3,5-Cl₂Ph | CF₃ | — | COC₂H₅ | H | N(COC₂H₅) | [85-87] |
| 14-10 | 3,5-Cl₂Ph | CF₃ | — | COPr-n | H | O | |
| 14-11 | 3,5-Cl₂Ph | CF₃ | — | COCH₂CH₂OCH₃ | H | NH | |
| 14-12 | 3,5-Cl₂Ph | CF₃ | — | COCH₂CH₂OCH₂CH₃ | H | NH₂ | |
| 14-13 | 3,5-Cl₂Ph | CF₃ | — | COCH₂CH(CH₃)OCH₃ | H | S | |
| 14-14 | 3,5-Cl₂Ph | CF₃ | — | COCH₂CH(CH₃)OCH₂CH₃ | H | O | |
| 14-15 | 3,5-Cl₂Ph | CF₃ | — | COCH₂CH(CH₃)OH | H | NH | |
| 14-16 | 3,5-Cl₂Ph | CF₃ | — | COCH₂CH₂OCH₂CH=CH₂ | H | CH₂ | |
| 14-17 | 3,5-Cl₂Ph | CF₃ | — | COCH₂COCH₃ | H | S | |
| 14-18 | 3,5-Cl₂Ph | CF₃ | — | COCH₂(1,3-dioxolane-2-yl) | H | O | |
| 14-19 | 3,5-Cl₂Ph | CF₃ | — | COCH₂(2-methyl-1,3-dioxolane-2-yl) | H | NH | |
| 14-20 | 3,5-Cl₂Ph | CF₃ | — | COCH₂(2-trifluoromethyl-1,3-dioxolane-2-yl) | H | CH₂ | |

TABLE 14-continued

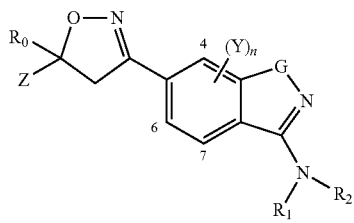

| Compound No. | Z | R₀ | (Y)n | R₁ | R₂ | G | Physical constant |
|---|---|---|---|---|---|---|---|
| 14-21 | 3,5-Cl₂Ph | CF₃ | — | COCH₂(2-methyl-1,3-dioxane-2-yl) | H | S | |
| 14-22 | 3,5-Cl₂Ph | CF₃ | — | COCH₂CH₂(1,3-dioxolane-2-yl) | H | O | |
| 14-23 | 3,5-Cl₂Ph | CF₃ | — | COCH₂CH₂(2-methyl-1,3-dioxolane-2-yl) | H | NH | |
| 14-24 | 3,5-Cl₂Ph | CF₃ | — | CO(tetrahydropyran-4-yl) | H | CH₂ | |
| 14-25 | 3,5-Cl₂Ph | CF₃ | — | CO(2,6-dimethyl-4H-pyran-4-one-3-yl) | H | S | |
| 14-26 | 3,5-Cl₂Ph | CF₃ | — | COCH₂CH₂CN | H | O | |
| 14-27 | 3,5-Cl₂Ph | CF₃ | — | COCH₂CH₂Ph | H | NH | |
| 14-28 | 3,5-Cl₂Ph | CF₃ | — | COCH₂CH₂(1,2,4-triazole-1-yl) | H | CH₂ | |
| 14-29 | 3,5-Cl₂Ph | CF₃ | — | COCH₂CH₂(pyrazole-1-yl) | H | S | |
| 14-30 | 3,5-CF₃Ph | CF₃ | — | COC₂H₅ | H | O | |
| 14-31 | 3-CF₃Ph | CF₃ | — | COCH₂CH₂OCH₃ | H | NH | |
| 14-32 | 3-CF₃Ph | CF₃ | — | COCH₂CH(CH₃)OCH₃ | H | CH₂ | |
| 14-33 | 3-CF₃Ph | CF₃ | — | COCH₂(2-methyl-1,3-dioxolane-2-yl) | H | S | |
| 14-34 | 3-CF₃Ph | CF₃ | — | COCH₂CH₂CN | H | O | |
| 14-35 | 3,5-Cl₂Ph | CF₃ | — | COPr-c | H | NH | |
| 14-36 | 3,5-Cl₂Ph | CF₃ | — | COHex-c | H | CH₂ | |
| 14-37 | 2-F-3-CF₃Ph | CF₃ | — | COC₂H₅ | H | S | |
| 14-38 | 2-F-3-CF₃Ph | CF₃ | — | COCH₂CH₂OCH₃ | H | O | |
| 14-39 | 3-CF₃-4-ClPh | CF₃ | — | COC₂H₅ | H | NH | |
| 14-40 | 3-CF₃-4-ClPh | CF₃ | — | COCH₂CH₂OCH₃ | H | CH₂ | |
| 14-41 | 3-CF₃-4-ClPh | CF₃ | — | COCH₂CH(CH₃)OCH₃ | H | S | |
| 14-42 | 3,5-Cl₂Ph | CF₃ | — | CSC₂H₅ | H | O | |
| 14-43 | 3,5-Cl₂Ph | CF₃ | — | 2-cyclohexenone-3-yl | H | NH | |
| 14-44 | 3,5-Cl₂Ph | CF₃ | — | CH₂(4-methyl-1,3-dioxolene-2-one-5-yl) | H | CH₂ | |
| 14-45 | 3,5-Cl₂Ph | CF₃ | — | CH₂(4-methyl-1,3-dioxolene-2-one-5-yl) | CH₂(4-methyl-1,3-dioxolene-2-one-5-yl) | S | |
| 14-46 | 3,5-Cl₂Ph | CF₃ | — | COC₂H₅ | CH₃ | O | |
| 14-47 | 3,5-Cl₂Ph | CF₃ | — | H | H | O | [>200] |
| 14-48 | 3,5-Cl₂Ph | CF₃ | — | H | H | NH | [>200] |
| 14-49 | 3-CF₃Ph | CF₃ | — | H | H | NH | |
| 14-50 | 2-F-3-CF₃Ph | CF₃ | — | H | H | CH₂ | |
| 14-51 | 3-CF₃-4-ClPh | CF₃ | — | H | H | S | |
| 14-52 | 3,5-Cl₂Ph | CF₃ | 4-F | COC₂H₅ | H | O | |
| 14-53 | 3,5-Cl₂Ph | CF₃ | 4-Cl | COC₂H₅ | H | NH | |
| 14-54 | 3,5-Cl₂Ph | CF₃ | 4-CH₃ | COC₂H₅ | H | CH₂ | |
| 14-55 | 3,5-Cl₂Ph | CF₃ | 4-CF₃ | COC₂H₅ | H | S | |
| 14-56 | 3,5-Cl₂Ph | CF₃ | 4-CH₂OCH₃ | COC₂H₅ | H | O | |
| 14-57 | 3,5-Cl₂Ph | CF₃ | 4-NO₂ | COC₂H₅ | H | NH | |
| 14-58 | 3,5-Cl₂Ph | CF₃ | 4-OH | COC₂H₅ | H | CH₂ | |
| 14-59 | 3,5-Cl₂Ph | CF₃ | 4-OCH₃ | COC₂H₅ | H | S | |
| 14-60 | 3,5-Cl₂Ph | CF₃ | 4-OCF₃ | COC₂H₅ | H | O | |
| 14-61 | 3,5-Cl₂Ph | CF₃ | 4-OCH₂COCH₃ | COC₂H₅ | H | NH | |
| 14-62 | 3,5-Cl₂Ph | CF₃ | 4-SH | COC₂H₅ | H | CH₂ | |
| 14-63 | 3,5-Cl₂Ph | CF₃ | 4-SCH₃ | COC₂H₅ | H | S | |
| 14-64 | 3,5-Cl₂Ph | CF₃ | 4-SCF₃ | COC₂H₅ | H | O | |
| 14-65 | 3,5-Cl₂Ph | CF₃ | 4-NH₂ | COC₂H₅ | H | NH | |
| 14-66 | 3,5-Cl₂Ph | CF₃ | 4-NHCH₃ | COC₂H₅ | H | CH₂ | |
| 14-67 | 3,5-Cl₂Ph | CF₃ | 4-N(CH₃)₂ | COC₂H₅ | H | S | |
| 14-68 | 3,5-Cl₂Ph | CF₃ | 4-NHPh | COC₂H₅ | H | O | |
| 14-69 | 3,5-Cl₂Ph | CF₃ | 4-NHCOCH₃ | COC₂H₅ | H | NH | |
| 14-70 | 3,5-Cl₂Ph | CF₃ | 4-NHCO₂C₂H₅ | COC₂H₅ | H | CH₂ | |
| 14-71 | 3,5-Cl₂Ph | CF₃ | 4-NHCO₂Bu-t | COC₂H₅ | H | S | |
| 14-72 | 3,5-Cl₂Ph | CF₃ | 4-NHCH₂Ph | COC₂H₅ | H | O | |
| 14-73 | 3,5-Cl₂Ph | CF₃ | 7-F | COC₂H₅ | H | NH | |
| 14-74 | 3,5-Cl₂Ph | NO₂ | — | COC₂H₅ | H | CH₂ | |
| 14-75 | 3,5-Cl₂Ph | OH | — | COC₂H₅ | H | S | |

TABLE 14-continued

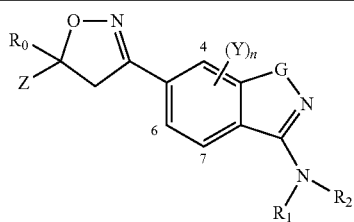

| Compound No. | Z | $R_0$ | $(Y)n$ | $R_1$ | $R_2$ | G | Physical constant |
|---|---|---|---|---|---|---|---|
| 14-76 | 3,5-Cl$_2$Ph | OMe | — | COC$_2$H$_5$ | H | O | |
| 14-77 | 3,5-Cl$_2$Ph | OCF$_3$ | — | COC$_2$H$_5$ | H | NH | |
| 14-78 | 3,5-Cl$_2$Ph | SH | — | COC$_2$H$_5$ | H | CH$_2$ | |
| 14-79 | 3,5-Cl$_2$Ph | SCF$_3$ | — | COC$_2$H$_5$ | H | S | |
| 14-80 | 3,5-Cl$_2$Ph | Cl | — | COC$_2$H$_5$ | H | O | |
| 14-81 | 3,5-Cl$_2$Ph | NH$_2$ | — | COC$_2$H$_5$ | H | NH | |
| 14-82 | 3,5-Cl$_2$Ph | NHCOCH$_3$ | — | COC$_2$H$_5$ | H | CH$_2$ | |
| 14-83 | 3,5-Cl$_2$Ph | NHCO$_2$C$_2$H$_5$ | — | COC$_2$H$_5$ | H | S | |
| 14-84 | 3,5-Cl$_2$Ph | CO$_2$C$_2$H$_5$ | — | COC$_2$H$_5$ | H | O | |
| 14-85 | 3,5-Cl$_2$Ph | SO$_2$CH$_3$ | — | COC$_2$H$_5$ | H | NH | |
| 14-86 | 3,5-Cl$_2$Ph | SO$_2$CF$_3$ | — | COC$_2$H$_5$ | H | CH$_2$ | |
| 14-87 | 3,5-Cl$_2$Ph | Ph | — | COC$_2$H$_5$ | H | S | |
| 14-88 | 3,5-Cl$_2$Ph | COCH$_3$ | — | COC$_2$H$_5$ | H | O | |
| 14-89 | 3,5-Cl$_2$Ph | Cl | — | COC$_2$H$_5$ | H | NH | |
| 14-90 | 3,5-Cl$_2$Ph | CF$_2$H | — | COC$_2$H$_5$ | H | CH$_2$ | |
| 14-91 | 3,5-Cl$_2$Ph | CCl$_3$ | — | COC$_2$H$_5$ | H | S | |
| 14-92 | 3,5-Cl$_2$Ph | CF$_2$Cl | — | COC$_2$H$_5$ | H | O | |
| 14-93 | CH$_3$CH=CH | CF$_3$ | — | COC$_2$H$_5$ | H | NH | |
| 14-94 | Propargyl | CF$_3$ | — | COC$_2$H$_5$ | H | CH$_2$ | |
| 14-95 | CH$_2$=CHCH$_2$ | CF$_3$ | — | COC$_2$H$_5$ | H | S | |
| 14-96 | 2-butynyl | CF$_3$ | — | COC$_2$H$_5$ | H | O | |
| 14-97 | 3,5-Cl$_2$Ph | CF$_3$ | — | =CHOCH$_3$ | | NH | |
| 14-98 | 3,5-Cl$_2$Ph | CF$_3$ | — | =C(OCH$_3$)$_2$ | | CH$_2$ | |
| 14-99 | 3,5-Cl$_2$Ph | CF$_3$ | — | =CHNO$_2$ | | S | |
| 14-100 | 3,5-Cl$_2$Ph | CF$_3$ | — | =C(OCH$_2$CH$_2$O) | | O | |
| 14-101 | 3,5-Cl$_2$Ph | CF$_3$ | — | CONHCH$_3$ | H | NH | |
| 14-102 | 3,5-Cl$_2$Ph | CF$_3$ | — | CONHC$_2$H$_5$ | H | CH$_2$ | |
| 14-103 | 3,5-Cl$_2$Ph | CF$_3$ | — | CONHPr-n | H | S | |
| 14-104 | 3,5-Cl$_2$Ph | CF$_3$ | — | CONHCH$_2$CH$_2$OCH$_3$ | H | O | |
| 14-105 | 3,5-Cl$_2$Ph | CF$_3$ | — | CONHCH$_2$CH$_2$OCH$_2$CH$_3$ | H | NH | |
| 14-106 | 3,5-Cl$_2$Ph | CF$_3$ | — | CONHCH$_2$CH(CH$_3$)OCH$_3$ | H | CH$_2$ | |
| 14-107 | 3,5-Cl$_2$Ph | CF$_3$ | — | CON(CH$_3$)$_2$ | H | S | |
| 14-108 | 3,5-Cl$_2$Ph | CF$_3$ | — | CONHCH$_2$CH$_2$CN | H | O | |
| 14-109 | 3,5-Cl$_2$Ph | CF$_3$ | — | CONHCH$_2$CH$_2$Ph | H | NH | |
| 14-110 | 3,5-Cl$_2$Ph | CF$_3$ | — | CONHCH$_2$CH$_2$ (1,2,4-trizole-1-yl) | H | CH$_2$ | |
| 14-111 | 3,5-Cl$_2$Ph | CF$_3$ | — | CONHCH$_2$CH$_2$ (pyrazole-1-yl) | H | S | |
| 14-112 | 3,5-Cl$_2$Ph | CF$_3$ | — | CONHOH | H | O | |
| 14-113 | 3,5-Cl$_2$Ph | CF$_3$ | — | CONHOCH$_3$ | H | NH | |
| 14-114 | 3,5-Cl$_2$Ph | CF$_3$ | — | CONHPr-c | H | CH$_2$ | |
| 14-115 | 3,5-Cl$_2$Ph | CF$_3$ | — | CONHPh | H | S | |
| 14-116 | 3,5-Cl$_2$Ph | CF$_3$ | — | CSNHCH$_3$ | H | O | |
| 14-117 | 3,5-Cl$_2$Ph | CF$_3$ | — | CO$_2$C$_2$H$_5$ | H | NH | |
| 14-118 | 3,5-Cl$_2$Ph | CF$_3$ | — | CO$_2$Pr-n | H | CH$_2$ | |
| 14-119 | 3,5-Cl$_2$Ph | CF$_3$ | — | CO$_2$Pr-c | H | S | |
| 14-120 | 3,5-Cl$_2$Ph | CF$_3$ | — | CO$_2$CH$_2$CH$_2$OCH$_3$ | H | O | |
| 14-121 | 3,5-Cl$_2$Ph | CF$_3$ | — | CO$_2$CH$_2$CH$_2$OCH$_2$CH$_3$ | H | NH | |
| 14-122 | 3,5-Cl$_2$Ph | CF$_3$ | — | CO$_2$CH$_2$CH(CH$_3$)OCH$_3$ | H | CH$_2$ | |
| 14-123 | 3,5-Cl$_2$Ph | CF$_3$ | — | CO$_2$CH$_2$CH$_2$CN | H | S | |
| 14-124 | 3,5-Cl$_2$Ph | CF$_3$ | — | CO$_2$CH$_2$CH$_2$Ph | H | O | |
| 14-125 | 3,5-Cl$_2$Ph | CF$_3$ | — | CO$_2$CH$_2$CH$_2$ (1,2,4-trizole-1-yl) | H | NH | |
| 14-126 | 3,5-Cl$_2$Ph | CF$_3$ | — | CO$_2$CH$_2$CH$_2$ (pyrazole-1-yl) | H | CH$_2$ | |
| 14-127 | 3,5-Cl$_2$Ph | CF$_3$ | — | CH$_2$CH$_2$CH$_2$CH$_2$ | | S | |
| 14-128 | 3,5-Cl$_2$Ph | CF$_3$ | — | C(=O)CH$_2$CH$_2$CH$_2$ | | O | |
| 14-129 | 3,5-Cl$_2$Ph | CF$_3$ | — | C(=O)CH$_2$CH$_2$C(=O) | | NH | |
| 14-130 | 3,5-Cl$_2$Ph | CF$_3$ | — | phthaloyl | | CH$_2$ | |
| 14-131 | 2,4-diCF$_3$-pyrimidine-6-yl | CF$_3$ | — | COCH$_2$CH(CH$_3$)OCH$_3$ | H | S | |
| 14-132 | 2-CH$_3$S-4-CF$_3$-pyrimidine-6-yl | CF$_3$ | — | COCH$_2$CH(CH$_3$)OCH$_3$ | H | O | |
| 14-133 | 2-CH$_3$O-4-CF$_3$-pyrimidine-6-yl | CF$_3$ | — | COCH$_2$CH(CH$_3$)OCH$_3$ | H | NH | |

TABLE 14-continued

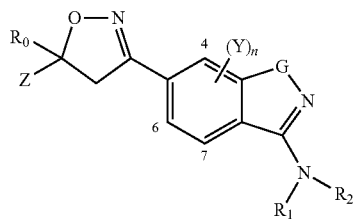

| Compound No. | Z | $R_0$ | (Y)n | $R_1$ | $R_2$ | G | Physical constant |
|---|---|---|---|---|---|---|---|
| 14-134 | 2-Cl-4-CF$_3$-pyrimidine-6-yl | CF$_3$ | — | COCH$_2$CH(CH$_3$)OCH$_3$ | H | CH$_2$ | |
| 14-135 | 2-Br-4-CF$_3$-pyrimidine-6-yl | CF$_3$ | — | COCH$_2$CH(CH$_3$)OCH$_3$ | H | S | |

TABLE 15

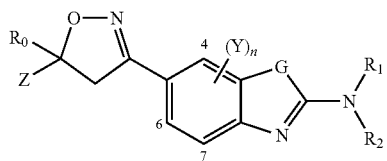

| Compound No. | Z | $R_0$ | (Y)n | $R_1$ | $R_2$ | G | Physical constant |
|---|---|---|---|---|---|---|---|
| 15-1 | 3,5-Cl$_2$Ph | CF$_3$ | — | n-Pr | H | O | |
| 15-2 | 3,5-Cl$_2$Ph | CF$_3$ | — | CH$_2$CH$_2$(2-Py) | H | NH | |
| 15-3 | 3,5-Cl$_2$Ph | CF$_3$ | — | CH$_2$CH$_2$COCH$_3$ | H | CH$_2$ | |
| 15-4 | 3,5-Cl$_2$Ph | CF$_3$ | — | CH$_2$CH$_2$OCH$_3$ | H | S | |
| 15-5 | 3,5-Cl$_2$Ph | CF$_3$ | — | COCH$_3$ | H | O | |
| 15-6 | 3,5-Cl$_2$Ph | CF$_3$ | — | COC$_2$H$_5$ | H | O | amorphous |
| 15-7 | 3,5-Cl$_2$Ph | CF$_3$ | — | COC$_2$H$_5$ | H | S | amorphous |
| 15-8 | 3,5-Cl$_2$Ph | CF$_3$ | — | COC$_2$H$_5$ | COC$_2$H$_5$ | O | |
| 15-9 | 3,5-Cl$_2$Ph | CF$_3$ | — | COC$_2$H$_5$ | H | NH | |
| 15-10 | 3,5-Cl$_2$Ph | CF$_3$ | — | COC$_2$H$_5$ | H | N(COC$_2$H$_5$) | |
| 15-11 | 3,5-Cl$_2$Ph | CF$_3$ | — | COPr-n | H | O | |
| 15-12 | 3,5-Cl$_2$Ph | CF$_3$ | — | COCH$_2$CH$_2$OCH$_3$ | H | NH | |
| 15-13 | 3,5-Cl$_2$Ph | CF$_3$ | — | COCH$_2$CH$_2$OCH$_2$CH$_3$ | H | CH$_2$ | |
| 15-14 | 3,5-Cl$_2$Ph | CF$_3$ | — | COCH$_2$CH(CH$_3$)OCH$_3$ | H | S | |
| 15-15 | 3,5-Cl$_2$Ph | CF$_3$ | — | COCH$_2$CH(CH$_3$)OCH$_2$CH$_3$ | H | O | |
| 15-16 | 3,5-Cl$_2$Ph | CF$_3$ | — | COCH$_2$CH(CH$_3$)OH | H | NH | |
| 15-17 | 3,5-Cl$_2$Ph | CF$_3$ | — | COCH$_2$CH$_2$OCH$_2$CH=CH$_2$ | H | CH$_2$ | |
| 15-18 | 3,5-Cl$_2$Ph | CF$_3$ | — | COCH$_2$COCH$_3$ | H | S | |
| 15-19 | 3,5-Cl$_2$Ph | CF$_3$ | — | COCH$_2$(1,3-dioxolane-2-yl) | H | O | |
| 15-20 | 3,5-Cl$_2$Ph | CF$_3$ | — | COCH$_2$(2-methyl-1,3-dioxolane-2-yl) | H | NH | |
| 15-21 | 3,5-Cl$_2$Ph | CF$_3$ | — | COCH$_2$(2-trifluoromethyl-1,3-dioxolane-2-yl) | H | CH$_2$ | |
| 15-22 | 3,5-Cl$_2$Ph | CF$_3$ | — | COCH$_2$(2-methyl-1,3-dioxane-2-yl) | H | S | |
| 15-23 | 3,5-Cl$_2$Ph | CF$_3$ | — | COCH$_2$CH$_2$(1,3-dioxolane-2-yl) | H | O | |
| 15-24 | 3,5-Cl$_2$Ph | CF$_3$ | — | COCH$_2$CH$_2$(2-methyl-1,3-dioxolane-2-yl) | H | NH | |
| 15-25 | 3,5-Cl$_2$Ph | CF$_3$ | — | CO(tetrahydropyran-4-yl) | H | CH$_2$ | |
| 15-26 | 3,5-Cl$_2$Ph | CF$_3$ | — | CO(2,6-dimethyl-4H-pyran-4-one-3-yl) | H | S | |
| 15-27 | 3,5-Cl$_2$Ph | CF$_3$ | — | COCH$_2$CH$_2$CN | H | O | |
| 15-28 | 3,5-Cl$_2$Ph | CF$_3$ | — | COCH$_2$CH$_2$Ph | H | NH | |
| 15-29 | 3,5-Cl$_2$Ph | CF$_3$ | — | COCH$_2$CH$_2$(1,2,4-triazole-1-yl) | H | CH$_2$ | |
| 15-30 | 3,5-Cl$_2$Ph | CF$_3$ | — | COCH$_2$CH$_2$(pyrazole-1-yl) | H | S | |
| 15-31 | 3-CF$_3$Ph | CF$_3$ | — | COC$_2$H$_5$ | H | O | |
| 15-32 | 3-CF$_3$Ph | CF$_3$ | — | COCH$_2$CH$_2$OCH$_3$ | H | NH | |
| 15-33 | 3-CF$_3$Ph | CF$_3$ | — | COCH$_2$CH(CH$_3$)OCH$_3$ | H | CH$_2$ | |
| 15-34 | 3-CF$_3$Ph | CF$_3$ | — | COCH$_2$(2-methyl-1,3-dioxolane-2-yl) | H | S | |
| 15-35 | 3-CF$_3$Ph | CF$_3$ | — | COCH$_2$CH$_2$CN | H | O | |
| 15-36 | 3,5-Cl$_2$Ph | CF$_3$ | — | COPr-c | H | NH | |

TABLE 15-continued

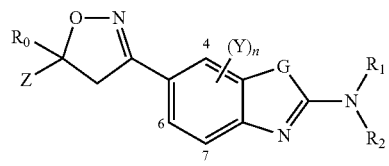

| Compound No. | Z | $R_0$ | $(Y)n$ | $R_1$ | $R_2$ | G | Physical constant |
|---|---|---|---|---|---|---|---|
| 15-37 | 3,5-$Cl_2$Ph | $CF_3$ | — | COHex-c | H | $CH_2$ | |
| 15-38 | 2-F-3-$CF_3$Ph | $CF_3$ | — | $COC_2H_5$ | H | S | |
| 15-39 | 2-F-3-$CF_3$Ph | $CF_3$ | — | $COCH_2CH_2OCH_3$ | H | O | |
| 15-40 | 3-$CF_3$-4-ClPh | $CF_3$ | — | $COC_2H_5$ | H | NH | |
| 15-41 | 3-$CF_3$-4-ClPh | $CF_3$ | — | $COCH_2CH_2OCH_3$ | H | $CH_2$ | |
| 15-42 | 3-$CF_3$-4-ClPh | $CF_3$ | — | $COCH_2CH(CH_3)OCH_3$ | H | S | |
| 15-43 | 3,5-$Cl_2$Ph | $CF_3$ | — | $CSC_2H_5$ | H | O | |
| 15-44 | 3,5-$Cl_2$Ph | $CF_3$ | — | 2-cyclohexenone-3-yl | H | NH | |
| 15-45 | 3,5-$Cl_2$Ph | $CF_3$ | — | $CH_2$(4-methyl-1,3-dioxolene-2-one-5-yl) | H | $CH_2$ | |
| 15-46 | 3,5-$Cl_2$Ph | $CF_3$ | — | $CH_2$(4-methyl-1,3-dioxolene-2-one-5-yl) | $CH_2$(4-methyl-1,3-dioxolene-2-one-5-yl) | S | |
| 15-47 | 3,5-$Cl_2$Ph | $CF_3$ | — | $COC_2H_5$ | $CH_3$ | O | |
| 15-48 | 3,5-$Cl_2$Ph | $CF_3$ | — | H | H | O | [>200] |
| 15-49 | 3,5-$Cl_2$Ph | $CF_3$ | — | H | H | NH | |
| 15-50 | 3-$CF_3$Ph | $CF_3$ | — | H | H | NH | |
| 15-51 | 2-F-3-$CF_3$Ph | $CF_3$ | — | H | H | $CH_2$ | |
| 15-52 | 3-$CF_3$-4-ClPh | $CF_3$ | — | H | H | S | |
| 15-53 | 3,5-$Cl_2$Ph | $CF_3$ | 4-F | $COC_2H_5$ | H | O | |
| 15-54 | 3,5-$Cl_2$Ph | $CF_3$ | 4-Cl | $COC_2H_5$ | H | NH | |
| 15-55 | 3,5-$Cl_2$Ph | $CF_3$ | 4-$CH_3$ | $COC_2H_5$ | H | $CH_2$ | |
| 15-56 | 3,5-$Cl_2$Ph | $CF_3$ | 4-$CF_3$ | $COC_2H_5$ | H | S | |
| 15-57 | 3,5-$Cl_2$Ph | $CF_3$ | 4-$CH_2OCH_3$ | $COC_2H_5$ | H | O | |
| 15-58 | 3,5-$Cl_2$Ph | $CF_3$ | 4-$NO_2$ | $COC_2H_5$ | H | NH | |
| 15-59 | 3,5-$Cl_2$Ph | $CF_3$ | 4-OH | $COC_2H_5$ | H | $CH_2$ | |
| 15-60 | 3,5-$Cl_2$Ph | $CF_3$ | 4-$OCH_3$ | $COC_2H_5$ | H | S | |
| 15-61 | 3,5-$Cl_2$Ph | $CF_3$ | 4-$OCF_3$ | $COC_2H_5$ | H | O | |
| 15-62 | 3,5-$Cl_2$Ph | $CF_3$ | 4-$OCH_2COCH_3$ | $COC_2H_5$ | H | NH | |
| 15-63 | 3,5-$Cl_2$Ph | $CF_3$ | 4-SH | $COC_2H_5$ | H | $CH_2$ | |
| 15-64 | 3,5-$Cl_2$Ph | $CF_3$ | 4-$SCH_3$ | $COC_2H_5$ | H | S | |
| 15-65 | 3,5-$Cl_2$Ph | $CF_3$ | 4-$SCF_3$ | $COC_2H_5$ | H | O | |
| 15-66 | 3,5-$Cl_2$Ph | $CF_3$ | 4-$NH_2$ | $COC_2H_5$ | H | NH | |
| 15-67 | 3,5-$Cl_2$Ph | $CF_3$ | 4-$NHCH_3$ | $COC_2H_5$ | H | $CH_2$ | |
| 15-68 | 3,5-$Cl_2$Ph | $CF_3$ | 4-$N(CH_3)_2$ | $COC_2H_5$ | H | S | |
| 15-69 | 3,5-$Cl_2$Ph | $CF_3$ | 4-NHPh | $COC_2H_5$ | H | O | |
| 15-70 | 3,5-$Cl_2$Ph | $CF_3$ | 4-$NHCOCH_3$ | $COC_2H_5$ | H | NH | |
| 15-71 | 3,5-$Cl_2$Ph | $CF_3$ | 4-$NHCO_2C_2H_5$ | $COC_2H_5$ | H | $CH_2$ | |
| 15-72 | 3,5-$Cl_2$Ph | $CF_3$ | 4-$NHCO_2$Bu-t | $COC_2H_5$ | H | S | |
| 15-73 | 3,5-$Cl_2$Ph | $CF_3$ | 4-$NHCH_2$Ph | $COC_2H_5$ | H | O | |
| 15-74 | 3,5-$Cl_2$Ph | $CF_3$ | 7-F | $COC_2H_5$ | H | NH | |
| 15-75 | 3,5-$Cl_2$Ph | $NO_2$ | — | $COC_2H_5$ | H | $CH_2$ | |
| 15-76 | 3,5-$Cl_2$Ph | OH | — | $COC_2H_5$ | H | S | |
| 15-77 | 3,5-$Cl_2$Ph | OMe | — | $COC_2H_5$ | H | O | |
| 15-78 | 3,5-$Cl_2$Ph | $OCF_3$ | — | $COC_2H_5$ | H | NH | |
| 15-79 | 3,5-$Cl_2$Ph | SH | — | $COC_2H_5$ | H | $CH_2$ | |
| 15-80 | 3,5-$Cl_2$Ph | $SCF_3$ | — | $COC_2H_5$ | H | S | |
| 15-81 | 3,5-$Cl_2$Ph | Cl | — | $COC_2H_5$ | H | O | |
| 15-82 | 3,5-$Cl_2$Ph | $NH_2$ | — | $COC_2H_5$ | H | NH | |
| 15-83 | 3,5-$Cl_2$Ph | $NHCOCH_3$ | — | $COC_2H_5$ | H | $CH_2$ | |
| 15-84 | 3,5-$Cl_2$Ph | $NHCO_2C_2H_5$ | — | $COC_2H_5$ | H | S | |
| 15-85 | 3,5-$Cl_2$Ph | $CO_2C_2H_5$ | — | $COC_2H_5$ | H | O | |
| 15-86 | 3,5-$Cl_2$Ph | $SO_2CH_3$ | — | $COC_2H_5$ | H | NH | |
| 15-87 | 3,5-$Cl_2$Ph | $SO_2CF_3$ | — | $COC_2H_5$ | H | $CH_2$ | |
| 15-88 | 3,5-$Cl_2$Ph | Ph | — | $COC_2H_5$ | H | S | |
| 15-89 | 3,5-$Cl_2$Ph | $COCH_3$ | — | $COC_2H_5$ | H | O | |
| 15-90 | 3,5-$Cl_2$Ph | Cl | — | $COC_2H_5$ | H | NH | |
| 15-91 | 3,5-$Cl_2$Ph | $CF_2H$ | — | $COC_2H_5$ | H | $CH_2$ | |
| 15-92 | 3,5-$Cl_2$Ph | $CCl_3$ | — | $COC_2H_5$ | H | S | |
| 15-93 | 3,5-$Cl_2$Ph | $CF_2Cl$ | — | $COC_2H_5$ | H | O | |
| 15-94 | $CH_3CH=CH$ | $CF_3$ | — | $COC_2H_5$ | H | NH | |
| 15-95 | Propargyl | $CF_3$ | — | $COC_2H_5$ | H | $CH_2$ | |
| 15-96 | $CH_2=CHCH_2$ | $CF_3$ | — | $COC_2H_5$ | H | S | |
| 15-97 | 2-butynyl | $CF_3$ | — | $COC_2H_5$ | H | O | |
| 15-98 | 3,5-$Cl_2$Ph | $CF_3$ | — | $=CHOCH_3$ | | NH | |
| 15-99 | 3,5-$Cl_2$Ph | $CF_3$ | — | $=C(OCH_3)_2$ | | $CH_2$ | |
| 15-100 | 3,5-$Cl_2$Ph | $CF_3$ | — | $=CHNO_2$ | | S | |
| 15-101 | 3,5-$Cl_2$Ph | $CF_3$ | — | $=C(OCH_2CH_2O)$ | | O | |

TABLE 15-continued

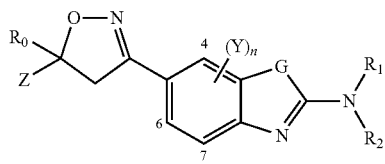

| Compound No. | Z | $R_0$ | $(Y)n$ | $R_1$ | $R_2$ | G | Physical constant |
|---|---|---|---|---|---|---|---|
| 15-102 | 3,5-$Cl_2$Ph | $CF_3$ | — | $CONHCH_3$ | H | NH | |
| 15-103 | 3,5-$Cl_2$Ph | $CF_3$ | — | $CONHC_2H_5$ | H | $CH_2$ | |
| 15-104 | 3,5-$Cl_2$Ph | $CF_3$ | — | CONHPr-n | H | S | |
| 15-105 | 3,5-$Cl_2$Ph | $CF_3$ | — | $CONHCH_2CH_2OCH_3$ | H | O | |
| 15-106 | 3,5-$Cl_2$Ph | $CF_3$ | — | $CONHCH_2CH_2OCH_2CH_3$ | H | NH | |
| 15-107 | 3,5-$Cl_2$Ph | $CF_3$ | — | $CONHCH_2CH(CH_3)OCH_3$ | H | $CH_2$ | |
| 15-108 | 3,5-$Cl_2$Ph | $CF_3$ | — | $CON(CH_3)_2$ | H | S | |
| 15-109 | 3,5-$Cl_2$Ph | $CF_3$ | — | $CONHCH_2CH_2CN$ | H | O | |
| 15-110 | 3,5-$Cl_2$Ph | $CF_3$ | — | $CONHCH_2CH_2Ph$ | H | NH | |
| 15-111 | 3,5-$Cl_2$Ph | $CF_3$ | — | $CONHCH_2CH_2$ (1,2,4-triazole-1-yl) | H | $CH_2$ | |
| 15-112 | 3,5-$Cl_2$Ph | $CF_3$ | — | $CONHCH_2CH_2$ (pyrazole-1-yl) | H | S | |
| 15-113 | 3,5-$Cl_2$Ph | $CF_3$ | — | CONHOH | H | O | |
| 15-114 | 3,5-$Cl_2$Ph | $CF_3$ | — | $CONHOCH_3$ | H | NH | |
| 15-115 | 3,5-$Cl_2$Ph | $CF_3$ | — | CONHPr-c | H | $CH_2$ | |
| 15-116 | 3,5-$Cl_2$Ph | $CF_3$ | — | CONHPh | H | S | |
| 15-117 | 3,5-$Cl_2$Ph | $CF_3$ | — | $CSNHCH_3$ | H | O | |
| 15-118 | 3,5-$Cl_2$Ph | $CF_3$ | — | $CO_2C_2H_5$ | H | NH | |
| 15-119 | 3,5-$Cl_2$Ph | $CF_3$ | — | $CO_2$Pr-n | H | $CH_2$ | |
| 15-120 | 3,5-$Cl_2$Ph | $CF_3$ | — | $CO_2$Pr-c | H | S | |
| 15-121 | 3,5-$Cl_2$Ph | $CF_3$ | — | $CO_2CH_2CH_2OCH_3$ | H | O | |
| 15-122 | 3,5-$Cl_2$Ph | $CF_3$ | — | $CO_2CH_2CH_2OCH_2CH_3$ | H | NH | |
| 15-123 | 3,5-$Cl_2$Ph | $CF_3$ | — | $CO_2CH_2CH(CH_3)OCH_3$ | H | $CH_2$ | |
| 15-124 | 3,5-$Cl_2$Ph | $CF_3$ | — | $CO_2CH_2CH_2CN$ | H | S | |
| 15-125 | 3,5-$Cl_2$Ph | $CF_3$ | — | $CO_2CH_2CH_2Ph$ | H | O | |
| 15-126 | 3,5-$Cl_2$Ph | $CF_3$ | — | $CO_2CH_2CH_2$ (1,2,4-triazole-1-yl) | H | NH | |
| 15-127 | 3,5-$Cl_2$Ph | $CF_3$ | — | $CO_2CH_2CH_2$ (pyrazole-1-yl) | H | $CH_2$ | |
| 15-128 | 3,5-$Cl_2$Ph | $CF_3$ | — | $CH_2CH_2CH_2CH_2$ | | S | |
| 15-129 | 3,5-$Cl_2$Ph | $CF_3$ | — | $C(=O)CH_2CH_2CH_2$ | | O | |
| 15-130 | 3,5-$Cl_2$Ph | $CF_3$ | — | $C(=O)CH_2CH_2C(=O)$ | | NH | |
| 15-131 | 3,5-$Cl_2$Ph | $CF_3$ | — | phthaloyl | | $CH_2$ | |
| 15-132 | 2,4-di$CF_3$-pyrimidine-6-yl | $CF_3$ | — | $COCH_2CH(CH_3)OCH_3$ | H | S | |
| 15-133 | 2-$CH_3$S-4-$CF_3$-pyrimidine-6-yl | $CF_3$ | — | $COCH_2CH(CH_3)OCH_3$ | H | O | |
| 15-134 | 2-$CH_3$O-4-$CF_3$-pyrimidine-6-yl | $CF_3$ | — | $COCH_2CH(CH_3)OCH_3$ | H | NH | |
| 15-135 | 2-Cl-4-$CF_3$-pyrimidine-6-yl | $CF_3$ | — | $COCH_2CH(CH_3)OCH_3$ | H | $CH_2$ | |
| 15-136 | 2-Br-4-$CF_3$-pyrimidine-6-yl | $CF_3$ | — | $COCH_2CH(CH_3)OCH_3$ | H | S | |

TABLE 16

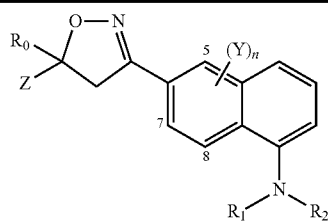

| Compound No. | Z | $R_0$ | (Yn) | $R_1$ | $R_2$ | Physical constant |
|---|---|---|---|---|---|---|
| 16-1 | 3,5-$Cl_2$Ph | $CF_3$ | — | n-Pr | H | |
| 16-2 | 3,5-$Cl_2$Ph | $CF_3$ | — | $CH_2CH_2$ (2-Py) | H | |
| 16-3 | 3,5-$Cl_2$Ph | $CF_3$ | — | $CH_2CH_2COCH_3$ | H | |
| 16-4 | 3,5-$Cl_2$Ph | $CF_3$ | — | $CH_2CH_2OCH_3$ | H | |
| 16-5 | 3,5-$Cl_2$Ph | $CF_3$ | — | $COCH_3$ | H | |

TABLE 16-continued

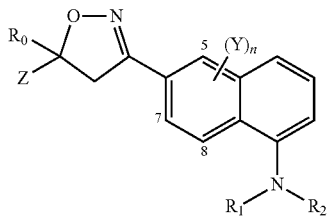

| Compound No. | Z | R₀ | (Yn) | R₁ | R₂ | Physical constant |
|---|---|---|---|---|---|---|
| 16-6 | 3,5-Cl₂Ph | CF₃ | — | COC₂H₅ | H | [223-225] |
| 16-7 | 3,5-Cl₂Ph | CF₃ | 2-Cl | COC₂H₅ | H | [116-119] |
| 16-8 | 3,5-Cl₂Ph | CF₃ | — | COPr-n | H | |
| 16-9 | 3,5-Cl₂Ph | CF₃ | — | COCH₂CH₂OCH₃ | H | |
| 16-10 | 3,5-Cl₂Ph | CF₃ | — | COCH₂CH₂OCH₂CH₃ | H | |
| 16-11 | 3,5-Cl₂Ph | CF₃ | — | COCH₂CH(CH₃)OCH₃ | H | |
| 16-12 | 3,5-Cl₂Ph | CF₃ | — | COCH₂CH(CH₃)OCH₂CH₃ | H | |
| 16-13 | 3,5-Cl₂Ph | CF₃ | — | COCH₂CH(CH₃)OH | H | |
| 16-14 | 3,5-Cl₂Ph | CF₃ | — | COCH₂CH₂OCH₂CH=CH₂ | H | |
| 16-15 | 3,5-Cl₂Ph | CF₃ | — | COCH₂COCH₃ | H | |
| 16-16 | 3,5-Cl₂Ph | CF₃ | — | COCH₂(1,3-dioxolane-2-yl) | H | |
| 16-17 | 3,5-Cl₂Ph | CF₃ | — | COCH₂(2-methyl-1,3-dioxolane-2-yl) | H | |
| 16-18 | 3,5-Cl₂Ph | CF₃ | — | COCH₂(2-trifluoromethyl-1,3-dioxolane-2-yl) | H | |
| 16-19 | 3,5-Cl₂Ph | CF₃ | — | COCH₂(2-methyl-1,3-dioxane-2-yl) | H | |
| 16-20 | 3,5-Cl₂Ph | CF₃ | — | COCH₂CH₂(1,3-dioxolane-2-yl) | H | |
| 16-21 | 3,5-Cl₂Ph | CF₃ | — | COCH₂CH₂(2-methyl-1,3-dioxolane-2-yl) | H | |
| 16-22 | 3,5-Cl₂Ph | CF₃ | — | CO(tetrahydropyran-4-yl) | H | |
| 16-23 | 3,5-Cl₂Ph | CF₃ | — | CO(2,6-dimethyl-4H-pyran-4-one-3-yl) | H | |
| 16-24 | 3,5-Cl₂Ph | CF₃ | — | COCH₂CH₂CN | H | |
| 16-25 | 3,5-Cl₂Ph | CF₃ | — | COCH₂CH₂Ph | H | |
| 16-26 | 3,5-Cl₂Ph | CF₃ | — | COCH₂CH₂(1,2,4-triazole-1-yl) | H | |
| 16-27 | 3,5-Cl₂Ph | CF₃ | — | COCH₂CH₂ (pyrazole-1-yl) | H | |
| 16-28 | 3-CF₃Ph | CF₃ | — | COC₂H₅ | H | |
| 16-29 | 3-CF₃Ph | CF₃ | — | COCH₂CH₂OCH₃ | H | |
| 16-30 | 3-CF₃Ph | CF₃ | — | COCH₂CH(CH₃)OCH₃ | H | |
| 16-31 | 3-CF₃Ph | CF₃ | — | COCH₂(2-methyl-1,3-dioxolane-2-yl) | H | |
| 16-32 | 3-CF₃Ph | CF₃ | — | COCH₂CH₂CN | H | |
| 16-33 | 3,5-Cl₂Ph | CF₃ | — | COPr-c | H | |
| 16-34 | 3,5-Cl₂Ph | CF₃ | — | COHex-c | H | |
| 16-35 | 2-F-3-CF₃Ph | CF₃ | — | COC₂H₅ | H | |
| 16-36 | 2-F-3-CF₃Ph | CF₃ | — | COCH₂CH₂OCH₃ | H | |
| 16-37 | 3-CF₃-4-ClPh | CF₃ | — | COC₂H₅ | H | |
| 16-38 | 3-CF₃-4-ClPh | CF₃ | — | COCH₂CH₂OCH₃ | H | |
| 16-39 | 3-CF₃-4-ClPh | CF₃ | — | COCH₂CH(CH₃)OCH₃ | H | |
| 16-40 | 3,5-Cl₂Ph | CF₃ | — | CSC₂H₅ | H | |
| 16-41 | 3,5-Cl₂Ph | CF₃ | — | 2-cyclohexenone-3-yl | H | |
| 16-42 | 3,5-Cl₂Ph | CF₃ | — | CH₂(4-methyl-1,3-dioxolene-2-one-5-yl) | H | |
| 16-43 | 3,5-Cl₂Ph | CF₃ | — | CH₂(4-methyl-1,3-dioxolene-2-one-5-yl) | CH₂(4-methyl-1,3-dioxolene-2-one-5-y1) | |
| 16-44 | 3,5-Cl₂Ph | CF₃ | — | COC₂H₅ | CH₃ | |
| 16-45 | 3,5-Cl₂Ph | CF₃ | — | H | H | |
| 16-46 | 3-CF₃Ph | CF₃ | — | H | H | |
| 16-47 | 2-F-3-CF₃Ph | CF₃ | — | H | H | |
| 16-48 | 3-CF₃-4-ClPh | CF₃ | — | H | H | |
| 16-49 | 3,5-Cl₂Ph | CF₃ | 5-F | COC₂H₅ | H | |
| 16-50 | 3,5-Cl₂Ph | CF₃ | 5-Cl | COC₂H₅ | H | |
| 16-51 | 3,5-Cl₂Ph | CF₃ | 5-CH₃ | COC₂H₅ | H | |
| 16-52 | 3,5-Cl₂Ph | CF₃ | 5-CF₃ | COC₂H₅ | H | |
| 16-53 | 3,5-Cl₂Ph | CF₃ | 5-CH₂OCH₃ | COC₂H₅ | H | |
| 16-54 | 3,5-Cl₂Ph | CF₃ | 5-NO₂ | COC₂H₅ | H | |
| 16-55 | 3,5-Cl₂Ph | CF₃ | 5-OH | COC₂H₅ | H | |
| 16-56 | 3,5-Cl₂Ph | CF₃ | 5-OCH₃ | COC₂H₅ | H | |
| 16-57 | 3,5-Cl₂Ph | CF₃ | 5-OCF₃ | COC₂H₅ | H | |
| 16-58 | 3,5-Cl₂Ph | CF₃ | 5-OCH₂COCH₃ | COC₂H₅ | H | |

TABLE 16-continued

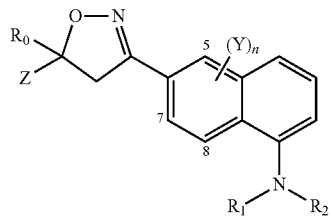

| Compound No. | Z | R₀ | (Yn) | R₁ | R₂ | Physical constant |
|---|---|---|---|---|---|---|
| 16-59 | 3,5-Cl₂Ph | CF₃ | 5-SH | COC₂H₅ | H | |
| 16-60 | 3,5-Cl₂Ph | CF₃ | 5-SCH₃ | COC₂H₅ | H | |
| 16-61 | 3,5-Cl₂Ph | CF₃ | 5-SCF₃ | COC₂H₅ | H | |
| 16-62 | 3,5-Cl₂Ph | CF₃ | 5-NH₂ | COC₂H₅ | H | |
| 16-63 | 3,5-Cl₂Ph | CF₃ | 5-NHCH₃ | COC₂H₅ | H | |
| 16-64 | 3,5-Cl₂Ph | CF₃ | 5-N(CH₃)₂ | COC₂H₅ | H | |
| 16-65 | 3,5-Cl₂Ph | CF₃ | 5-NHPh | COC₂H₅ | H | |
| 16-66 | 3,5-Cl₂Ph | CF₃ | 5-NHCOCH₃ | COC₂H₅ | H | |
| 16-67 | 3,5-Cl₂Ph | CF₃ | 5-NHCO₂C₂H₅ | COC₂H₅ | H | |
| 16-68 | 3,5-Cl₂Ph | CF₃ | 5-NHCO₂Bu-t | COC₂H₅ | H | |
| 16-69 | 3,5-Cl₂Ph | CF₃ | 5-NHCH₂Ph | COC₂H₅ | H | |
| 16-70 | 3,5-Cl₂Ph | CF₃ | 8-F | COC₂H₅ | H | |
| 16-71 | 3,5-Cl₂Ph | NO₂ | — | COC₂H₅ | H | |
| 16-72 | 3,5-Cl₂Ph | OH | — | COC₂H₅ | H | |
| 16-73 | 3,5-Cl₂Ph | OMe | — | COC₂H₅ | H | |
| 16-74 | 3,5-Cl₂Ph | OCF₃ | — | COC₂H₅ | H | |
| 16-75 | 3,5-Cl₂Ph | SH | — | COC₂H₅ | H | |
| 16-76 | 3,5-Cl₂Ph | SCF₃ | — | COC₂H₅ | H | |
| 16-77 | 3,5-Cl₂Ph | Cl | — | COC₂H₅ | H | |
| 16-78 | 3,5-Cl₂Ph | NH₂ | — | COC₂H₅ | H | |
| 16-79 | 3,5-Cl₂Ph | NHCOCH₃ | — | COC₂H₅ | H | |
| 16-80 | 3,5-Cl₂Ph | NHCO₂C₂H₅ | — | COC₂H₅ | H | |
| 16-81 | 3,5-Cl₂Ph | CO₂C₂H₅ | — | COC₂H₅ | H | |
| 16-82 | 3,5-Cl₂Ph | SO₂CH₃ | — | COC₂H₅ | H | |
| 16-83 | 3,5-Cl₂Ph | SO₂CF₃ | — | COC₂H₅ | H | |
| 16-84 | 3,5-Cl₂Ph | Ph | — | COC₂H₅ | H | |
| 16-85 | 3,5-Cl₂Ph | COCH₃ | — | COC₂H₅ | H | |
| 16-86 | 3,5-Cl₂Ph | Cl | — | COC₂H₅ | H | |
| 16-87 | 3,5-Cl₂Ph | CF₂H | — | COC₂H₅ | H | |
| 16-88 | 3,5-Cl₂Ph | CCl₃ | — | COC₂H₅ | H | |
| 16-89 | 3,5-Cl₂Ph | CF₂Cl | — | COC₂H₅ | H | |
| 16-90 | CH₃CH=CH | CF₃ | — | COC₂H₅ | H | |
| 16-91 | Propargyl | CF₃ | — | COC₂H₅ | H | |
| 16-92 | CH₂=CHCH₂ | CF₃ | — | COC₂H₅ | H | |
| 16-93 | 2-butynyl | CF₃ | — | COC₂H₅ | H | |
| 16-94 | 3,5-Cl₂Ph | CF₃ | — | =CHOCH₃ | | |
| 16-95 | 3,5-Cl₂Ph | CF₃ | — | =C(OCH₃)₂ | | |
| 16-96 | 3,5-Cl₂Ph | CF₃ | — | =CHNO₂ | | |
| 16-97 | 3,5-Cl₂Ph | CF₃ | — | =C(OCH₂CH₂O) | | |
| 16-98 | 3,5-Cl₂Ph | CF₃ | — | CONHCH₃ | H | |
| 16-99 | 3,5-Cl₂Ph | CF₃ | — | CONHC₂H₅ | H | |
| 16-100 | 3,5-Cl₂Ph | CF₃ | — | CONHPr-n | H | |
| 16-101 | 3,5-Cl₂Ph | CF₃ | — | CONHCH₂CH₂OCH₃ | H | |
| 16-102 | 3,5-Cl₂Ph | CF₃ | — | CONHCH₂CH₂OCH₂CH₃ | H | |
| 16-103 | 3,5-Cl₂Ph | CF₃ | — | CONHCH₂CH(CH₃)OCH₃ | H | |
| 16-104 | 3,5-Cl₂Ph | CF₃ | — | CON(CH₃)₂ | H | |
| 16-105 | 3,5-Cl₂Ph | CF₃ | — | CONHCH₂CH₂CN | H | |
| 16-106 | 3,5-Cl₂Ph | CF₃ | — | CONHCH₂CH₂Ph | H | |
| 16-107 | 3,5-Cl₂Ph | CF₃ | — | CONHCH₂CH₂(1,2,4-triazole-1-yl) | H | |
| 16-108 | 3,5-Cl₂Ph | CF₃ | — | CONHCH₂CH₂(pyrazole-1-yl) | H | |
| 16-109 | 3,5-Cl₂Ph | CF₃ | — | CONHOH | H | |
| 16-110 | 3,5-Cl₂Ph | CF₃ | — | CONHOCH₃ | H | |
| 16-111 | 3,5-Cl₂Ph | CF₃ | — | CONHPr-c | H | |
| 16-112 | 3,5-Cl₂Ph | CF₃ | — | CONHPh | H | |
| 16-113 | 3,5-Cl₂Ph | CF₃ | — | CSNHCH₃ | H | |
| 16-114 | 3,5-Cl₂Ph | CF₃ | — | CO₂C₂H₅ | H | |
| 16-115 | 3,5-Cl₂Ph | CF₃ | — | CO₂Pr-n | H | |
| 16-116 | 3,5-Cl₂Ph | CF₃ | — | CO₂Bu-t | H | [188-190] |
| 16-117 | 3,5-Cl₂Ph | CF₃ | — | CO₂Pr-c | H | |
| 16-118 | 3,5-Cl₂Ph | CF₃ | — | CO₂CH₂CH₂OCH₃ | H | |
| 16-119 | 3,5-Cl₂Ph | CF₃ | — | CO₂CH₂CH₂OCH₂CH₃ | H | |
| 16-120 | 3,5-Cl₂Ph | CF₃ | — | CO₂CH₂CH(CH₃)OCH₃ | H | |
| 16-121 | 3,5-Cl₂Ph | CF₃ | — | CO₂CH₂CH₂CN | H | |
| 16-122 | 3,5-Cl₂Ph | CF₃ | — | CO₂CH₂CH₂Ph | H | |
| 16-123 | 3,5-Cl₂Ph | CF₃ | — | CO₂CH₂CH₂(1,2,4-triazole-1-yl) | H | |

TABLE 16-continued

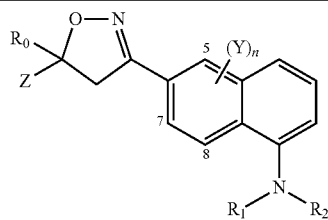

| Compound No. | Z | $R_0$ | (Yn) | $R_1$ | $R_2$ | Physical constant |
|---|---|---|---|---|---|---|
| 16-124 | 3,5-$Cl_2$Ph | $CF_3$ | — | $CO_2CH_2CH_2$(pyrazole-1-yl) | H | |
| 16-125 | 3,5-$Cl_2$Ph | $CF_3$ | — | $CH_2CH_2CH_2CH_2$ | | |
| 16-126 | 3,5-$Cl_2$Ph | $CF_3$ | — | $C(=O)CH_2CH_2CH_2$ | | |
| 16-127 | 3,5-$Cl_2$Ph | $CF_3$ | — | $C(=O)CH_2CH_2C(=O)$ | | |
| 16-128 | 3,5-$Cl_2$Ph | $CF_3$ | — | phthaloyl | | |
| 16-129 | 2,4-di$CF_3$-pyrimidine-6-yl | $CF_3$ | — | $COCH_2CH(CH_3)OCH_3$ | H | |
| 16-130 | 2-$CH_3$S-4-$CF_3$-pyrimidine-6-yl | $CF_3$ | — | $COCH_2CH(CH_3)OCH_3$ | H | |
| 16-131 | 2-$CH_3$O-4-$CF_3$-pyrimidine-6-yl | $CF_3$ | — | $COCH_2CH(CH_3)OCH_3$ | H | |
| 16-132 | 2-Cl-4-$CF_3$-pyrimidine-6-yl | $CF_3$ | — | $COCH_2CH(CH_3)OCH_3$ | H | |
| 16-133 | 2-Br-4-$CF_3$-pyrimidine-6-yl | $CF_3$ | — | $COCH_2CH(CH_3)OCH_3$ | H | |

TABLE 17

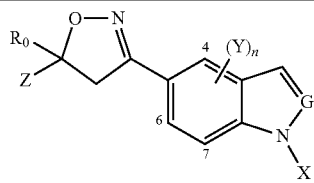

| Compound No. | Z | $R_0$ | (Y)n | X | G | Physical constant |
|---|---|---|---|---|---|---|
| 17-1 | 3,5-$Cl_2$Ph | $CF_3$ | — | — | CH | [157-159] |
| 17-2 | 3,5-$Cl_2$Ph | $CF_3$ | — | $COCH_3$ | CH | amorphous |
| 17-3 | 3,5-$Cl_2$Ph | $CF_3$ | — | $COC_2H_5$ | CH | amorphous |
| 17-4 | 3,5-$Cl_2$Ph | $CF_3$ | — | COPr-n | CH | |
| 17-5 | 3,5-$Cl_2$Ph | $CF_3$ | — | $COCH_2CH_2OCH_3$ | N | |
| 17-6 | 3,5-$Cl_2$Ph | $CF_3$ | — | $COCH_2CH_2OCH_2CH_3$ | CH | |
| 17-7 | 3,5-$Cl_2$Ph | $CF_3$ | — | $COCH_2CH(CH_3)OCH_3$ | N | |
| 17-8 | 3,5-$Cl_2$Ph | $CF_3$ | — | $COCH_2CH(CH_3)OCH_2CH_3$ | CH | |
| 17-9 | 3,5-$Cl_2$Ph | $CF_3$ | — | $COCH_2CH(CH_3)OH$ | N | |
| 17-10 | 3,5-$Cl_2$Ph | $CF_3$ | — | $COCH_2CH_2OCH_2CH=CH_2$ | CH | |
| 17-11 | 3,5-$Cl_2$Ph | $CF_3$ | — | $COCH_2COCH_3$ | N | |
| 17-12 | 3,5-$Cl_2$Ph | $CF_3$ | — | $COCH_2$(1,3-dioxolane-2-yl) | CH | |
| 17-13 | 3,5-$Cl_2$Ph | $CF_3$ | — | $COCH_2$(2-methyl-1,3-dioxolane-2-yl) | N | |
| 17-14 | 3,5-$Cl_2$Ph | $CF_3$ | — | $COCH_2$(2-trifluoromethyl-1,3-dioxolane-2-yl) | CH | |
| 17-15 | 3,5-$Cl_2$Ph | $CF_3$ | — | $COCH_2$(2-methyl-1,3-dioxane-2-yl) | N | |
| 17-16 | 3,5-$Cl_2$Ph | $CF_3$ | — | $COCH_2CH_2$(1,3-dioxolane-2-yl) | CH | |
| 17-17 | 3,5-$Cl_2$Ph | $CF_3$ | — | $COCH_2CH_2$(2-methyl-1,3-dioxolane-2-yl) | N | |
| 17-18 | 3,5-$Cl_2$Ph | $CF_3$ | — | CO(tetrahydropyran-4-yl) | CH | |
| 17-19 | 3,5-$Cl_2$Ph | $CF_3$ | — | CO(2,6-dimethyl-4H-pyran-4-one-3-yl) | N | |
| 17-20 | 3,5-$Cl_2$Ph | $CF_3$ | — | $COCH_2CH_2CN$ | CH | |
| 17-21 | 3,5-$Cl_2$Ph | $CF_3$ | — | $COCH_2CH_2Ph$ | N | |
| 17-22 | 3,5-$Cl_2$Ph | $CF_3$ | — | $COCH_2CH_2$(1,2,4-triazole-1-yl) | CH | |
| 17-23 | 3,5-$Cl_2$Ph | $CF_3$ | — | $COCH_2CH_2$(pyrazole-1-yl) | N | |

TABLE 17-continued

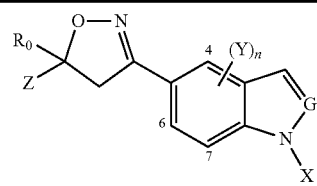

| Compound No. | Z | $R_0$ | (Y)n | X | G | Physical constant |
|---|---|---|---|---|---|---|
| 17-24 | 3-CF$_3$Ph | CF$_3$ | — | COC$_2$H$_5$ | CH | |
| 17-25 | 3-CF$_3$Ph | CF$_3$ | — | COCH$_2$CH$_2$OCH$_3$ | N | |
| 17-26 | 3-CF$_3$Ph | CF$_3$ | — | COCH$_2$CH(CH$_3$)OCH$_3$ | CH | |
| 17-27 | 3-CF$_3$Ph | CF$_3$ | — | COCH$_2$(2-methyl-1,3-dioxolane-2-yl) | N | |
| 17-28 | 3-CF$_3$Ph | CF$_3$ | — | COCH$_2$CH$_2$CN | CH | |
| 17-29 | 3,5-Cl$_2$Ph | CF$_3$ | — | COPr-c | N | |
| 17-30 | 3,5-Cl$_2$Ph | CF$_3$ | — | COHex-c | CH | |
| 17-31 | 2-F-3-CF$_3$Ph | CF$_3$ | — | COC$_2$H$_5$ | N | |
| 17-32 | 2-F-3-CF$_3$Ph | CF$_3$ | — | COCH$_2$CH$_2$OCH$_3$ | CH | |
| 17-33 | 3-CF$_3$-4-ClPh | CF$_3$ | — | COC$_2$H$_5$ | N | |
| 17-34 | 3-CF$_3$-4-ClPh | CF$_3$ | — | COCH$_2$CH$_2$OCH$_3$ | CH | |
| 17-35 | 3-CF$_3$-4-ClPh | CF$_3$ | — | COCH$_2$CH(CH$_3$)OCH$_3$ | N | |
| 17-36 | 3,5-Cl$_2$Ph | CF$_3$ | — | CSC$_2$H$_5$ | CH | |
| 17-37 | 3,5-Cl$_2$Ph | CF$_3$ | — | 2-cyclohexenone-3-yl | N | |
| 17-38 | 3,5-Cl$_2$Ph | CF$_3$ | — | H | CH | |
| 17-39 | 3-CF$_3$Ph | CF$_3$ | — | H | N | |
| 17-40 | 2-F-3-CF$_3$Ph | CF$_3$ | — | H | CH | |
| 17-41 | 3-CF$_3$-4-ClPh | CF$_3$ | — | H | N | |
| 17-42 | 3,5-Cl$_2$Ph | CF$_3$ | 4-F | COC$_2$H$_5$ | CH | |
| 17-43 | 3,5-Cl$_2$Ph | CF$_3$ | 4-Cl | COC$_2$H$_5$ | N | |
| 17-44 | 3,5-Cl$_2$Ph | CF$_3$ | 4-CH$_3$ | COC$_2$H$_5$ | CH | |
| 17-45 | 3,5-Cl$_2$Ph | CF$_3$ | 4-CF$_3$ | COC$_2$H$_5$ | N | |
| 17-46 | 3,5-Cl$_2$Ph | CF$_3$ | 4-CH$_2$OCH$_3$ | COC$_2$H$_5$ | CH | |
| 17-47 | 3,5-Cl$_2$Ph | CF$_3$ | 4-NO$_2$ | COC$_2$H$_5$ | N | |
| 17-48 | 3,5-Cl$_2$Ph | CF$_3$ | 4-OH | COC$_2$H$_5$ | CH | |
| 17-49 | 3,5-Cl$_2$Ph | CF$_3$ | 4-OCH$_3$ | COC$_2$H$_5$ | N | |
| 17-50 | 3,5-Cl$_2$Ph | CF$_3$ | 4-OCF$_3$ | COC$_2$H$_5$ | CH | |
| 17-51 | 3,5-Cl$_2$Ph | CF$_3$ | 4-OCH$_2$COCH$_3$ | COC$_2$H$_5$ | N | |
| 17-52 | 3,5-Cl$_2$Ph | CF$_3$ | 4-SH | COC$_2$H$_5$ | CH | |
| 17-53 | 3,5-Cl$_2$Ph | CF$_3$ | 4-SCH$_3$ | COC$_2$H$_5$ | N | |
| 17-54 | 3,5-Cl$_2$Ph | CF$_3$ | 4-SCF$_3$ | COC$_2$H$_5$ | CH | |
| 17-55 | 3,5-Cl$_2$Ph | CF$_3$ | 4-NH$_2$ | COC$_2$H$_5$ | N | |
| 17-56 | 3,5-Cl$_2$Ph | CF$_3$ | 4-NHCH$_3$ | COC$_2$H$_5$ | CH | |
| 17-57 | 3,5-Cl$_2$Ph | CF$_3$ | 4-N(CH$_3$)$_2$ | COC$_2$H$_5$ | N | |
| 17-58 | 3,5-Cl$_2$Ph | CF$_3$ | 4-NHPh | COC$_2$H$_5$ | CH | |
| 17-59 | 3,5-Cl$_2$Ph | CF$_3$ | 4-NHCOCH$_3$ | COC$_2$H$_5$ | N | |
| 17-60 | 3,5-Cl$_2$Ph | CF$_3$ | 4-NHCO$_2$C$_2$H$_5$ | COC$_2$H$_5$ | CH | |
| 17-61 | 3,5-Cl$_2$Ph | CF$_3$ | 4-NHCO$_2$Bu-t | COC$_2$H$_5$ | N | |
| 17-62 | 3,5-Cl$_2$Ph | CF$_3$ | 4-NHCH$_2$Ph | COC$_2$H$_5$ | CH | |
| 17-63 | 3,5-Cl$_2$Ph | CF$_3$ | 7-F | COC$_2$H$_5$ | N | |
| 17-64 | 3,5-Cl$_2$Ph | NO$_2$ | — | COC$_2$H$_5$ | CH | |
| 17-65 | 3,5-Cl$_2$Ph | OH | — | COC$_2$H$_5$ | N | |
| 17-66 | 3,5-Cl$_2$Ph | OMe | — | COC$_2$H$_5$ | CH | |
| 17-67 | 3,5-Cl$_2$Ph | OCF$_3$ | — | COC$_2$H$_5$ | N | |
| 17-68 | 3,5-Cl$_2$Ph | SH | — | COC$_2$H$_5$ | CH | |
| 17-69 | 3,5-Cl$_2$Ph | SCF$_3$ | — | COC$_2$H$_5$ | N | |
| 17-70 | 3,5-Cl$_2$Ph | Cl | — | COC$_2$H$_5$ | CH | |
| 17-71 | 3,5-Cl$_2$Ph | NH$_2$ | — | COC$_2$H$_5$ | N | |
| 17-72 | 3,5-Cl$_2$Ph | NHCOCH$_3$ | — | COC$_2$H$_5$ | CH | |
| 17-73 | 3,5-Cl$_2$Ph | NHCO$_2$C$_2$H$_5$ | — | COC$_2$H$_5$ | N | |
| 17-74 | 3,5-Cl$_2$Ph | CO$_2$C$_2$H$_5$ | — | COC$_2$H$_5$ | CH | |
| 17-75 | 3,5-Cl$_2$Ph | SO$_2$CH$_3$ | — | COC$_2$H$_5$ | N | |
| 17-76 | 3,5-Cl$_2$Ph | SO$_2$CF$_3$ | — | COC$_2$H$_5$ | CH | |
| 17-77 | 3,5-Cl$_2$Ph | Ph | — | COC$_2$H$_5$ | N | |
| 17-78 | 3,5-Cl$_2$Ph | COCH$_3$ | — | COC$_2$H$_5$ | CH | |
| 17-79 | 3,5-Cl$_2$Ph | Cl | — | COC$_2$H$_5$ | N | |
| 17-80 | 3,5-Cl$_2$Ph | CF$_2$H | — | COC$_2$H$_5$ | CH | |
| 17-81 | 3,5-Cl$_2$Ph | CCl$_3$ | — | COC$_2$H$_5$ | N | |
| 17-82 | 3,5-Cl$_2$Ph | CF$_2$Cl | — | COC$_2$H$_5$ | CH | |
| 17-83 | CH$_3$CH=CH | CF$_3$ | — | COC$_2$H$_5$ | N | |
| 17-84 | Propargyl | CF$_3$ | — | COC$_2$H$_5$ | CH | |
| 17-85 | CH$_2$=CHCH$_2$ | CF$_3$ | — | COC$_2$H$_5$ | N | |
| 17-86 | 2-butynyl | CF$_3$ | — | COC$_2$H$_5$ | CH | |
| 17-87 | 3,5-Cl$_2$Ph | CF$_3$ | — | CONHCH$_3$ | N | [165-169] |
| 17-88 | 3,5-Cl$_2$Ph | CF$_3$ | — | CONHC$_2$H$_5$ | CH | [189-191] |
| 17-89 | 3,5-Cl$_2$Ph | CF$_3$ | — | CONHC$_2$H$_5$ | N | amorphous |
| 17-90 | 3,5-Cl$_2$Ph | CF$_3$ | — | CONHPr-n | N | |

TABLE 17-continued

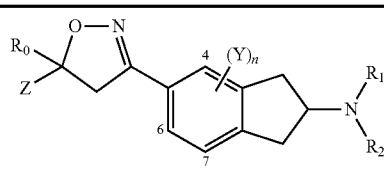

| Compound No. | Z | $R_0$ | (Y)n | X | G | Physical constant |
|---|---|---|---|---|---|---|
| 17-91 | 3,5-$Cl_2$Ph | $CF_3$ | — | CONHPr-i | CH | [216-219] |
| 17-92 | 3,5-$Cl_2$Ph | $CF_3$ | — | CONHPr-i | N | amorphous |
| 17-93 | 3,5-$Cl_2$Ph | $CF_3$ | — | CONHCH$_2$CH$_2$OCH$_3$ | CH | |
| 17-94 | 3,5-$Cl_2$Ph | $CF_3$ | — | CONHCH$_2$CH$_2$OCH$_2$CH$_3$ | N | |
| 17-95 | 3,5-$Cl_2$Ph | $CF_3$ | — | CONHCH$_2$CH(CH$_3$)OCH$_3$ | CH | |
| 17-96 | 3,5-$Cl_2$Ph | $CF_3$ | — | CON(CH$_3$)$_2$ | N | |
| 17-97 | 3,5-$Cl_2$Ph | $CF_3$ | — | CON(CH$_2$CH$_3$)$_2$ | CH | amorphous |
| 17-98 | 3,5-$Cl_2$Ph | $CF_3$ | — | CONHCH$_2$CH$_2$CN | N | |
| 17-99 | 3,5-$Cl_2$Ph | $CF_3$ | — | CONHCH$_2$Ph | CH | [162-165] |
| 17-100 | 3,5-$Cl_2$Ph | $CF_3$ | — | CONHCH$_2$CH$_2$Ph | N | |
| 17-101 | 3,5-$Cl_2$Ph | $CF_3$ | — | CONHCH$_2$CH$_2$(1,2,4-triazole-1-yl) | CH | |
| 17-102 | 3,5-$Cl_2$Ph | $CF_3$ | — | CONHCH$_2$CH$_2$(pyrazole-1-yl) | N | |
| 17-103 | 3,5-$Cl_2$Ph | $CF_3$ | — | CONHCH$_2$(2-Py) | CH | amorphous |
| 17-104 | 3,5-$Cl_2$Ph | $CF_3$ | — | CONHCH$_2$(2-Py) | N | [182-185] |
| 17-105 | 3,5-$Cl_2$Ph | $CF_3$ | — | CONHOH | CH | |
| 17-106 | 3,5-$Cl_2$Ph | $CF_3$ | — | CONHOCH$_3$ | N | |
| 17-107 | 3,5-$Cl_2$Ph | $CF_3$ | — | CONHPr-c | CH | |
| 17-108 | 3,5-$Cl_2$Ph | $CF_3$ | — | CONHPh | N | [196-199] |
| 17-109 | 3,5-$Cl_2$Ph | $CF_3$ | — | CSNHCH$_3$ | CH | |
| 17-110 | 3,5-$Cl_2$Ph | $CF_3$ | — | CSNHCH$_2$CH$_3$ | N | amorphous |
| 17-111 | 3,5-$Cl_2$Ph | $CF_3$ | — | CO$_2$CH$_3$ | CH | [138-140] |
| 17-112 | 3,5-$Cl_2$Ph | $CF_3$ | — | CO$_2$C$_2$H$_5$ | N | |
| 17-113 | 3,5-$Cl_2$Ph | $CF_3$ | — | CO$_2$Pr-n | CH | |
| 17-114 | 3,5-$Cl_2$Ph | $CF_3$ | — | CO$_2$Bu-t | CH | amorphous |
| 17-115 | 3,5-$Cl_2$Ph | $CF_3$ | — | CO$_2$Pr-c | N | |
| 17-116 | 3,5-$Cl_2$Ph | $CF_3$ | — | CO$_2$CH$_2$CH$_2$OCH$_3$ | CH | |
| 17-117 | 3,5-$Cl_2$Ph | $CF_3$ | — | CO$_2$CH$_2$CH$_2$OCH$_2$CH$_3$ | N | |
| 17-118 | 3,5-$Cl_2$Ph | $CF_3$ | — | CO$_2$CH$_2$CH(CH$_3$)OCH$_3$ | CH | |
| 17-119 | 3,5-$Cl_2$Ph | $CF_3$ | — | CO$_2$CH$_2$CH$_2$CN | N | |
| 17-120 | 3,5-$Cl_2$Ph | $CF_3$ | — | CO$_2$CH$_2$CH$_2$Ph | CH | |
| 17-121 | 3,5-$Cl_2$Ph | $CF_3$ | — | CO$_2$CH$_2$CH$_2$(1,2,4-triazole-1-yl) | N | |
| 17-122 | 3,5-$Cl_2$Ph | $CF_3$ | — | CO$_2$CH$_2$CH$_2$(pyrazole-1-yl) | CH | |
| 17-123 | 2,4-di$CF_3$-pyrimidine-6-yl | $CF_3$ | — | COCH$_2$CH(CH$_3$)OCH$_3$ | N | |
| 17-124 | 2-CH$_3$S-4-CF$_3$-pyrimidine-6-yl | $CF_3$ | — | COCH$_2$CH(CH$_3$)OCH$_3$ | CH | |
| 17-125 | 2-CH$_3$O-4-CF$_3$-pyrimidine-6-yl | $CF_3$ | — | COCH$_2$CH(CH$_3$)OCH$_3$ | N | |
| 17-126 | 2-Cl-4-CF$_3$-pyrimidine-6-yl | $CF_3$ | — | COCH$_2$CH(CH$_3$)OCH$_3$ | CH | |
| 17-127 | 2-Br-4-CF$_3$-pyrimidine-6-yl | $CF_3$ | — | COCH$_2$CH(CH$_3$)OCH$_3$ | N | |

TABLE 18

| Compound No. | Z | $R_0$ | (Y)n | $R_1$ | $R_2$ | Physical constant |
|---|---|---|---|---|---|---|
| 18-1 | 3,5-$Cl_2$Ph | $CF_3$ | — | n-Pr | H | |
| 18-2 | 3,5-$Cl_2$Ph | $CF_3$ | — | CH$_2$CH$_2$(2-Py) | H | |
| 18-3 | 3,5-$Cl_2$Ph | $CF_3$ | — | CH$_2$CH$_2$COCH$_3$ | H | |
| 18-4 | 3,5-$Cl_2$Ph | $CF_3$ | — | CH$_2$CH$_2$OCH$_3$ | H | |
| 18-5 | 3,5-$Cl_2$Ph | $CF_3$ | — | COCH$_3$ | H | [197-200] |
| 18-6 | 3,5-$Cl_2$Ph | $CF_3$ | — | COC$_2$H$_5$ | H | [78-95] |
| 18-7 | 3,5-$Cl_2$Ph | $CF_3$ | — | COPr-n | H | amorphous |

TABLE 18-continued

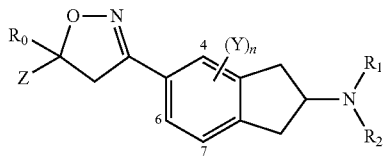

| Compound No. | Z | $R_0$ | $(Y)n$ | $R_1$ | $R_2$ | Physical constant |
|---|---|---|---|---|---|---|
| 18-8 | 3,5-Cl$_2$Ph | CF$_3$ | — | COCH$_2$CH$_2$OCH$_3$ | H | |
| 18-9 | 3,5-Cl$_2$Ph | CF$_3$ | — | COCH$_2$CH$_2$OCH$_2$CH$_3$ | H | |
| 18-10 | 3,5-Cl$_2$Ph | CF$_3$ | — | COCH$_2$CH(CH$_3$)OCH$_3$ | H | amorphous |
| 18-11 | 3,5-Cl$_2$Ph | CF$_3$ | — | COCH$_2$CH(CH$_3$)OCH$_2$CH$_3$ | H | |
| 18-12 | 3,5-Cl$_2$Ph | CF$_3$ | — | COCH$_2$CH(CH$_3$)OH | H | |
| 18-13 | 3,5-Cl$_2$Ph | CF$_3$ | — | COCH$_2$CH$_2$OCH$_2$CH=CH$_2$ | H | |
| 18-14 | 3,5-Cl$_2$Ph | CF$_3$ | — | COCH$_2$COCH$_3$ | H | |
| 18-15 | 3,5-Cl$_2$Ph | CF$_3$ | — | COCH$_2$(1,3-dioxolane-2-yl) | H | |
| 18-16 | 3,5-Cl$_2$Ph | CF$_3$ | — | COCH$_2$(2-methyl-1,3-dioxolane-2-yl) | H | amorphous |
| 18-17 | 3,5-Cl$_2$Ph | CF$_3$ | — | COCH$_2$(2-trifluoromethyl-1,3-dioxolane-2-yl) | H | |
| 18-18 | 3,5-Cl$_2$Ph | CF$_3$ | — | COCH$_2$(2-methyl-1,3-dioxane-2-yl) | H | |
| 18-19 | 3,5-Cl$_2$Ph | CF$_3$ | — | COCH$_2$CH$_2$(1,3-dioxolane-2-yl) | H | |
| 18-20 | 3,5-Cl$_2$Ph | CF$_3$ | — | COCH$_2$CH$_2$(2-methyl-1,3-dioxolane-2-yl) | H | |
| 18-21 | 3,5-Cl$_2$Ph | CF$_3$ | — | CO(tetrahydropyran-4-yl) | H | |
| 18-22 | 3,5-Cl$_2$Ph | CF$_3$ | — | CO(2,6-dimethyl-4H-pyran-4-one-3-yl) | H | |
| 18-23 | 3,5-Cl$_2$Ph | CF$_3$ | — | COCH$_2$CH$_2$CN | H | amorphous |
| 18-24 | 3,5-Cl$_2$Ph | CF$_3$ | — | COCH$_2$CH$_2$Ph | H | |
| 18-25 | 3,5-Cl$_2$Ph | CF$_3$ | — | COCH$_2$CH$_2$(1,2,4-triazole-1-yl) | H | |
| 18-26 | 3,5-Cl$_2$Ph | CF$_3$ | — | COCH$_2$CH$_2$(pyrazole-1-yl) | H | |
| 18-27 | 3-CF$_3$Ph | CF$_3$ | — | COC$_2$H$_5$ | H | |
| 18-28 | 3-CF$_3$Ph | CF$_3$ | — | COCH$_2$CH$_2$OCH$_3$ | H | |
| 18-29 | 3-CF$_3$Ph | CF$_3$ | — | COCH$_2$CH(CH$_3$)OCH$_3$ | H | |
| 18-30 | 3-CF$_3$Ph | CF$_3$ | — | COCH$_2$(2-methyl-1,3-dioxolane-2-yl) | H | |
| 18-31 | 3-CF$_3$Ph | CF$_3$ | — | COCH$_2$CH$_2$CN | H | amorphous |
| 18-32 | 3,5-Cl$_2$Ph | CF$_3$ | — | COPr-c | H | amorphous |
| 18-33 | 3,5-Cl$_2$Ph | CF$_3$ | — | COHex-c | H | |
| 18-34 | 2-F-3-CF$_3$Ph | CF$_3$ | — | COC$_2$H$_5$ | H | |
| 18-35 | 2-F-3-CF$_3$Ph | CF$_3$ | — | COCH$_2$CH$_2$OCH$_3$ | H | |
| 18-36 | 3-CF$_3$-4-ClPh | CF$_3$ | — | COC$_2$H$_5$ | H | |
| 18-37 | 3-CF$_3$-4-ClPh | CF$_3$ | — | COCH$_2$CH$_2$OCH$_3$ | H | |
| 18-38 | 3-CF$_3$-4-ClPh | CF$_3$ | — | COCH$_2$CH(CH$_3$)OCH$_3$ | H | |
| 18-39 | 3,5-Cl$_2$Ph | CF$_3$ | — | CSC$_2$H$_5$ | H | |
| 18-40 | 3,5-Cl$_2$Ph | CF$_3$ | — | 2-cyclohexenone-3-yl | H | |
| 18-41 | 3,5-Cl$_2$Ph | CF$_3$ | — | CH$_2$(4-methyl-1,3-dioxolene-2-one-5-yl) | H | |
| 18-42 | 3,5-Cl$_2$Ph | CF$_3$ | — | CH$_2$(4-methyl-1,3-dioxolene-2-one-5-yl) | CH$_2$(4-methyl-1,3-dioxolene-2-one-5-yl) | |
| 18-43 | 3,5-Cl$_2$Ph | CF$_3$ | — | COC$_2$H$_5$ | CH$_3$ | |
| 18-44 | 3,5-Cl$_2$Ph | CF$_3$ | — | H | H | amorphous |
| 18-45 | 3-CF$_3$Ph | CF$_3$ | — | H | H | |
| 18-46 | 2-F-3-CF$_3$Ph | CF$_3$ | — | H | H | |
| 18-47 | 3-CF$_3$-4-ClPh | CF$_3$ | — | H | H | |
| 18-48 | 3,5-Cl$_2$Ph | CF$_3$ | 4-F | COC$_2$H$_5$ | H | |
| 18-49 | 3,5-Cl$_2$Ph | CF$_3$ | 4-Cl | COC$_2$H$_5$ | H | |
| 18-50 | 3,5-Cl$_2$Ph | CF$_3$ | 4-CH$_3$ | COC$_2$H$_5$ | H | |
| 18-51 | 3,5-Cl$_2$Ph | CF$_3$ | 4-CF$_3$ | COC$_2$H$_5$ | H | |
| 18-52 | 3,5-Cl$_2$Ph | CF$_3$ | 4-CH$_2$OCH$_3$ | COC$_2$H$_5$ | H | |
| 18-53 | 3,5-Cl$_2$Ph | CF$_3$ | 4-NO$_2$ | COC$_2$H$_5$ | H | |
| 18-54 | 3,5-Cl$_2$Ph | CF$_3$ | 4-OH | COC$_2$H$_5$ | H | |
| 18-55 | 3,5-Cl$_2$Ph | CF$_3$ | 4-OCH$_3$ | COC$_2$H$_5$ | H | |
| 18-56 | 3,5-Cl$_2$Ph | CF$_3$ | 4-OCF$_3$ | COC$_2$H$_5$ | H | |
| 18-57 | 3,5-Cl$_2$Ph | CF$_3$ | 4-OCH$_2$COCH$_3$ | COC$_2$H$_5$ | H | |
| 18-58 | 3,5-Cl$_2$Ph | CF$_3$ | 4-SH | COC$_2$H$_5$ | H | |

TABLE 18-continued

| Compound No. | Z | $R_0$ | $(Y)n$ | $R_1$ | $R_2$ | Physical constant |
|---|---|---|---|---|---|---|
| 18-59 | 3,5-$Cl_2$Ph | $CF_3$ | 4-$SCH_3$ | $COC_2H_5$ | H | |
| 18-60 | 3,5-$Cl_2$Ph | $CF_3$ | 4-$SCF_3$ | $COC_2H_5$ | H | |
| 18-61 | 3,5-$Cl_2$Ph | $CF_3$ | 4-$NH_2$ | $COC_2H_5$ | H | |
| 18-62 | 3,5-$Cl_2$Ph | $CF_3$ | 4-$NHCH_3$ | $COC_2H_5$ | H | |
| 18-63 | 3,5-$Cl_2$Ph | $CF_3$ | 4-$N(CH_3)_2$ | $COC_2H_5$ | H | |
| 18-64 | 3,5-$Cl_2$Ph | $CF_3$ | 4-NHPh | $COC_2H_5$ | H | |
| 18-65 | 3,5-$Cl_2$Ph | $CF_3$ | 4-$NHCOCH_3$ | $COC_2H_5$ | H | |
| 18-66 | 3,5-$Cl_2$Ph | $CF_3$ | 4-$NHCO_2C_2H_5$ | $COC_2H_5$ | H | |
| 18-67 | 3,5-$Cl_2$Ph | $CF_3$ | 4-$NHCO_2$Bu-t | $COC_2H_5$ | H | |
| 18-68 | 3,5-$Cl_2$Ph | $CF_3$ | 4-$NHCH_2$Ph | $COC_2H_5$ | H | |
| 18-69 | 3,5-$Cl_2$Ph | $CF_3$ | 7-F | $COC_2H_5$ | H | |
| 18-70 | 3,5-$Cl_2$Ph | $NO_2$ | — | $COC_2H_5$ | H | |
| 18-71 | 3,5-$Cl_2$Ph | OH | — | $COC_2H_5$ | H | |
| 18-72 | 3,5-$Cl_2$Ph | OMe | — | $COC_2H_5$ | H | |
| 18-73 | 3,5-$Cl_2$Ph | $OCF_3$ | — | $COC_2H_5$ | H | |
| 18-74 | 3,5-$Cl_2$Ph | SH | — | $COC_2H_5$ | H | |
| 18-75 | 3,5-$Cl_2$Ph | $SCF_3$ | — | $COC_2H_5$ | H | |
| 18-76 | 3,5-$Cl_2$Ph | Cl | — | $COC_2H_5$ | H | |
| 18-77 | 3,5-$Cl_2$Ph | $NH_2$ | — | $COC_2H_5$ | H | |
| 18-78 | 3,5-$Cl_2$Ph | $NHCOCH_3$ | — | $COC_2H_5$ | H | |
| 18-79 | 3,5-$Cl_2$Ph | $NHCO_2C_2H_5$ | — | $COC_2H_5$ | H | |
| 18-80 | 3,5-$Cl_2$Ph | $CO_2C_2H_5$ | — | $COC_2H_5$ | H | |
| 18-81 | 3,5-$Cl_2$Ph | $SO_2CH_3$ | — | $COC_2H_5$ | H | |
| 18-82 | 3,5-$Cl_2$Ph | $SO_2CF_3$ | — | $COC_2H_5$ | H | |
| 18-83 | 3,5-$Cl_2$Ph | Ph | — | $COC_2H_5$ | H | |
| 18-84 | 3,5-$Cl_2$Ph | $COCH_3$ | — | $COC_2H_5$ | H | |
| 18-85 | 3,5-$Cl_2$Ph | Cl | — | $COC_2H_5$ | H | |
| 18-86 | 3,5-$Cl_2$Ph | $CF_2$H | — | $COC_2H_5$ | H | |
| 18-87 | 3,5-$Cl_2$Ph | $CCl_3$ | — | $COC_2H_5$ | H | |
| 18-88 | 3,5-$Cl_2$Ph | $CF_2Cl$ | — | $COC_2H_5$ | H | |
| 18-89 | $CH_3CH=CH$ | $CF_3$ | — | $COC_2H_5$ | H | |
| 18-90 | Propargyl | $CF_3$ | — | $COC_2H_5$ | H | |
| 18-91 | $CH_2=CHCH_2$ | $CF_3$ | — | $COC_2H_5$ | H | |
| 18-92 | 2-butynyl | $CF_3$ | — | $COC_2H_5$ | H | |
| 18-93 | 3,5-$Cl_2$Ph | $CF_3$ | — | $COC_2H_5$ | -(nitrogen atom forms double bond with indane ring) | |
| 18-94 | 3,5-$Cl_2$Ph | $CF_3$ | — | =$CHOCH_3$ | | |
| 18-95 | 3,5-$Cl_2$Ph | $CF_3$ | — | =$C(OCH_3)_2$ | | |
| 18-96 | 3,5-$Cl_2$Ph | $CF_3$ | — | =$CHNO_2$ | | |
| 18-97 | 3,5-$Cl_2$Ph | $CF_3$ | — | =$C(OCH_2CH_2O)$ | | |
| 18-98 | 3,5-$Cl_2$Ph | $CF_3$ | — | $CONHCH_3$ | H | |
| 18-99 | 3,5-$Cl_2$Ph | $CF_3$ | — | $CONHC_2H_5$ | H | |
| 18-100 | 3,5-$Cl_2$Ph | $CF_3$ | — | CONHPr-n | H | |
| 18-101 | 3,5-$Cl_2$Ph | $CF_3$ | — | $CONHCH_2CH_2OCH_3$ | H | |
| 18-102 | 3,5-$Cl_2$Ph | $CF_3$ | — | $CONHCH_2CH_2OCH_2CH_3$ | H | |
| 18-103 | 3,5-$Cl_2$Ph | $CF_3$ | — | $CONHCH_2CH(CH_3)OCH_3$ | H | |
| 18-104 | 3,5-$Cl_2$Ph | $CF_3$ | — | $CON(CH_3)_2$ | H | |
| 18-105 | 3,5-$Cl_2$Ph | $CF_3$ | — | $CONHCH_2CH_2CN$ | H | |
| 18-106 | 3,5-$Cl_2$Ph | $CF_3$ | — | $CONHCH_2CH_2$Ph | H | |
| 18-107 | 3,5-$Cl_2$Ph | $CF_3$ | — | $CONHCH_2CH_2$(1,2,4-triazole-1-yl) | H | |
| 18-108 | 3,5-$Cl_2$Ph | $CF_3$ | — | $CONHCH_2CH_2$ (pyrazole-1-yl) | H | |
| 18-109 | 3,5-$Cl_2$Ph | $CF_3$ | — | CONHOH | H | |
| 18-110 | 3,5-$Cl_2$Ph | $CF_3$ | — | $CONHOCH_3$ | H | |
| 18-111 | 3,5-$Cl_2$Ph | $CF_3$ | — | CONHPr-c | H | |
| 18-112 | 3,5-$Cl_2$Ph | $CF_3$ | — | CONHPh | H | |
| 18-113 | 3,5-$Cl_2$Ph | $CF_3$ | — | $CSNHCH_3$ | H | |
| 18-114 | 3,5-$Cl_2$Ph | $CF_3$ | — | $CO_2C_2H_5$ | H | |
| 18-115 | 3,5-$Cl_2$Ph | $CF_3$ | — | $CO_2$Pr-n | H | |
| 18-116 | 3,5-$Cl_2$Ph | $CF_3$ | — | $CO_2$Pr-c | H | |
| 18-117 | 3,5-$Cl_2$Ph | $CF_3$ | — | $CO_2CH_2CH_2OCH_3$ | H | |
| 18-118 | 3,5-$Cl_2$Ph | $CF_3$ | — | $CO_2CH_2CH_2OCH_2CH_3$ | H | |
| 18-119 | 3,5-$Cl_2$Ph | $CF_3$ | — | $CO_2CH_2CH(CH_3)OCH_3$ | H | |
| 18-120 | 3,5-$Cl_2$Ph | $CF_3$ | — | $CO_2CH_2CH_2CN$ | H | |
| 18-121 | 3,5-$Cl_2$Ph | $CF_3$ | — | $CO_2CH_2CH_2$Ph | H | |

TABLE 18-continued

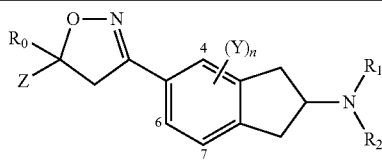

| Compound No. | Z | $R_0$ | (Y)n | $R_1$ | $R_2$ | Physical constant |
|---|---|---|---|---|---|---|
| 18-122 | 3,5-$Cl_2$Ph | $CF_3$ | — | $CO_2CH_2CH_2$(1,2,4-triazole-1-yl) | H | |
| 18-123 | 3,5-$Cl_2$Ph | $CF_3$ | — | $CO_2CH_2CH_2$(pyrazole-1-yl) | H | |
| 18-124 | 3,5-$Cl_2$Ph | $CF_3$ | — | $CH_2CH_2CH_2CH_2$ | | |
| 18-125 | 3,5-$Cl_2$Ph | $CF_3$ | — | C(=O)$CH_2CH_2CH_2$ | | |
| 18-126 | 3,5-$Cl_2$Ph | $CF_3$ | — | C(=O)$CH_2CH_2$C(=O) | | |
| 18-127 | 3,5-$Cl_2$Ph | $CF_3$ | — | phthaloyl | | |
| 18-128 | 2,4-di$CF_3$-pyrimidine-6-yl | $CF_3$ | — | $COCH_2CH(CH_3)OCH_3$ | H | |
| 18-129 | 2-$CH_3$S-4-$CF_3$-pyrimidine-6-yl | $CF_3$ | — | $COCH_2CH(CH_3)OCH_3$ | H | |
| 18-130 | 2-$CH_3$O-4-$CF_3$-pyrimidine-6-yl | $CF_3$ | — | $COCH_2CH(CH_3)OCH_3$ | H | |
| 18-131 | 2-Cl-4-$CF_3$-pyrimidine-6-yl | $CF_3$ | — | $COCH_2CH(CH_3)OCH_3$ | H | |
| 18-132 | 2-Br-4-$CF_3$-pyrimidine-6-yl | $CF_3$ | — | $COCH_2CH(CH_3)OCH_3$ | H | |

TABLE 19

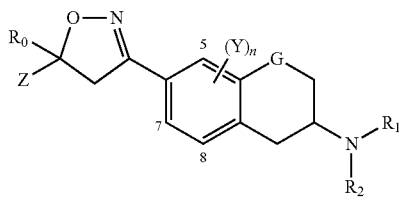

| Compound No. | Z | $R_0$ | (Y)n | $R_1$ | $R_2$ | G | Physical constant |
|---|---|---|---|---|---|---|---|
| 19-1 | 3,5-$Cl_2$Ph | $CF_3$ | — | n-Pr | H | $CH_2$ | |
| 19-2 | 3,5-$Cl_2$Ph | $CF_3$ | — | $CH_2CH_2$(2-Py) | H | O | |
| 19-3 | 3,5-$Cl_2$Ph | $CF_3$ | — | $CH_2CH_2COCH_3$ | H | $CH_2$ | |
| 19-4 | 3,5-$Cl_2$Ph | $CF_3$ | — | $CH_2CH_2OCH_3$ | H | O | |
| 19-5 | 3,5-$Cl_2$Ph | $CF_3$ | — | $COCH_3$ | H | $CH_2$ | |
| 19-6 | 3,5-$Cl_2$Ph | $CF_3$ | — | $COC_2H_5$ | H | $CH_2$ | amorphous |
| 19-7 | 3,5-$Cl_2$Ph | $CF_3$ | — | $COC_2H_5$ | H | O | |
| 19-8 | 3,5-$Cl_2$Ph | $CF_3$ | — | COPr-n | H | $CH_2$ | |
| 19-9 | 3,5-$Cl_2$Ph | $CF_3$ | — | $COCH_2CH_2OCH_3$ | H | $CH_2$ | |
| 19-10 | 3,5-$Cl_2$Ph | $CF_3$ | — | $COCH_2CH_2OCH_3$ | H | O | |
| 19-11 | 3,5-$Cl_2$Ph | $CF_3$ | — | $COCH_2CH_2OCH_2CH_3$ | H | O | |
| 19-12 | 3,5-$Cl_2$Ph | $CF_3$ | — | $COCH_2CH(CH_3)OCH_3$ | H | $CH_2$ | |
| 19-13 | 3,5-$Cl_2$Ph | $CF_3$ | — | $COCH_2CH(CH_3)OCH_2CH_3$ | H | O | |
| 19-14 | 3,5-$Cl_2$Ph | $CF_3$ | — | $COCH_2CH(CH_3)OH$ | H | $CH_2$ | |
| 19-15 | 3,5-$Cl_2$Ph | $CF_3$ | — | $COCH_2CH_2OCH_2CH=CH_2$ | H | O | |
| 19-16 | 3,5-$Cl_2$Ph | $CF_3$ | — | $COCH_2COCH_3$ | H | $CH_2$ | |
| 19-17 | 3,5-$Cl_2$Ph | $CF_3$ | — | $COCH_2$(1,3-dioxolane-2-yl) | H | O | |
| 19-18 | 3,5-$Cl_2$Ph | $CF_3$ | — | $COCH_2$(2-methyl-1,3-dioxolane-2-yl) | H | $CH_2$ | |
| 19-19 | 3,5-$Cl_2$Ph | $CF_3$ | — | $COCH_2$(2-trifluoromethyl-1,3-dioxolane-2-yl) | H | O | |
| 19-20 | 3,5-$Cl_2$Ph | $CF_3$ | — | $COCH_2$(2-methyl-1,3-dioxane-2-yl) | H | $CH_2$ | |
| 19-21 | 3,5-$Cl_2$Ph | $CF_3$ | — | $COCH_2CH_2$(1,3-dioxolane-2-yl) | H | O | |
| 19-22 | 3,5-$Cl_2$Ph | $CF_3$ | — | $COCH_2CH_2$(2-methyl-1,3-dioxolane-2-yl) | H | $CH_2$ | |
| 19-23 | 3,5-$Cl_2$Ph | $CF_3$ | — | CO(tetrahydropyran-4-yl) | H | O | |
| 19-24 | 3,5-$Cl_2$Ph | $CF_3$ | — | CO(2,6-dimethyl-4H-pyran-4-one-3-yl) | H | $CH_2$ | |
| 19-25 | 3,5-$Cl_2$Ph | $CF_3$ | — | $COCH_2CH_2CN$ | H | O | |
| 19-26 | 3,5-$Cl_2$Ph | $CF_3$ | — | $COCH_2CH_2Ph$ | H | $CH_2$ | |

TABLE 19-continued

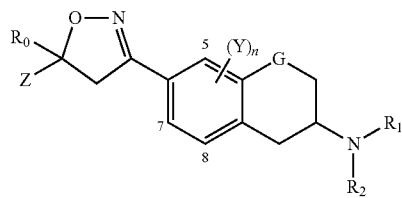

| Compound No. | Z | $R_0$ | $(Y)n$ | $R_1$ | $R_2$ | G | Physical constant |
|---|---|---|---|---|---|---|---|
| 19-27 | 3,5-Cl$_2$Ph | CF$_3$ | — | COCH$_2$CH$_2$(1,2,4-triazole-1-yl) | H | O | |
| 19-28 | 3,5-Cl$_2$Ph | CF$_3$ | — | COCH$_2$CH$_2$(pyrazole-1-yl) | H | CH$_2$ | |
| 19-29 | 3-CF$_3$Ph | CF$_3$ | — | COC$_2$H$_5$ | H | O | |
| 19-30 | 3-CF$_3$Ph | CF$_3$ | — | COCH$_2$CH$_2$OCH$_3$ | H | CH$_2$ | |
| 19-31 | 3-CF$_3$Ph | CF$_3$ | — | COCH$_2$CH(CH$_3$)OCH$_3$ | H | O | |
| 19-32 | 3-CF$_3$Ph | CF$_3$ | — | COCH$_2$(2-methyl-1,3-dioxolane-2-yl) | H | CH$_2$ | |
| 19-33 | 3-CF$_3$Ph | CF$_3$ | — | COCH$_2$CH$_2$CN | H | O | |
| 19-34 | 3,5-Cl$_2$Ph | CF$_3$ | — | COPr-c | H | CH$_2$ | |
| 19-35 | 3,5-Cl$_2$Ph | CF$_3$ | — | COHex-c | H | O | |
| 19-36 | 2-F-3-CF$_3$Ph | CF$_3$ | — | COC$_2$H$_5$ | H | CH$_2$ | |
| 19-37 | 2-F-3-CF$_3$Ph | CF$_3$ | — | COCH$_2$CH$_2$OCH$_3$ | H | O | |
| 19-38 | 3-CF$_3$-4-ClPh | CF$_3$ | — | COC$_2$H$_5$ | H | CH$_2$ | |
| 19-39 | 3-CF$_3$-4-ClPh | CF$_3$ | — | COCH$_2$CH$_2$OCH$_3$ | H | O | |
| 19-40 | 3-CF$_3$-4-ClPh | CF$_3$ | — | COCH$_2$CH(CH$_3$)OCH$_3$ | H | CH$_2$ | |
| 19-41 | 3,5-Cl$_2$Ph | CF$_3$ | — | CSC$_2$H$_5$ | H | O | |
| 19-42 | 3,5-Cl$_2$Ph | CF$_3$ | — | 2-cyclohexenone-3-yl | H | CH$_2$ | |
| 19-43 | 3,5-Cl$_2$Ph | CF$_3$ | — | CH$_2$(4-methyl-1,3-dioxolene-2-one-5-yl) | H | O | |
| 19-44 | 3,5-Cl$_2$Ph | CF$_3$ | — | CH$_2$(4-methyl-1,3-dioxolene-2-one-5-yl) | CH$_2$(4-methyl-1,3-dioxolene-2-one-5-yl) | CH$_2$ | |
| 19-45 | 3,5-Cl$_2$Ph | CF$_3$ | — | COC$_2$H$_5$ | CH$_3$ | O | |
| 19-46 | 3,5-Cl$_2$Ph | CF$_3$ | — | H | H | CH$_2$ | |
| 19-47 | 3,5-Cl$_2$Ph | CF$_3$ | — | H | H | O | |
| 19-48 | 3-CF$_3$Ph | CF$_3$ | — | H | H | CH$_2$ | |
| 19-49 | 2-F-3-CF$_3$Ph | CF$_3$ | — | H | H | O | |
| 19-50 | 3-CF$_3$-4-ClPh | CF$_3$ | — | H | H | CH$_2$ | |
| 19-51 | 3,5-Cl$_2$Ph | CF$_3$ | 5-F | COC$_2$H$_5$ | H | O | |
| 19-52 | 3,5-Cl$_2$Ph | CF$_3$ | 5-Cl | COC$_2$H$_5$ | H | CH$_2$ | |
| 19-53 | 3,5-Cl$_2$Ph | CF$_3$ | 5-CH$_3$ | COC$_2$H$_5$ | H | O | |
| 19-54 | 3,5-Cl$_2$Ph | CF$_3$ | 5-CF$_3$ | COC$_2$H$_5$ | H | CH$_2$ | |
| 19-55 | 3,5-Cl$_2$Ph | CF$_3$ | 5-CH$_2$OCH$_3$ | COC$_2$H$_5$ | H | O | |
| 19-56 | 3,5-Cl$_2$Ph | CF$_3$ | 5-NO$_2$ | COC$_2$H$_5$ | H | CH$_2$ | |
| 19-57 | 3,5-Cl$_2$Ph | CF$_3$ | 5-OH | COC$_2$H$_5$ | H | O | |
| 19-58 | 3,5-Cl$_2$Ph | CF$_3$ | 5-OCH$_3$ | COC$_2$H$_5$ | H | CH$_2$ | |
| 19-59 | 3,5-Cl$_2$Ph | CF$_3$ | 5-OCF$_3$ | COC$_2$H$_5$ | H | O | |
| 19-60 | 3,5-Cl$_2$Ph | CF$_3$ | 5-OCH$_2$COCH$_3$ | COC$_2$H$_5$ | H | CH$_2$ | |
| 19-61 | 3,5-Cl$_2$Ph | CF$_3$ | 5-SH | COC$_2$H$_5$ | H | O | |
| 19-62 | 3,5-Cl$_2$Ph | CF$_3$ | 5-SCH$_3$ | COC$_2$H$_5$ | H | CH$_2$ | |
| 19-63 | 3,5-Cl$_2$Ph | CF$_3$ | 5-SCF$_3$ | COC$_2$H$_5$ | H | O | |
| 19-64 | 3,5-Cl$_2$Ph | CF$_3$ | 5-NH$_2$ | COC$_2$H$_5$ | H | CH$_2$ | |
| 19-65 | 3,5-Cl$_2$Ph | CF$_3$ | 5-NHCH$_3$ | COC$_2$H$_5$ | H | O | |
| 19-66 | 3,5-Cl$_2$Ph | CF$_3$ | 5-N(CH$_3$)$_2$ | COC$_2$H$_5$ | H | CH$_2$ | |
| 19-67 | 3,5-Cl$_2$Ph | CF$_3$ | 5-NHPh | COC$_2$H$_5$ | H | O | |
| 19-68 | 3,5-Cl$_2$Ph | CF$_3$ | 5-NHCOCH$_3$ | COC$_2$H$_5$ | H | CH$_2$ | |
| 19-69 | 3,5-Cl$_2$Ph | CF$_3$ | 5-NHCO$_2$C$_2$H$_5$ | COC$_2$H$_5$ | H | O | |
| 19-70 | 3,5-Cl$_2$Ph | CF$_3$ | 5-NHCO$_2$Bu-t | COC$_2$H$_5$ | H | CH$_2$ | |
| 19-71 | 3,5-Cl$_2$Ph | CF$_3$ | 5-NHCH$_2$Ph | COC$_2$H$_5$ | H | O | |
| 19-72 | 3,5-Cl$_2$Ph | CF$_3$ | 8-F | COC$_2$H$_5$ | H | CH$_2$ | |
| 19-73 | 3,5-Cl$_2$Ph | NO$_2$ | — | COC$_2$H$_5$ | H | O | |
| 19-74 | 3,5-Cl$_2$Ph | OH | — | COC$_2$H$_5$ | H | CH$_2$ | |
| 19-75 | 3,5-Cl$_2$Ph | OMe | — | COC$_2$H$_5$ | H | O | |
| 19-76 | 3,5-Cl$_2$Ph | OCF$_3$ | — | COC$_2$H$_5$ | H | CH$_2$ | |
| 19-77 | 3,5-Cl$_2$Ph | SH | — | COC$_2$H$_5$ | H | O | |
| 19-78 | 3,5-Cl$_2$Ph | SCF$_3$ | — | COC$_2$H$_5$ | H | CH$_2$ | |
| 19-79 | 3,5-Cl$_2$Ph | Cl | — | COC$_2$H$_5$ | H | O | |
| 19-80 | 3,5-Cl$_2$Ph | NH$_2$ | — | COC$_2$H$_5$ | H | CH$_2$ | |
| 19-81 | 3,5-Cl$_2$Ph | NHCOCH$_3$ | — | COC$_2$H$_5$ | H | O | |
| 19-82 | 3,5-Cl$_2$Ph | NHCO$_2$C$_2$H$_5$ | — | COC$_2$H$_5$ | H | CH$_2$ | |
| 19-83 | 3,5-Cl$_2$Ph | CO$_2$C$_2$H$_5$ | — | COC$_2$H$_5$ | H | O | |
| 19-84 | 3,5-Cl$_2$Ph | SO$_2$CH$_3$ | — | COC$_2$H$_5$ | H | CH$_2$ | |
| 19-85 | 3,5-Cl$_2$Ph | SO$_2$CF$_3$ | — | COC$_2$H$_5$ | H | O | |
| 19-86 | 3,5-Cl$_2$Ph | Ph | — | COC$_2$H$_5$ | H | CH$_2$ | |

TABLE 19-continued

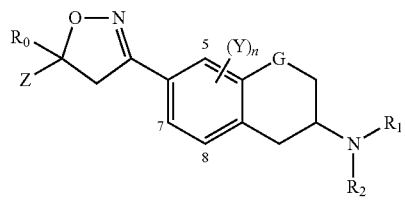

| Compound No. | Z | R₀ | (Y)n | R₁ | R₂ | G | Physical constant |
|---|---|---|---|---|---|---|---|
| 19-87 | 3,5-Cl₂Ph | COCH₃ | — | COC₂H₅ | H | O | |
| 19-88 | 3,5-Cl₂Ph | Cl | — | COC₂H₅ | H | CH₂ | |
| 19-89 | 3,5-Cl₂Ph | CF₂H | — | COC₂H₅ | H | O | |
| 19-90 | 3,5-Cl₂Ph | CCl₃ | — | COC₂H₅ | H | CH₂ | |
| 19-91 | 3,5-Cl₂Ph | CF₂Cl | — | COC₂H₅ | H | O | |
| 19-92 | CH₃CH=CH | CF₃ | — | COC₂H₅ | H | CH₂ | |
| 19-93 | Propargyl | CF₃ | — | COC₂H₅ | H | O | |
| 19-94 | CH₂=CHCH₂ | CF₃ | — | COC₂H₅ | H | CH₂ | |
| 19-95 | 2-butynyl | CF₃ | — | COC₂H₅ | H | O | |
| 19-96 | 3,5-Cl₂Ph | CF₃ | — | COC₂H₅ | -(nitrogen atom forms double bond with indane ring) | CH₂ | |
| 19-97 | 3,5-Cl₂Ph | CF₃ | — | =CHOCH₃ | | CH₂ | |
| 19-98 | 3,5-Cl₂Ph | CF₃ | — | =C(OCH₃)₂ | | O | |
| 19-99 | 3,5-Cl₂Ph | CF₃ | — | =CHNO₂ | | CH₂ | |
| 19-100 | 3,5-Cl₂Ph | CF₃ | — | =C(OCH₂CH₂O) | | O | |
| 19-101 | 3,5-Cl₂Ph | CF₃ | — | CONHCH₃ | H | CH₂ | |
| 19-102 | 3,5-Cl₂Ph | CF₃ | — | CONHC₂H₅ | H | O | |
| 19-103 | 3,5-Cl₂Ph | CF₃ | — | CONHPr-n | H | CH₂ | |
| 19-104 | 3,5-Cl₂Ph | CF₃ | — | CONHCH₂CH₂OCH₃ | H | O | |
| 19-105 | 3,5-Cl₂Ph | CF₃ | — | CONHCH₂CH₂OCH₂CH₃ | H | CH₂ | |
| 19-106 | 3,5-Cl₂Ph | CF₃ | — | CONHCH₂CH(CH₃)OCH₃ | H | O | |
| 19-107 | 3,5-Cl₂Ph | CF₃ | — | CON(CH₃)₂ | H | CH₂ | |
| 19-108 | 3,5-Cl₂Ph | CF₃ | — | CONHCH₂CH₂CN | H | O | |
| 19-109 | 3,5-Cl₂Ph | CF₃ | — | CONHCH₂CH₂Ph | H | CH₂ | |
| 19-110 | 3,5-Cl₂Ph | CF₃ | — | CONHCH₂CH2(1,2,4-triazole-1-yl) | H | O | |
| 19-111 | 3,5-Cl₂Ph | CF₃ | — | CONHCH₂CH₂(pyrazole-1-yl) | H | CH₂ | |
| 19-112 | 3,5-Cl₂Ph | CF₃ | — | CONHOH | H | O | |
| 19-113 | 3,5-Cl₂Ph | CF₃ | — | CONHOCH₃ | H | CH₂ | |
| 19-114 | 3,5-Cl₂Ph | CF₃ | — | CONHPr-c | H | O | |
| 19-115 | 3,5-Cl₂Ph | CF₃ | — | CONHPh | H | CH₂ | |
| 19-116 | 3,5-Cl₂Ph | CF₃ | — | CSNHCH₃ | H | O | |
| 19-117 | 3,5-Cl₂Ph | CF₃ | — | CO₂C₂H₅ | H | CH₂ | |
| 19-118 | 3,5-Cl₂Ph | CF₃ | — | CO₂Pr-n | H | O | |
| 19-119 | 3,5-Cl₂Ph | CF₃ | — | CO₂Pr-c | H | CH₂ | |
| 19-120 | 3,5-Cl₂Ph | CF₃ | — | CO₂CH₂CH₂OCH₃ | H | O | |
| 19-121 | 3,5-Cl₂Ph | CF₃ | — | CO₂CH₂CH₂OCH₂CH₃ | H | CH₂ | |
| 19-122 | 3,5-Cl₂Ph | CF₃ | — | CO₂CH₂CH(CH₃)OCH₃ | H | O | |
| 19-123 | 3,5-Cl₂Ph | CF₃ | — | CO₂CH₂CH₂CN | H | CH₂ | |
| 19-124 | 3,5-Cl₂Ph | CF₃ | — | CO₂CH₂CH₂Ph | H | O | |
| 19-125 | 3,5-Cl₂Ph | CF₃ | — | CO₂CH₂CH₂(1,2,4-triazole-1-yl) | H | CH₂ | |
| 19-126 | 3,5-Cl₂Ph | CF₃ | — | CO₂CH₂CH₂(pyrazole-1-yl) | H | O | |
| 19-127 | 3,5-Cl₂Ph | CF₃ | — | CH₂CH₂CH₂CH₂ | | CH₂ | |
| 19-128 | 3,5-Cl₂Ph | CF₃ | — | C(=O)CH₂CH₂CH₂ | | O | |
| 19-129 | 3,5-Cl₂Ph | CF₃ | — | C(=O)CH₂CH₂C(=O) | | CH₂ | |
| 19-130 | 3,5-Cl₂Ph | CF₃ | — | phthaloyl | | O | |
| 19-131 | 2,4-diCF₃-pyrimidine-6-yl | CF₃ | — | COCH₂CH(CH₃)OCH₃ | H | CH₂ | |
| 19-132 | 2-CH₃S-4-CF₃-pyrimidine-6-yl | CF₃ | — | COCH₂CH(CH₃)OCH₃ | H | O | |
| 19-133 | 2-CH₃O-4-CF₃-pyrimidine-6-yl | CF₃ | — | COCH₂CH(CH₃)OCH₃ | H | CH₂ | |
| 19-134 | 2-Cl-4-CF₃-pyrimidine-6-yl | CF₃ | — | COCH₂CH(CH₃)OCH₃ | H | O | |
| 19-135 | 2-Br-4-CF₃-pyrimidine-6-yl | CF₃ | — | COCH₂CH(CH₃)OCH₃ | H | CH₂ | |

TABLE 20

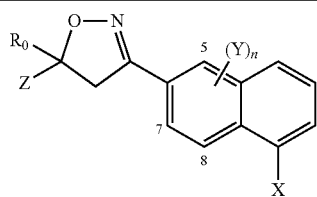

| Compound No. | Z | R₀ | (Y)n | X | Physical constant |
|---|---|---|---|---|---|
| 20-1 | 3,5-Cl₂Ph | CF₃ | — | — | |
| 20-2 | 3,5-Cl₂Ph | CF₃ | — | COCH₃ | |
| 20-3 | 3,5-Cl₂Ph | CF₃ | — | COC₂H₅ | |
| 20-4 | 3,5-Cl₂Ph | CF₃ | — | COPr-n | |
| 20-5 | 3,5-Cl₂Ph | CF₃ | — | COCH₂CH₂OCH₃ | |
| 20-6 | 3,5-Cl₂Ph | CF₃ | — | COCH₂CH₂OCH₂CH₃ | |
| 20-7 | 3,5-Cl₂Ph | CF₃ | — | COCH₂CH(CH₃)OCH₃ | |
| 20-8 | 3,5-Cl₂Ph | CF₃ | — | COCH₂CH(CH₃)OCH₂CH₃ | |
| 20-9 | 3,5-Cl₂Ph | CF₃ | — | COCH₂CH(CH₃)OH | |
| 20-10 | 3,5-Cl₂Ph | CF₃ | — | COCH₂CH₂OCH₂CH=CH₂ | |
| 20-11 | 3,5-Cl₂Ph | CF₃ | — | COCH₂COCH₃ | |
| 20-12 | 3,5-Cl₂Ph | CF₃ | — | COCH₂(1,3-dioxolane-2-yl) | |
| 20-13 | 3,5-Cl₂Ph | CF₃ | — | COCH₂(2-methyl-1,3-dioxolane-2-yl) | |
| 20-14 | 3,5-Cl₂Ph | CF₃ | — | COCH₂(2-trifluoromethyl-1,3-dioxolane-2-yl) | |
| 20-15 | 3,5-Cl₂Ph | CF₃ | — | COCH₂(2-methyl-1,3-dioxane-2-yl) | |
| 20-16 | 3,5-Cl₂Ph | CF₃ | — | COCH₂CH₂(1,3-dioxolane-2-yl) | |
| 20-17 | 3,5-Cl₂Ph | CF₃ | — | COCH₂CH₂(2-methyl-1,3-dioxolane-2-yl) | |
| 20-18 | 3,5-Cl₂Ph | CF₃ | — | CO(tetrahydropyran-4-yl) | |
| 20-19 | 3,5-Cl₂Ph | CF₃ | — | CO(2,6-dimethyl-4H-pyran-4-one-3-yl) | |
| 20-20 | 3,5-Cl₂Ph | CF₃ | — | COCH₂CH₂CN | |
| 20-21 | 3,5-Cl₂Ph | CF₃ | — | COCH₂CH₂Ph | |
| 20-22 | 3,5-Cl₂Ph | CF₃ | — | COCH₂CH₂(1,2,4-triazole-1-yl) | |
| 20-23 | 3,5-Cl₂Ph | CF₃ | — | COCH₂CH₂(pyrazole-1-yl) | |
| 20-24 | 3-CF₃Ph | CF₃ | — | COC₂H₅ | |
| 20-25 | 3-CF₃Ph | CF₃ | — | COCH₂CH₂OCH₃ | |
| 20-26 | 3-CF₃Ph | CF₃ | — | COCH₂CH(CH₃)OCH₃ | |
| 20-27 | 3-CF₃Ph | CF₃ | — | COCH₂(2-methyl-1,3-dioxolane-2-yl) | |
| 20-28 | 3-CF₃Ph | CF₃ | — | COCH₂CH₂CN | |
| 20-29 | 3,5-Cl₂Ph | CF₃ | — | COPr-c | |
| 20-30 | 3,5-Cl₂Ph | CF₃ | — | COHex-c | |
| 20-31 | 2-F-3-CF₃Ph | CF₃ | — | COC₂H₅ | |
| 20-32 | 2-F-3-CF₃Ph | CF₃ | — | COCH₂CH₂OCH₃ | |
| 20-33 | 3-CF₃-4-ClPh | CF₃ | — | COC₂H₅ | |
| 20-34 | 3-CF₃-4-ClPh | CF₃ | — | COCH₂CH₂OCH₃ | |
| 20-35 | 3-CF₃-4-ClPh | CF₃ | — | COCH₂CH(CH₃)OCH₃ | |
| 20-36 | 3,5-Cl₂Ph | CF₃ | — | CSC₂H₅ | |
| 20-37 | 3,5-Cl₂Ph | CF₃ | — | 2-cyclohexenone-3-yl | |
| 20-38 | 3,5-Cl₂Ph | CF₃ | — | H | |
| 20-39 | 3-CF₃Ph | CF₃ | — | H | |
| 20-40 | 2-F-3-CF₃Ph | CF₃ | — | H | |
| 20-41 | 3-CF₃-4-ClPh | CF₃ | — | H | |
| 20-42 | 3,5-Cl₂Ph | CF₃ | 5-F | COC₂H₅ | |
| 20-43 | 3,5-Cl₂Ph | CF₃ | 5-Cl | COC₂H₅ | |
| 20-44 | 3,5-Cl₂Ph | CF₃ | 5-CH₃ | COC₂H₅ | |
| 20-45 | 3,5-Cl₂Ph | CF₃ | 5-CF₃ | COC₂H₅ | |
| 20-46 | 3,5-Cl₂Ph | CF₃ | 5-CH₂OCH₃ | COC₂H₅ | |
| 20-47 | 3,5-Cl₂Ph | CF₃ | 5-NO₂ | COC₂H₅ | |
| 20-48 | 3,5-Cl₂Ph | CF₃ | 5-OH | COC₂H₅ | |
| 20-49 | 3,5-Cl₂Ph | CF₃ | 5-OCH₃ | COC₂H₅ | |
| 20-50 | 3,5-Cl₂Ph | CF₃ | 5-OCF₃ | COC₂H₅ | |
| 20-51 | 3,5-Cl₂Ph | CF₃ | 5-OCH₂COCH₃ | COC₂H₅ | |
| 20-52 | 3,5-Cl₂Ph | CF₃ | 5-SH | COC₂H₅ | |
| 20-53 | 3,5-Cl₂Ph | CF₃ | 5-SCH₃ | COC₂H₅ | |
| 20-54 | 3,5-Cl₂Ph | CF₃ | 5-SCF₃ | COC₂H₅ | |
| 20-55 | 3,5-Cl₂Ph | CF₃ | 5-NH₂ | COC₂H₅ | |
| 20-56 | 3,5-Cl₂Ph | CF₃ | 5-NHCH₃ | COC₂H₅ | |
| 20-57 | 3,5-Cl₂Ph | CF₃ | 5-N(CH₃)₂ | COC₂H₅ | |
| 20-58 | 3,5-Cl₂Ph | CF₃ | 5-NHPh | COC₂H₅ | |

TABLE 20-continued

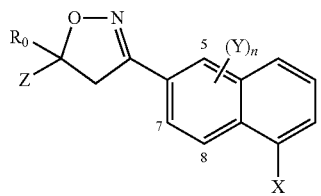

| Compound No. | Z | R₀ | (Y)n | X | Physical constant |
|---|---|---|---|---|---|
| 20-59 | 3,5-Cl₂Ph | CF₃ | 5-NHCOCH₃ | COC₂H₅ | |
| 20-60 | 3,5-Cl₂Ph | CF₃ | 5-NHCO₂C₂H₅ | COC₂H₅ | |
| 20-61 | 3,5-Cl₂Ph | CF₃ | 5-NHCO₂Bu-t | COC₂H₅ | |
| 20-62 | 3,5-Cl₂Ph | CF₃ | 5-NHCH₂Ph | COC₂H₅ | |
| 20-63 | 3,5-Cl₂Ph | CF₃ | 8-F | COC₂H₅ | |
| 20-64 | 3,5-Cl₂Ph | NO₂ | — | COC₂H₅ | |
| 20-65 | 3,5-Cl₂Ph | OH | — | COC₂H₅ | |
| 20-66 | 3,5-Cl₂Ph | OMe | — | COC₂H₅ | |
| 20-67 | 3,5-Cl₂Ph | OCF₃ | — | COC₂H₅ | |
| 20-68 | 3,5-Cl₂Ph | SH | — | COC₂H₅ | |
| 20-69 | 3,5-Cl₂Ph | SCF₃ | — | COC₂H₅ | |
| 20-70 | 3,5-Cl₂Ph | Cl | — | COC₂H₅ | |
| 20-71 | 3,5-Cl₂Ph | NH₂ | — | COC₂H₅ | |
| 20-72 | 3,5-Cl₂Ph | NHCOCH₃ | — | COC₂H₅ | |
| 20-73 | 3,5-Cl₂Ph | NHCO₂C₂H₅ | — | COC₂H₅ | |
| 20-74 | 3,5-Cl₂Ph | CO₂C₂H₅ | — | COC₂H₅ | |
| 20-75 | 3,5-Cl₂Ph | SO₂CH₃ | — | COC₂H₅ | |
| 20-76 | 3,5-Cl₂Ph | SO₂CF₃ | — | COC₂H₅ | |
| 20-77 | 3,5-Cl₂Ph | Ph | — | COC₂H₅ | |
| 20-78 | 3,5-Cl₂Ph | COCH₃ | — | COC₂H₅ | |
| 20-79 | 3,5-Cl₂Ph | Cl | — | COC₂H₅ | |
| 20-80 | 3,5-Cl₂Ph | CF₂H | — | COC₂H₅ | |
| 20-81 | 3,5-Cl₂Ph | CCl₃ | — | COC₂H₅ | |
| 20-82 | 3,5-Cl₂Ph | CF₂Cl | — | COC₂H₅ | |
| 20-83 | CH₃CH=CH | CF₃ | — | COC₂H₅ | |
| 20-84 | Propargyl | CF₃ | — | COC₂H₅ | |
| 20-85 | CH₂=CHCH₂ | CF₃ | — | COC₂H₅ | |
| 20-86 | 2-butynyl | CF₃ | — | COC₂H₅ | |
| 20-87 | 3,5-Cl₂Ph | CF₃ | — | CONHCH₃ | |
| 20-88 | 3,5-Cl₂Ph | CF₃ | — | CONHC₂H₅ | |
| 20-89 | 3,5-Cl₂Ph | CF₃ | — | CONHPr-n | |
| 20-90 | 3,5-Cl₂Ph | CF₃ | — | CONHCH₂CH₂OCH₃ | |
| 20-91 | 3,5-Cl₂Ph | CF₃ | — | CONHCH₂CH₂OCH₂CH₃ | |
| 20-92 | 3,5-Cl₂Ph | CF₃ | — | CONHCH₂CH(CH₃)OCH₃ | |
| 20-93 | 3,5-Cl₂Ph | CF₃ | — | CON(CH₃)₂ | |
| 20-94 | 3,5-Cl₂Ph | CF₃ | — | CONHCH₂CH₂CN | |
| 20-95 | 3,5-Cl₂Ph | CF₃ | — | CONHCH₂CH₂Ph | |
| 20-96 | 3,5-Cl₂Ph | CF₃ | — | CONHCH₂CH₂ (1,2,4-triazole-1-yl) | |
| 20-97 | 3,5-Cl₂Ph | CF₃ | — | CONHCH₂CH₂ (pyrazole-1-yl) | |
| 20-98 | 3,5-Cl₂Ph | CF₃ | — | CONHCH₂ (2-Py) | [141-143] |
| 20-99 | 3,5-Cl₂Ph | CF₃ | — | CONHOH | |
| 20-100 | 3,5-Cl₂Ph | CF₃ | — | CONHOCH₃ | |
| 20-101 | 3,5-Cl₂Ph | CF₃ | — | CONHPr-c | |
| 20-102 | 3,5-Cl₂Ph | CF₃ | — | CONHPh | |
| 20-103 | 3,5-Cl₂Ph | CF₃ | — | CSNHCH₃ | |
| 20-104 | 3,5-Cl₂Ph | CF₃ | — | CO₂C₂H₅ | |
| 20-105 | 3,5-Cl₂Ph | CF₃ | — | CO₂Pr-n | |
| 20-106 | 3,5-Cl₂Ph | CF₃ | — | CO₂Pr-c | |
| 20-107 | 3,5-Cl₂Ph | CF₃ | — | CO₂CH₂CH₂OCH₃ | |
| 20-108 | 3,5-Cl₂Ph | CF₃ | — | CO₂CH₂CH₂OCH₂CH₃ | |
| 20-109 | 3,5-Cl₂Ph | CF₃ | — | CO₂CH₂CH(CH₃)OCH₃ | |
| 20-110 | 3,5-Cl₂Ph | CF₃ | — | CO₂CH₂CH₂CN | |
| 20-111 | 3,5-Cl₂Ph | CF₃ | — | CO₂CH₂CH₂Ph | |
| 20-112 | 3,5-Cl₂Ph | CF₃ | — | CO₂CH₂CH₂ (1,2,4-triazole-1-yl) | |
| 20-113 | 3,5-Cl₂Ph | CF₃ | — | CO₂CH₂CH₂ (pyrazole-1-yl) | |
| 20-114 | 2,4-diCF₃-pyrimidine-6-yl | CF₃ | — | COCH₂CH(CH₃)OCH₃ | |
| 20-115 | 2-CH₃S-4-CF₃-pyrimidine-6-yl | CF₃ | — | COCH₂CH(CH₃)OCH₃ | |
| 20-116 | 2-CH₃O-4-CF₃-pyrimidine-6-yl | CF₃ | — | COCH₂CH(CH₃)OCH₃ | |

TABLE 20-continued

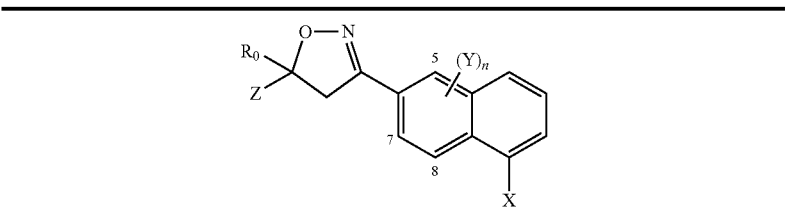

| Compound No. | Z | $R_0$ | (Y)n | X | Physical constant |
|---|---|---|---|---|---|
| 20-117 | 2-Cl-4-$CF_3$-pyrimidine-6-yl | $CF_3$ | — | $COCH_2CH(CH_3)OCH_3$ | |
| 20-118 | 2-Br-4-$CF_3$-pyrimidine-6-yl | $CF_3$ | — | $COCH_2CH(CH_3)OCH_3$ | |

TABLE 21

| Compound No. | $^1$H-NMR ($CDCl_3$, δ ppm) |
|---|---|
| 1-5 | 2.05 (s, 3H), 1.78-1.87 (m, 1H), 2.59-2.69 (m, 1H), 2.85-3.02 (m, 2H), 3.68 (d, 1H), 4.07 (d, 1H), 5.53 (q, 1H), 5.71 (m, 1H), 7.32-7.68 (m, 6H) |
| 1-9 | 1.12 (t, 3H), 1.75-1.86 (m, 1H), 2.59-2.69 (m, 1H), 2.85-3.02 (m, 2H), 3.68 (d, 1H), 4.07 (d, 1H), 5.50 (q, 1H), 6.62 (m, 1H), 7.32-7.57 (m, 6H) |
| 1-12 | 1.24-1.28 (m, 3H), 1.80-1.87 (m, 1H), 2.30-2.50 (m, 2H), 2.60-2.69 (m, 1H) 2.87-3.00 (m, 2H), 3.43 (s, 1H), 3.68 (d, 1H), 4.05 (d, 1H), 4.11-4.15 (m, 1H), 5.53 (q,1H), 6.00 (d,1H), 7.32-7.58 (m, 7H) |
| 1-13 | 1.77-1.84 (m, 1H), 2.54 (t, 2H), 2.62-2.67 (m, 1H), 2.88-2.95 (m, 2H), 3.66-3.75 (m, 3H), 3.98-4.08 (m, 3H), 5.14-5.25 (m, 2H), 5.51 (q, 1H), 5.79-5.88 (m, 1H), 6.47 (d, 1H), 7.32-7.57 (m, 7H) |
| 1-14 | 1.80-1.93 (m, 1H), 2.28 (s, 3H), 2.58-2.68 (m, 1H), 2.83-3.07 (m, 2H), 3.50 (s, 2H), 3.68 (d, 1H), 4.07 (d, 1H), 5.51 (q, 1H), 7.32-7.60 (m, 6H) |
| 1-15 | 1.77-1.87 (m, 1H), 2.59-2.70 (m, 3H), 2.85-2.99 (m, 2H), 3.69 (d, 1H), 3.88-4.13 (m, 5H), 5.15-5.18 (m, 1H), 5.53 (q, 1H), 6.37 (m, 1H), 7.32-7.57 (m, 6H) |
| 1-16 | 1.44 (s, 3H), 1.78-1.85 (m, 1H), 2.61-2.69 (m, 3H), 2.84-3.00 (m, 2H), 3.69 (d, 1H), 3.89-4.00 (m, 4H), 4.04 (d, 1H), 5.53 (q, 1H), 6.63 (d, 1H), 7.32-7.58 (m, 7H) |
| 1-17 | 1.75-1.88 (m, 1H), 2.58-2.69 (m, 1H), 2.85-3.01 (m, 4H), 3.69 (d, 1H), 4.05-4.20 (m, 5H), 5.56 (q, 1H), 6.18 (m, 1H), 7.32-7.58 (m, 6H) |
| 1-18 | 1.44-1.54 (m, 4H), 1.76-1.84 (m, 2H), 2.58-2.69 (m, 3H), 2.88-2.99 (m, 2H), 3.70 (d, 1H), 3.81-4.15 (m, 5H), 5.55 (q, 1H), 6.88 (m, 1H), 7.35-7.57 (m, 6H) |
| 1-19 | 1.71-1.87 (m, 1H), 1.94-2.11 (m, 2H), 2.36-2.43 (m, 2H), 2.58-2.78 (m, 1H), 2.81-3.02 (m, 2H), 3.69 (d, 1H), 3.82-4.10 (m, 5H), 4.93-4.97 (m, 1H), 5.50 (q, 1H), 6.03 (m, 1H), 7.31-7.57 (m, 6H) |
| 1-20 | 1.33 (s, 3H), 1.74-1.86 (m, 1H), 2.31-2.38 (m, 2H), 2.56-2.68 (m, 2H), 3 .68 (d, 1H), 3.88-4.14 (m, 5H), 5.53 (q, 1H), 5.93 (m, 1H), 7.32-7.57 (m, 6H) |
| 1-21 | 1.74-1.88 (m, 5H), 2.33-2.42 (m, 1H), 2.59-2.70 (m, 1H), 2.87-3.05 (m, 2H), 3.38-3.46 (m, 2H), 3.68 (d, 1H), 4.02-4.11 (m, 3H), 5.49-5.64 (m, 2H), 7.27-7.58 (m, 6H) |
| 1-22 | 1.93-2.00 (m, 1H), 2.30 (s, 3H), 2.61-2.72 (m, 1H), 2.85 (s, 3H), 2.88-3.09 (m, 3H), 3.69 (d, 1H), 4.07 (d, 1H), 5.59 (q, 1H), 6.20 (s, 1H), 7.37-7.57 (m, 6H) |
| 1-24 | 1.58-1.73 (m, 1H), 2.49-2.58 (m, 3H), 2.77-3.04 (m, 4H), 3.67 (d, 1H), 4.04 (d, 1H), 5.38-5.47 (m, 2H), 7.02-7.52 (m, 11H) |
| 1-25 | 1.66-1.73 (m, 1H), 2.51-2.58 (m, 1H), 2.80-2.94 (m, 3H), 3.68 (d, 1H), 4.07 (d, 1H), 4.54-4.59 (m, 2H), 5.42 (q, 1H), 5.70 (m, 1H), 7.41-7.56 (m, 6H), 7.92 (s, 1H), 8.16 (s, 1H) |
| 1-26 | 1.61-1.71 (m, 1H), 2.46-2.57 (m, 1H), 2.77-2.92 (m, 4H), 3.68 (d, 1H), 4.07 (d, 1H), 4.42-4.53 (m, 2H), 5.40 (q, 1H), 6.04 (m, 1H), 6.23 (s, 1H), 7.08 (d, 1H), 7.40-7.52 (m, 5H) |
| 1-30 | 1.75-1.87 (m, 1H), 2.58-2.72 (m, 4H), 2.85-3.02 (m, 2H), 3.74 (d, 1H), 3.89-4.03 (m, 4H), 4.14 (d, 1H), 5.49 (q, 1H), 6.64 (m, 1H), 7.32-7.87 (m, 7H) |
| 1-31 | 1.80-1.92 (m, 1H), 2.54-3.04 (m, 7H), 3.74 (d, 1H), 4.13 (d, 1H), 5.50 (q, 1H), 6.05 (m, 1H), 7.32-7.87 (m, 7H) |
| 1-38 | 1.59 (d, 3H), 1.75-1.86 (m, 1H), 2.39-2.46 (m, 2H), 2.59-2.68 (m, 1H), 2.85-3.01 (m, 2H), 3.32 (s, 3H), 3.69-3.78 (m, 2H), 4.14 (d, 1H), 5.52 (q, 1H), 6.48 (m, 1H), 7.32-7.82 (m, 6H) |
| 1-39 | 1.34 (t, 3H), 1.91-2.01 (m, 1H), 2.68-3.04 (m, 5H), 3.69 (d, 1H), 4.07 (d, 1H), 6.18 (q, 1H), 7.42-7.62 (m, 6H) |
| 1-40 | 1.94-2.05 (m, 3H), 2.33-2.38 (m, 2H), 2.55-2.63 (m, 2H), 2.89-3.05 (m, 2H), 3.69 (d, 1H), 4.07 (d, 1H), 4.88-4.98 (m, 1H), 7.34-7.61 (m, 7H) |

TABLE 21-continued

| Compound No. | $^1$H-NMR (CDCl$_3$, δ ppm) |
| --- | --- |
| 1-41 | 1.79-1.92 (m, 1H), 2.14 (s, 3H), 2.41-2.50 (m, 1H), 2.83-3.09 (m, 2H), 3.66 (s, 2H), 3.69 (d, 1H), 4.07 (d, 1H), 4.13 (t, 1H), 7.36-7.58 (m, 6H) |
| 1-42 | 1.91-2.26 (m, 8H), 2.63-3.01 (m, 2H), 3.48 (s, 4H), 3.69 (d, 1H), 4.08 (d, 1H), 4.57 (t, 1H), 7.40-7.60 (m, 6H) |
| 1-44 | 1.97-2.02 (m, 1H), 2.38-2.58 (m, 1H), 2.82-3.10 (m, 2H), 3.68 (d, 1H), 4.06 (d, 1H), 4.95 (t, 1H), 7.10 (d, 1H), 7.37-7.57 (m, 5H) |
| 1-45 | 1.83-1.90 (m, 1H), 2.48-3.04 (m, 3H), 3.74 (d, 1H), 4.13 (d, 1H), 4.48 (t, 1H), 7.31-7.87 (m, 7H) |
| 1-46 | 1.83-1.89 (m, 1H), 2.47-3.02 (m, 2H), 3.86 (d, 1H), 4.21 (d, 1H), 4.50 (t, 1H), 7.31-7.75 (m, 5H), 7.98 (t, 1H) |
| 1-47 | 1.86-1 92 (m, 1H) 2.45-3.10 (m, 2H), 3.72 (d, 1H), 4.12 (d, 1H), 4.53 (t, 1H), 7.32-7.92 (m, 6H) |
| 1-129 | 1.22 (d, 3H), 1.75-1.85 (m, 1H), 2.38-2.50 (m, 2H), 2.62 (s, 3H), 2.80-3.10 (m, 2H), 3.31 (s, 3H), 3.70-3.80 (m, 1H), 3.99 (d, 1H), 4.23 (d, 1H), 5.52 (q, 1H), 6.47 (m, 1H), 7.29-7.62 (m, 3H), 7.77 (s, 1H) |
| 1-130 | 1.24 (d, 3H), 1.77-1.84 (m, 1H), 2.37-2.50 (m, 2H), 2.55-2.70 (m, 1H), 2.80-3 12 (m, 2H), 3.31 (s, 3H), 3.72-3.80 (m, 1H), 4.00 (d, 1H), 4.13 (s, 3H), 4.26 (d, 1H), 5.52 (q, 1H), 6.47 (d, 1H), 7.32-7.59 (m, 3H), 7.81 (s, 1H) |
| 1-132 | 1.23 (d, 3H), 1.70-1.90 (m, 1H), 2.35-2.50 (m, 2H), 2.60-2.72 (m, 1H), 2.80-3.16 (m, 2H), 3.32 (s, 3H), 3.71-3.81 (m, 1H), 4.04 (d, 1H), 4.28 (d, 1H), 5.52 (q, 1H), 6.49 (m, 1H), 7.33-7.60 (m, 3H), 8.16 (s, 1H) |
| 1-134 | 1.93-2.05 (m, 1H), 2.41-3.11 (m, 6H), 3.69 (d, 1H), 4.08 (d, 1H), 4.94 (q, 1H), 5.22 (m, 2H), 7.33-7.61 (m, 6H) |
| 1-136 | 1.21 (t, 3H), 1.79-1.87 (m, 1H), 2.24 (q, 2H), 2.59-2.70 (m, 1H), 2.75-3.05 (m, 2H), 3.71 (d, 1H), 3.94 (s, 3H), 4.08 (d, 1H), 5.51-5.61 (m, 2H), 7.05-7.59 (m, 6H) |
| 1-137 | 1.21 (t, 3H), 1.78-1.85 (m, 1H), 2.27 (q, 2H), 2.59-2.68 (m, 1H), 2.86-3.02 (m, 2H), 3.71 (d, 1H), 4.18 (d, 1H), 5.50-5.63 (m, 2H), 7.32-8.05 (m, 6H) |
| 1-138 | 1.21 (t, 3H), 1.74-1.87 (m, 1H), 2.27 (q, 2H), 2.47 (s, 3H), 2.58-2.68 (m, 1H), 2.82-3.04 (m, 2H), 3.72 (d, 1H), 4.11 (d, 1H), 5.51 (q, 1H), 5.65 (m, 1H), 7.30-7.64 (m, 6H) |
| 1-139 | 1.20 (t, 3H), 1.59-1.87 (m, 1H), 2.25 (q, 2H), 2.60-2.69 (m, 1H), 2.84-3.04 (m, 2H), 3.74 (d, 1H), 3.89 (s, 3H), 4.09 (d, 1H), 5.49-5.62 (m, 2H), 7.17-7.58 (m, 6H) |
| 1-141 | 1.25 (d, 3H), 1.75-1.85 (m, 1H), 2.39-2.48 (m, 2H), 2.60-2.66 (m, 1H), 2.83-3.02 (m, 5H), 3.33 (s, 3H), 3.73-3.79 (m, 1H), 4.01 (d, 1H), 4.33 (d, 1H), 5.51 (q, 1H), 6.52 (m, 1H), 7.31-7.59 (m, 3H), 7.99 (s, 1H) |
| 1-143 | 1.21 (t, 3H), 1.75-1.88 (m, 1H), 2.27 (q, 2H), 2.59-2.70 (m, 1H), 2.84-3.04 (m, 2H), 3.67 (d, 1H), 4.08 (d, 1H), 5.49-5.62 (m, 2H), 7.29-7.56 (m, 5H) |
| 1-144 | 1.22 (t, 3H), 1.78-1.85 (m, 1H), 2.27 (q, 2H), 2.62-2.68 (m, 1H), 2.77-3.03 (m, 2H), 3.69 (d, 1H), 4.03 (d, 1H), 5.52-5.63 (m, 2H), 7.30-7.79 (m, 9H), 8.11 (s, 1H) |
| 3-6 | 1.18 (t, 3H), 2.28 (q, 2H), 2.49-2.70 (m, 2H), 2.98-3.39 (m, 2H), 3.68 (d, 1H), 4.05 (d, 1H), 5.74 (d, 1H), 7.42-7.50 (m, 3H), 8.01 (s, 1H), 8.51 (s, 1H) |
| 3-44 | 1.95-2.01 (m, 1H), 2.48-3.05 (m, 2H), 3.69 (d, 1H), 4.08 (d, 1H), 4.60 (t, 1H), 7.40-7.52 (m, 3H), 7.88 (s, 1H), 8.46 (s, 1H) |
| 5-7 | 1.19 (t, 3H), 2.53 (q, 2H), 3.65 (d, 1H), 4.04 (d, 1H), 4.83 (s, 2H), 5.33 (s, 2H), 7.14-7.50 (m, 6H) |
| 5-12 | 1.22 (d, 3H), 1.73-1.90 (m, 3H), 2.03-2.13 (m, 1H), 2.33-2.48 (m, 2H), 2.77-2.83 (m, 2H), 3.29 (s, 3H), 3.67 (d, 1H), 3.69-3.76 (m, 1H), 4.06 (d, 1H), 5.18-5.25 (m, 1H), 6.46 (m, 1H), 7.34-7.51 (m, 6H) |
| 5-46 | 1.64-2.08 (m, 4H), 2.71-2.86 (m, 2H), 3.67 (d, 1H), 3.97 (t, 1H), 4.04 (d, 1H), 7.36-7.51 (m, 6H) |
| 5-47 | 1.85-2.18 (m, 2H), 3.65 (d, 1H), 4.04 (d, 1H), 4.20-4.33 (m, 3H), 7.13-7.54 (m, 6H) |
| 8-1 | 3.14-3.36 (m, 2H), 3.61-4.15 (m, 4H), 7.42-7.71 (m, 6H) |
| 14-7 | 1.44 (t, 6H), 2.57 (q, 4H), 3.77 (d, 1H), 4.14 (d, 1H), 7.43 -7 .70 (m, 6H) |
| 14-47 | 3.84 (d, 1H), 4.16 (d, 1H), 7.37-7.77 (m, 6H) |
| 15-6 | 1.26 (t, 3H), 2.63 (q, 2H), 3.68 (d, 1H), 4.05 (d, 1H), 7.44-7.68 (m, 6H) |
| 15-7 | 1.26 (d, 3H), 2.40 (q, 2H), 3.75 (d, 1H), 4.14 (q, 1H), 7.42-7.84 (m, 6H) |
| 15-48 | 3.72 (d, 1H), 4.12 (d, 1H), 7.35-7.71 (m, 6H) |
| 17-2 | 2.66 (s, 3H), 3.77 (d, 1H), 4.15 (d, 1H), 6.68 (d, 1H), 7.42-7.87 (m, 6H), 8.49 (d, 1H) |
| 17-3 | 1.33 (t, 3H), 2.97 (q, 2H), 3.78 (d, 1H), 4.17 (d, 1H), 6.66 (d, 1H), 7.41-7.86 (m, 6H), 8.51 (d, 1H) |
| 17-89 | 1.28 (t, 3H), 3.53 (q, 2H), 3.77 (d, 1H), 4.17 (d, 1H), 6.62 (d, 1H), 7.32-7.83 (m, 7H) |
| 17-92 | 1.30 (d, 6H), 3.78 (d, 1H), 4.14-4.25 (m, 2H), 6.97 (m, 1H), 7.42-8.48 (m, 7H) |
| 17-97 | 1.25 (t, 6H), 3.47 (q, 4H), 3.78 (d, 1H), 4.17 (d, 1H), 6.62 (d, 1H), 7.32-7.83 (m,7H) |
| 17-103 | 3.78 (d, 1H), 4.18 (d, 1H), 4.79 (d, 2H), 6.67 (d, 1H), 7.24-7.86 (m, 9H), 8.29 (d, 1H), 8.59 (d, 1H) |

TABLE 21-continued

| Compound No. | $^1$H-NMR (CDCl$_3$, δ ppm) |
|---|---|
| 17-110 | 1.39 (t, 3H), 3.75-3.88 (m, 2H), 4.16 (d, 1H), 7.43-8.10 (m, 6H), 9.36 (d, 1H) |
| 17-114 | 1.68 (s, 9H), 3.78 (d, 1H), 4.18 (d, 1H), 6.59 (d, 1H), 7.41-7.82 (m, 6H), 8.19 (d, 1H) |
| 18-7 | 0.93 (t, 3H), 1.59-1.71 (m, 2H), 2.11 (t, 2H), 2.78-2.84 (m, 2H), 3.30-3.38 (m, 2H), 3.68 (d, 1H), 4.07 (d, 1H), 4.74-4.81 (m, 1H), 5.59 (m, 1H), 7.29-7.56 (m, 6H) |
| 18-10 | 1.17 (d, 3H), 2.29-2.32 (m, 2H), 2.75-2.84 (m, 2H), 3.26-3.37 (m, 6H), 3.64-3.71 (m, 2H), 4.08 (d, 1H), 4.75-4.82 (m, 1H), 5.80 (m, 1H), 7.26-7.57 (m, 6H) |
| 18-16 | 1.38 (s, 3H), 2.58 (s, 2H), 2.78-2.87 (m, 2H), 3.28-3.37 (m, 2H), 3.69 (d, 1H), 3.81-3.95 (m, 4H), 4.07 (d, 1H), 4.72-4.78 (m, 1H), 6.58 (m, 1H), 7.18-7.56 (m, 6H) |
| 18-31 | 2.45 (t, 2H), 2.69 (t, 2H), 2.72-2.87 (m, 2H), 3.29-3.39 (m, 2H), 3.68 (d, 1H), 4.07 (d, 1H), 4.75-4.79 (m, 1H), 5.71 (m, 1H), 7.18-7.57 (m, 6H) |
| 18-32 | 0.69-0.75 (m, 2H), 0.95-1.00 (m, 2H), 1.14-1.28 (m, 1H), 2.81-2.88 (m, 2H), 3.29-3.37 (m, 2H), 3.68 (d, 1H), 4.08 (d, 1H), 4.75-4.82 (m, 1H), 5.80 (m, 1H), 7.26-7.57 (m, 6H) |
| 19-6 | 1.11 (t, 3H), 1.72-1.82 (m, 1H), 1.98-2.12 (m, 1H), 2.20 (q, 2H), 2.23-3.20 (m, 4H), 3.67 (d, 1H), 4.07 (d, 1H), 4.25-4.33 (m, 1H), 5.40 (m, 1H), 7.10-7.51 (m, 6H) |

Although the following indicates several examples of compositions according to the present invention, the additives and ratios at which the additives are added are not limited to these examples, but rather can be varied over a wide range. In addition, the term "parts" in the preparation examples indicates "parts by weight".

Preparation Example 1

Wettable Powder

| | |
|---|---|
| Compound according to the present invention | 40 parts |
| Clay | 48 parts |
| Sodium dioctyl sulfosuccinate | 4 parts |
| Sodium lignin sulfonate | 8 parts |

The above components are uniformly mixed and finely crushed to obtain a wettable powder containing 40% active ingredient.

Preparation Example 2

Emulsion

| | |
|---|---|
| Compound according to the present invention | 10 parts |
| Solvesso 200 | 53 parts |
| Cyclohexanone | 26 parts |
| Calcium dodecylbenzene sulfonate | 1 part |
| Polyoxyethylene alkyl allyl ether | 10 parts |

The above components are mixed and dissolved to obtain an emulsion containing 10% active ingredient.

Preparation Example 3

Powder

| | |
|---|---|
| Compound according to the present invention | 10 parts |
| Clay | 90 parts |

The above components are uniformly mixed and finely crushed to obtain a powder containing 10% active ingredient.

Preparation Example 4

Granules

| | |
|---|---|
| Compound according to the present invention | 5 parts |
| Clay | 73 parts |
| Bentonite | 20 parts |
| Sodium dioctyl sulfosuccinate | 1 part |
| Potassium phosphate | 1 part |

The above components are thoroughly crushed and mixed followed by the addition of water, mixing well, granulating and drying to obtain granules containing 5% active ingredient.

Preparation Example 5

Suspension

| | |
|---|---|
| Compound according to the present invention | 10 parts |
| Polyoxyethylene alkyl allyl ether | 4 parts |

-continued

| | |
|---|---|
| Sodium polycarboxylate | 2 parts |
| Glycerin | 10 parts |
| Xanthan gum | 0.2 parts |
| Water | 73.8 parts |

The above components are mixed and wet-crushed to a grain size of 3 microns or less to obtain a suspension containing 10% active ingredient.

Preparation Example 6

Water-Dispersible Granules

| | |
|---|---|
| Compound according to the present invention | 40 parts |
| Clay | 36 parts |
| Potassium chloride | 10 parts |
| Sodium alkylbenzene sulfonate | 1 part |
| Sodium lignin sulfonate | 8 parts |
| Formaldehyde condensation product of sodium alkylbenzene sulfonate | 5 parts |

The above components are uniformly mixed and finely crushed followed by adding a suitable amount of water and mixing to obtain a clay-like material. The clay-like material is granulated and then dried to obtain water-dispersible granules containing 40% active ingredient.

Test examples of the pest control agents according to the present invention obtained in the manner described above are indicated below.

Test Example 1

Efficacy Against *Aphis gossypii*

Cucumber plants planted in a no. 3 pot for which 10 days had elapsed since germination were inoculated with adult *Aphis gossypii*. The adult insects were removed after 1 day, and a chemical liquid diluted with water to a compound concentration of 125 ppm was sprayed onto the cucumber plants infested with nymphs laid by the adults in accordance with the emulsion formula indicated in the aforementioned Preparation Example 2. The cucumber plants were placed in a constant temperature chamber at a temperature of 25° C. and humidity of 65% and insect viability was investigated 5 days later followed by determination of insect mortality rate. The test was repeated twice. As a result, the following compounds demonstrated insect mortality rates of 100%.

Compound Nos. (compound numbers correspond to the compound numbers of Tables 1 to 20, and to apply similarly hereinafter): 1-5, 1-6, 1-7, 1-8, 1-9, 1-10, 1-11, 1-12, 1-13, 1-14, 1-15, 1-16, 1-17, 1-18, 1-19, 1-20, 1-21, 1-23, 1-25, 1-26, 1-27, 1-28, 1-29, 1-30, 1-31, 1-32, 1-34, 1-35, 1-36, 1-37, 1-38, 1-39, 1-128, 1-135, 1-136, 1-137, 1-138, 1-139, 1-140, 1-141, 1-142, 1-143, 3-6, 5-6, 5-8, 5-12, 18-6

The insect mortality rate of pirimicarb used as a control was 9%.

Test Example 2

Efficacy Against *Spodoptera litura*

The emulsion indicated in the aforementioned Preparation Example 2 was diluted with water to a compound concentration of 125 ppm in accordance with the formula thereof. After immersing cabbage leaves in the chemical liquid for 30 seconds and allowing to air dry, the cabbage leaves were placed in a Petri dish lined with filter paper and inoculated with five 2nd instar *Spodoptera litura* larvae. A glass cover was placed over the Petri dish, the dish was placed in a constant temperature chamber at a temperature of 25° C. and humidity of 65%, and viability was investigated 5 days later followed by determination of insect mortality rate. The test was repeated twice. As a result, the following compounds demonstrated insect mortality rates of 100%.

Compound Nos.: 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-34, 1-35, 1-36, 1-37, 1-38, 1-39, 1-40, 1-41, 1-128, 1-129, 1-130, 1-134, 1-135, 1-136, 1-137, 1-138, 1-139, 1-140, 1-141, 1-142, 1-143, 3-6, 5-6, 5-8, 5-12, 5-7, 5-10, 13-5, 13-6, 16-6, 18-5, 18-6, 18-7, 18-32, 18-10, 18-16, 18-23

The insect mortality rate of chlordimeform used as a control was 40%.

Test Example 3

Efficacy Against *Tetranychus urticae*

After inoculating the first true leaves of kidney bean plants planted in a no. 3 pot for which 7 to 10 days had elapsed since germination with female adult *Tetranychus urticae* resistant to organic phosphorous agents, a chemical liquid diluted with water to a compound concentration of 125 ppm was sprayed onto the kidney bean plants in accordance with the formula of the wettable powder indicated in the aforementioned Preparation Example 1. The kidney bean plants were placed in a constant temperature chamber at a temperature of 25° C. and humidity of 65% and insect mortality rate was investigated 3 days later. The test was repeated twice. As a result, the following compounds demonstrated insect mortality rates of 100%.

Compound Nos.: 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-34, 1-35, 1-36, 1-37, 1-38, 1-39, 1-40, 1-128, 1-129, 1-130, 1-134, 1-135, 1-136, 1-137, 1-138, 1-139, 1-140, 1-141, 1-142, 1-143, 3-6, 5-6, 5-8, 5-12, 5-10

The insect mortality rate of chlordimeform used as a control was 40%.

Test Example 4

Efficacy Against *Pseudaletia separata*

The wettable powder indicated in the aforementioned Preparation Example 1 was diluted with water to a compound concentration of 125 ppm in accordance with the formula thereof. After immersing corn leaves in the chemical liquid for 30 seconds and allowing to air dry, the corn leaves were placed in a Petri dish lined with filter paper and inoculated with five 2nd instar *Pseudaletia separata* larvae. A glass cover was placed over the Petri dish, the dish was placed in a constant temperature chamber at a temperature of 25° C. and humidity of 65%, and viability was investigated 5 days later followed by determination of insect mortality rate. The test was repeated twice. As a result, the following compounds demonstrated insect mortality rates of 100%.

Compound Nos.: 1-6, 3-6, 5-6, 5-8, 17-88, 17-111, 14-7, 14-8, 14-9, 14-48

The insect mortality rate of chlordimeform used as a control was 40%.

Test Example 5

Efficacy Against *Culex pipiens molestus*

0.225 ml of distilled water containing 10 *Culex pipiens molestus* larvae 1 day after hatching and aquarium fish food (TetraMin, Tetra Japan) were placed in a 0.3 ml polystyrene test container.

The compounds were prepared as 1% solutions using DMSO (containing 0.5% Tween 20), and further diluted to 0.01% with distilled water. 0.025 ml of the diluted chemical liquid were added to the test container containing the *Culex pipiens molestus* larvae followed by stirring (final compound concentration: 0.001%).

Insect mortality rates were invested 2 days after allowing to stand at 25° C. The test was repeated twice.

In this test, the following compounds demonstrated insect mortality rates of 90% or higher and were determined to be effective.

Compound Nos.: 1-6, 1-7, 1-8, 1-10, 1-11, 1-16, 1-20, 1-22, 1-26, 1-27, 1-31, 1-34, 1-35, 1-36, 1-40, 1-41, 1-128, 3-6, 5-6, 5-7, 5-8, 5-10, 5-12, 8-88, 13-5, 13-6, 16-6, 16-7, 16-116, 17-3, 17-91, 17-111, 20-98

Test Example 6

Efficacy Against *Reticulitermes speratus*

1% compound stock solutions prepared by diluting with DMSO (containing 0.5% Tween 20) were diluted 100-fold with water to obtain desired 0.01% diluted chemical liquids. Filter paper having a diameter of 5.5 cm was placed on the bottom of a PET plastic cup having a volume of 90 ml followed by dropping in 0.7 ml of chemical liquid over the entire surface of the filter paper and allowing to stand for 30 minutes. 10 *Reticulitermes speratus* worker ants were released into the cup followed by covering with a lid containing air holes.

Subsequently, the cup was placed in an observation chamber (25° C., 60% Rh, 14 L) and viability was evaluated 5 days after treatment. The test was repeated twice.

In this test, the following compound demonstrated an insect mortality rate of 90% or higher.

Compound No.: 1-6

Test Example 7

Efficacy Against *Blattella germanica*

0.5 ml of 10% aqueous sucrose solution were placed in a 1.5 ml Eppendorf tube followed by the addition of 10 μl of a 1% compound stock solution prepared by diluting with DMSO (containing 0.5% Tween 20) and 0.5 ml of melted 2% aqueous agar solution and stirring well. This was promptly centrifuged to obtain a poison bait containing 0.01% of the compound.

Filter paper having a diameter of 5.5 cm and the poison bait were placed in a 90 ml PET plastic cup, after which 20 1st instar *Blattella germanica* larvae were released into the cup followed by covering with a lid containing air holes.

Subsequently, the cup was placed in an observation chamber (25° C., 60% Rh, 14 L) and viability was evaluated 5 days after treatment. The test was repeated twice.

In this test, the following compound demonstrated an insect mortality rate of 90% or higher.

Compound No.: 1-6

INDUSTRIAL APPLICABILITY

According to the present invention, novel nitrogen-containing heterocyclic compounds or salts thereof, which can be advantageously synthesized industrially and can function as an active ingredient of a pest control agent that has reliable effects and can be used safely, as well as an insecticide, miticide and pest control agent, which contain as an active ingredient thereof at least one type of these compounds, are provided.

The invention claimed is:

1. A nitrogen-containing heterocyclic compound represented by the following formula (I), or a salt thereof:

wherein,
$R_0$ represents a nitro group, a hydroxyl group, a mercapto group, a halogen atom, an unsubstituted or substituted amino group, or an organic group;

Z represents an unsubstituted or substituted phenyl group, or an unsubstituted or substituted 5-membered or 6-membered heterocyclic group comprising at least one heteroatom selected from the group consisting of a nitrogen atom, an oxygen atom and a sulfur atom; and, Q represents a group represented by the following formula (I'):

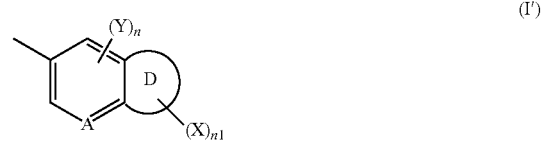

selected from the group consisting of:

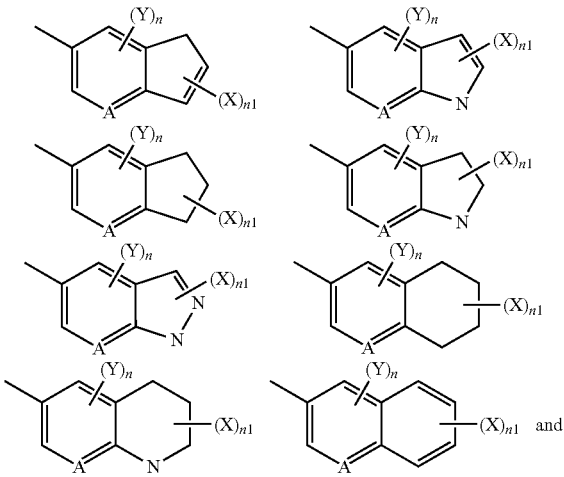

-continued

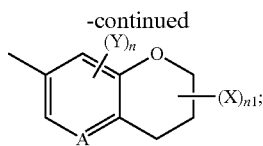

wherein,
Y represents a nitro group, a hydroxyl group, a mercapto group, a halogen atom, an unsubstituted or substituted amino group, or an organic group;
n represents an integer of 0 to 3, a plurality of Y is identical to or different from each other when n is 2 or more, and two Y may form a 4-membered to 6-membered ring by bonding together when two Y are mutually adjacent;
D represents a 5-membered to 8-membered hydrocarbon ring group or heterocyclic group that has or does not have a substituent other than a substituent X;
X represents a functional group represented by the following formula (II)-1 or formula (II)-2:

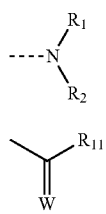

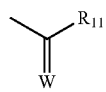

wherein,
in the formula (II)-1, a dotted line represents a single bond or double bond, and either
$R_1$ or $R_2$ is bonded to a nitrogen atom when the dotted line represents a double bond; and
$R_1$ and $R_2$ respectively and independently represent a hydrogen atom, a nitro group, a hydroxyl group, a mercapto group, an unsubstituted or substituted amino group, or an organic group, $R_1$ and $R_2$ may bond together to fortn a 3-membered to 8-membered ring, or $R_1$ and $R_2$ may together form a double bond to represent a group represented by the following formula:

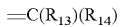

wherein,
$R_{13}$ and $R_{14}$ respectively and independently represent a hydrogen atom, a nitro group, a hydroxyl group, a mercapto group, a halogen atom, an unsubstituted or substituted amino group, or an organic group, or $R_1$ or $R_2$ may bond with A to form a 5-membered to 8-membered ring; and,
in the formula (II-2), W represents an oxygen atom or a sulfur atom; and,
$R_{11}$ represents a hydrogen atom, a hydroxyl group, a mercapto group, an unsubstituted or substituted amino group, or an organic group;
n1 represents an integer of 1; and,
A represents a carbon atom or a nitrogen atom, and when A is a carbon atom and does not have a substituent represented by Y on the carbon atom, a hydrogen atom bonds thereto or A forms a ring by bonding with $R_1$ or $R_2$.

2. The nitrogen-containing heterocyclic compound or the salt thereof, according to claim 1, wherein, in the formula (I'), X is represented by formula (II)-1.

3. The nitrogen-containing heterocyclic compound or the salt thereof, according to claim 2, wherein, in the formula (II)-1, $R_1$ is a group represented by formula (III):

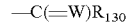

wherein,
$R_{130}$ represents a hydrogen atom, an unsubstituted or substituted amino group or an organic group, and W represents an oxygen atom or a sulfur atom.

4. The nitrogen-containing heterocyclic compound or the salt thereof, according to any one of claims 1 to 3, wherein, in the formula (I), $R_0$ represents a $C_1$ to $C_{12}$ haloallcyl group.

5. The nitrogen-containing heterocyclic compound or the salt thereof, according to any one of claims 1 to 3, wherein, in the formula (I'), Y represents a halogen atom, a $C_1$ to $C_6$ alkyl group, a $C_1$ to $C_6$ alkoxy group, a $C_1$ to $C_6$ haloalkyl group or a $C_1$ to $C_6$ haloalkoxy group, or n represents 0.

6. An insecticide comprising as an active ingredient thereof at least one type of the nitrogen-containing heterocyclic compound or salt thereof, according to any one of claims 1 to 3.

7. A miticide comprising as an active ingredient thereof at least one type of the nitrogen-containing heterocyclic compound or salt thereof, according to any one of claims 1 to 3.

8. A sanitary pest control agent comprising as an active ingredient thereof at least one type of the nitrogen-containing heterocyclic compound or salt thereof, according to any one of claims 1 to 3.

9. An insecticide comprising as an active ingredient thereof at least one type of the nitrogen-containing heterocyclic compound or salt thereof, according to claim 1.

10. An insecticide comprising as an active ingredient thereof at least one type of the nitrogen-containing heterocyclic compound or salt thereof, according to claim 4.

11. An insecticide comprising as an active ingredient thereof at least one type of the nitrogen-containing heterocyclic compound or salt thereof, according to claim 5.

12. A miticide comprising as an active ingredient thereof at least one type of the nitrogen-containing heterocyclic compound or salt thereof, according to claim 1.

13. A miticide comprising as an active ingredient thereof at least one type of the nitrogen-containing heterocyclic compound or salt thereof, according to claim 4.

14. A miticide comprising as an active ingredient thereof at least one type of the nitrogen-containing heterocyclic compound or salt thereof, according to claim 5.

15. A sanitary pest control agent comprising as an active ingredient thereof at least one type of the nitrogen-containing heterocyclic compound or salt thereof, according to claim 1.

16. A sanitary pest control agent comprising as an active ingredient thereof at least one type of the nitrogen-containing heterocyclic compound or salt thereof, according to claim 4.

17. A sanitary pest control agent comprising as an active ingredient thereof at least one type of the nitrogen-containing heterocyclic compound or salt thereof, according to claim 5.

18. The nitrogen-containing heterocyclic compound or the salt thereof, according to claim 1, wherein Z is unsubstituted or Z is substituted with a halogen atom, a cyano group, a $C_1$ to $C_6$ alkyl group, a $C_1$ to $C_6$ haloalkyl group, a $C_1$ to $C_6$ alkoxy group, or a $C_1$ to $C_6$ alkylthio group.

* * * * *